United States Patent
Lee et al.

(10) Patent No.: US 10,985,329 B2
(45) Date of Patent: Apr. 20, 2021

(54) CONDENSED CYCLIC COMPOUND AND ORGANIC LIGHT-EMITTING DEVICE INCLUDING THE SAME

(71) Applicants: Samsung Electronics Co., Ltd., Suwon-si (KR); Samsung SDI Co., Ltd., Yongin-si (KR)

(72) Inventors: Seungjae Lee, Suwon-si (KR); Byungku Kim, Suwon-si (KR); Youngkwon Kim, Suwon-si (KR); Changwoo Kim, Suwon-si (KR); Hyungsun Kim, Suwon-si (KR); Changju Shin, Suwon-si (KR); Eunsun Yu, Suwon-si (KR); Byoungki Choi, Hwaseong-si (KR); Kyu-Young Hwang, Suwon-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 0 days.

(21) Appl. No.: 16/177,914

(22) Filed: Nov. 1, 2018

(65) Prior Publication Data
US 2019/0074451 A1    Mar. 7, 2019

Related U.S. Application Data

(63) Continuation-in-part of application No. 14/573,422, filed on Dec. 17, 2014, now Pat. No. 10,158,085.

(30) Foreign Application Priority Data

Dec. 17, 2013  (KR) .................. 10-2013-0157532

(51) Int. Cl.
*H01L 51/00* (2006.01)
*C07D 405/14* (2006.01)
(Continued)

(52) U.S. Cl.
CPC ........ *H01L 51/0072* (2013.01); *C07D 405/14* (2013.01); *C07D 491/048* (2013.01);
(Continued)

(58) Field of Classification Search
None
See application file for complete search history.

(56) References Cited

U.S. PATENT DOCUMENTS 7,846,560 B2   12/2010   Nakano et al.
8,080,658 B2   12/2011   Iwakura et al.
(Continued)

FOREIGN PATENT DOCUMENTS

JP   2009-155300 A   7/2009
JP   2010-215759 A   9/2010
(Continued)

OTHER PUBLICATIONS

Machine English Translation of JP 2013-026529 A (Ito).
(Continued)

*Primary Examiner* — Jay Yang
(74) *Attorney, Agent, or Firm* — Cantor Colburn LLP

(57) ABSTRACT

A condensed-cyclic compound represented by Formula 1A:

Formula 1A (Continued)

10

| 19 |
|---|
| 15 |
| 11 | wherein in Formula 1A, groups, substituents, and variables are the same as defined in the specification.

7 Claims, 1 Drawing Sheet

(51) Int. Cl.
*C09K 11/06* (2006.01)
*C07D 491/048* (2006.01)
*H01L 51/50* (2006.01)

(52) U.S. Cl.
CPC .......... *C09K 11/06* (2013.01); *H01L 51/0067* (2013.01); *H01L 51/0071* (2013.01); *H01L 51/0073* (2013.01); *C09K 2211/1018* (2013.01); *H01L 51/0081* (2013.01); *H01L 51/0085* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

| | | |
|---|---|---|
| 9,847,501 B2 | 12/2017 | Mizutani et al. |
| 2010/0032658 A1 | 2/2010 | Lee et al. |
| 2012/0086329 A1 | 4/2012 | Dyatkin |
| 2013/0062597 A1 | 3/2013 | Yoshida et al. |
| 2014/0077179 A1 | 3/2014 | Shin et al. |
| 2014/0312338 A1 | 10/2014 | Mizutani et al. |
| 2015/0025239 A1 | 1/2015 | Ahn et al. |
| 2015/0228909 A1 | 8/2015 | Kim et al. |

FOREIGN PATENT DOCUMENTS

| | | |
|---|---|---|
| JP | 2010-267847 A | 11/2010 |
| JP | 2013-026529 A | 2/2013 |
| JP | 5317470 B2 | 7/2013 |
| JP | 5444594 B2 | 1/2014 |
| KR | 10-2008-0080306 A | 9/2008 |
| KR | 10-2010-0007780 A | 1/2010 |
| KR | 10-2010-0031736 A | 3/2010 |
| KR | 10-2010-0032888 A | 3/2010 |
| KR | 1020120052879 A | 5/2012 |
| KR | 10-2012-0116282 A | 10/2012 |
| KR | 10-2013-0094903 A | 8/2013 |
| KR | 20140046541 A | 4/2014 |
| WO | 2010-004877 A1 | 1/2010 |
| WO | 2012-015017 A1 | 2/2012 |
| WO | 2012-033062 A1 | 3/2012 |
| WO | 2012-133644 A1 | 10/2012 |
| WO | 2012-137958 A1 | 10/2012 |
| WO | 2013-077362 A1 | 5/2013 |
| WO | 2013077362 A1 | 5/2013 |
| WO | 2013-122402 A1 | 8/2013 |
| WO | 2013-165192 A1 | 11/2013 |

OTHER PUBLICATIONS

Office Action issued by the Korean Patent Office dated Nov. 21, 2018, in the examination of the Korean Patent Application No. 10-2013-0157532.
Office Action issued by the Korean Patent Office dated Apr. 18, 2019 in the examination of the Korean Patent Application No. 10-2013-0157532, with English Translation.
Korean Office Action dated Dec. 12, 2019 issued in corresponding Korean Patent Application No. 10-2019-0020496, 136 pages.
Office Action dated Dec. 17, 2019 in corresponding Korean Patent Application No. 10-2013-0157532.

10

| 19 |
|---|
| 15 |
| 11 |

CONDENSED CYCLIC COMPOUND AND ORGANIC LIGHT-EMITTING DEVICE INCLUDING THE SAME

CROSS-REFERENCE TO RELATED APPLICATIONS

This application is a continuation-in-part of U.S. patent application Ser. No. 14/573,422, filed on Dec. 17, 2014, which claims priority to Korean Patent Application No. 10-2013-0157532, filed on Dec. 17, 2013, and all the benefits accruing therefrom under 35 U.S.C. § 119, the contents of which are incorporated herein in their entireties by reference.

BACKGROUND

1. Field

One or more embodiments of the present disclosure relate to condensed-cyclic compounds and organic light-emitting devices including the condensed-cyclic compounds.

2. Description of the Related Art

Organic light-emitting devices (OLEDs) are self-emitting devices that have advantages such as wide viewing angles, excellent contrast ratios, and quick response times. In addition, OLEDs exhibit excellent brightness, driving voltage, and response speed characteristics, and can provide multi-colored images.

A typical OLED has a structure including an anode, a cathode, and an organic layer disposed between the anode and the cathode and including an emission layer. A hole transporting region may be disposed between the anode and the cathode, and an electron transporting region may be disposed between the emission layer and the cathode. Holes injected from the anode move to the EML via the hole transport region, and electrons injected from the cathode move to the EML via the electron transport region. Carriers such as holes and electrons recombine in the EML to generate excitons. When the excitons drop from an excited state to a ground state, light is emitted.

Different types of organic light emitting devices are known. However, there still remains a need in OLEDs having low driving voltage, high efficiency, high brightness, and long lifespan.

SUMMARY

One or more embodiments include novel condensed-cyclic compounds and organic light-emitting devices including the condensed-cyclic compounds.

Additional aspects will be set forth in part in the description which follows and, in part, will be apparent from the description, or may be learned by practice of the presented embodiments.

According to one or more embodiments, provided is a condensed-cyclic compound represented by Formula 1A or 1B:

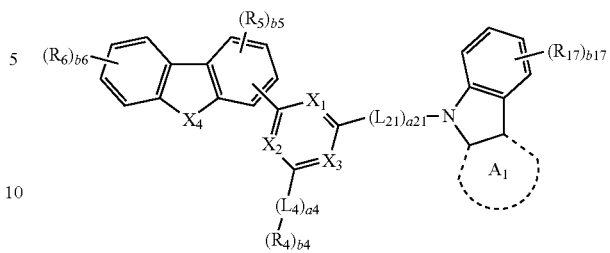

Formula 1A

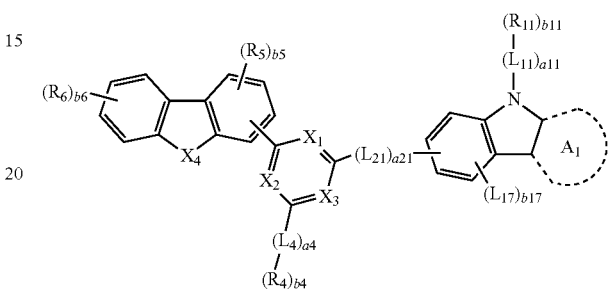

Formula 1B

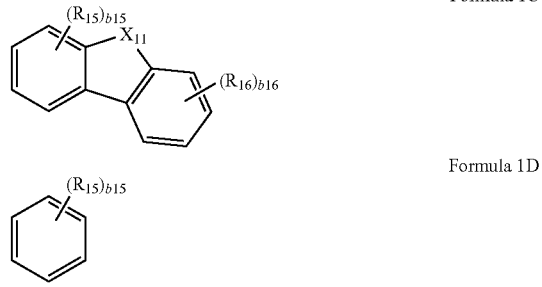

Formula 1C

Formula 1D

In the Formulae above,
ring $A_1$ in Formulae 1A and 1B is represented by Formula 1C or 1D;
$X_1$ is N or C-$[(L_1)_{a1}$-$(R_1)_{b1}]$,
$X_2$ is N or C-$[(L_2)_{a2}$-$(R_2)_{b2}]$,
$X_3$ is N or C-$[(L_3)_{a3}$-$(R_3)_{b3}]$, and
at least one of $X_1$ to $X_3$ is N;
$X_4$ is O or S;
$X_{11}$ is selected from N-$[(L_{12})_{a12}$-$(R_{12})_{b12}]$, S, O, S(=O), S(=O)$_2$, C(=O), C($R_{13}$)($R_{14}$), Si($R_{13}$)($R_{14}$), P($R_{13}$), P(=O)($R_{13}$), and C=N($R_{12}$);
$L_1$ to $L_4$, $L_{11}$, $L_{12}$ and $L_{21}$ may be each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic hetero-condensed polycyclic group;
a1 to a4, a11, a12, and a21 may be each independently selected from integers of 0 to 3;
$R_1$ to $R_3$, $R_5$, $R_6$, and $R_{11}$ to $R_{17}$ may be each independently selected from a hydrogen, a deuterium, —F (a fluoro group), —Cl (a chloro group), —Br (a bromo group), —I (an iodo group), a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic hetero-condensed polycyclic group, $-N(Q_1)(Q_2)$, $-Si(Q_3)(Q_4)(Q_5)$, and $-B(Q_6)(Q_7)$, $R_4$ is selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, and a substituted or unsubstituted monovalent non-aromatic hetero-condensed polycyclic group;

b1 to b6 and b11 to b17 may be each independently selected from integers of 1 to 3;

at least one substituent of the substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted divalent non-aromatic condensed polycyclic group, substituted divalent non-aromatic hetero-condensed polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, and substituted monovalent non-aromatic hetero-condensed polycyclic group may be selected from:

a deuterium, $-F$, $-Cl$, $-Br$, $-I$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, $-F$, $-Cl$, $-Br$, $-I$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, $-N(Q_{11})(Q_{12})$, $-Si(Q_{13})(Q_{14})(Q_{15})$ and $-B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, each substituted with at least one of a deuterium, $-F$, $-Cl$, $-Br$, $-I$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, $-N(Q_{21})(Q_{22})$, $-Si(Q_{23})(Q_{24})(Q_{25})$, and $-B(Q_{26})(Q_{27})$; and $-N(Q_{31})(Q_{32})$, $-Si(Q_{33})(Q_{34})(Q_{35})$ and $-B(Q_{36})(Q_{37})$;

wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, monovalent a non-aromatic condensed polycyclic group, and a monovalent non-aromatic hetero-condensed polycyclic group.

According to one or more other embodiments, provided is a condensed-cyclic compound represented by Formula 1A:

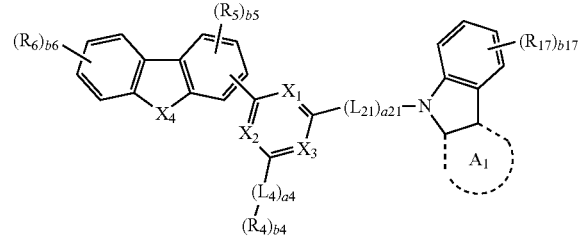

Formula 1A wherein in Formula 1A,
ring $A_1$ is represented by Formula 1D;

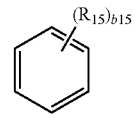

Formula 1D $X_1$ to $X_3$ is N;

$X_4$ is O or S;

$L_4$ and $L_{21}$ are each independently selected from groups represented by Formulae 2-1, 2-2 and 2-34;

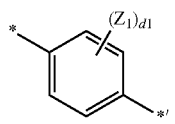

Formula 2-1

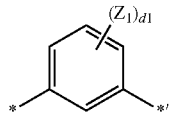

Formula 2-2

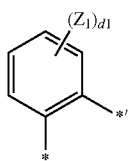

Formula 2-34 wherein in Formulae 2-1, 2-2 and 2-34, $Z_1$ is selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group and a phenyl group and d1 is selected from integers of 1 to 4;

a4 is selected from integers 0 to 3 and a21 is 0, 1, 2 or 3;

$R_5$, $R_6$, $R_{15}$ and $R_{17}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

$R_4$ is selected from:

a phenyl group; and a phenyl group, substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, and a biphenyl group; and b4 to b6, b15 and b17 are each independently selected from integers of 1 to 3.

According to one or more other embodiments, provided is an organic light-emitting device including a first electrode;

a second electrode; and an organic layer disposed between the first electrode and the second electrode, wherein the organic layer includes an emission layer and at least one condensed-cyclic compound described above.

The condensed-cyclic compound may be included in the emission layer, wherein the emission layer further includes a dopant, and the condensed-cyclic compound included in the emission layer may act as a host.

BRIEF DESCRIPTION OF THE DRAWING

These and/or other aspects will become apparent and more readily appreciated from the following description of the embodiments, taken in conjunction with the accompanying drawing in which:

the FIGURE is a schematic view showing an organic light-emitting device according to an embodiment.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

A condensed-cyclic compound according to an embodiment may be represented by Formula 1A or 1B:

Formula 1A

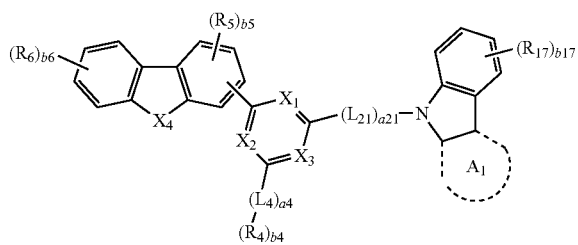

Formula 1B

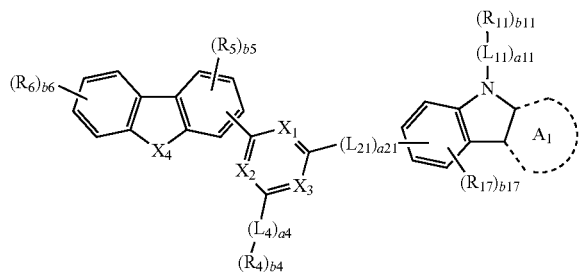

ring $A_1$ in Formula 1A and 1B may be represented by Formula 1C or 1D.

Formula 1C

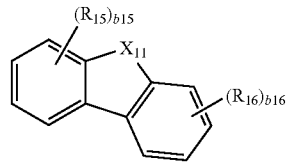

Formula 1D

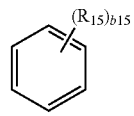

In Formulae 1A and 1B, ring $A_1$ may be fused with an adjacent 5-membered cyclic ring by sharing the carbon atoms disposed therebetween. Accordingly, the condensed-cyclic compound represented by Formula 1A or 1B may be represented by any one of Formulae 1A-1 to 1A-7 and 1B-1 to 1B-4:

Formula 1A-1

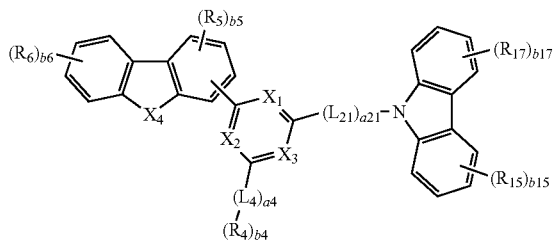

Formula 1A-2

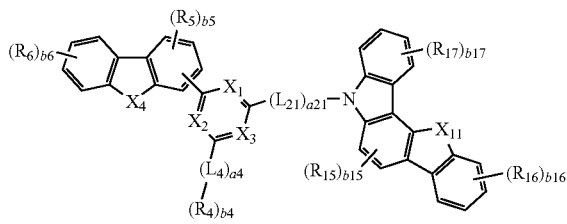

Formula 1A-3

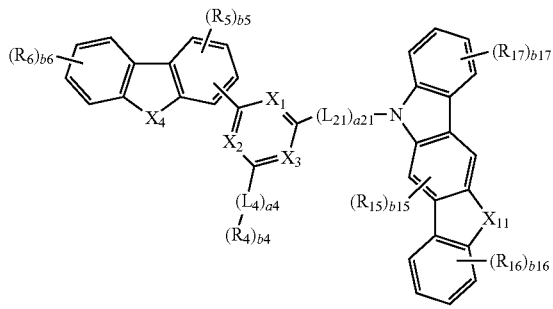

Formula 1A-4

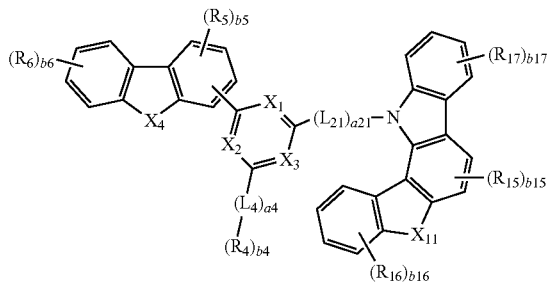

Formula 1A-5
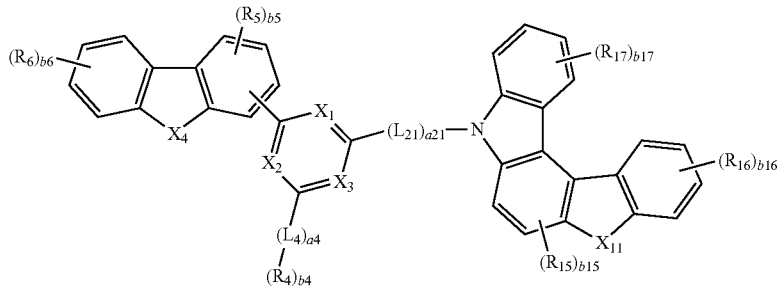
Formula 1A-6
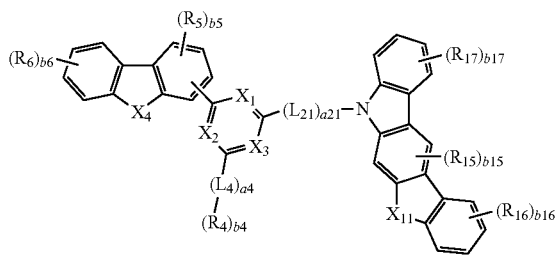
Formula 1A-7
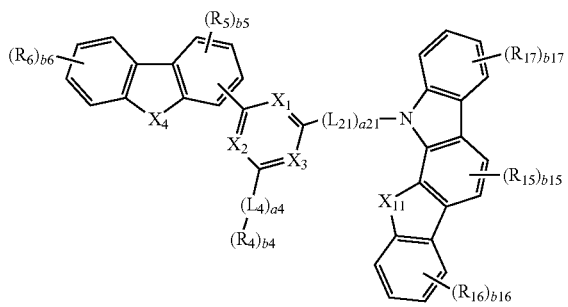
Formula 1B-1
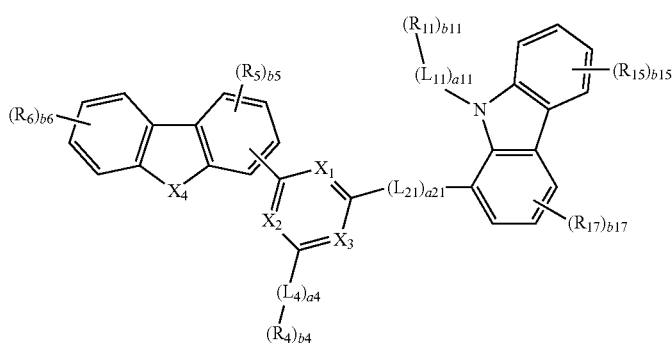
Formula 1B-2
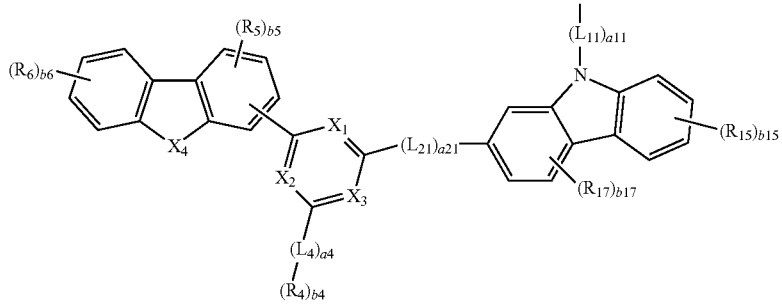
Formula 1B-3
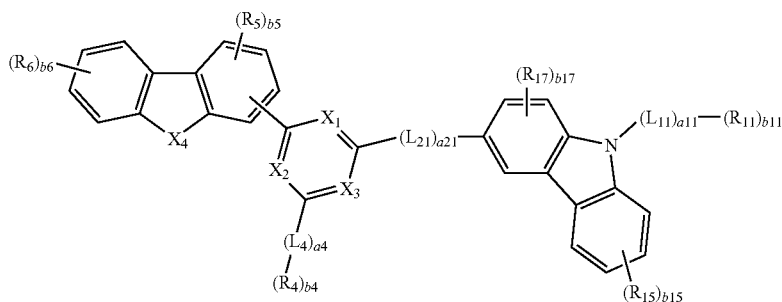

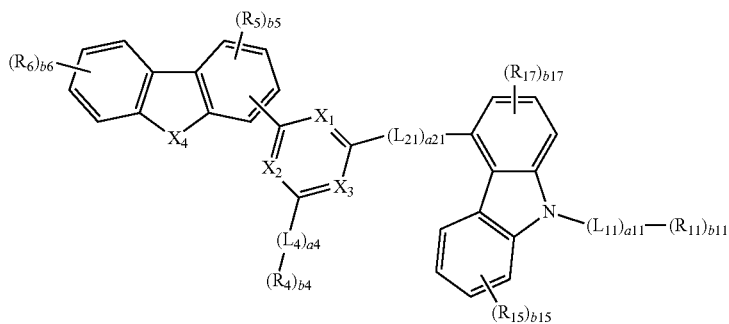

Formula 1B-4

Descriptions of Formulae 1A-1 to 1A-7 and 1B-1 to 1B-4, $X_1$ to $X_4$, $X_{11}$, $L_1$ to $L_4$, $L_{11}$, $L_{12}$, $L_{21}$, a1 to a4, a11, a12, a21, $R_1$ to $R_6$, $R_{11}$ to $R_{17}$, b1 to b6, and b11 to b17 are given below.

According to an embodiment, the condensed-cyclic compound may be represented by Formula 1A-1, 1A-2, 1A-3, 1B-1, 1B-2, 1B-3, or 1B-4, but it is not limited thereto.

According to another embodiment, the condensed-cyclic compound may be represented by Formula 1A-1 or 1A-2, but it is not limited thereto.

Formulae 1A and 1B may be represented by any one of Formulae 1A(1) to 1A(4) and 1B(1) to 1B(4), but they are not limited thereto:

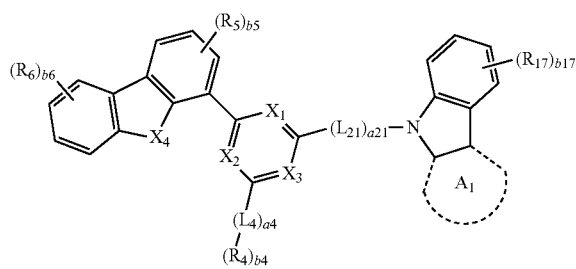

Formula 1A(1)

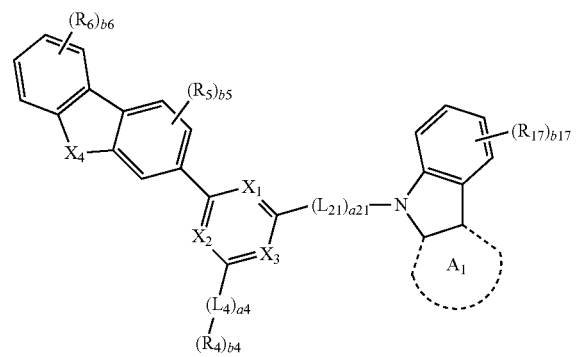

Formula 1A(2)

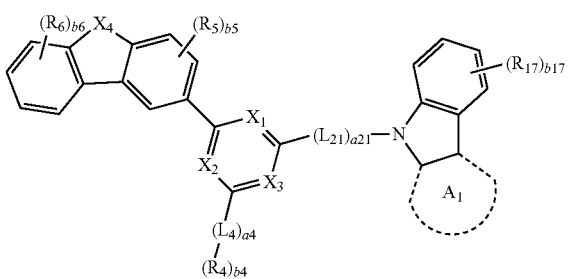

Formula 1A(3)

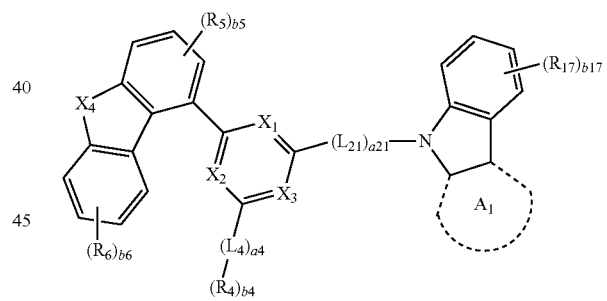

Formula 1A(4)

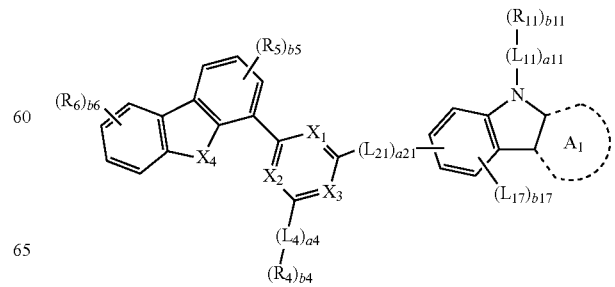

Formula 1B(1)

-continued

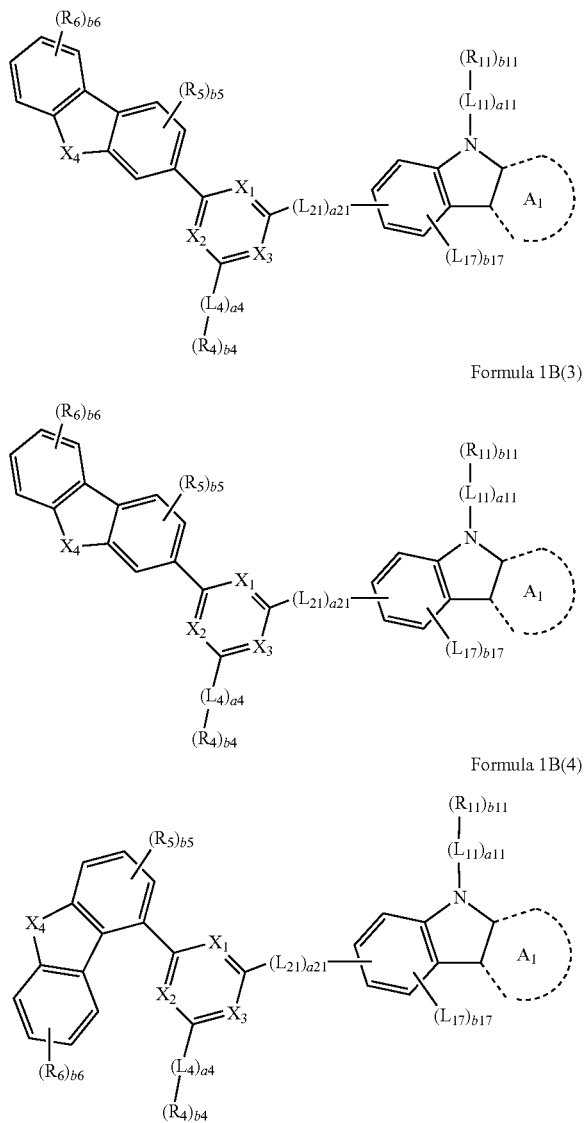

Formula 1B(2)

Formula 1B(3)

Formula 1B(4)

In Formulae 1A(1) to 1A(4) and 1B(1) to 1B(4), descriptions of ring $A_1$, $X_1$ to $X_4$, $X_{11}$, $L_1$ to $L_4$, $L_{11}$, $L_{12}$, $L_{21}$, a1 to a4, a11, a12, a21, $R_1$ to $R_6$, $R_{11}$ to $R_{17}$, b1 to b6, and b11 to b17 are given below.

In Formula 1C, $X_{11}$ is selected from N-[$(L_{12})_{a12}$-$(R_{12})_{b12}$], S, O, S(=O), S(=O)$_2$, C(=O), C($R_{13}$)($R_{14}$), Si($R_{13}$)($R_{14}$), P($R_{13}$), P(=O)($R_{13}$), and C=N($R_{12}$). For example, in Formula 1C, $X_{11}$ may be selected from N-[$(L_{12})_{a12}$-$(R_{12})_{b12}$], S, O, and C($R_{13}$)($R_{14}$), but it is not limited thereto. Descriptions of $L_{12}$, a12, $R_{12}$ to $R_{14}$, and b12 may be understood by referring to the description below.

In Formula 1A and 1B, $X_1$ is N or C-[$(L_1)_{a1}$-$(R_1)_{b1}$], $X_2$ is N or C-[$(L_2)_{a2}$-$(R_2)_{b2}$], $X_3$ is N or C-[$(L_3)_{a3}$-$(R_3)_{b3}$], and at least one of $X_1$ to $X_3$ is N.

For example, in Formulae 1A and 1B, $X_1$ to $X_3$ may be N;

$X_1$ may be C-[$(L_1)_{a1}$-$(R_1)_{b1}$], $X_2$ and $X_3$ may be N;

$X_1$ may be N, $X_2$ may be C-[$(L_2)_{a2}$-$(R_2)_{b2}$], and $X_3$ may be N;

$X_1$ and $X_2$ may be N, and $X_3$ may be C-[$(L_3)_{a3}$-$(R_3)_{b3}$];

$X_1$ may be C-[$(L_1)_{a1}$-$(R_1)_{b1}$], $X_2$ may be N, and $X_3$ may be C-[$(L_3)_{a3}$-$(R_3)_{b3}$];

$X_1$ may be C-[$(L_1)_{a1}$-$(R_1)_{b1}$], $X_2$ may be C-[$(L_2)_{a2}$-$(R_2)_{b2}$], and $X_3$ may be N; or $X_1$ may be N, $X_2$ may be C-[$(L_2)_{a2}$-$(R_2)_{b2}$], and $X_3$ may be C-[$(L_3)_{a3}$-$(R_3)_{b3}$]

According to an embodiment, $X_1$ may be C-[$(L_1)_{a1}$-$(R_1)_{b1}$], $X_2$ and $X_3$ may be N; or $X_1$ and $X_2$ may be N, and $X_3$ may be C-[$(L_3)_{a3}$-$(R_3)_{b3}$], but they are not limited thereto.

Descriptions of $L_1$ to $L_3$, a1 to a3, $R_1$ to $R_3$, and b1 to b3 may be understood by referring to the description below.

In Formulae 1A, 1B, and 1C, $L_1$ to $L_4$, $L_{11}$, $L_{12}$, and $L_{21}$ may be each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic hetero-condensed polycyclic group.

For example, in Formulae 1A, 1B, and 1C, $L_1$ to $L_4$, $L_{11}$, Lie, and $L_{21}$ may be each independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, a isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, a isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group an imidazopyrimidinylene group, and an imidazopyridinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{20}$ aryl group, a $C_2$-$C_{60}$ heteroaryl group, a monovalent non-aromatic condensed polycyclic group, a monovalent non-aromatic hetero-condensed cyclic group, and —Si($Q_{33}$)($Q_{34}$)($Q_{35}$), $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, but they are not limited thereto.

For example, in Formulae 1A, 1B, and 1C, $L_1$ to $L_4$, $L_{11}$, $L_{1c}$, and $L_{21}$ may be each independently selected from Formulae 2-1 to 2-34:

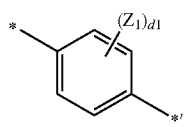

Formula 2-1

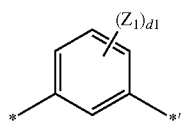

Formula 2-2

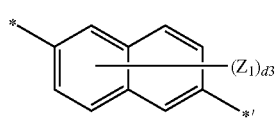

Formula 2-3

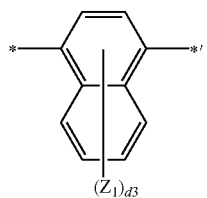

Formula 2-4

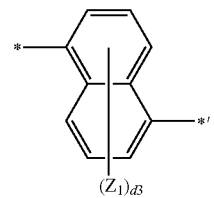

Formula 2-5

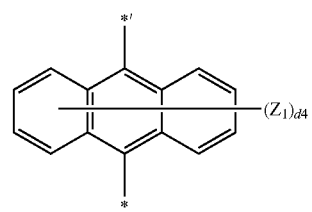

Formula 2-6

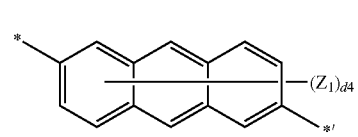

Formula 2-7

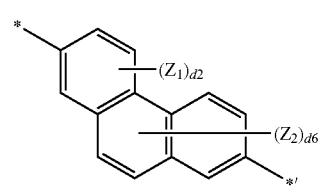

Formula 2-8

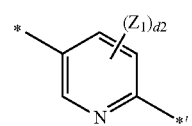

Formula 2-9

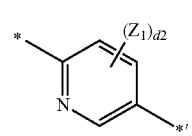

Formula 2-10

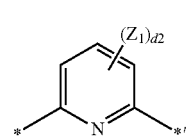

Formula 2-11

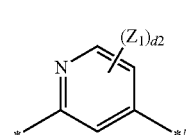

Formula 2-12

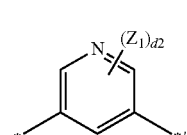

Formula 2-13

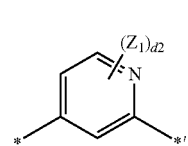

Formula 2-14

Formula 2-15
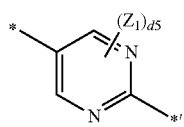
Formula 2-16
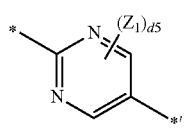
Formula 2-17
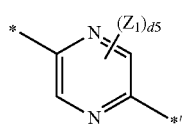
Formula 2-18
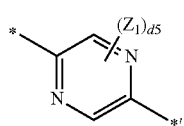
Formula 2-19
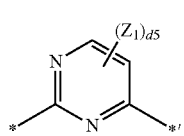
Formula 2-20
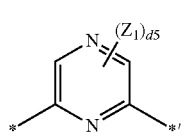
Formula 2-21
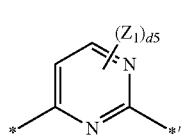
Formula 2-22
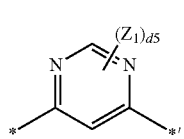
Formula 2-23
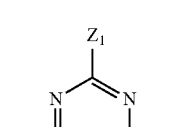
Formula 2-24
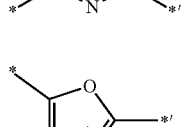
Formula 2-25
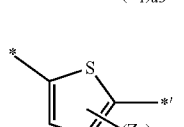
Formula 2-26
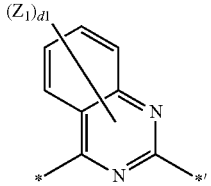
Formula 2-27
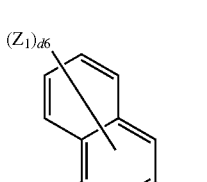
Formula 2-28
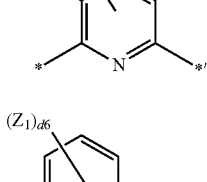
Formula 2-29
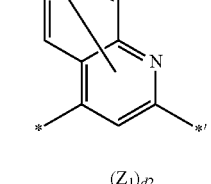
Formula 2-30
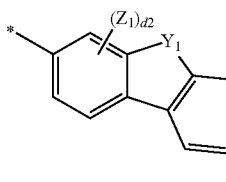
Formula 2-31
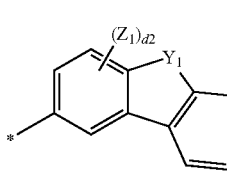
Formula 2-32
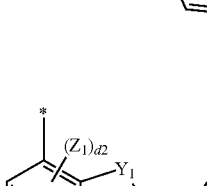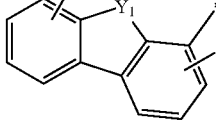
Formula 2-33
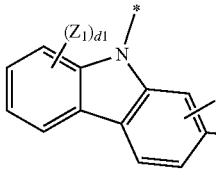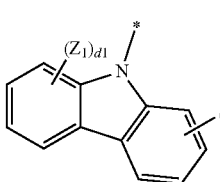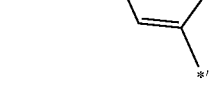

-continued

Formula 2-34

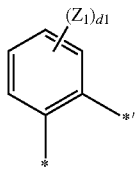

In Formula 2-1 to 2-34, $Y_1$ may be selected from O, S, S(=O), S(=O)$_2$, C($Z_3$)($Z_4$), N($Z_5$), or Si($Z_6$)($Z_7$);

$Z_1$ to $Z_7$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group, and —Si($Q_{33}$)($Q_{34}$)($Q_{35}$);

wherein $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

d1 is selected from integers of 1 to 4,
d2 is selected from integers of 1 to 3,
d3 is selected from integers of 1 to 6,
d4 is selected from integers of 1 to 8,
d5 is 1 or 2,
d6 is selected from integers of 1 to 5, and
each of * and *' indicates a bonding site to neighboring atoms.

For example, in Formulae 2-1 to 2-34, *' indicates a bonding site to neighboring atoms of $L_1$ to $L_4$, $L_{11}$, $L_{12}$, and $L_{21}$ or bonding site to each of $R_1$ to $R_4$, $R_{11}$, $R_{12}$, and $R_{21}$.

According to an embodiment, in Formulae 1A and 1B, $L_1$ to $L_4$, $L_{11}$, $L_{12}$, and $L_{21}$ may be each independently selected from Formulae 2-1 to 2-5, 2-9 to 2-23, and 2-34, but they are not limited thereto.

According to another embodiment, in Formulae 1A and 1B, $L_1$ to $L_4$, $L_{11}$, $L_{12}$, and $L_{21}$ may be each independently selected from:

a phenylene group and a naphthylene group; and a phenylene group and a naphthylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group, and —Si($Q_{33}$)($Q_{34}$)($Q_{35}$) (wherein $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, but they are not limited thereto.

In Formula 1A, a1 represents the number of groups $L_1$, which may be 0, 1, 2, or 3, for example, 0, 1, or 2, or may be 0 or 1. When a1 is 0, -($L_1$)$_{a1}$- is a single bond. When a1 is 2 or greater, two or more groups $L_1$ may be the same or different. Descriptions of a2 to a4, a11, a12, and a21 may be understood by referring to the description of a1 and structures of Formulae 1A and 1B.

According to an embodiment, in Formulae above, a1 to a4, a11, a12, and a21 may be each independently, 0, 1, or 2.

According to another embodiment, in Formulae above, a21 may be 1, but it is not limited thereto.

In Formulae 1A, 1B, 1C, and 1D, $R_1$ to $R_3$, $R_5$, $R_6$, and $R_{11}$ to $R_{17}$ may be each independently selected from a hydrogen, a deuterium, —F (a fluoro group), —Cl (a chloro group), —Br (a bromo group), —I (an iodo group), a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic hetero-condensed polycyclic group, —N($Q_1$)($Q_2$), —Si($Q_3$)($Q_4$)($Q_5$), and —B($Q_6$)($Q_7$). Here, descriptions of $Q_1$ to $Q_7$ are as described below.

In Formulae 1A and 1B, $R_4$ is selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, and a substituted or unsubstituted monovalent non-aromatic hetero-condensed polycyclic group. For example, $R_4$ may be selected from a substituted or unsubstituted $C_6$-$C_{20}$ aryl group, a substituted or unsubstituted $C_2$-$C_{30}$ heteroaryl group, a substituted or unsubstituted monovalent non-aromatic condensed polycyclic group, and a substituted or unsubstituted monovalent non-aromatic hetero-condensed polycyclic group, but it is not limited thereto.

According to an embodiment, in Formulae 1A and 1B, $R_{11}$ and $R_{17}$ may be each independently selected from a substituted or unsubstituted $C_6$-$C_{30}$ aryl group, a substituted or unsubstituted $C_2$-$C_{30}$ heteroaryl group, a substituted or unsubstituted monovalent non-aromatic condensed polycyclic group, and a substituted or unsubstituted monovalent non-aromatic hetero-condensed polycyclic group.

For example, in Formulae 1A, 1B, 1C, and 1D, $R_1$ to $R_3$, $R_5$, $R_6$, and $R_{13}$ to $R_{17}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof and a phosphoric acid or a salt thereof;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_{33}$)($Q_{34}$)($Q_{35}$), a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and a biphenyl group; and —Si($Q_3$)($Q_4$)($Q_5$) (provided that, $R_{13}$ and $R_{14}$ are not —Si($Q_3$)($Q_4$)($Q_5$));

wherein $Q_3$ to $Q_5$ and $Q_{33}$ to $Q_{35}$ may be each independently selected from a hydrogen, $C_1$-$C_{20}$ alkyl group, $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, but they are not limited thereto.

According to another embodiment, in Formulae 1A, 1B, 1C, and 1D, $R_1$ to $R_3$, $R_5$, $R_6$, and $R_{13}$ to $R_{17}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_{33}$)($Q_{34}$)($Q_{35}$), a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group; and —Si($Q_3$)($Q_4$)($Q_5$), provided that $R_{13}$ and $R_{14}$ are not —Si($Q_3$)($Q_4$)($Q_5$);

wherein $Q_3$ to $Q_5$ and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

Meanwhile, in Formulae 1A and 1B, $R_4$, $R_{11}$, and $R_{12}$ may be each independently selected from:

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_{33}$)($Q_{34}$)($Q_{35}$), a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and a biphenyl group; and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

According to another embodiment, in Formulae 1A, 1B, 1C, and 1D, $R_1$ to $R_3$, $R_5$, $R_6$, and $R_{13}$ to $R_{17}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

Formulae 4-1 to 4-31 below (for example, Formulae 4-1 to 4-3 and 4-6 to 4-13); and —Si($Q_3$)($Q_4$)($Q_5$) (provided that, $R_{13}$ and $R_{14}$ are not —Si($Q_3$)($Q_4$)($Q_5$));

wherein, $R_4$, $R_{11}$, and $R_{17}$ may be each independently selected from Formulae 4-1 to 4-31 (for example, Formulae 4-1 to 4-3 and 4-6 to 4-13), but they are not limited thereto.

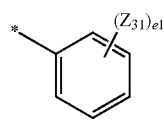

Formula 4-1

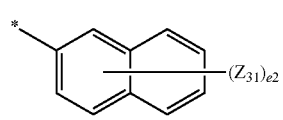

Formula 4-2

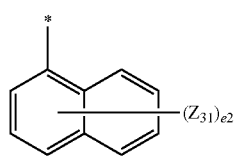

Formula 4-3

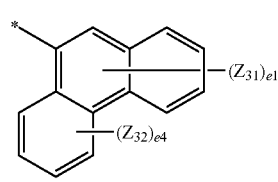

Formula 4-4

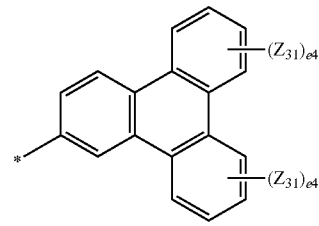

Formula 4-5

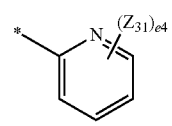

Formula 4-6

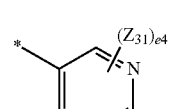

Formula 4-7

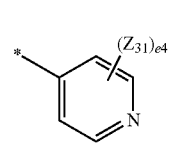

Formula 4-8

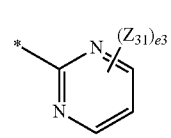

Formula 4-9

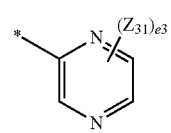

Formula 4-10

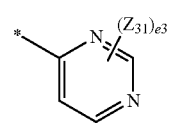

Formula 4-11

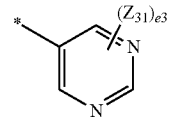

Formula 4-12

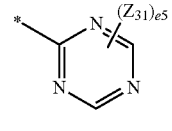

Formula 4-13

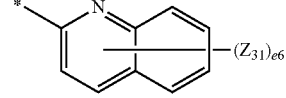

Formula 4-14

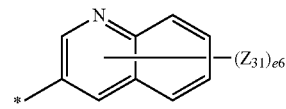

Formula 4-15

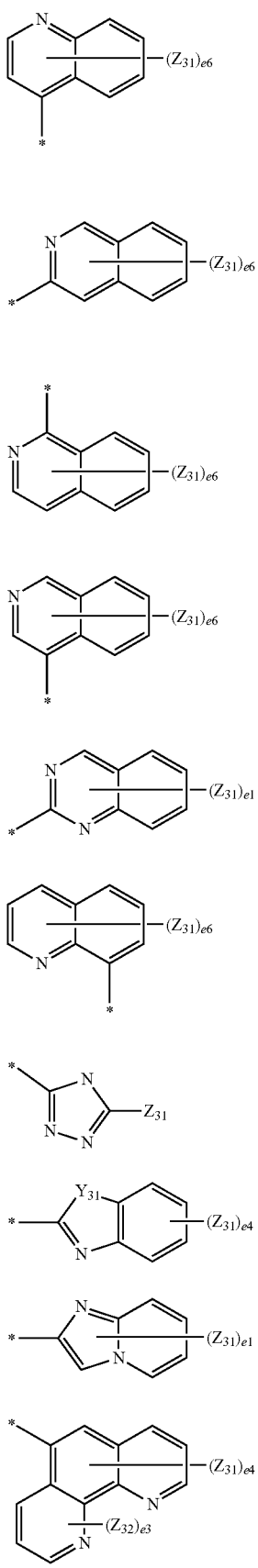
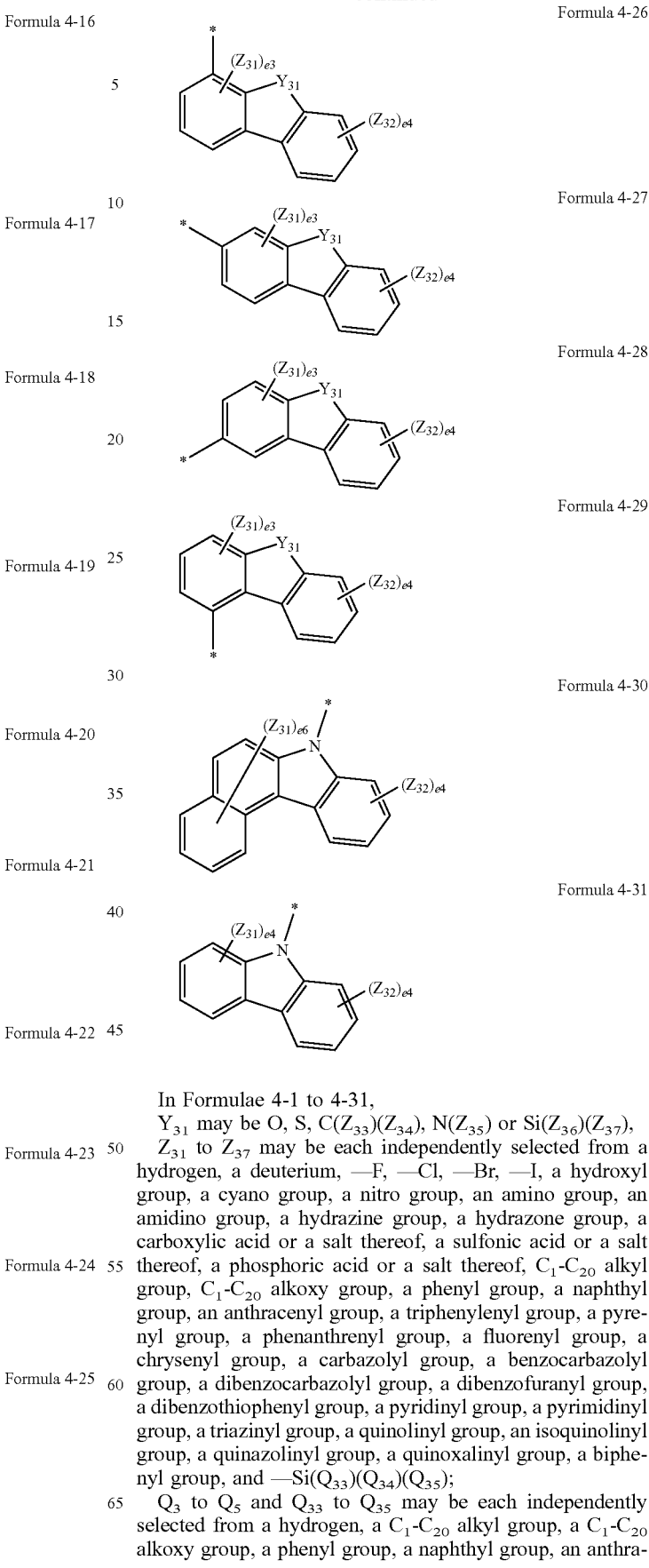

In Formulae 4-1 to 4-31, $Y_{31}$ may be O, S, $C(Z_{33})(Z_{34})$, $N(Z_{35})$ or $Si(Z_{36})(Z_{37})$, $Z_{31}$ to $Z_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, $C_1$-$C_{20}$ alkyl group, $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group, and —$Si(Q_{33})(Q_{34})(Q_{35})$;

$Q_3$ to $Q_5$ and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

e1 may be selected from integers of 1 to 5,
e2 is selected from integers of 1 to 7,
e3 is selected from integers of 1 to 3,
e4 is selected from integers of 1 to 4,
e5 is 1 or 2,
e6 is selected from integers of 1 to 6, and
* indicates a bonding site to a neighboring atom.

According to another embodiment, $R_1$ to $R_3$, $R_5$, $R_6$, and $R_{13}$ to $R_{17}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group and a naphthyl group;

a phenyl group and a naphthyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, and a naphthyl group; and —Si($Q_3$)($Q_4$)($Q_5$) (provided that, $R_{13}$ and $R_{14}$ are not —Si($Q_3$)($Q_4$)($Q_5$) and $Q_3$ to $Q_5$ are each independently selected from a hydrogen, a $C_1$-$C_{20}$ alkyl group, a $C_1$-$C_{20}$ alkoxy group, a phenyl group, and a naphthyl group);

$R_4$, $R_{11}$, and $R_{12}$ are each independently selected from:

a phenyl group and a naphthyl group; and a phenyl group and a naphthyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, and a naphthyl group; but, they are not limited thereto.

According to another embodiment, $R_5$, $R_6$, and $R_{15}$ to $R_{17}$ may all be hydrogen, but they are not limited thereto.

In Formulae 1A and 1B, b1 represents the number of groups $R_1$ and may be selected from integers of 1 to 3. For example, b1 may be 1 or 2. In greater detail, b1 may be 1. When b1 is 2 or greater, two or more of groups $R_1$ may be the same or different. Descriptions of b2 to b6 and b11 to b17 may be understood by referring to the description of b1 and structures of Formulae 1A, 1B, 1C, and 1D.

According to an embodiment, at least one substituent of the substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted divalent non-aromatic condensed polycyclic group, substituted divalent non-aromatic hetero-condensed polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, and substituted monovalent non-aromatic hetero-condensed polycyclic group may be selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, —N($Q_{11}$)($Q_{12}$), —Si($Q_{13}$)($Q_{14}$)($Q_{15}$) and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$) and —B($Q_{36}$)($Q_{37}$);

wherein $Q_1$ to $Q_7$, $Q_{11}$ to $Q_{17}$, $Q_{21}$ to $Q_{27}$ and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group.

According to one or more embodiments, provided is a condensed-cyclic compound represented by Formula 1A:

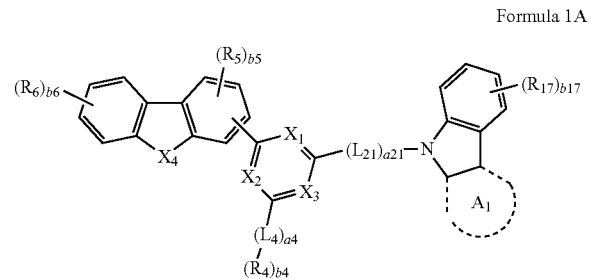

Formula 1A wherein in Formula 1A,
ring $A_1$ is represented by Formula 1D;

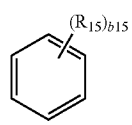

Formula 1D $X_1$ to $X_3$ is N;
$X_4$ is O or S;
$L_4$ and $L_{21}$ are each independently selected from groups represented by Formulae 2-1, 2-2 and 2-34;

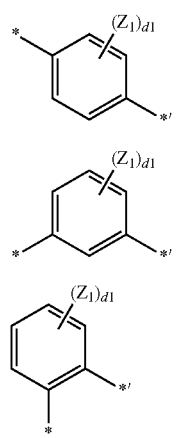

Formula 2-1

Formula 2-2

Formula 2-34 wherein in Formulae 2-1, 2-2 and 2-34, $Z_1$ is selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group and a phenyl group and d1 is selected from integers of 1 to 4;

a4 is selected from integers 0 to 3 and a21 is 0, 1, 2 or 3 (or a21 may be 1 or 2);

$R_5$, $R_6$, $R_{15}$ and $R_{17}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

$R_4$ is selected from:

a phenyl group; and a phenyl group, substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, and a biphenyl group; and b4 to b6, b15 and b17 are each independently selected from integers of 1 to 3.

For example, a condensed-cyclic compound represented by Formula 1A described above may be represented by one of Formulae 1A(1) to 1A(4) described herein.

The condensed-cyclic compound may be any one of Compounds 1 to 825, but it is not limited thereto:

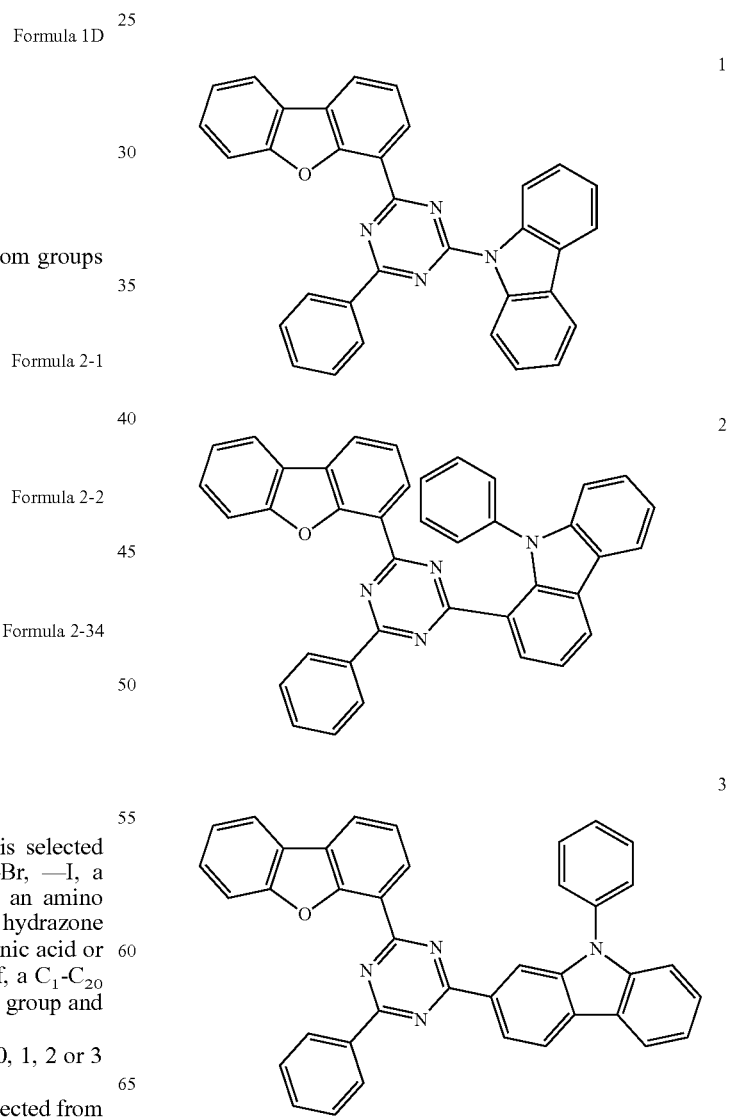

4
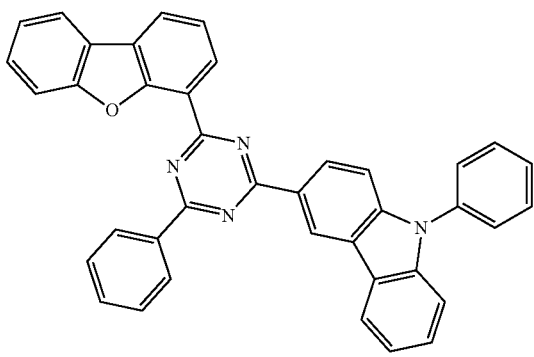
5
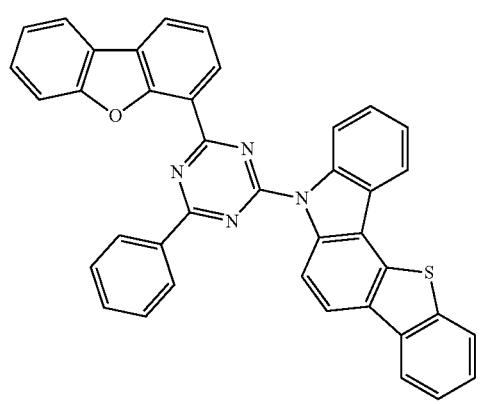
6
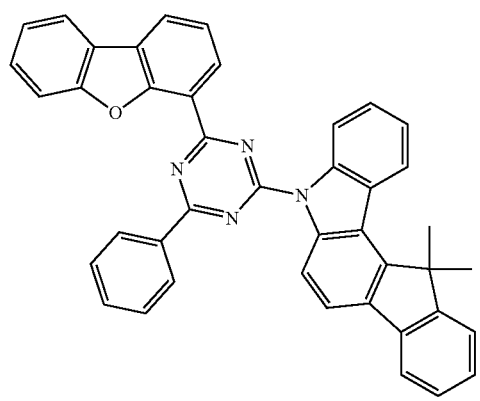
7
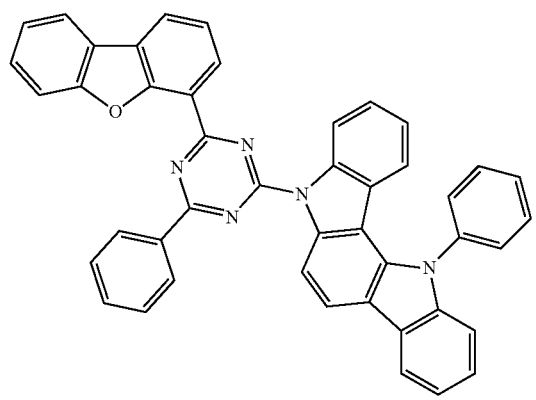
8
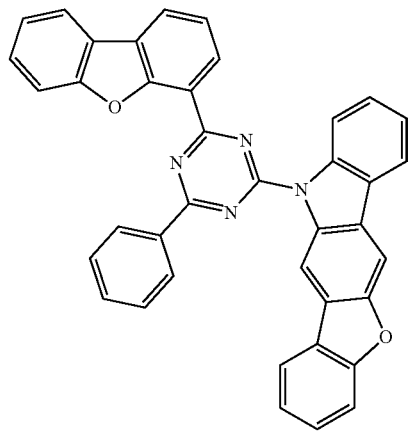
9
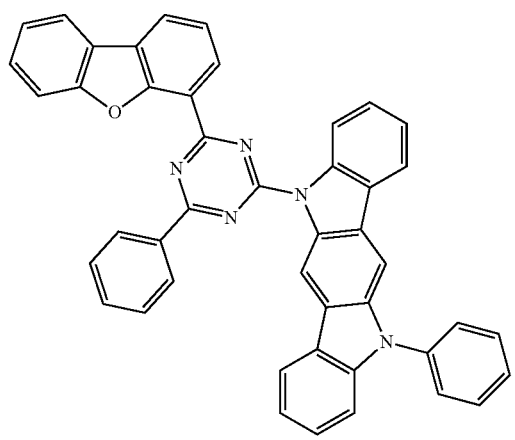
10
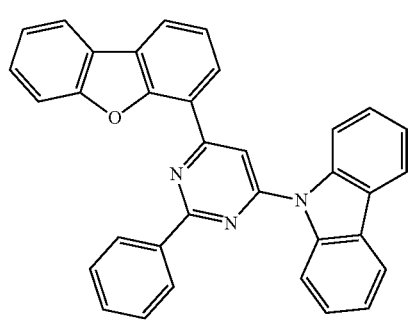
11
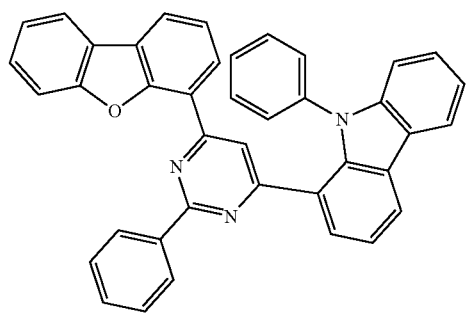

12
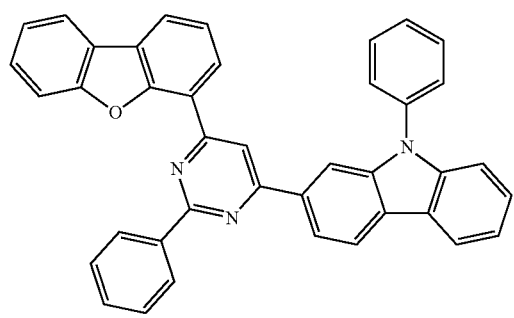
13
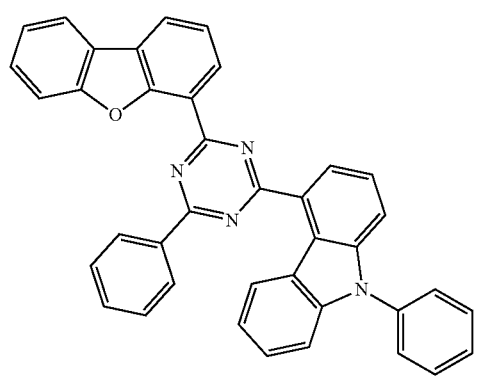
14
15
16
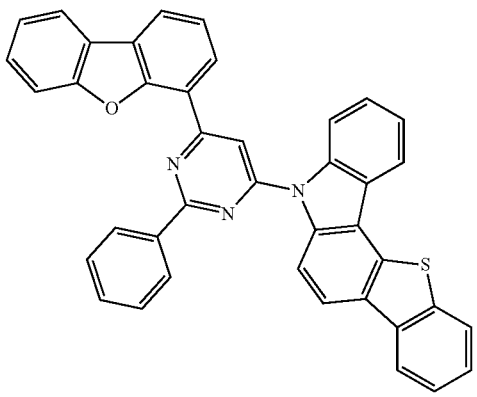
17
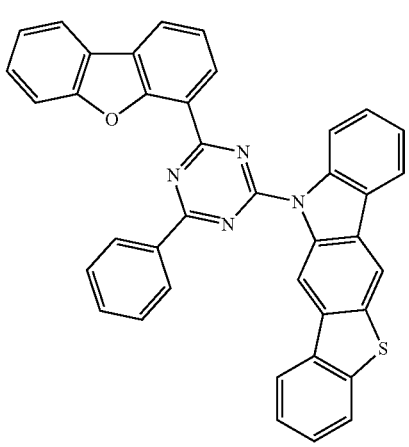
18
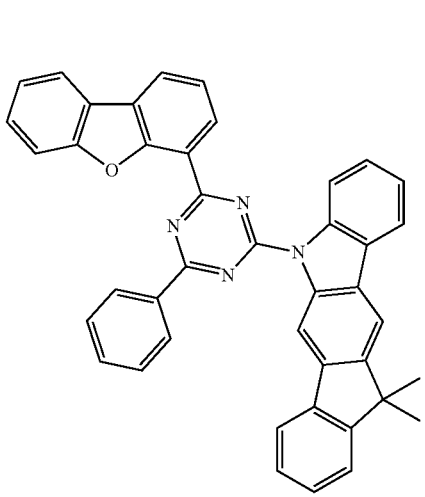

19
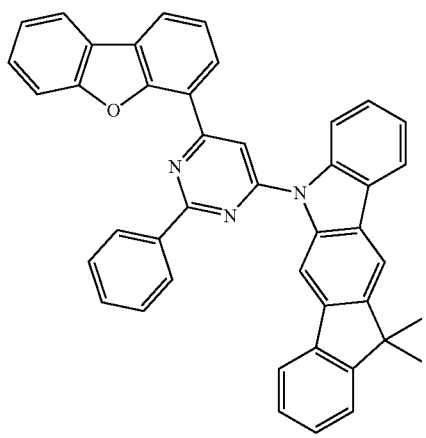
20
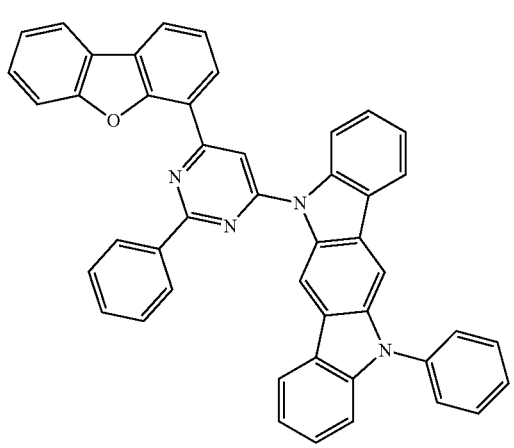
21
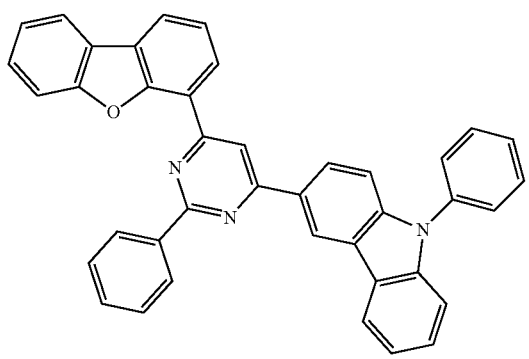
22
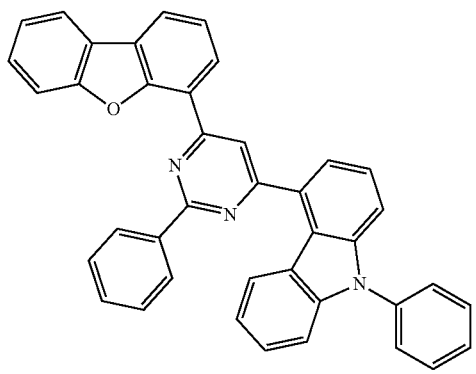
23
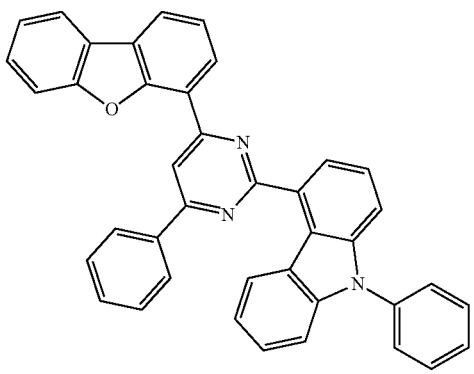
24
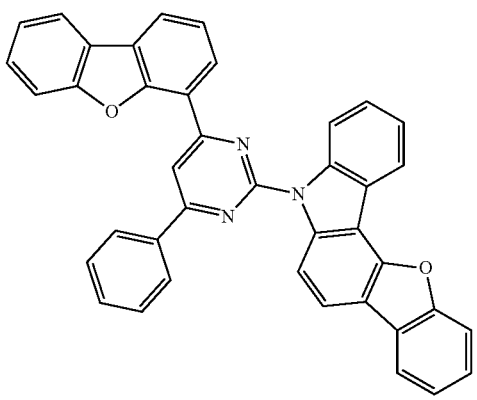
25
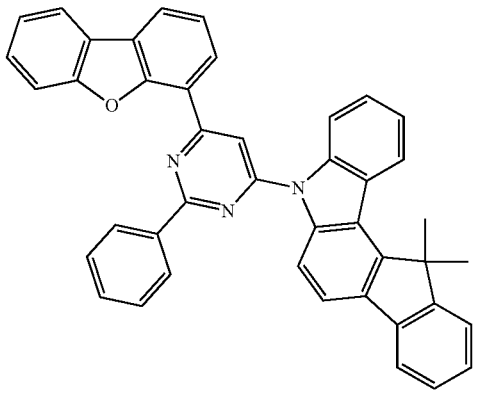
26
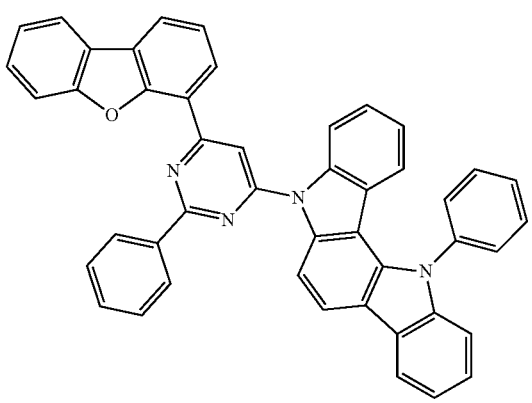

27
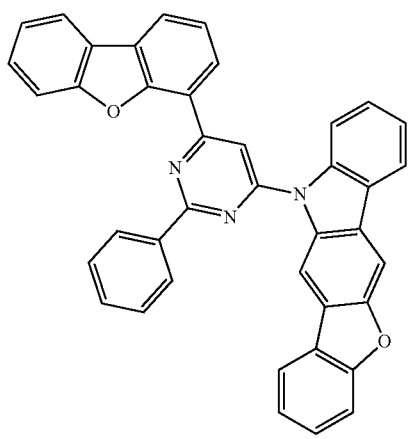
28
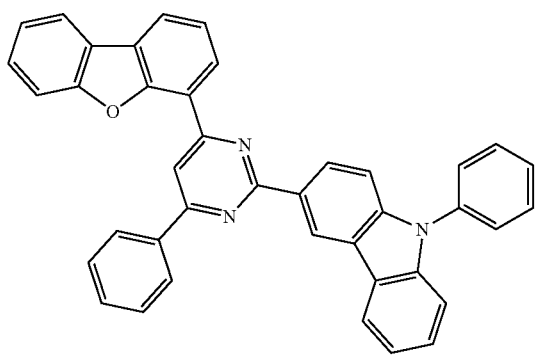
29
30
31
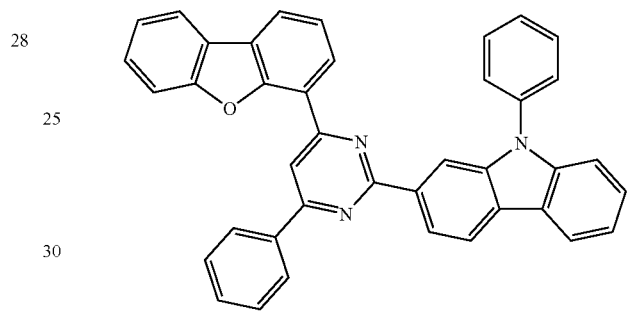
32
33
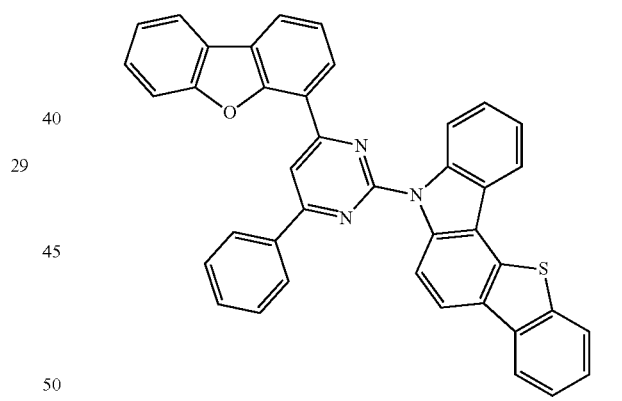
34
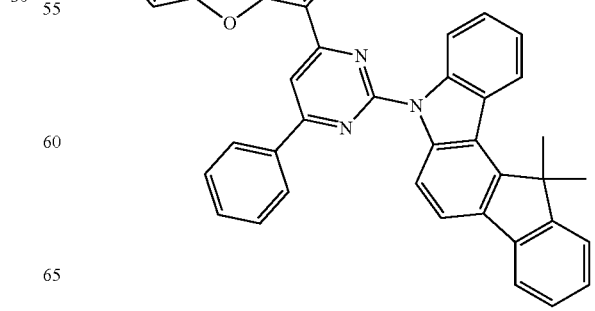

35
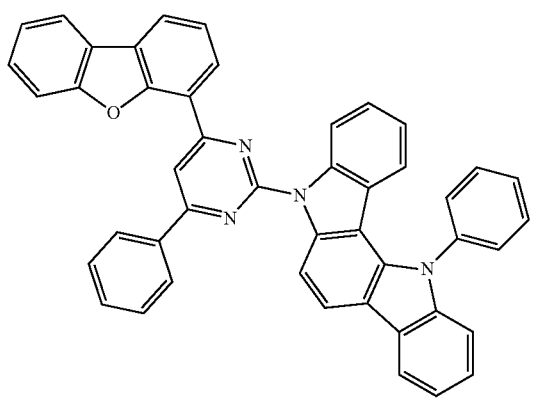
36
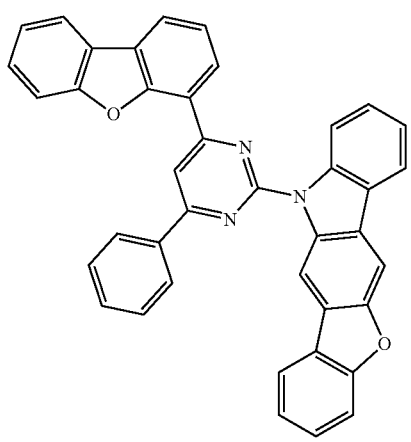
37
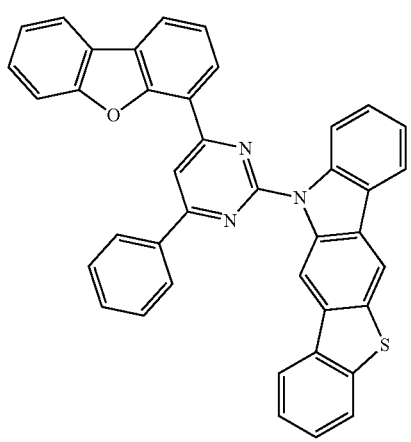
38
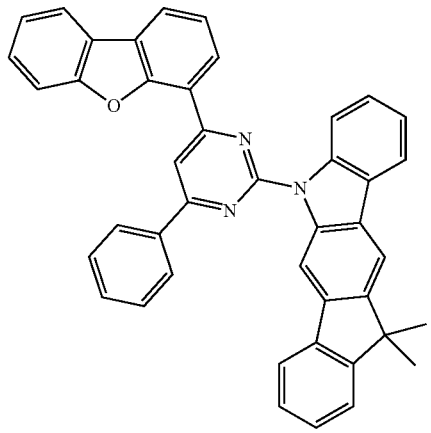
39
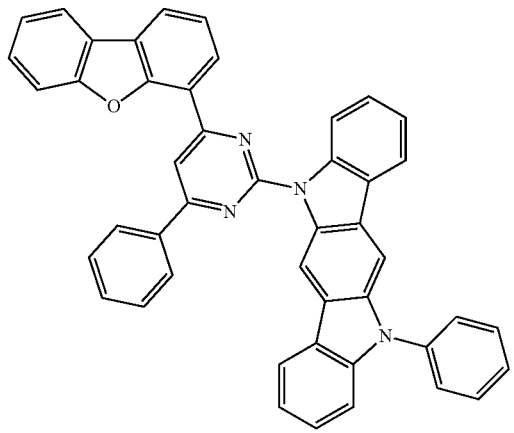
40
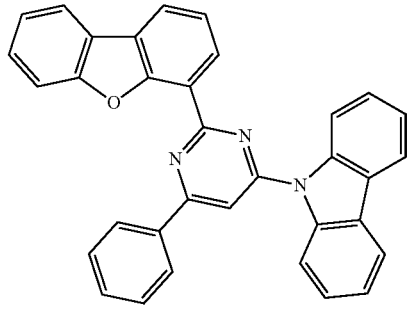
41
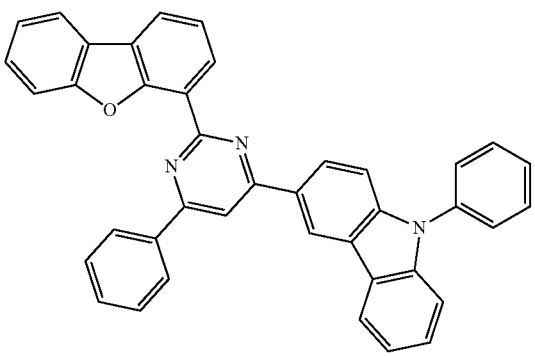

42
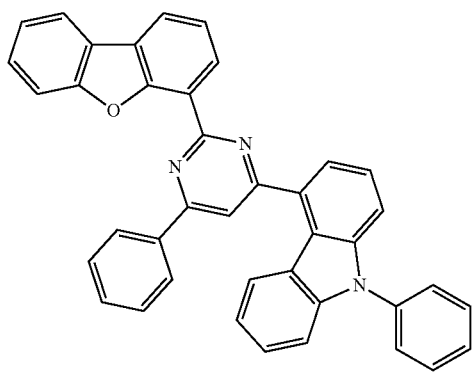
43
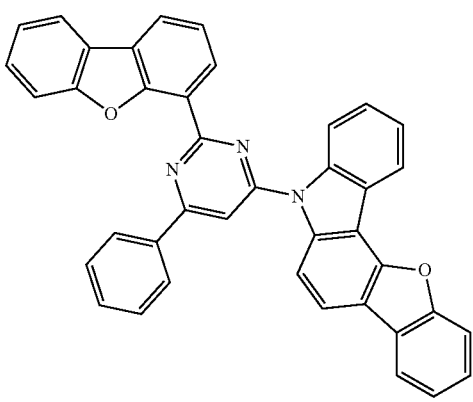
44
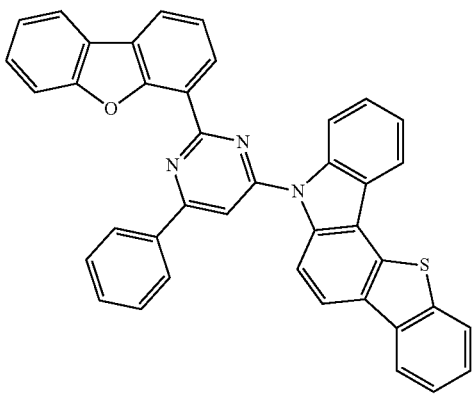
45
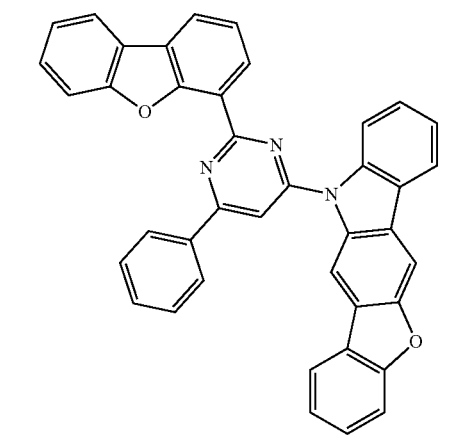
46
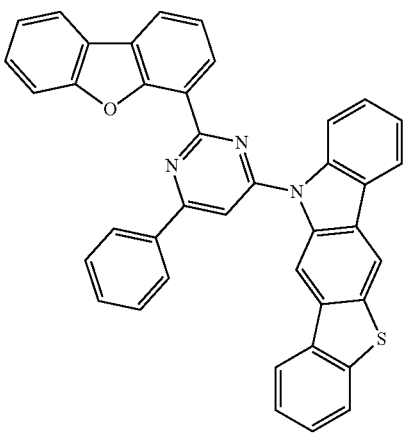
47
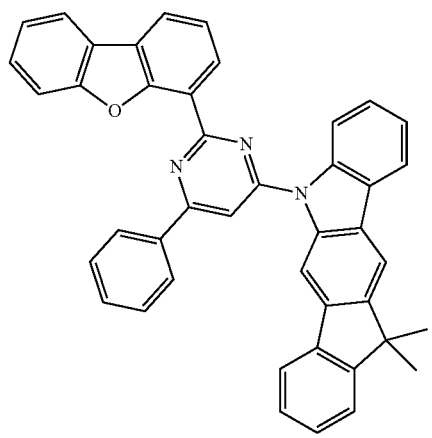
48
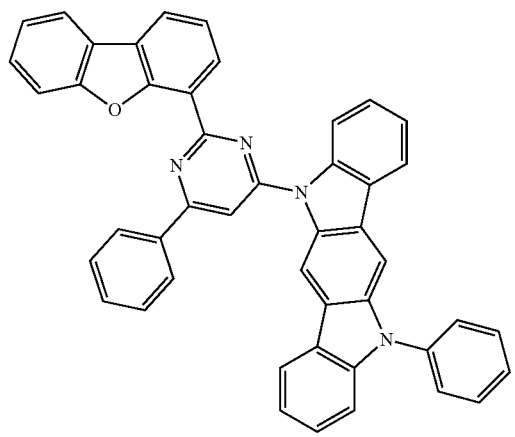
49
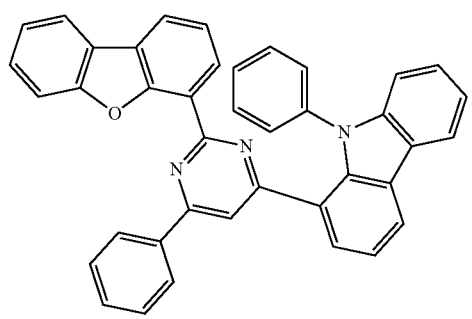

50
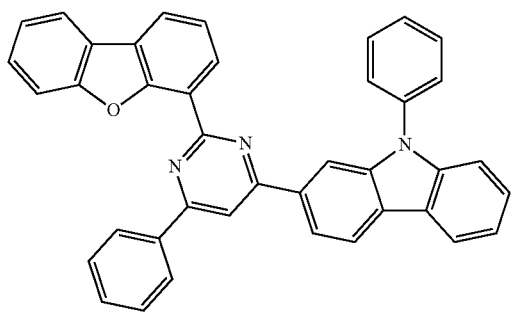
51
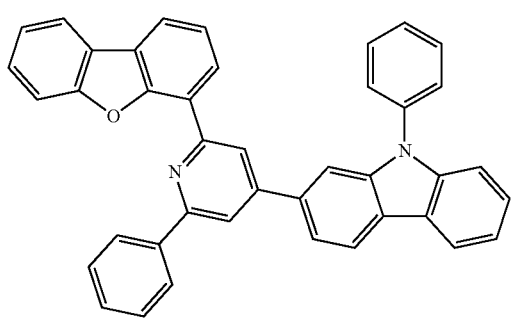
52
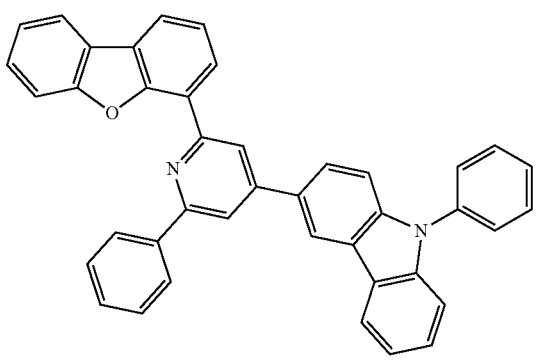
53
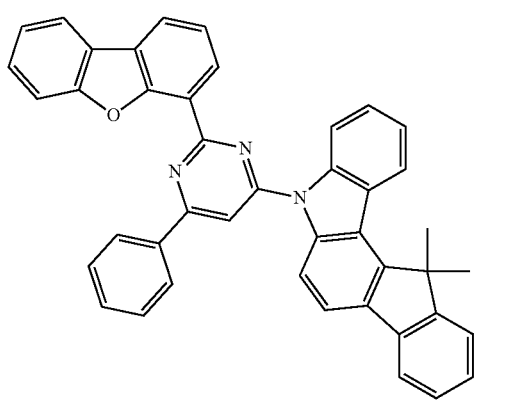
54
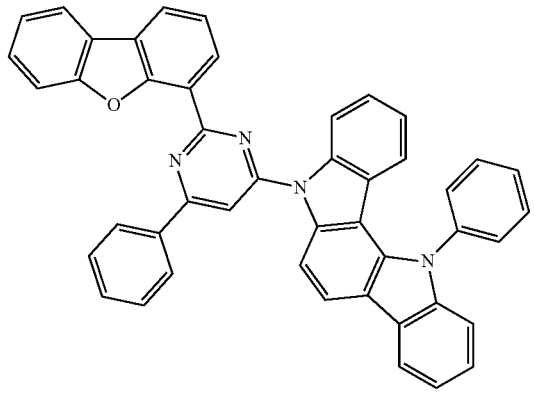
55
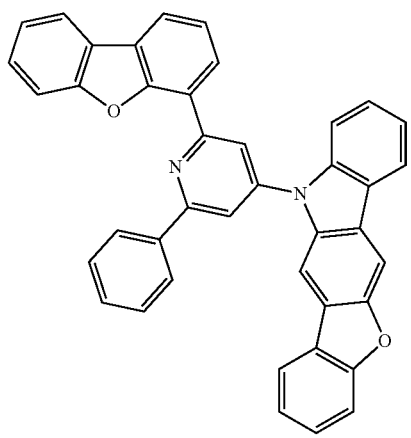
56
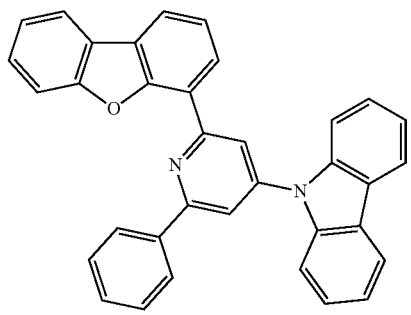
57

58
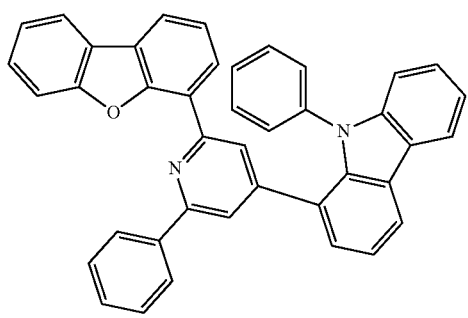
59
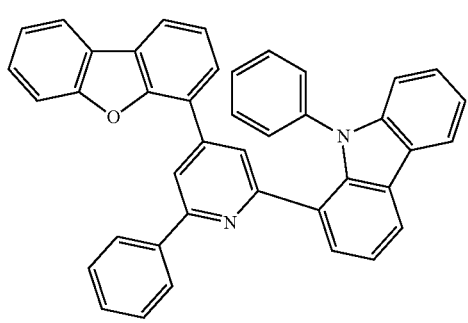
60
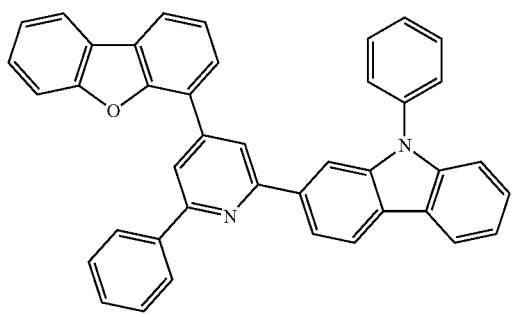
61
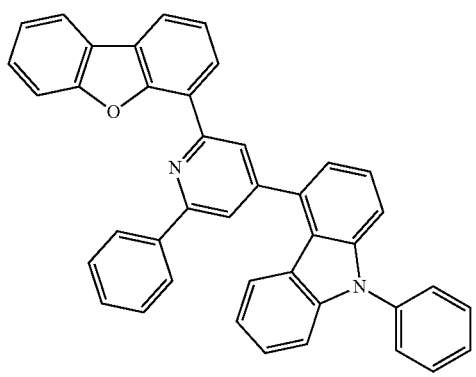
62
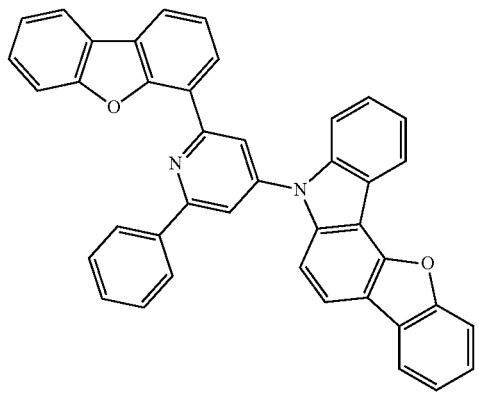
63
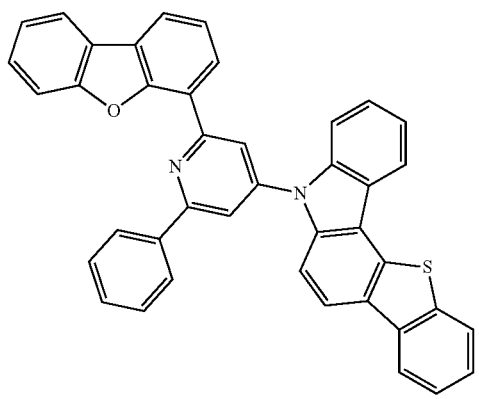
64
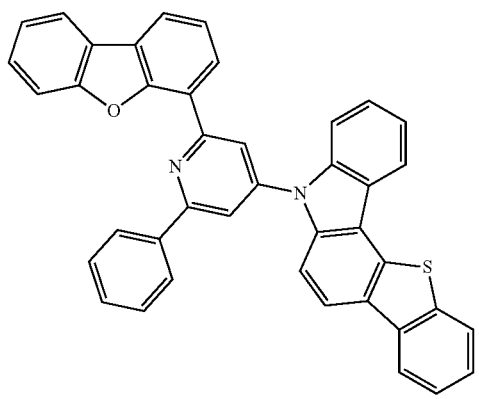
65
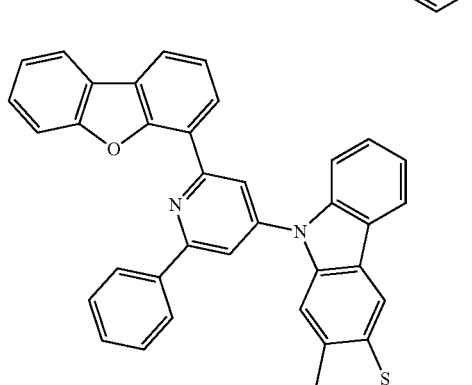

-continued
66
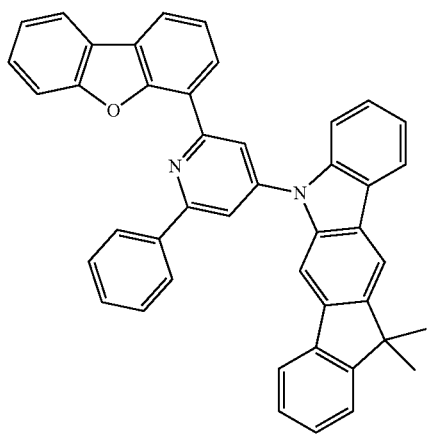
67
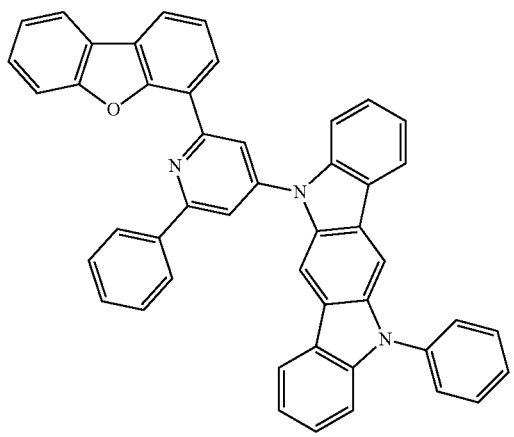
68
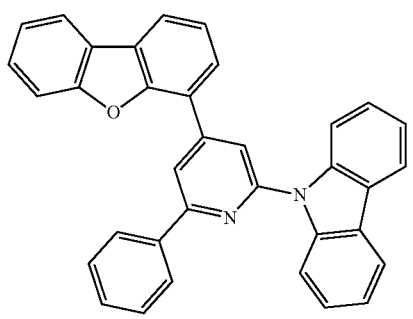
69
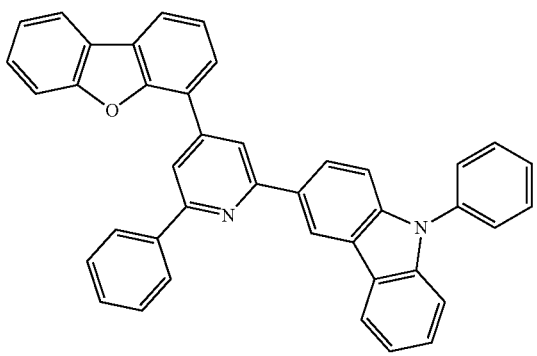
-continued
70
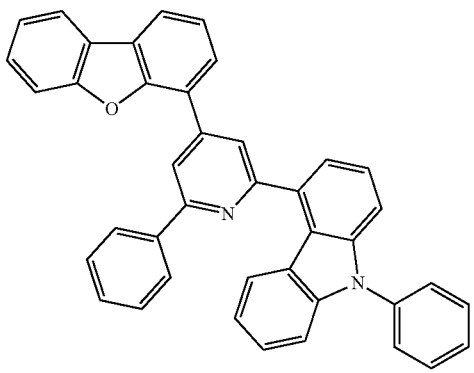
71
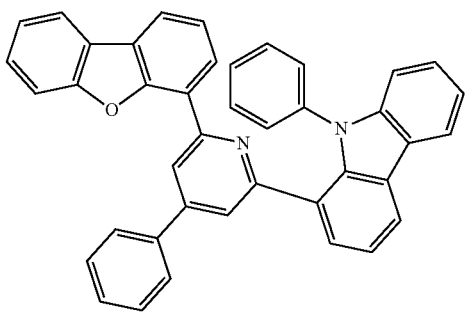
72
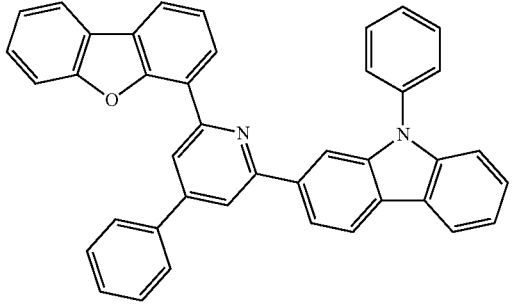
73

74
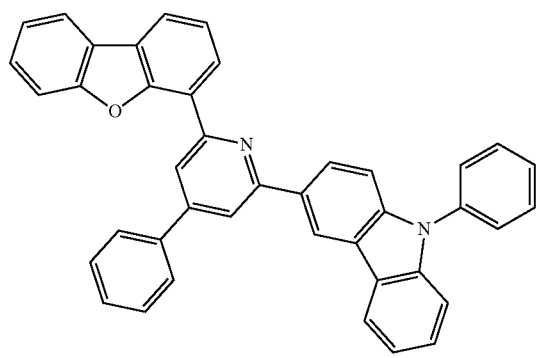
75
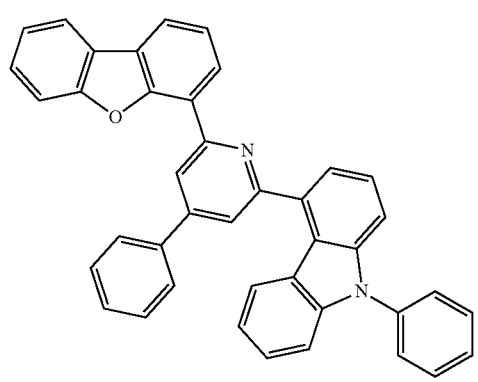
76
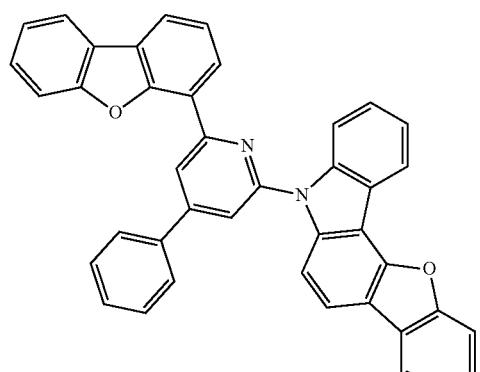
77
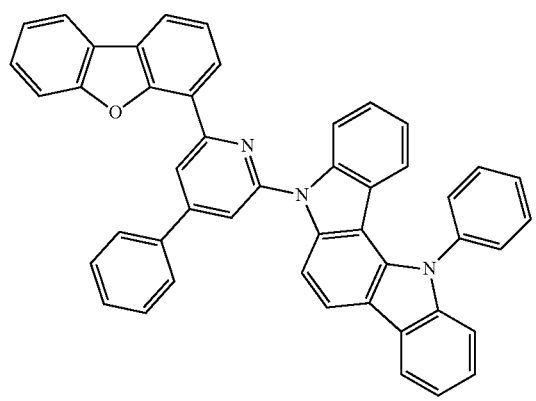
78
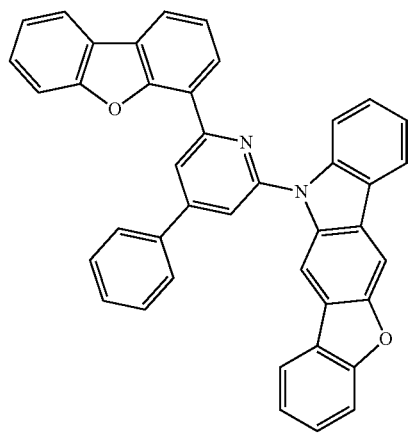
79
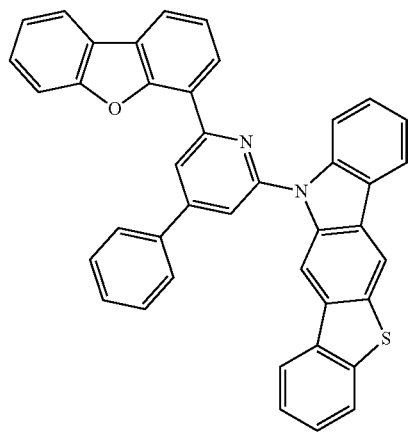
80
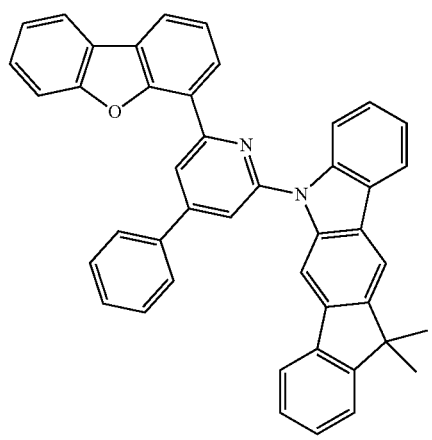

81
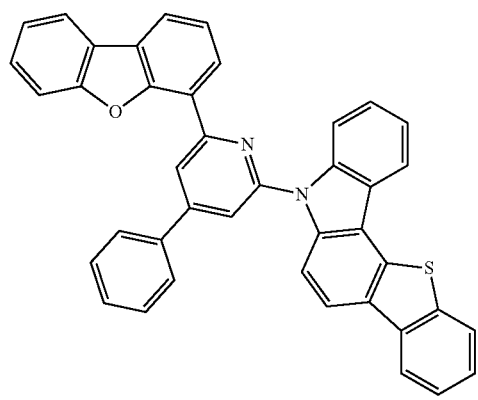
82
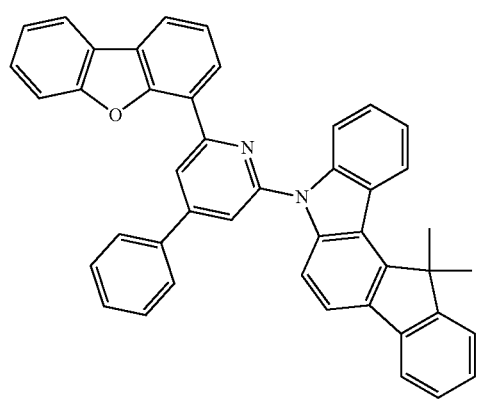
83
84
85
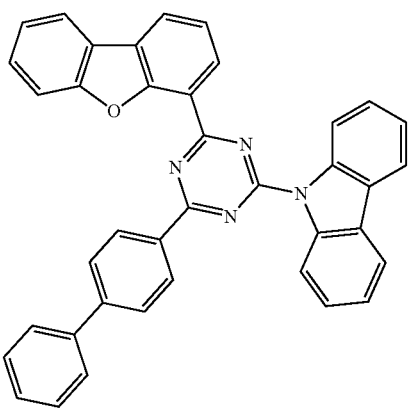
86
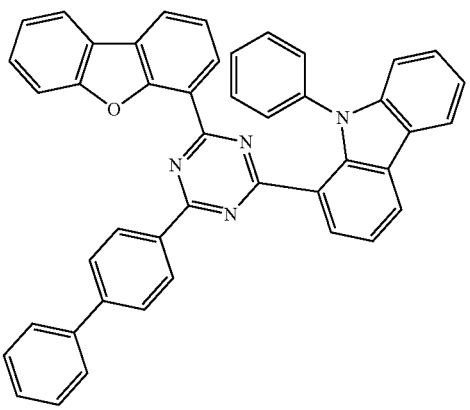
87
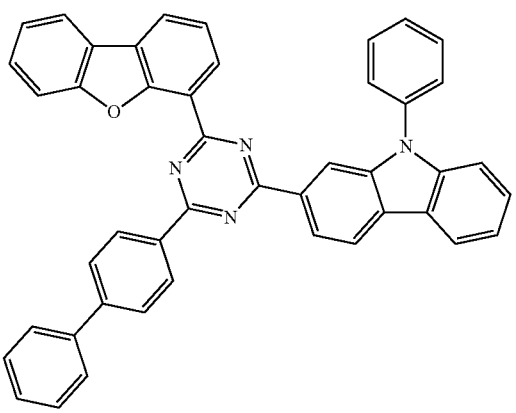

88
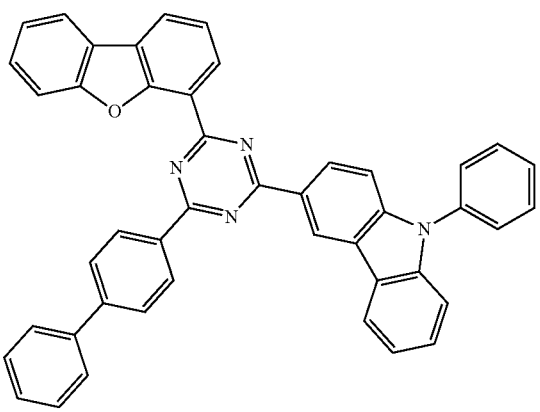
89
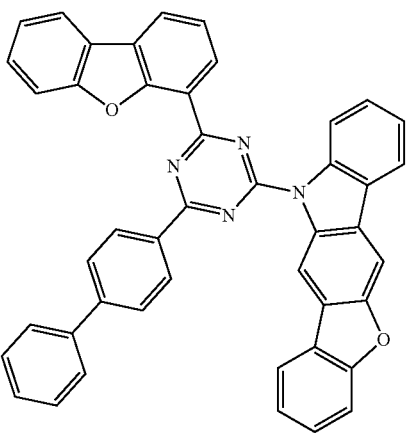
90
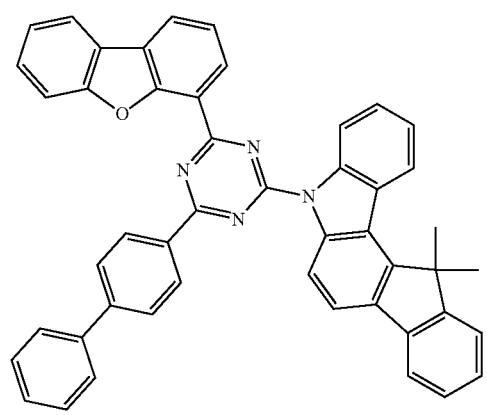
91
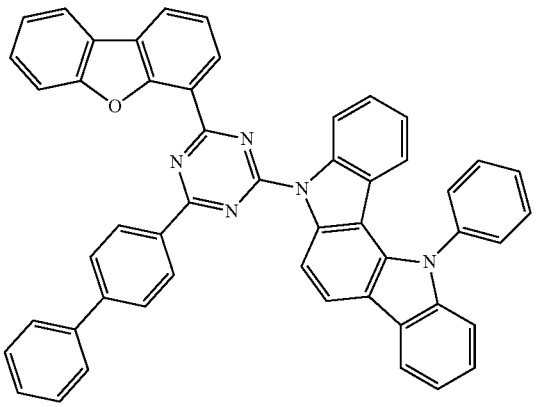
92
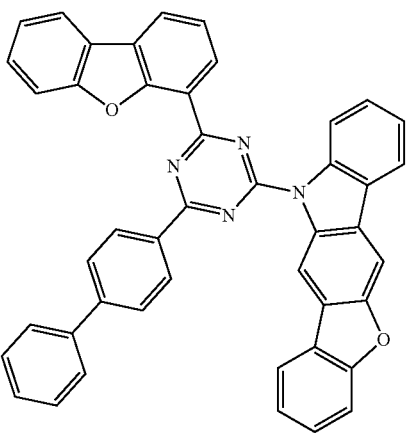
93
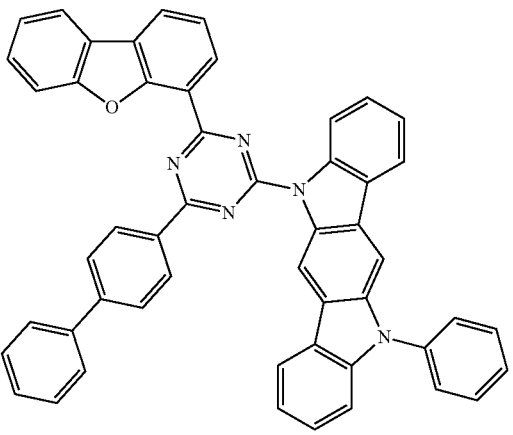

94
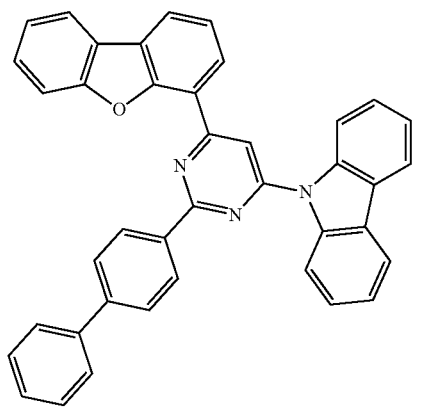
95
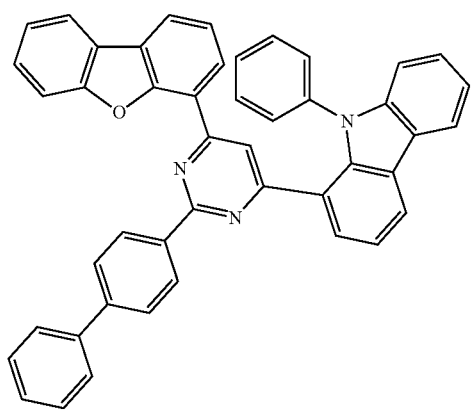
96
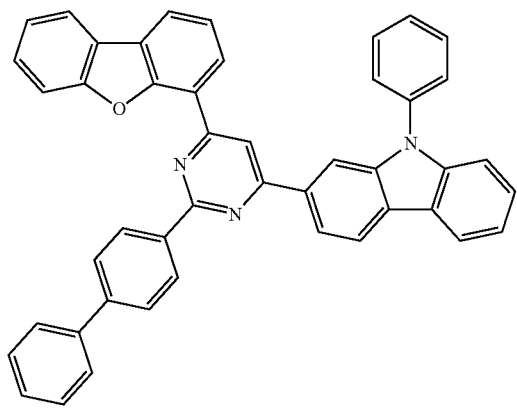
97
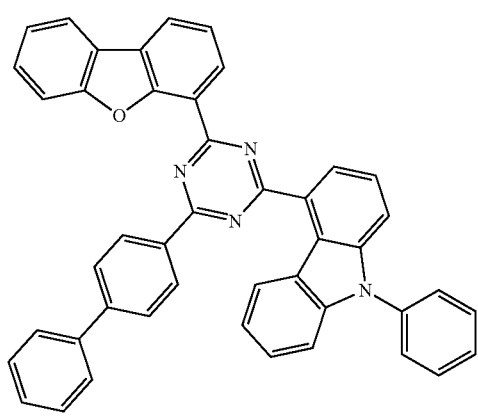
98
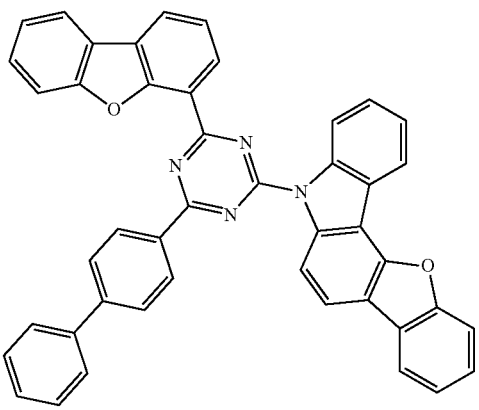
99
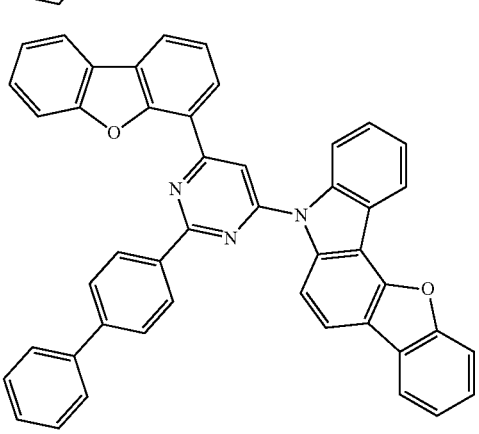
100
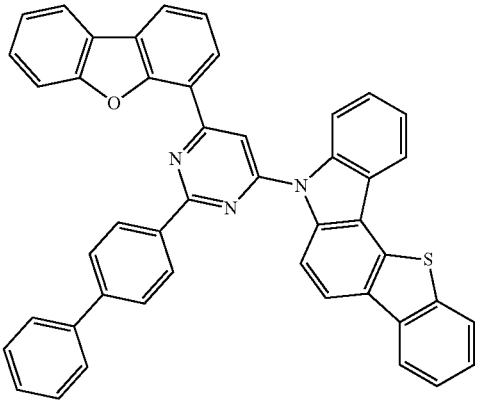
101
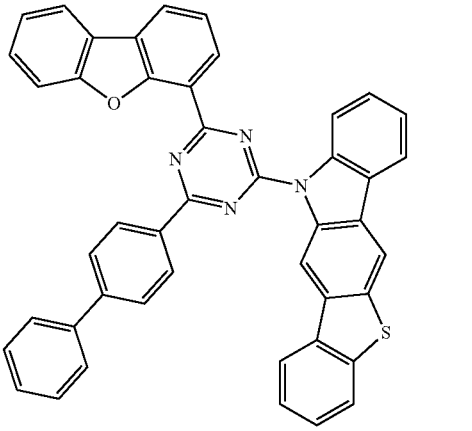

102
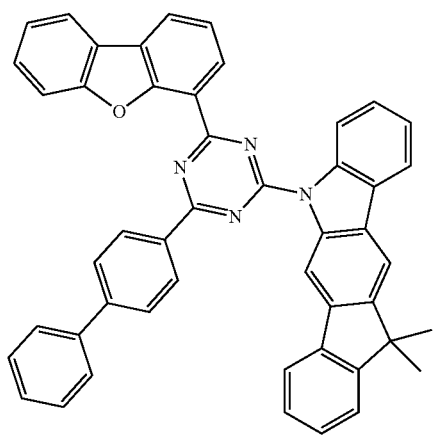
103
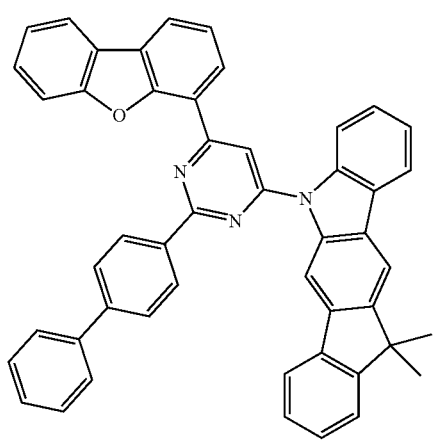
104
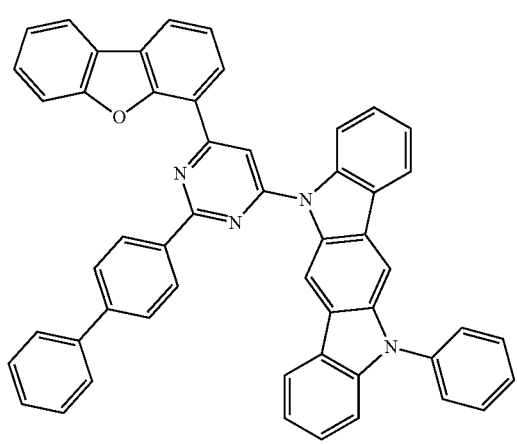
105
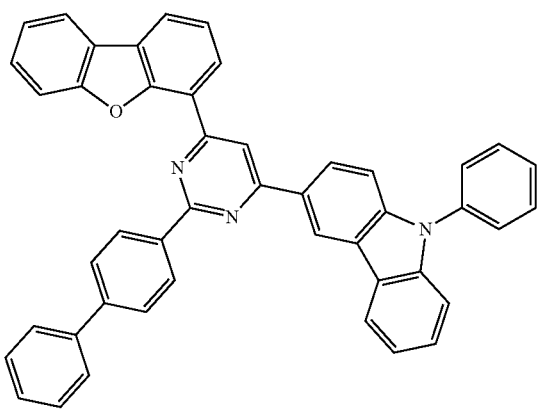
106
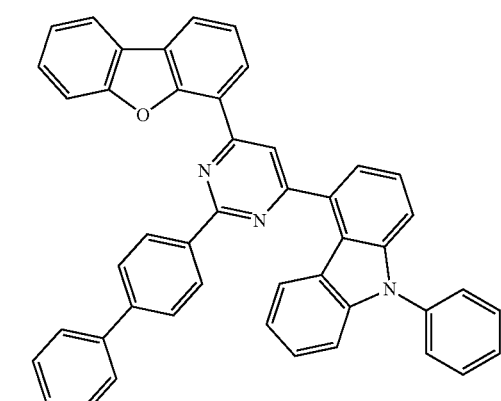
107
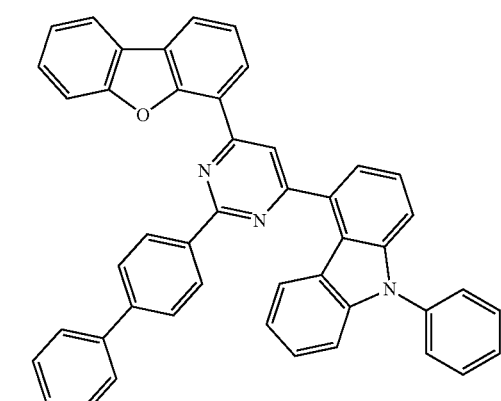
108
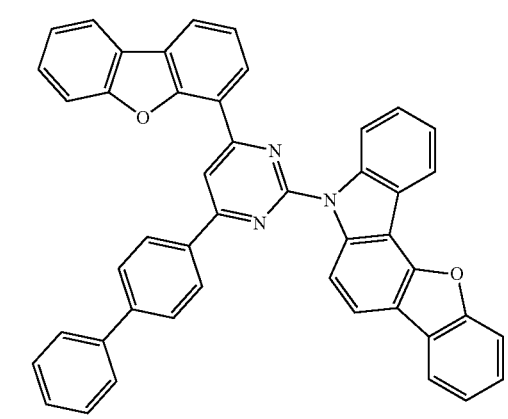

109
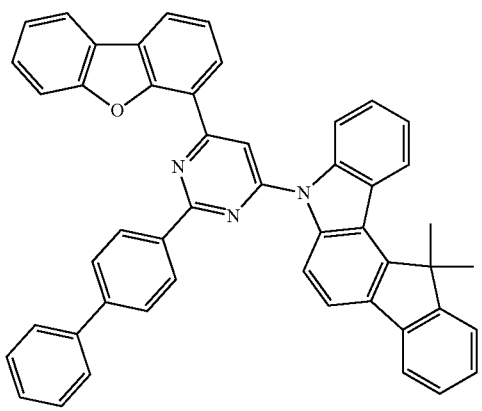
110
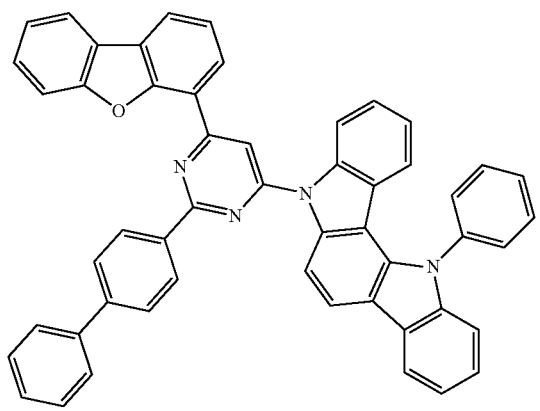
111
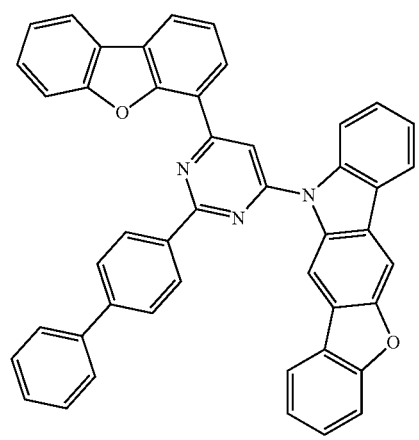
112
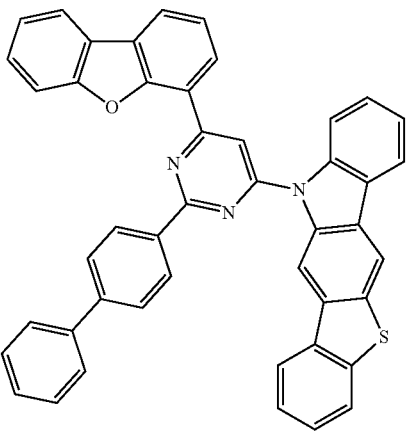
113
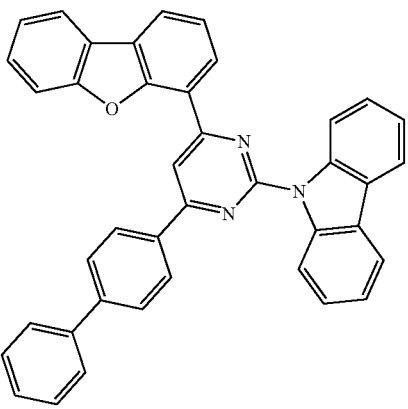
114
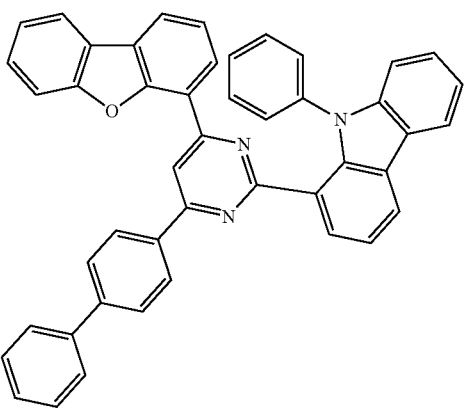

115
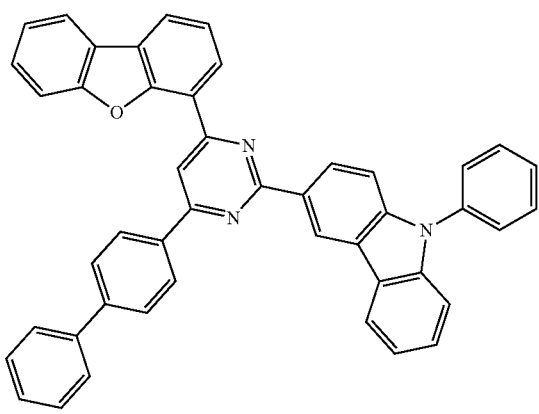
116
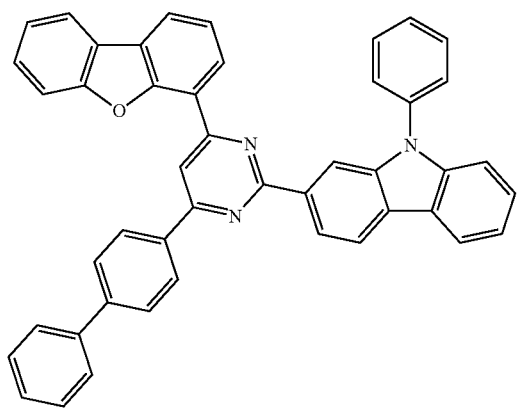
117
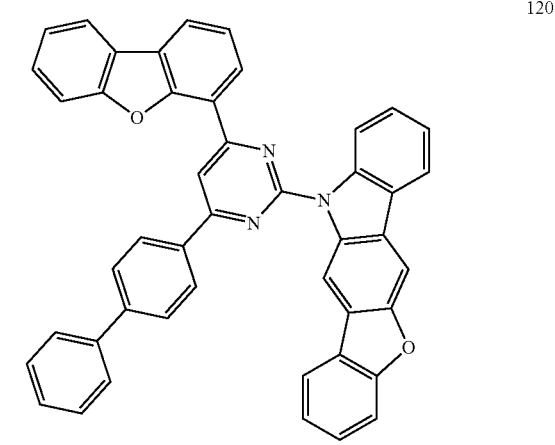
118
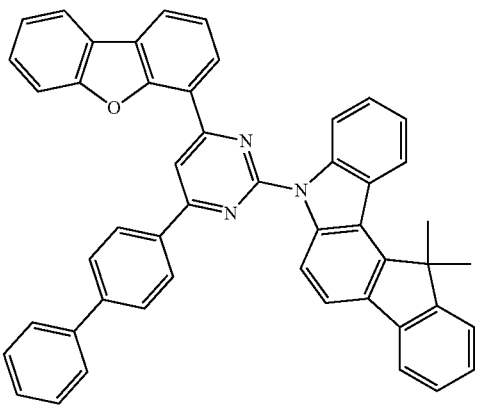
119
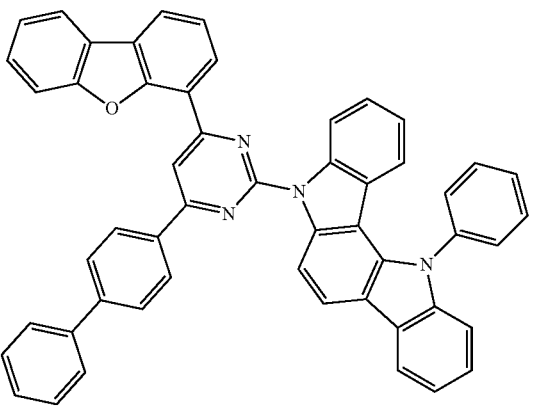
120
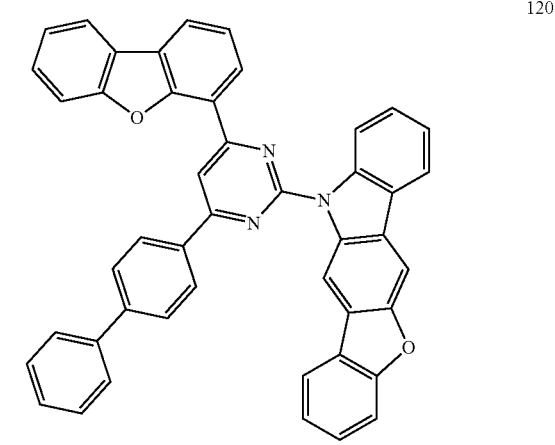

121
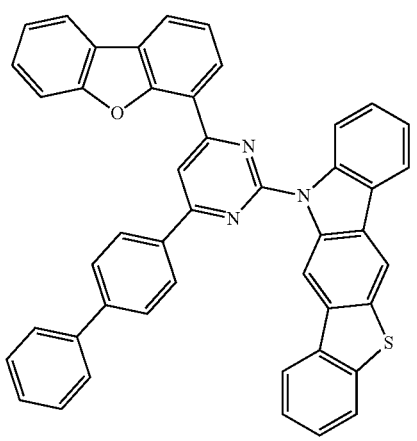
122
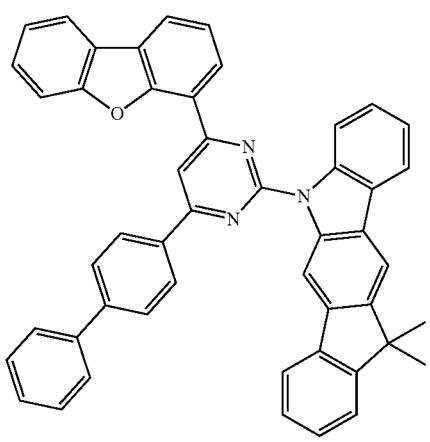
123
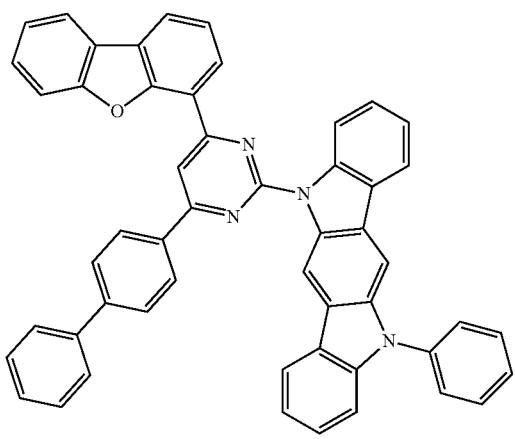
124
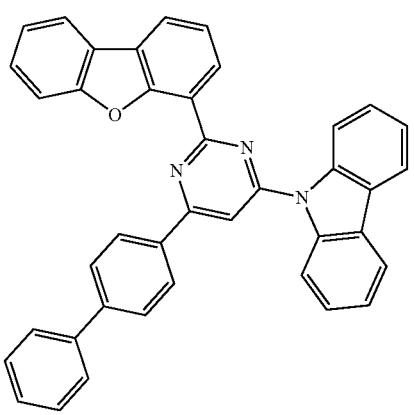
125
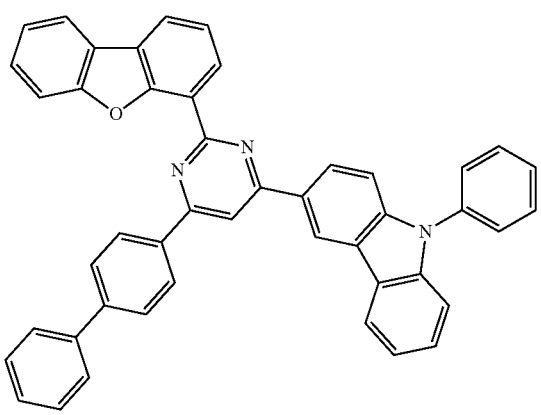
126
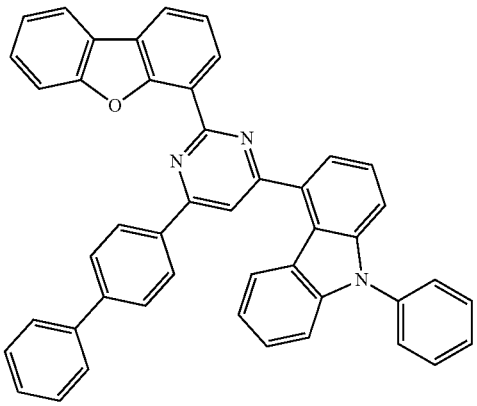
127
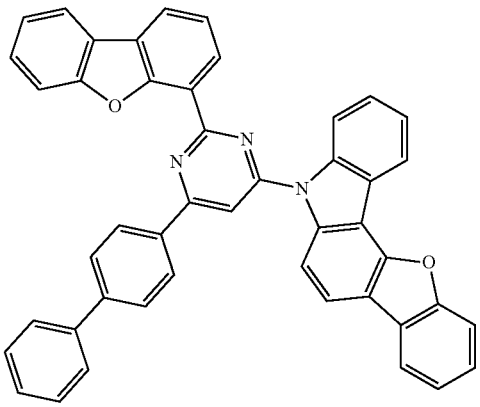

-continued
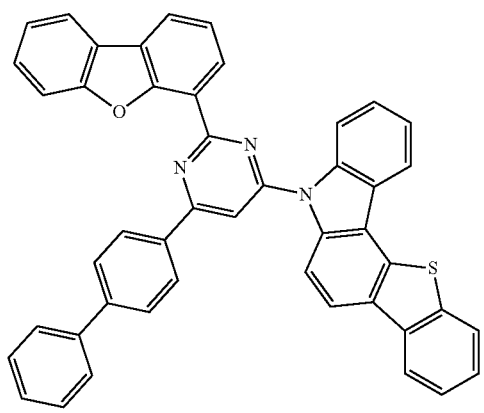
128
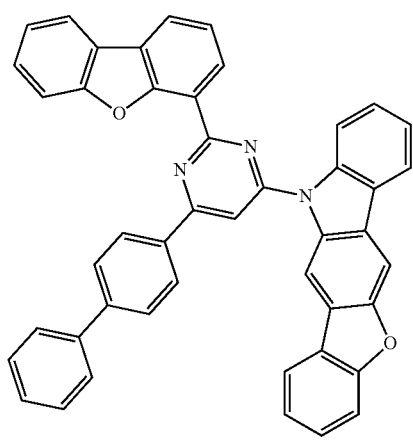
129
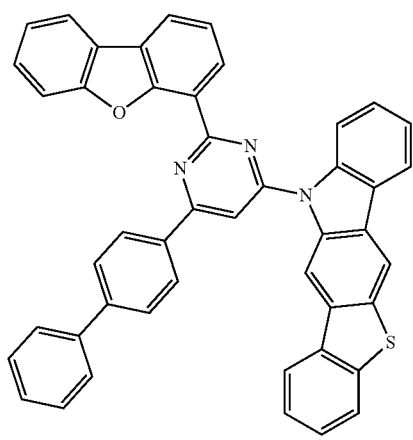
130
-continued
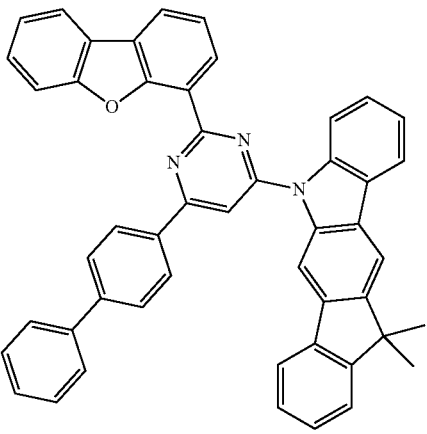
131
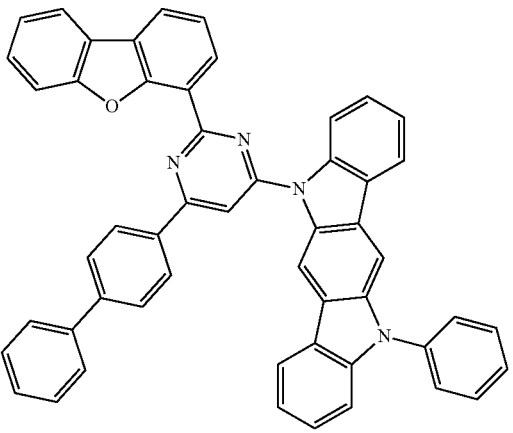
132
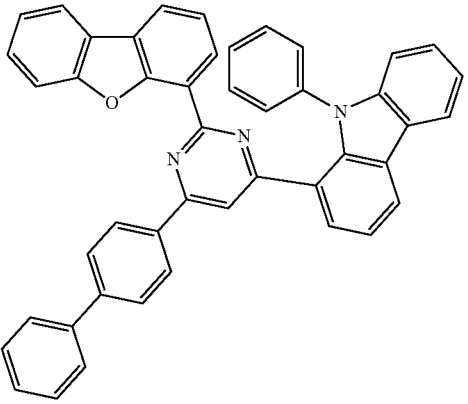
133

-continued
134
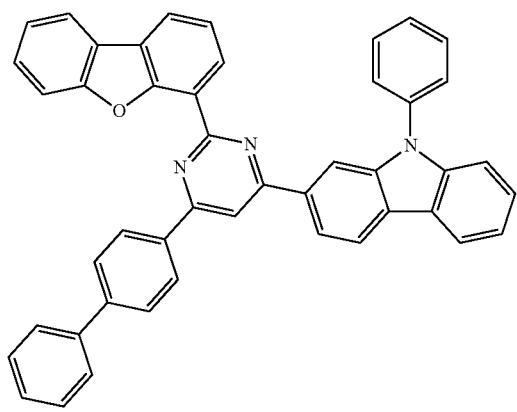
135
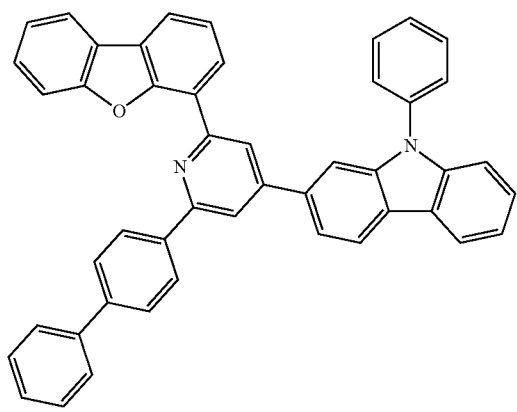
136
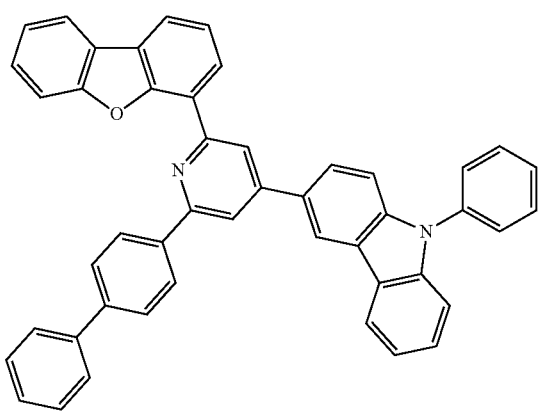
-continued
137
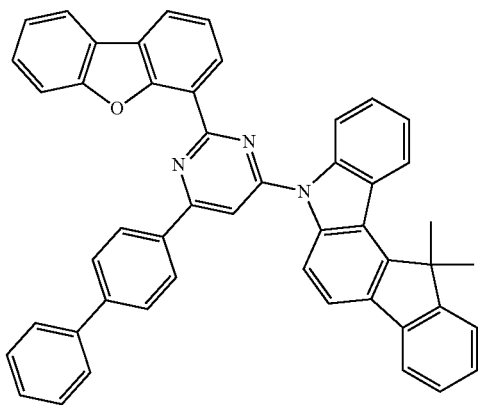
138
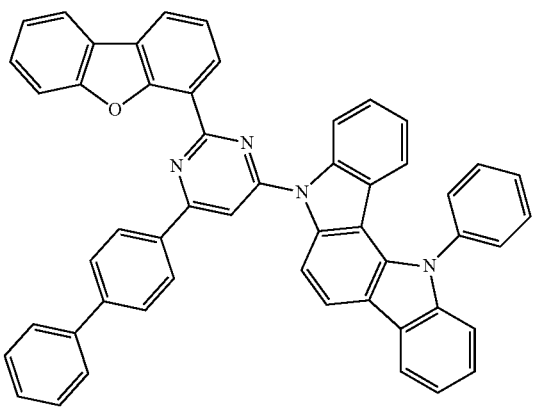
139
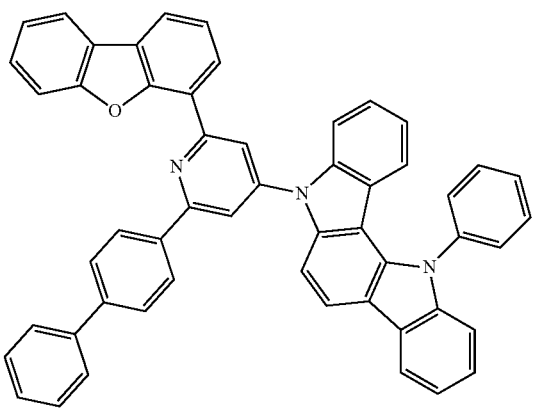

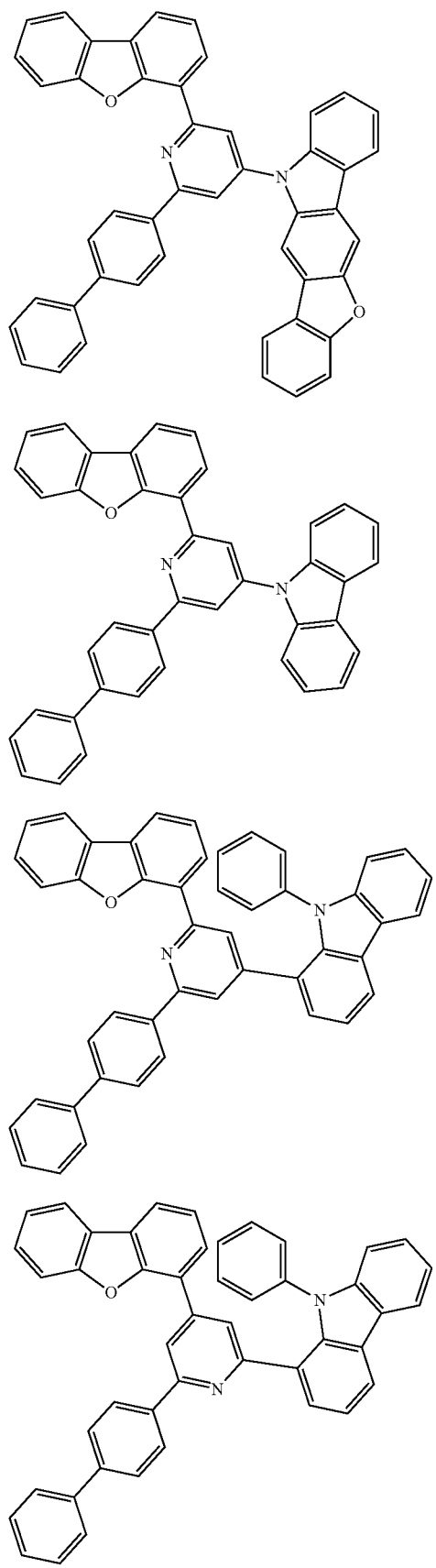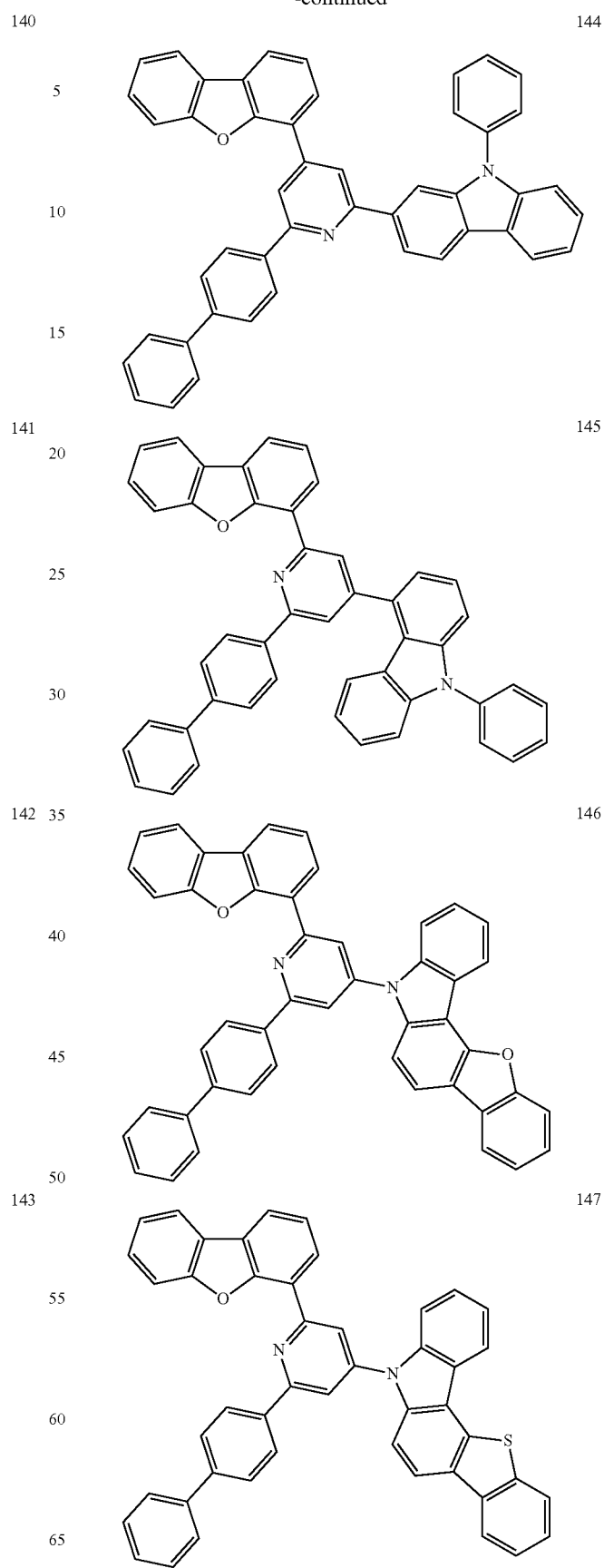

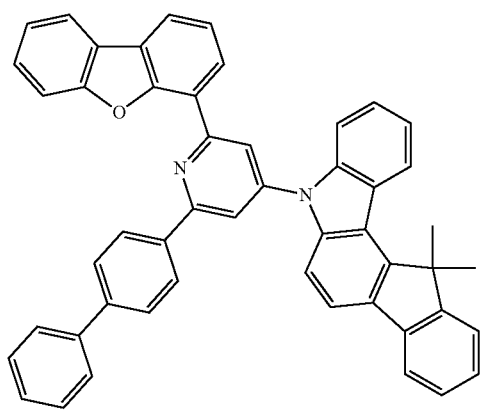
148
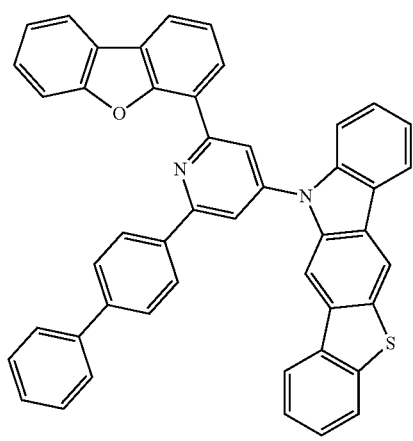
149
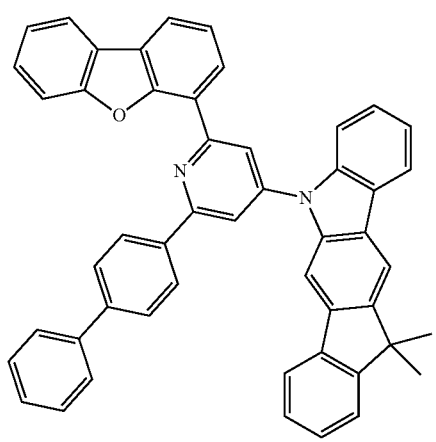
150
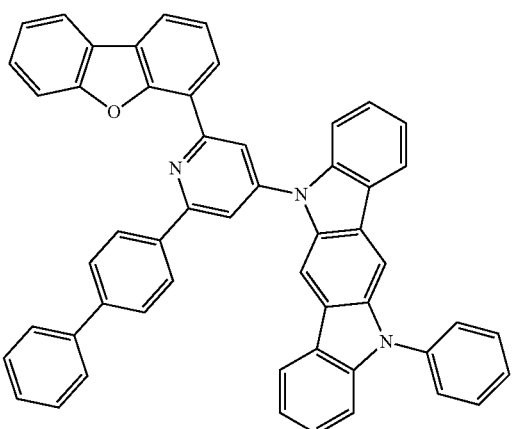
151
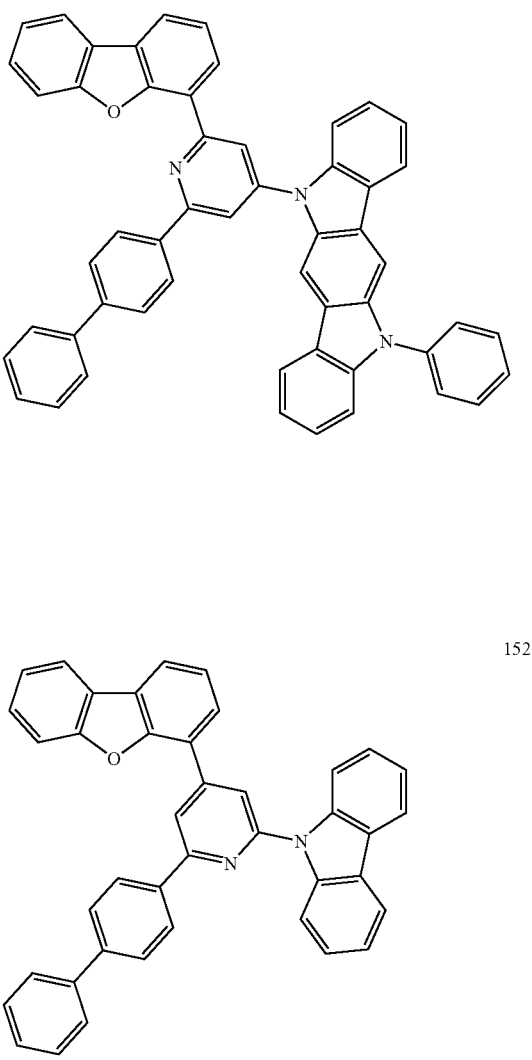
152
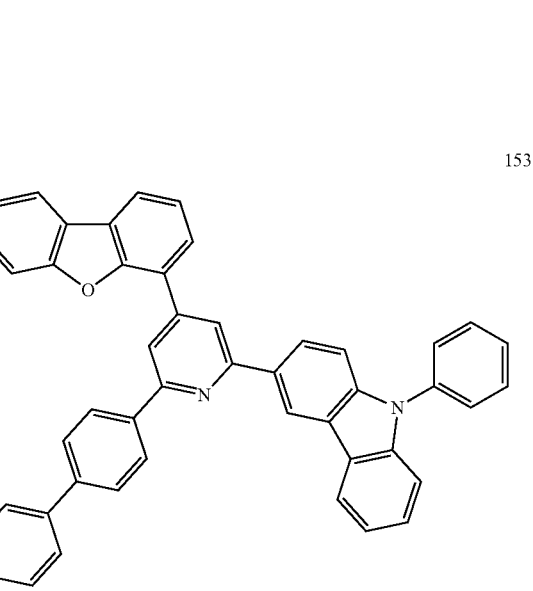
153

154 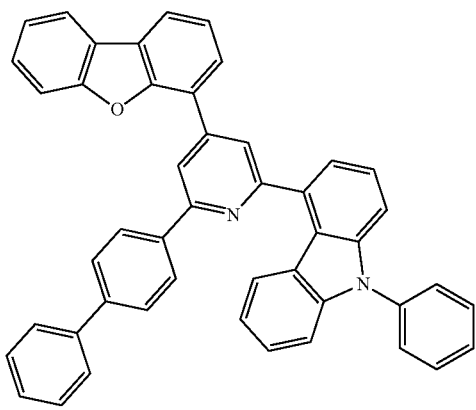
155 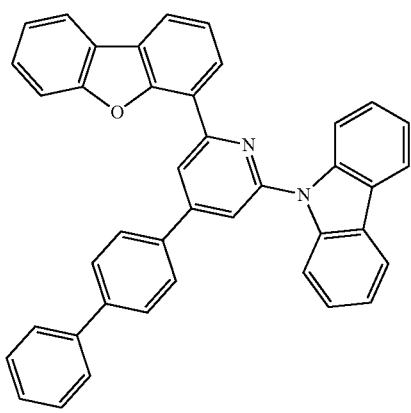
156 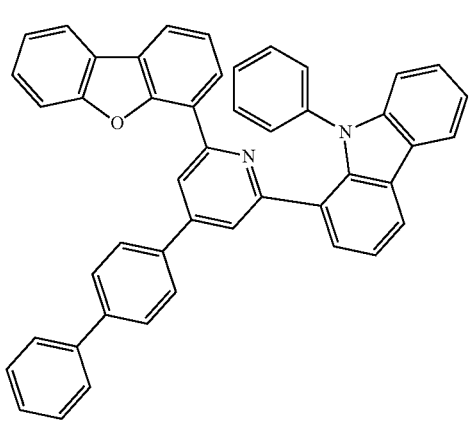
157 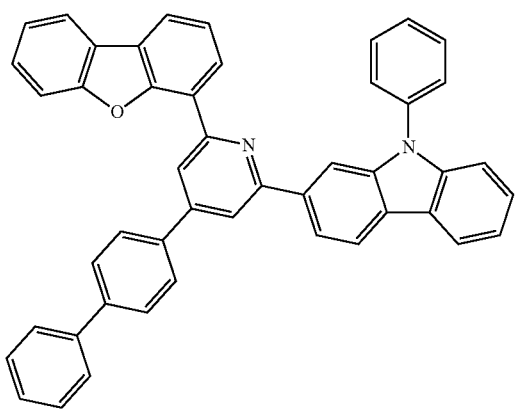
158 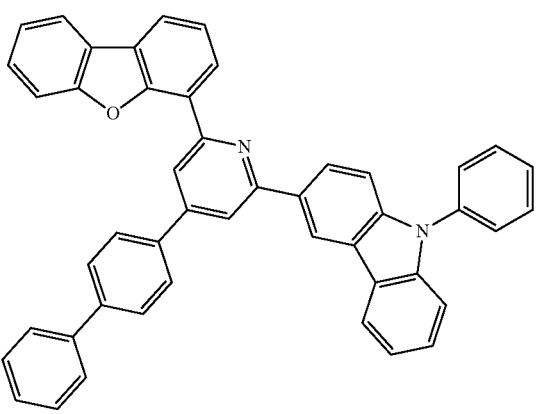
159 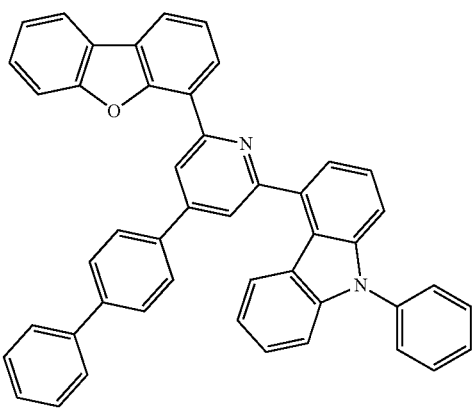
160 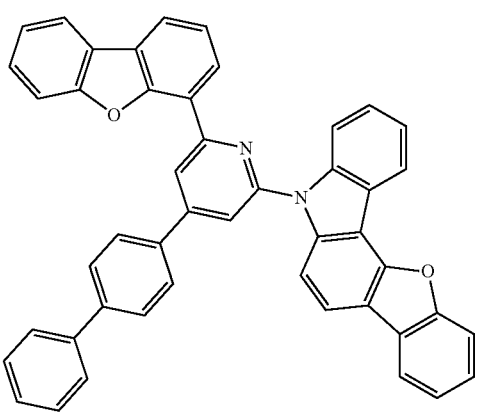

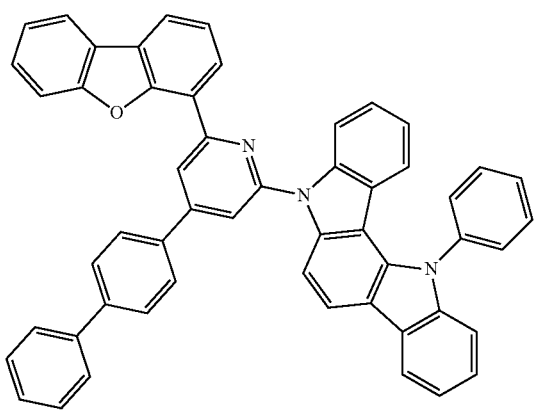
161
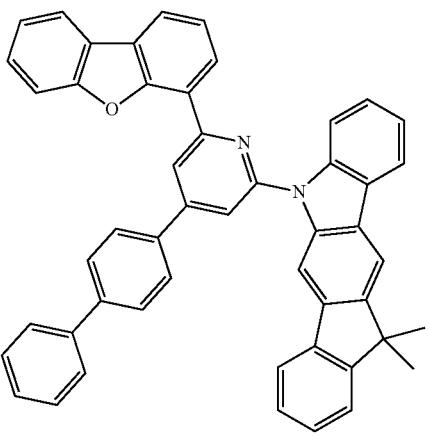
164
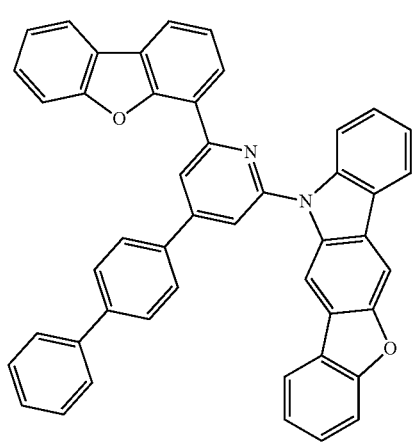
162
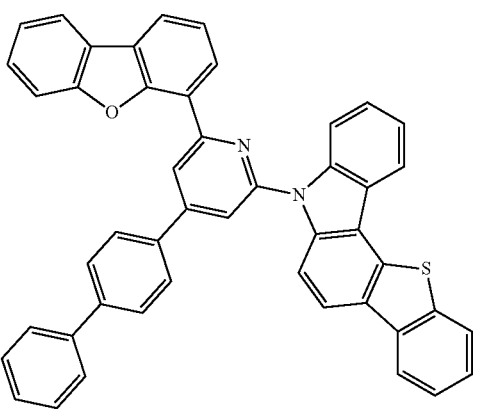
165
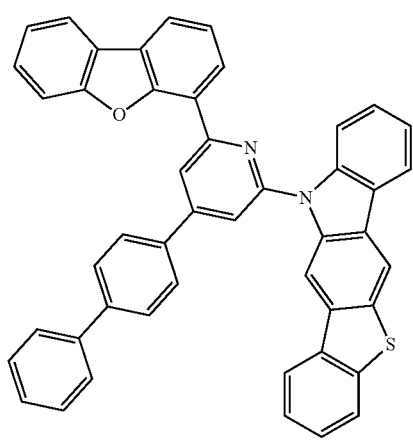
163
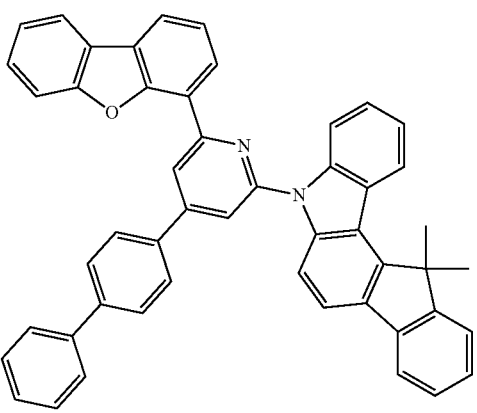
166

167
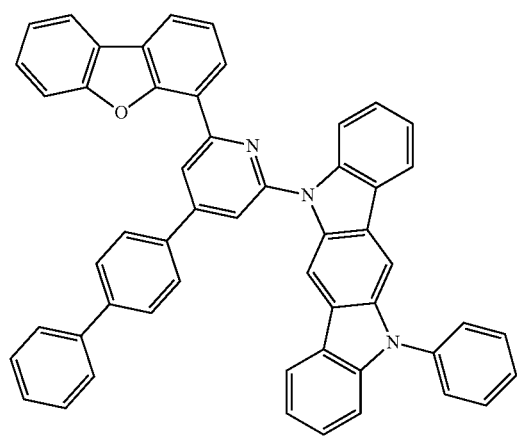
168
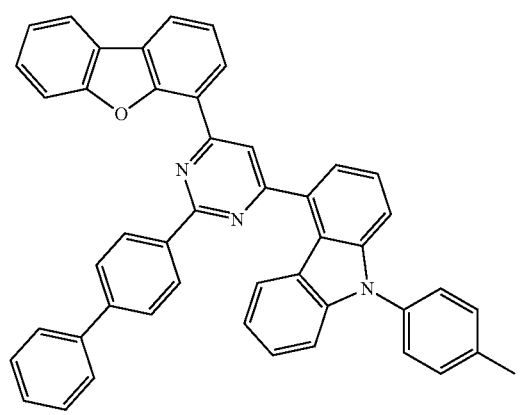
169
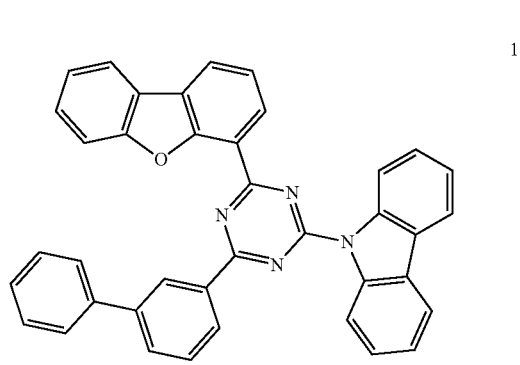
170
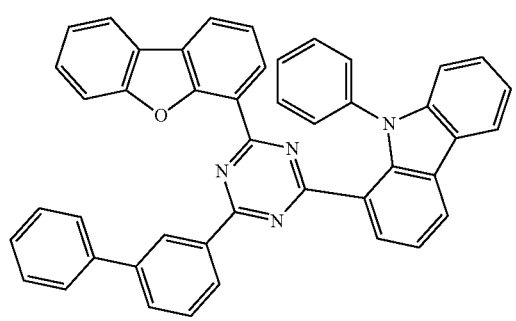
171
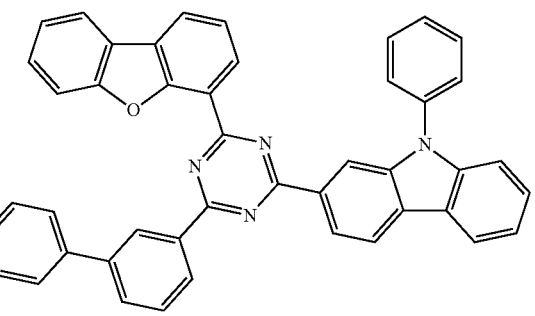
172
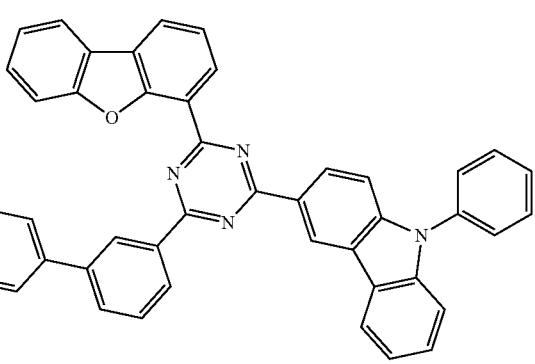
173
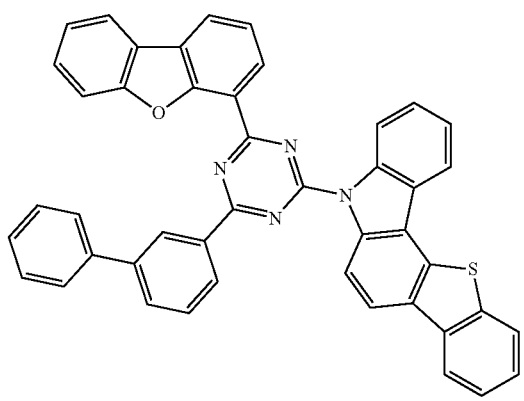
174
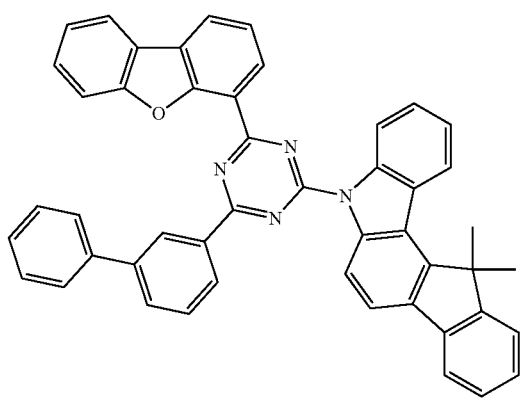

175
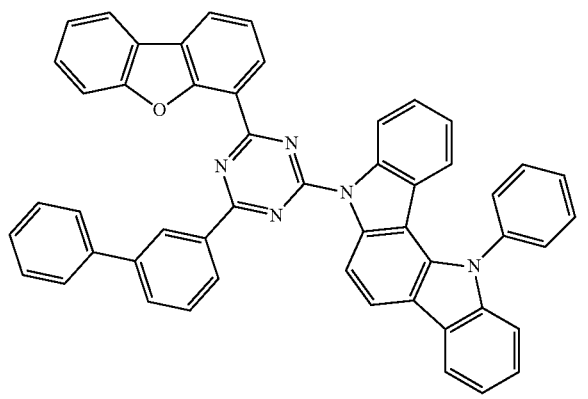
176
179
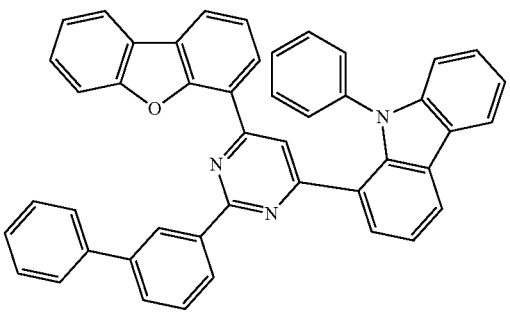
180
177
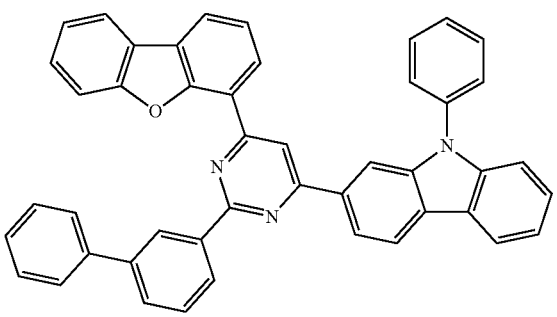
181
178
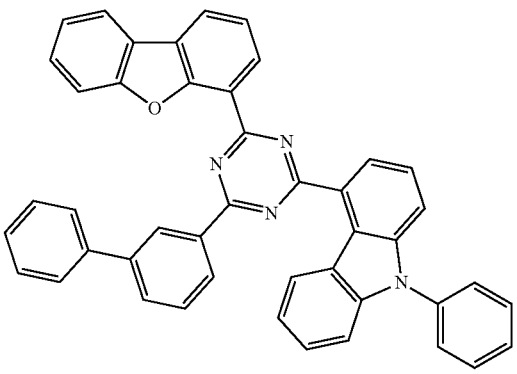
182
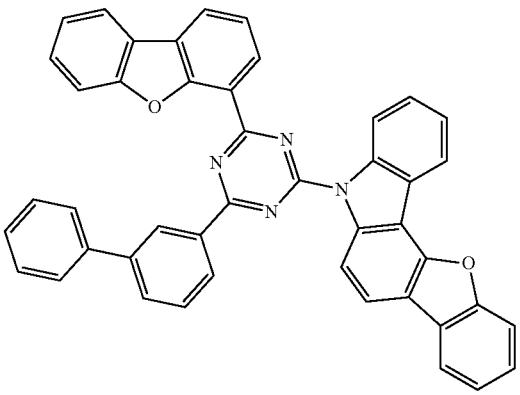

183
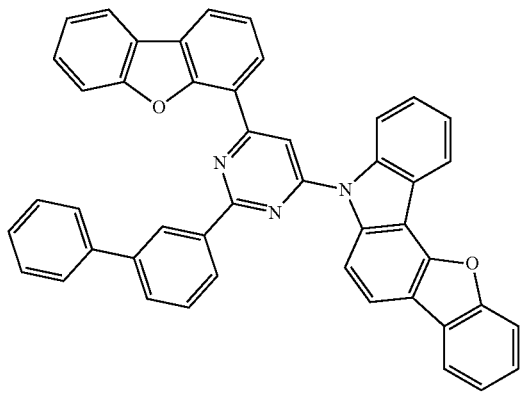
184
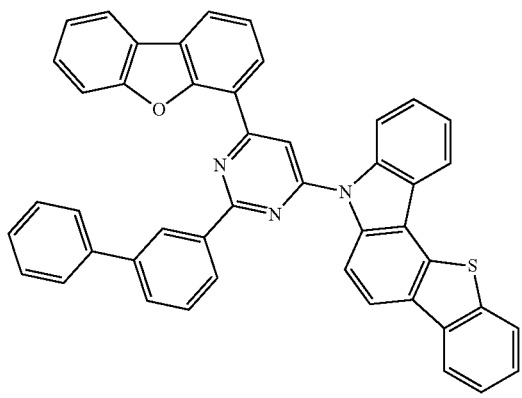
185
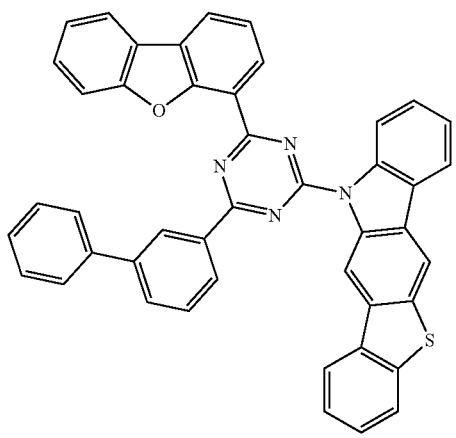
186
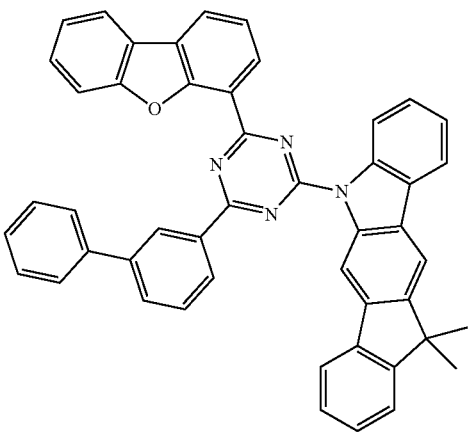
187
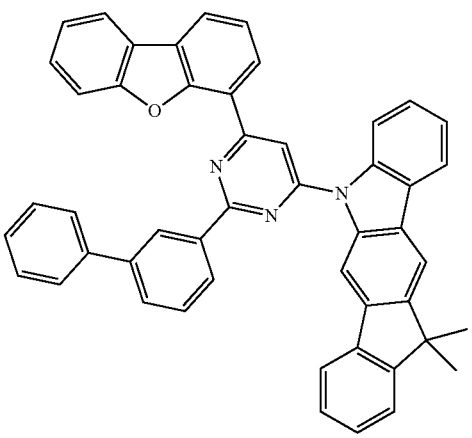
188
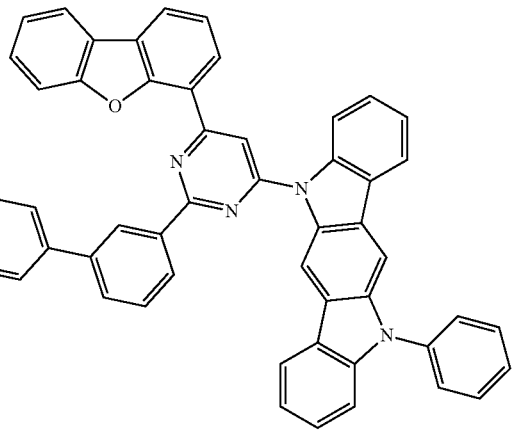

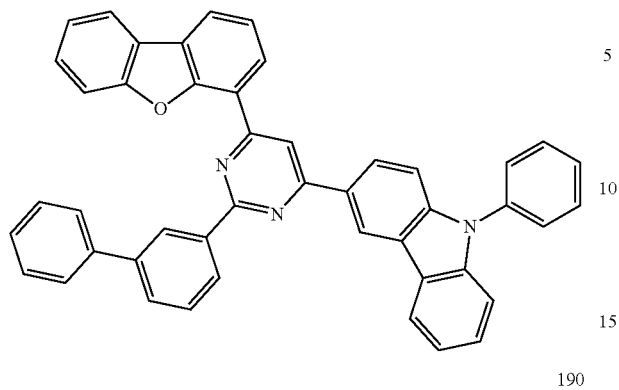
189
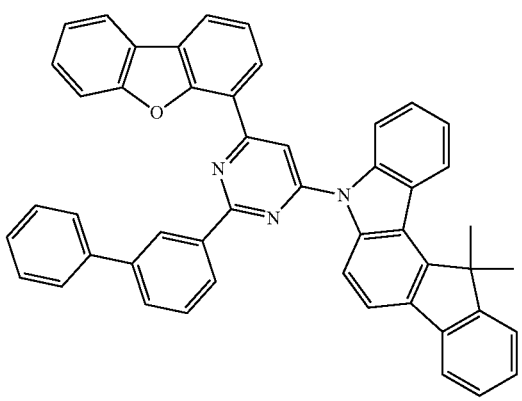
193
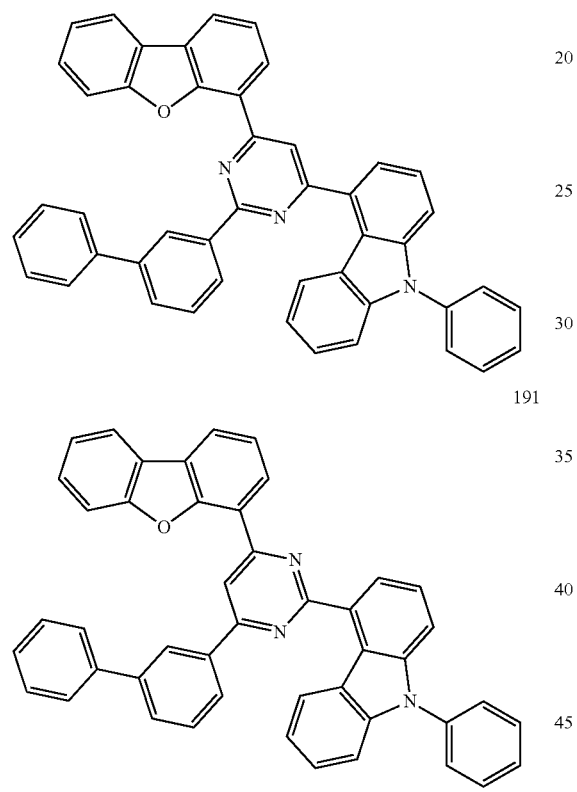
190
191
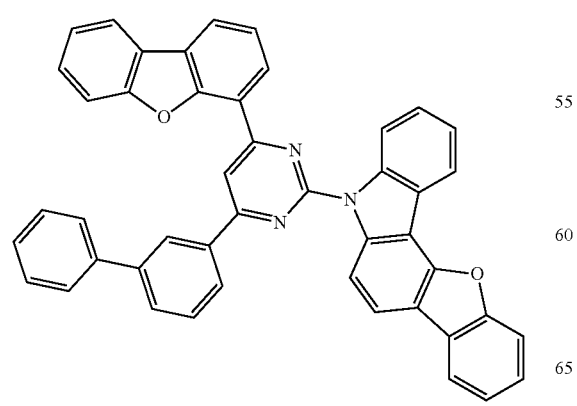
192
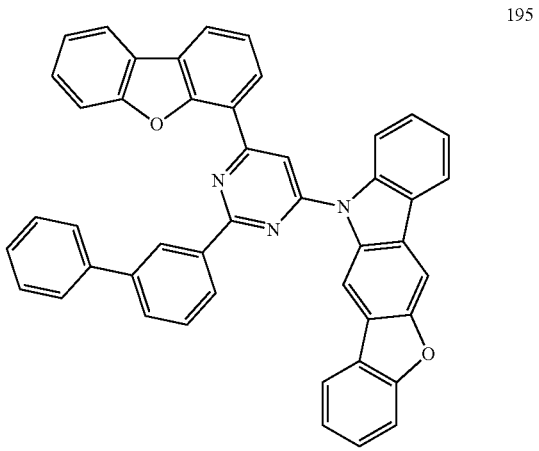
194
195

-continued
196
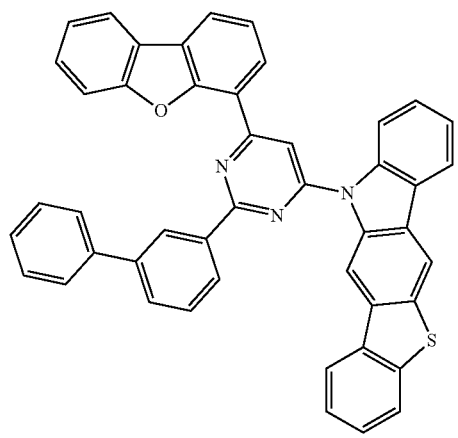
197
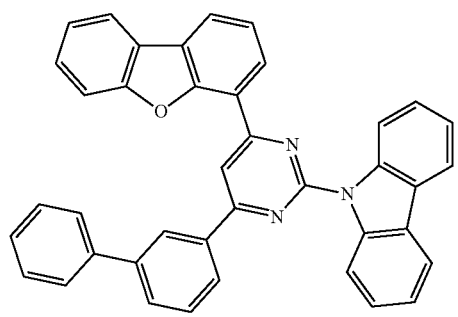
198
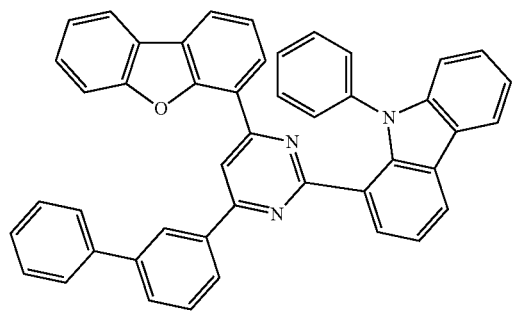
199
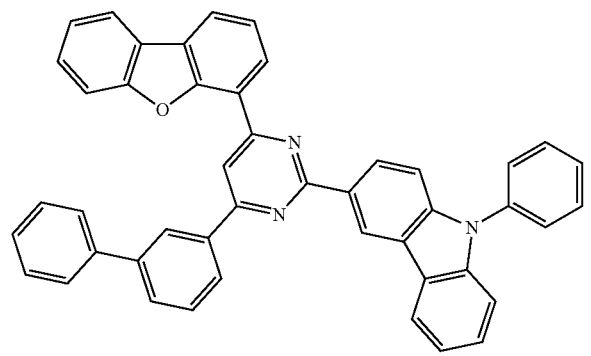
-continued
200
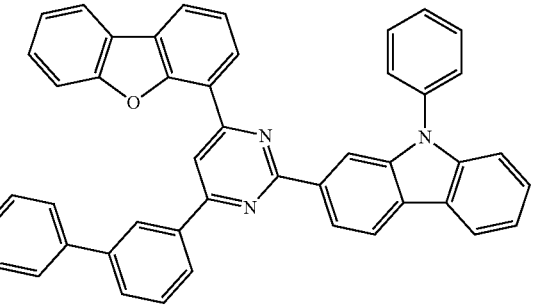
201
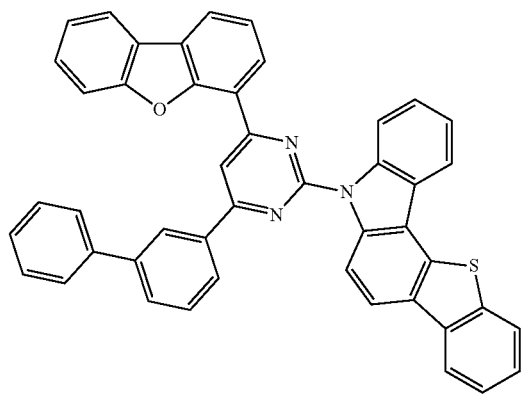
202
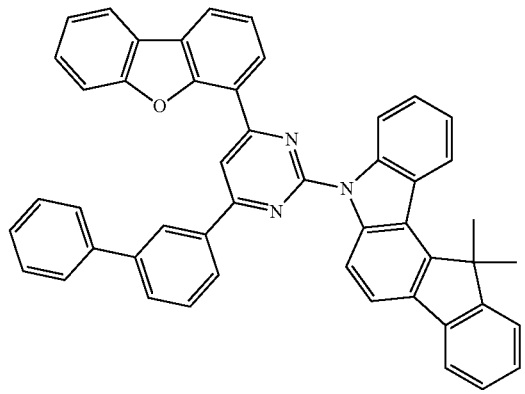
203
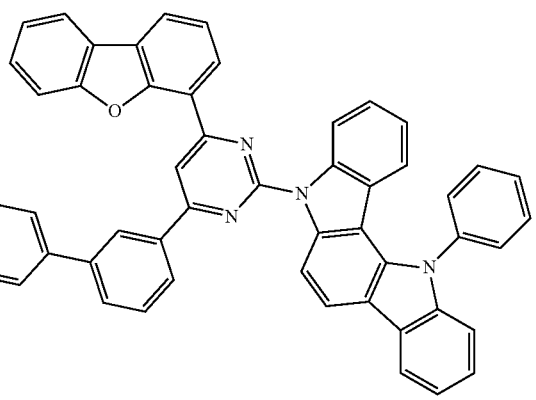

204
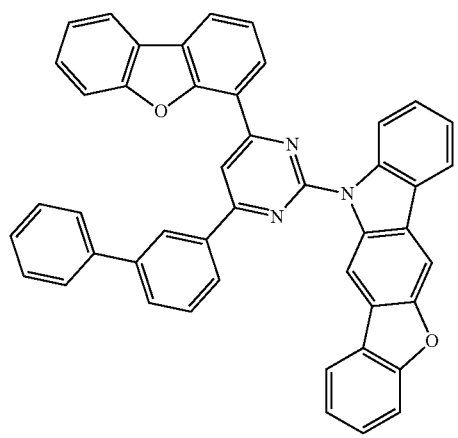
205
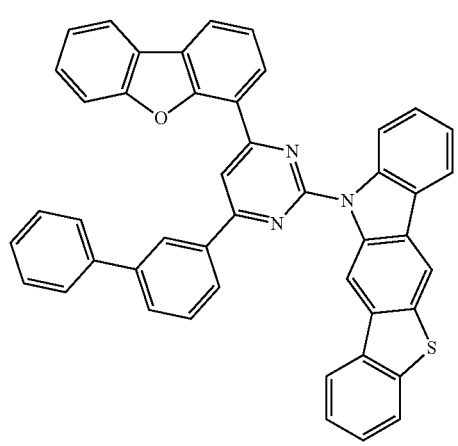
206
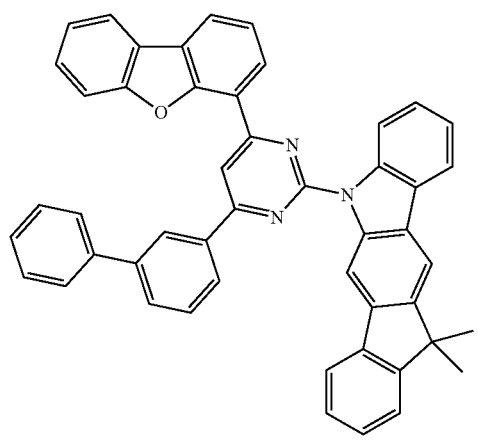
207
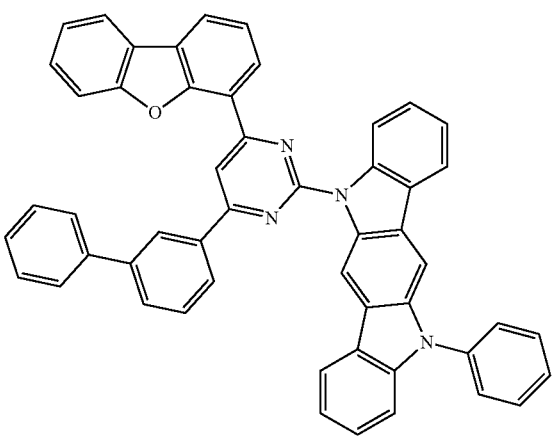
208
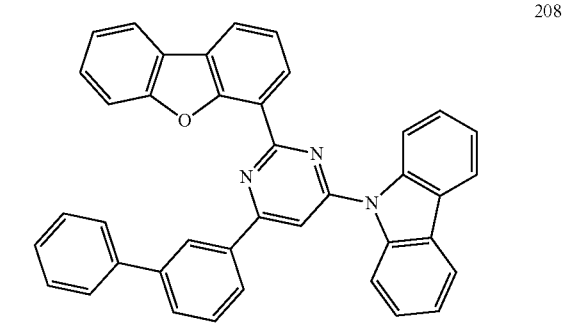
209
210
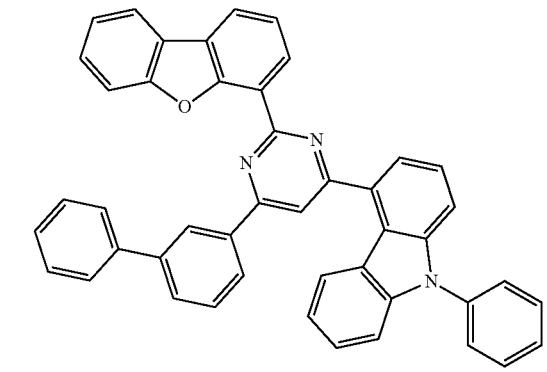

211
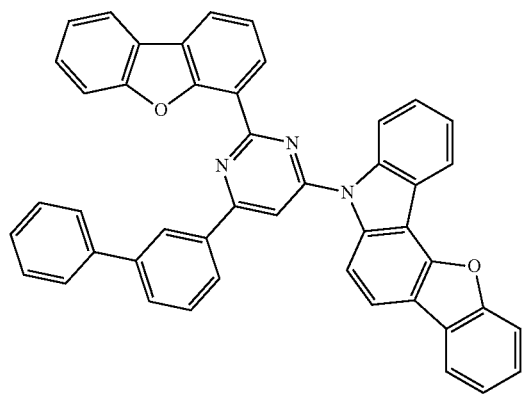
212
213
214
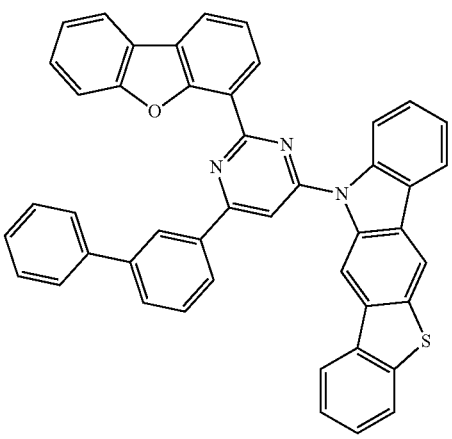
215
216
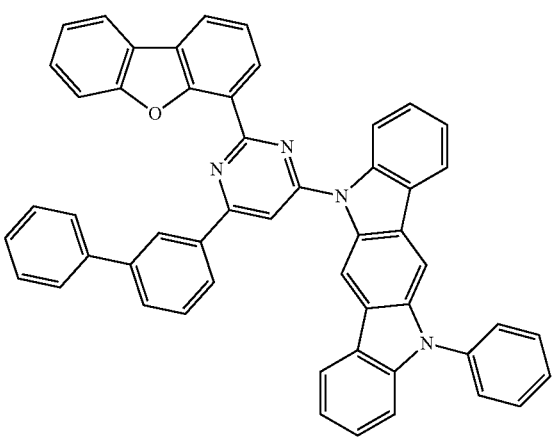
217
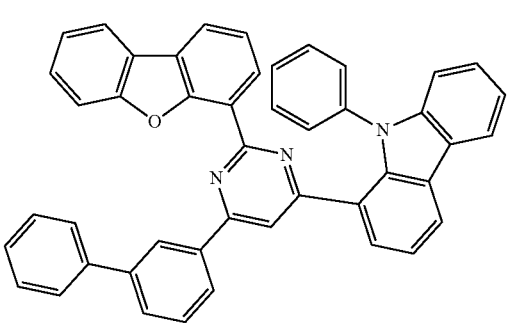

218
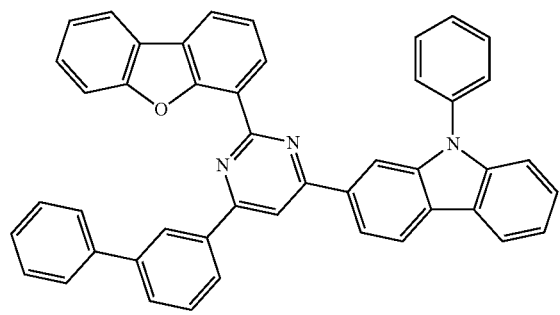
219
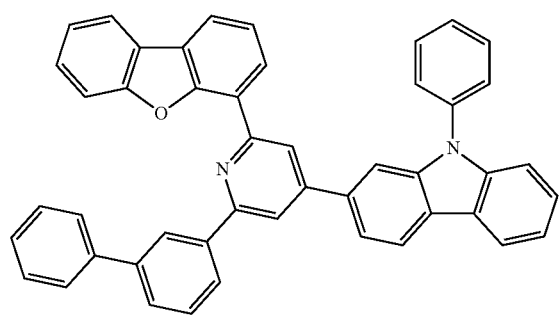
220
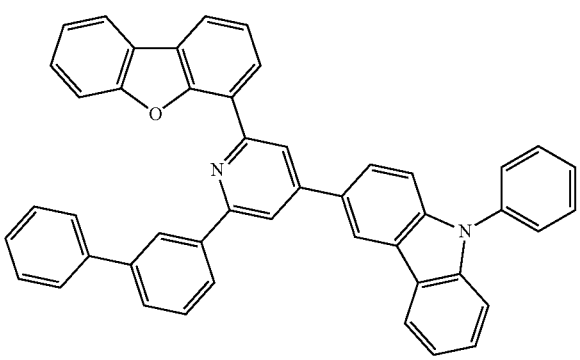
221
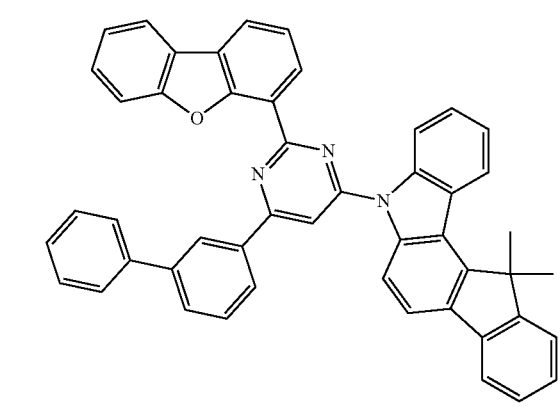
222
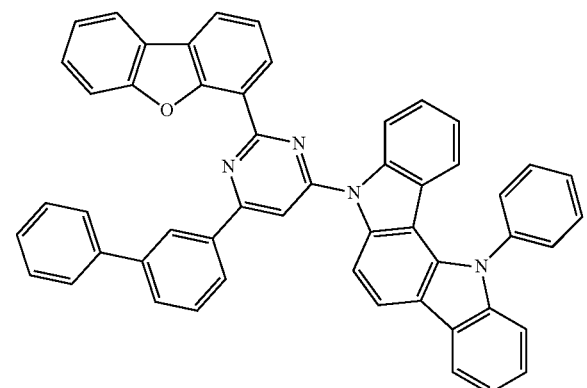
223
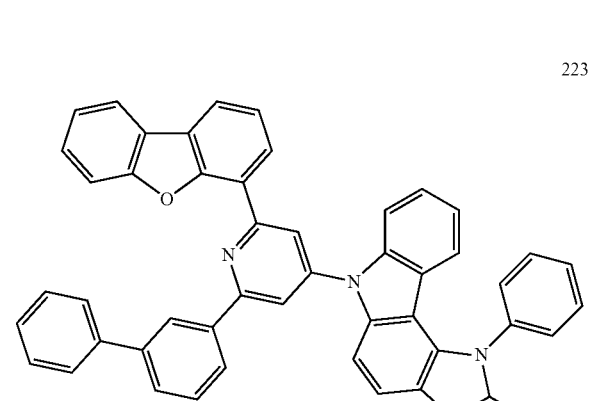
224
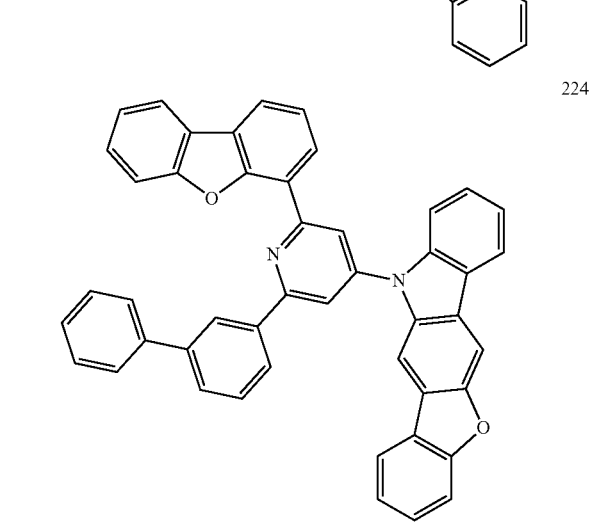
225
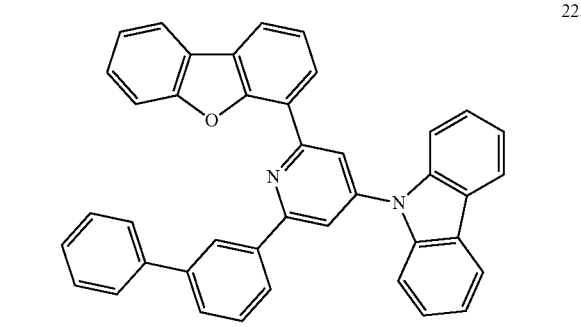

226
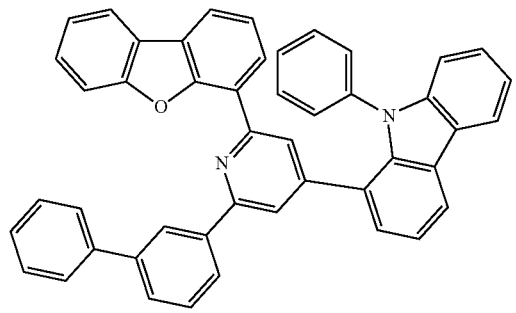
227
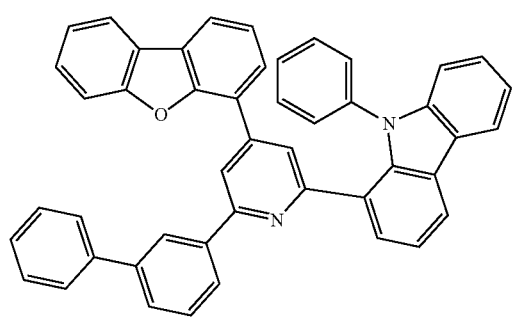
228
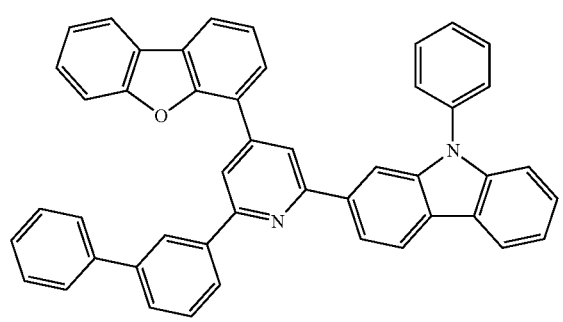
229
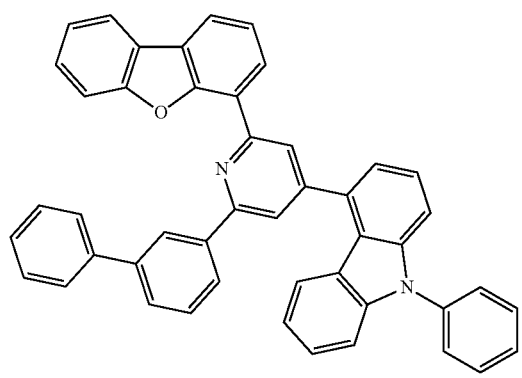
230
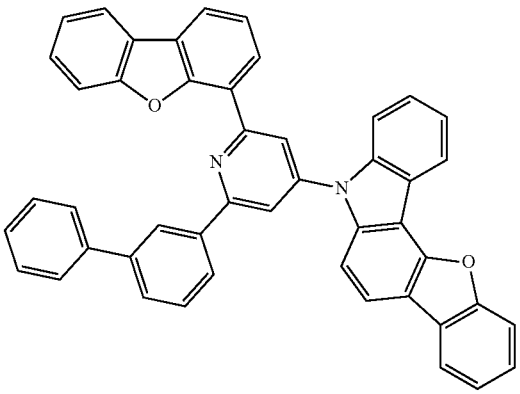
231
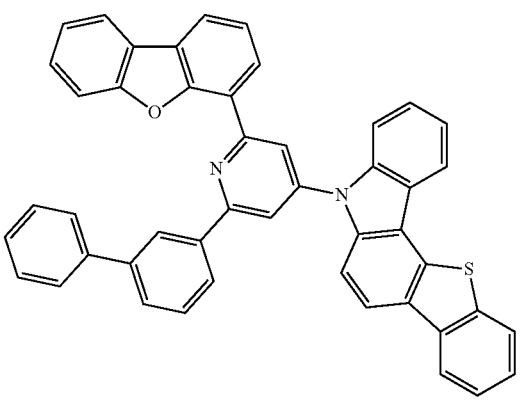
232
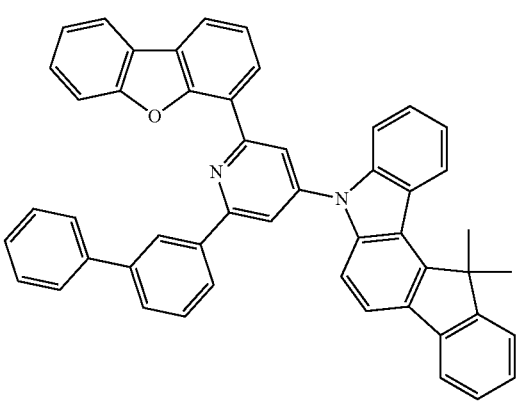

233
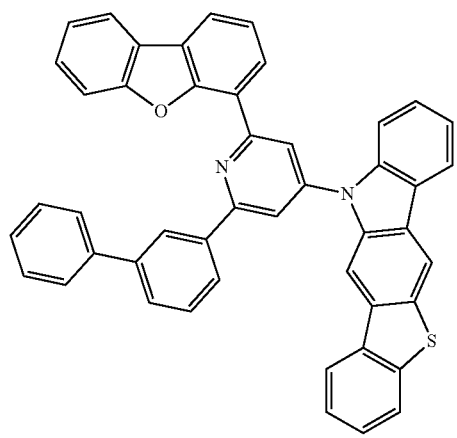
234
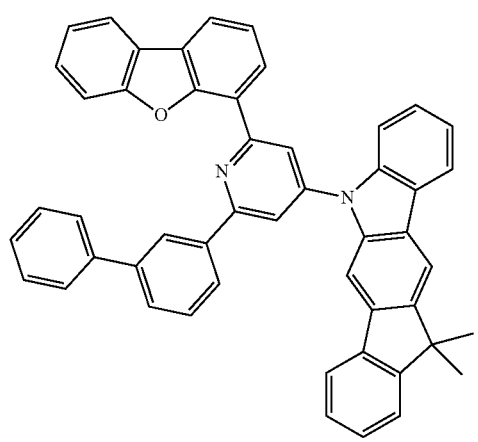
235
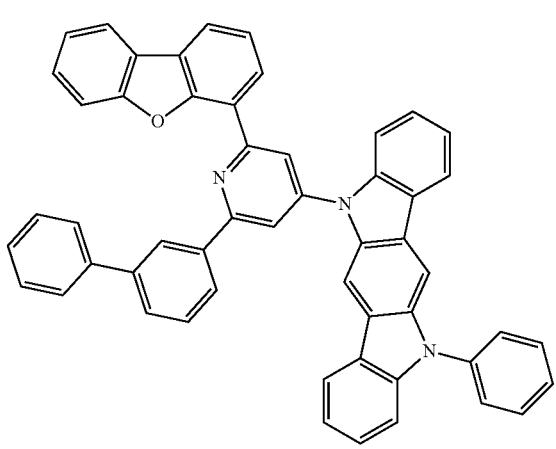
236
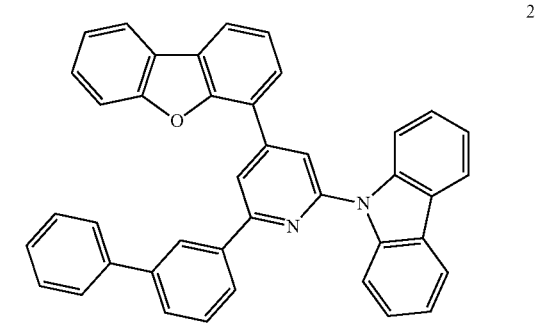
237
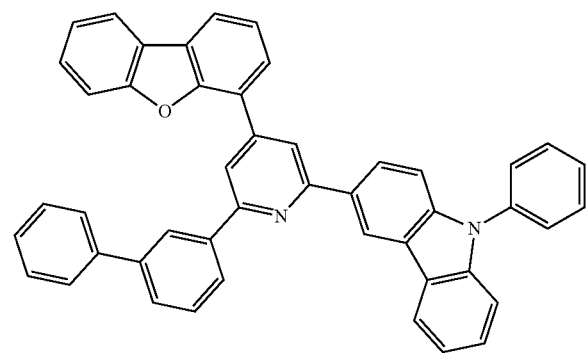
238
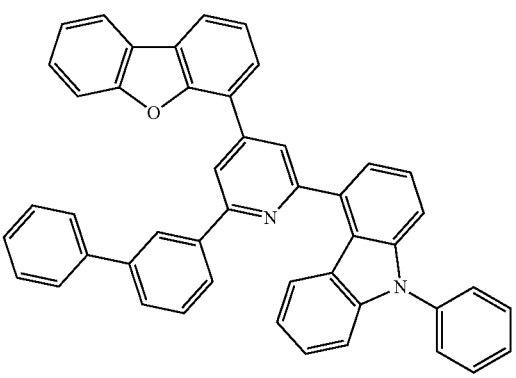
239
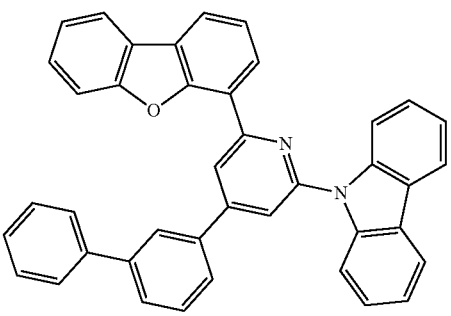
240
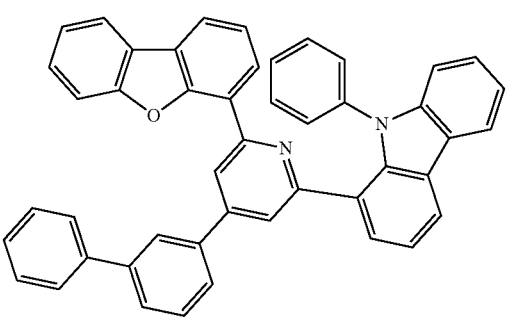

241
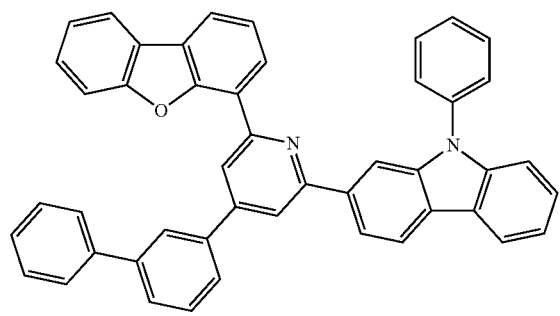
242
243
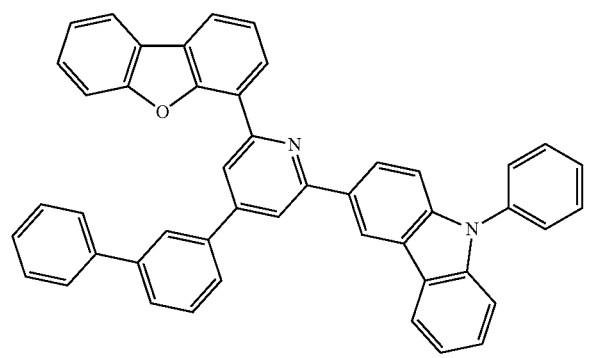
244
245
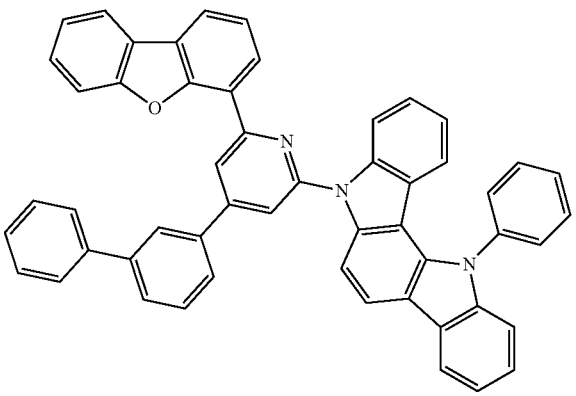
246
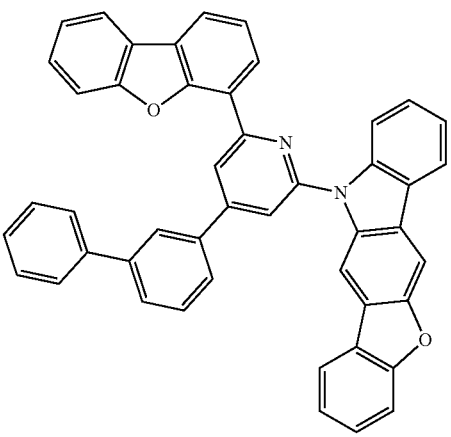
247
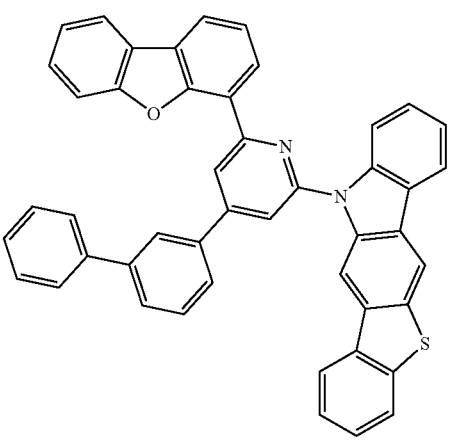

101
-continued
248
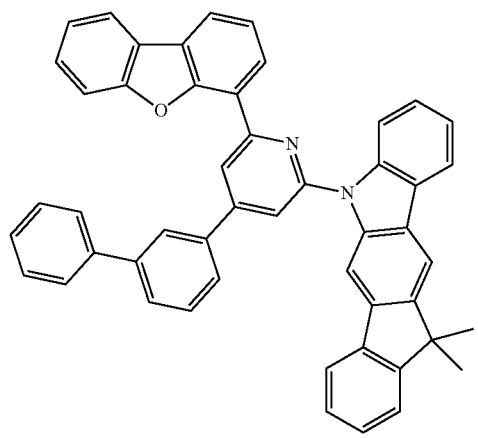
249
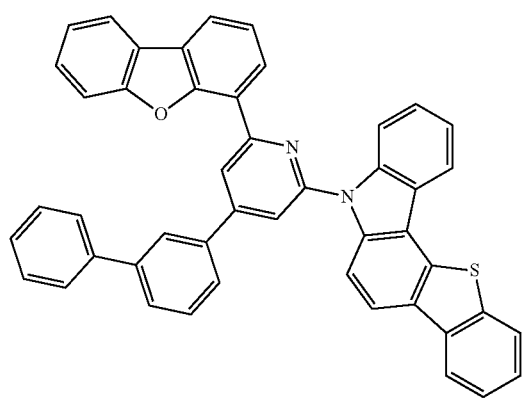
250
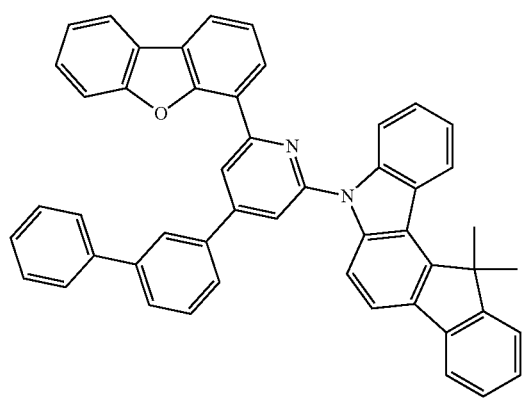
102
-continued
251
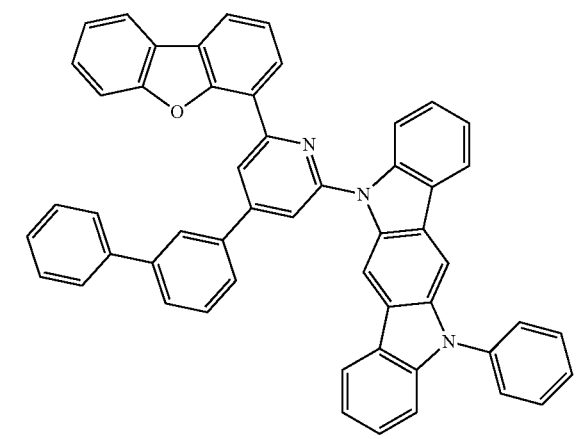
252
253
254
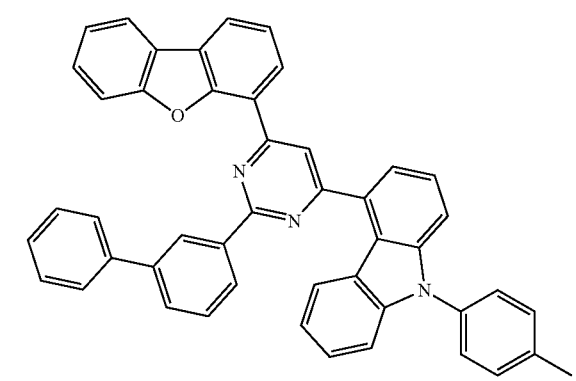
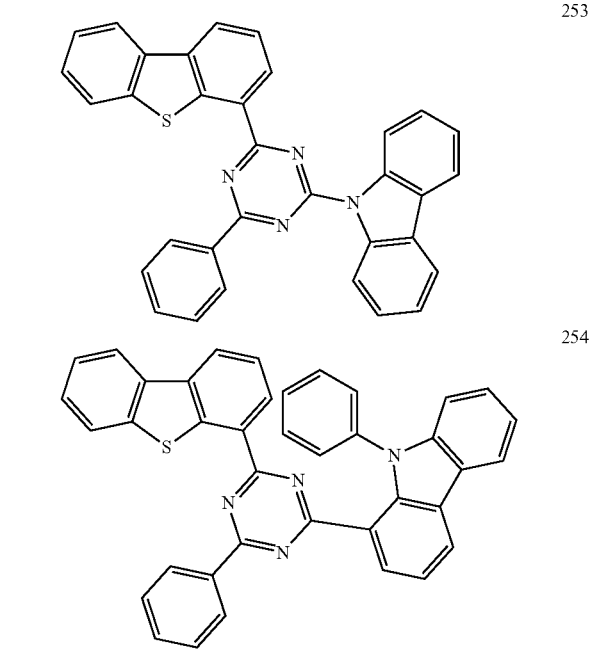

255
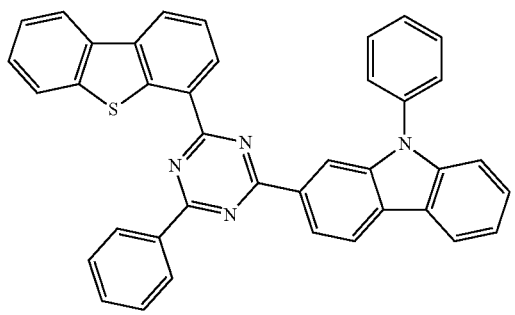
256
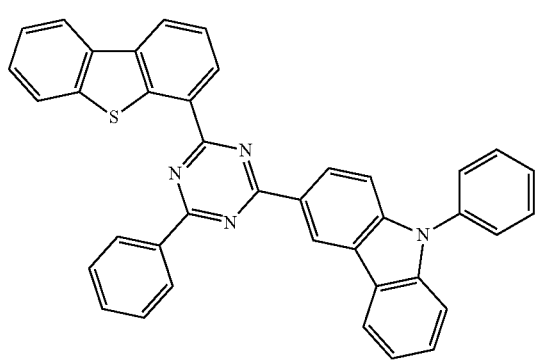
257
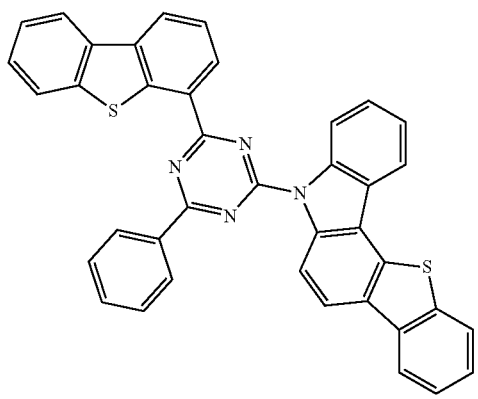
258
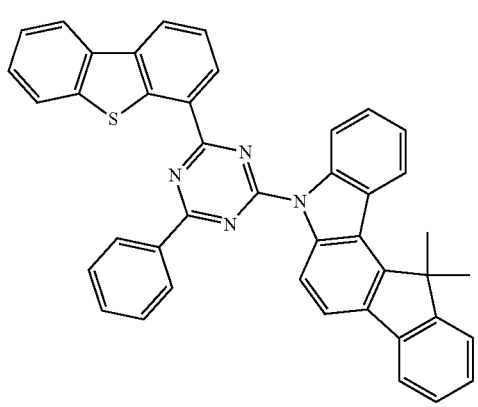
259
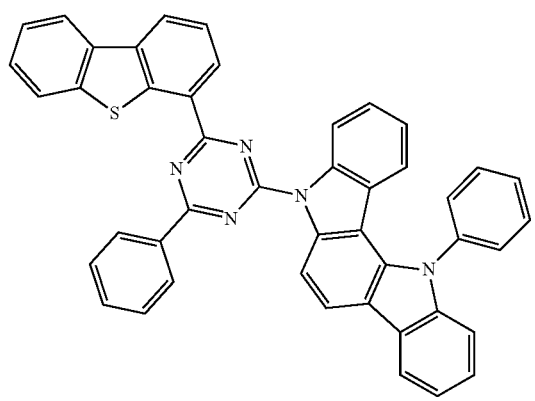
260
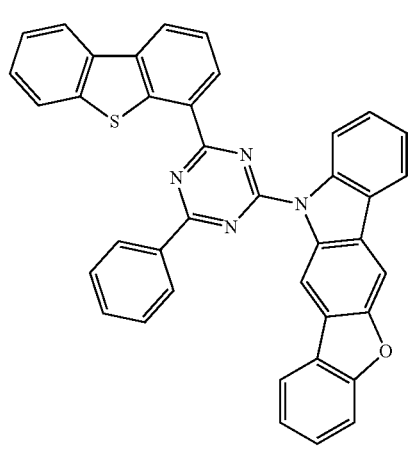
261
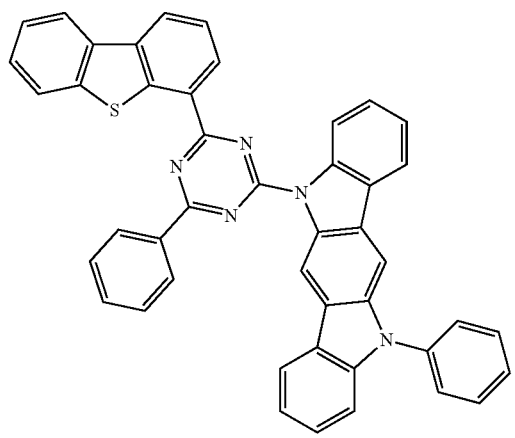
262
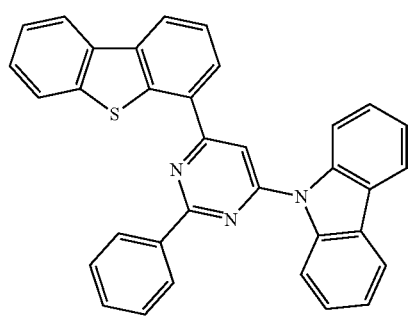

263
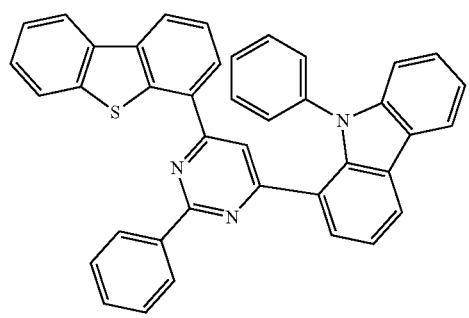
264
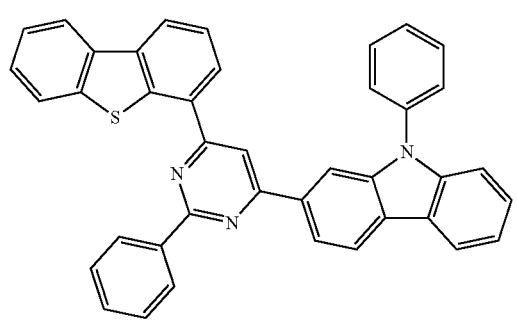
265
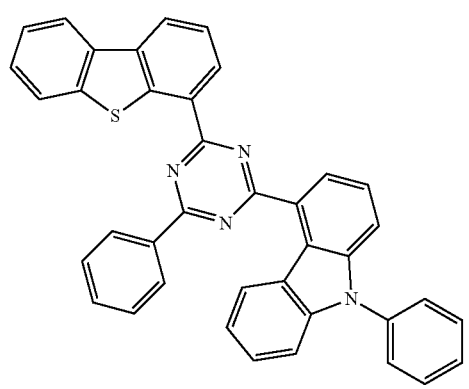
266
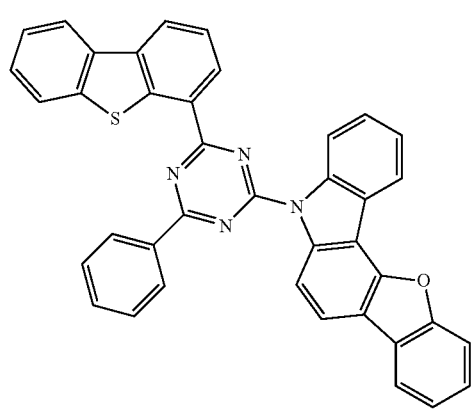
267
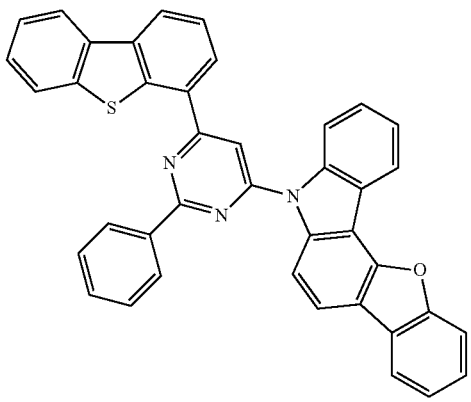
268
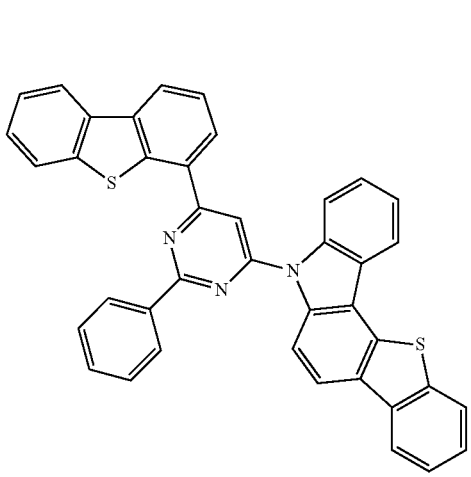
269
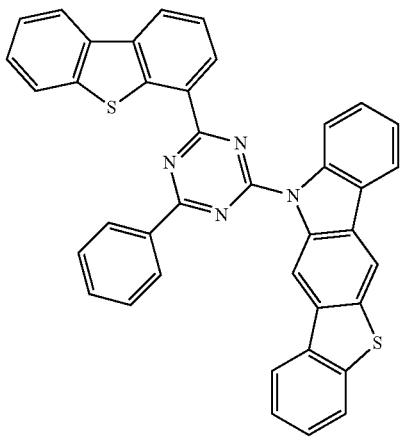

270
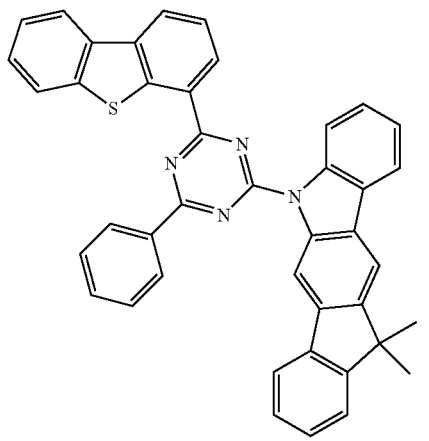
271
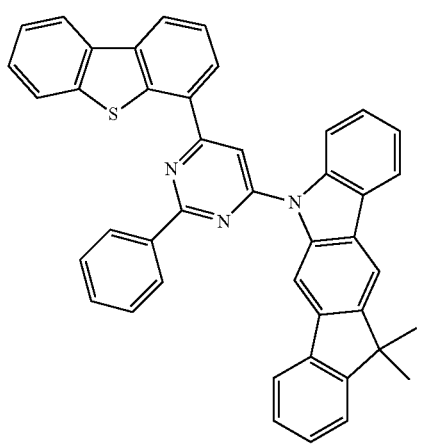
272
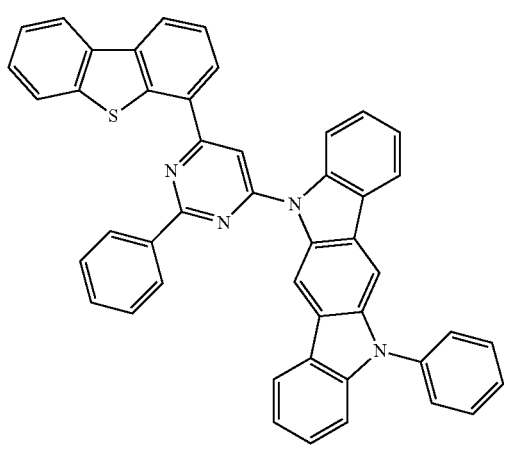
273
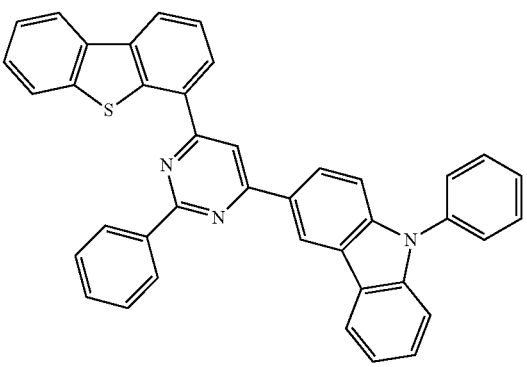
274
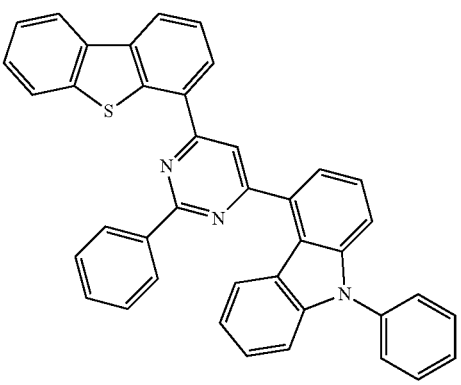
275
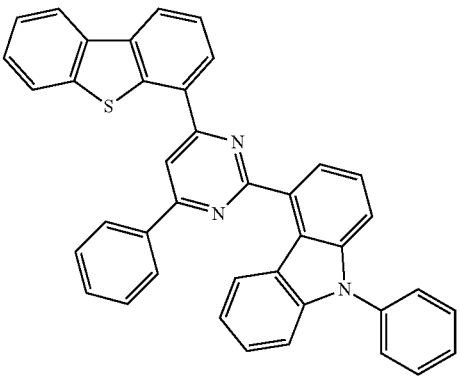
276
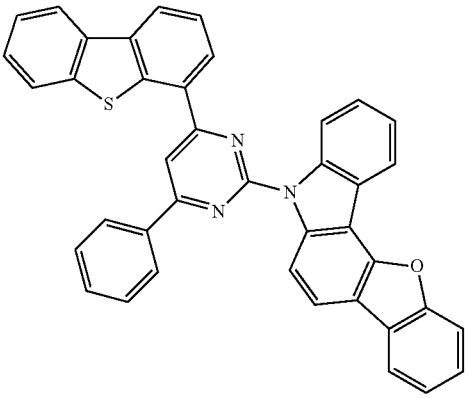

277
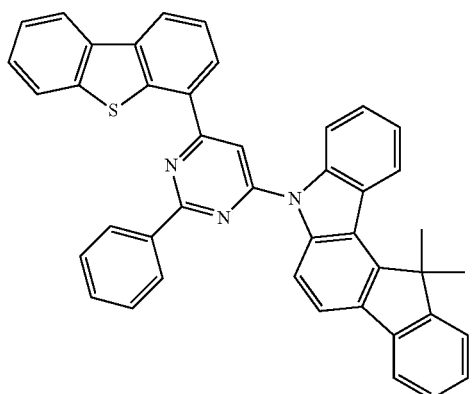
278
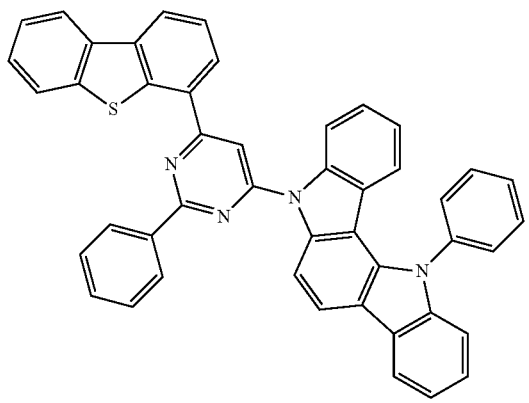
279
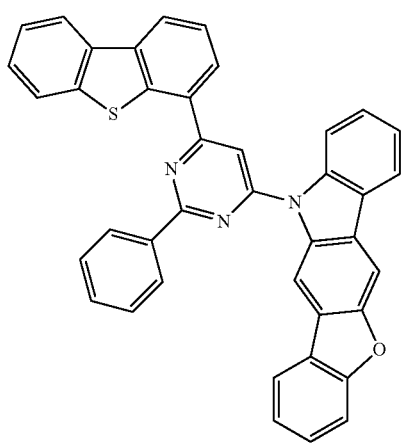
280
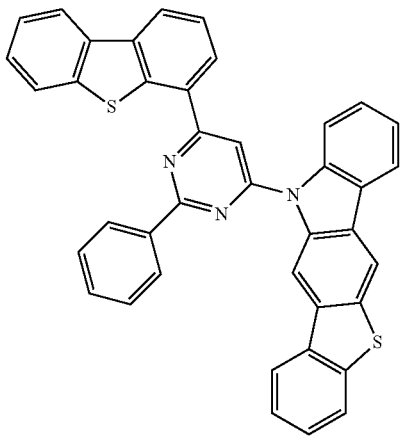
281
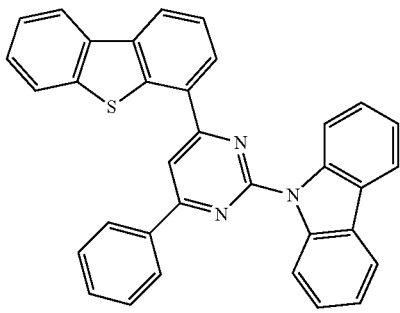
282
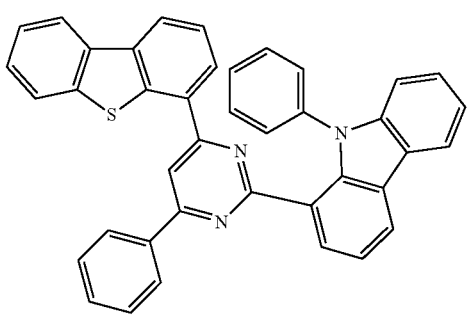
283
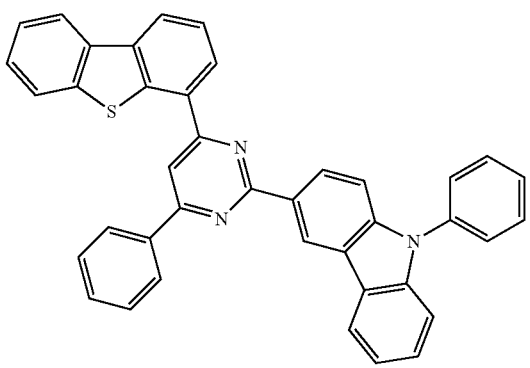

284
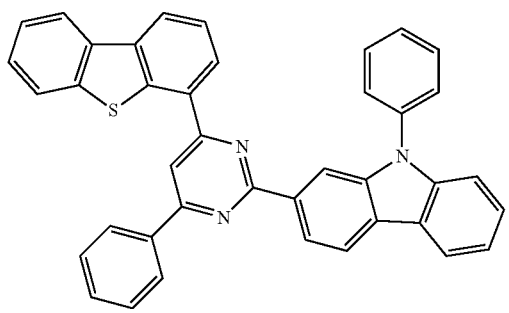
285
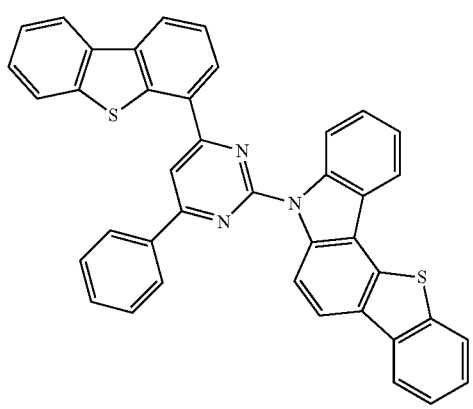
286
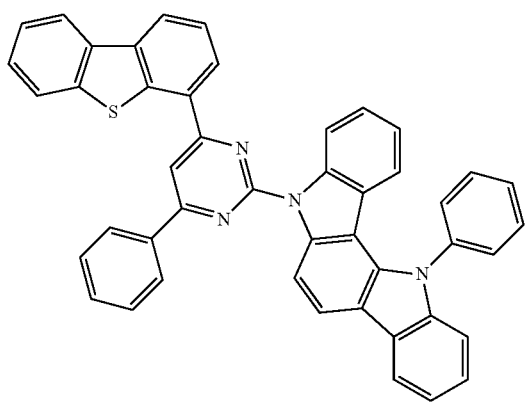
287
288
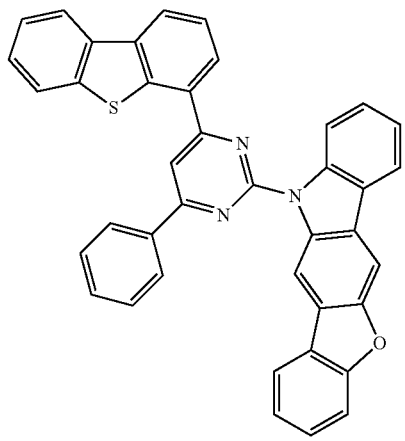
289
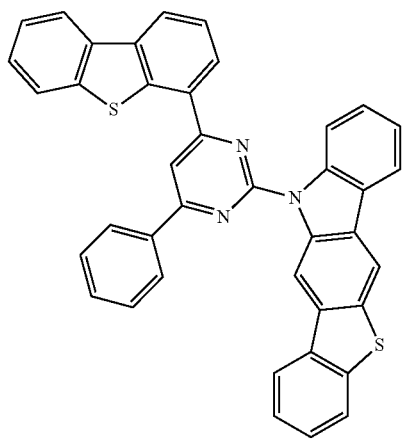
290
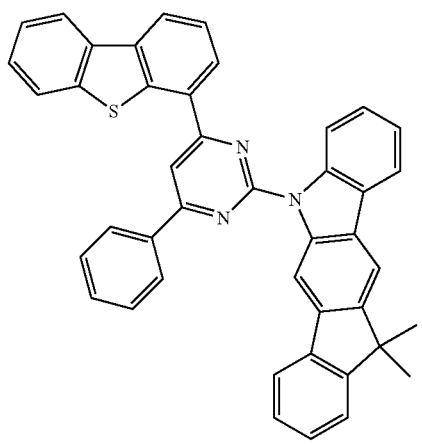

291
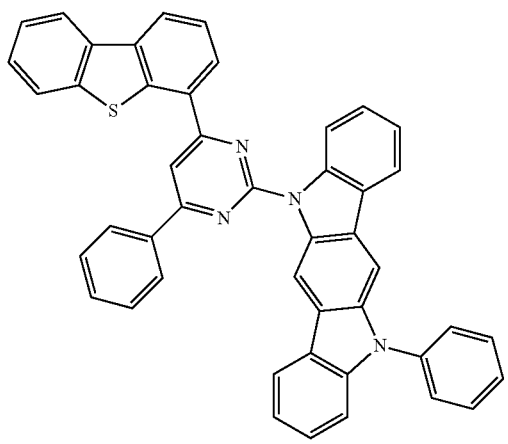
292
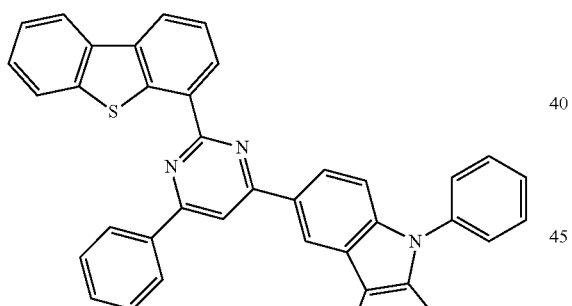
293
294
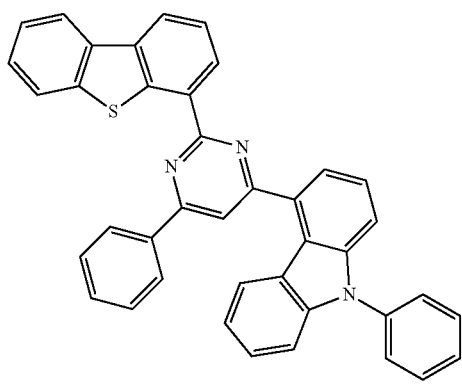
295
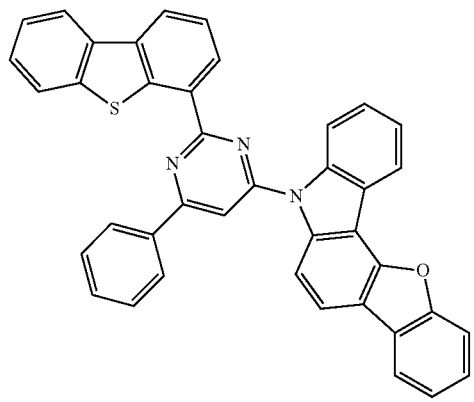
296
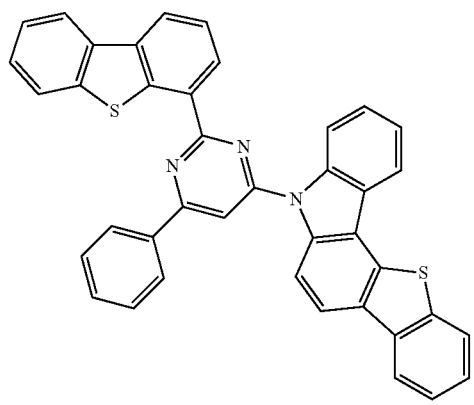
297
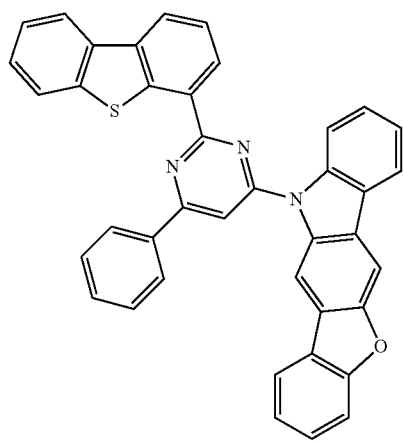

298
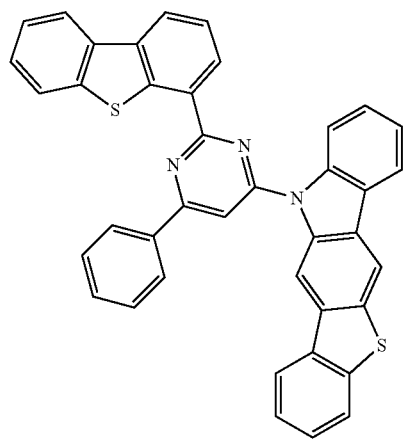
299
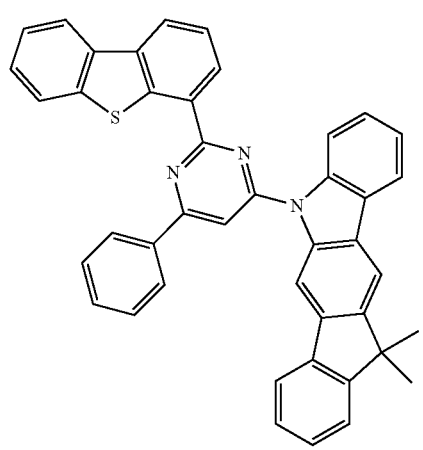
300
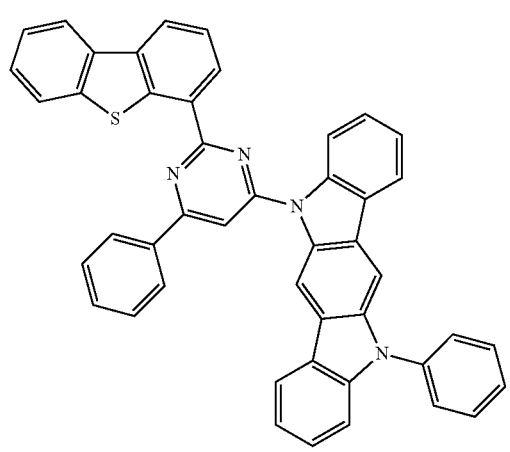
301
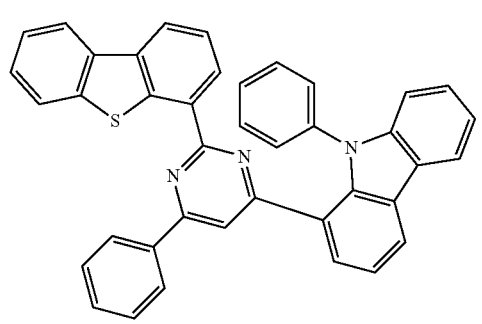
302
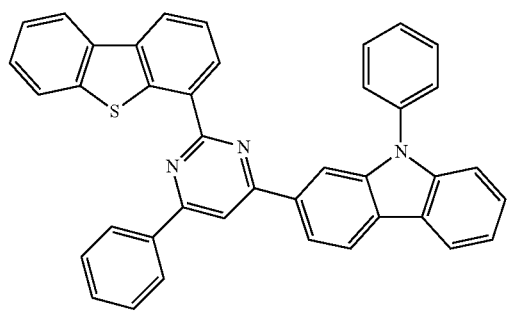
303
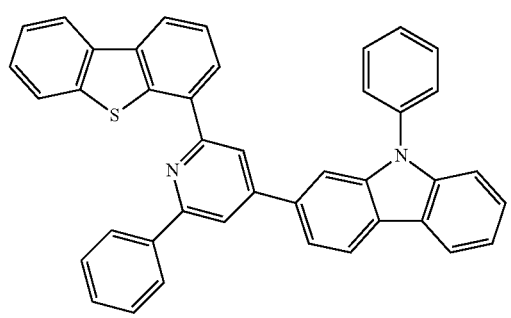
304
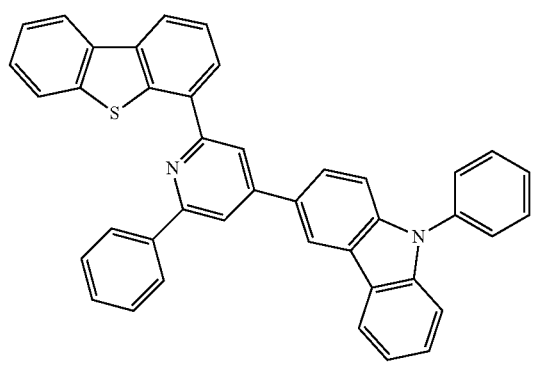
305
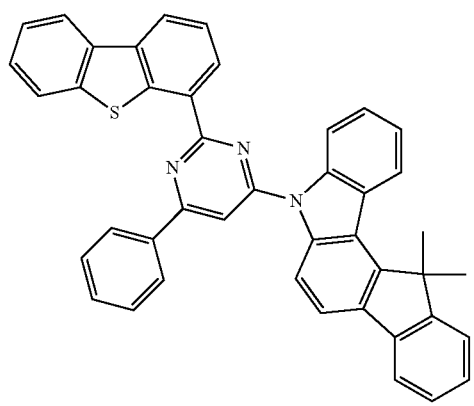

306
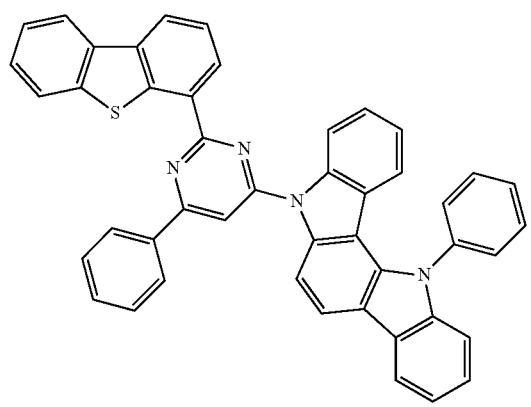
307
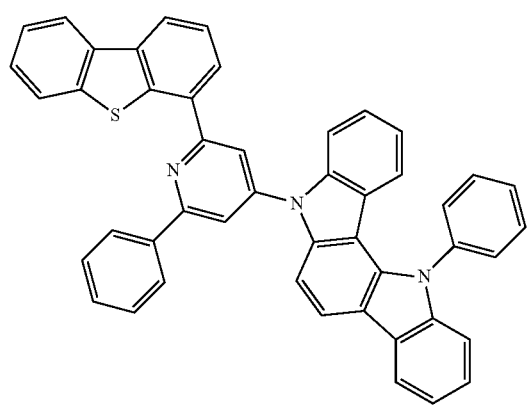
308
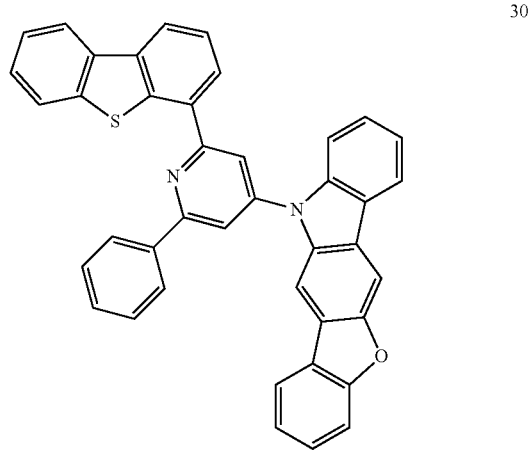
309
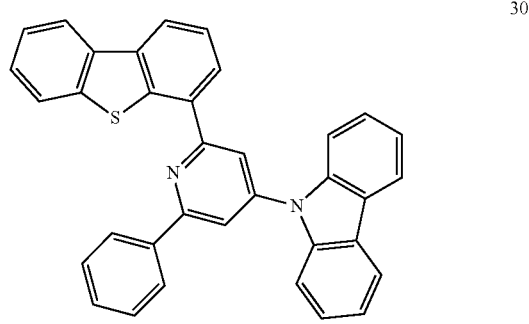
310
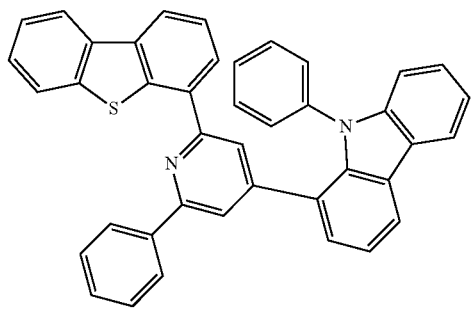
311
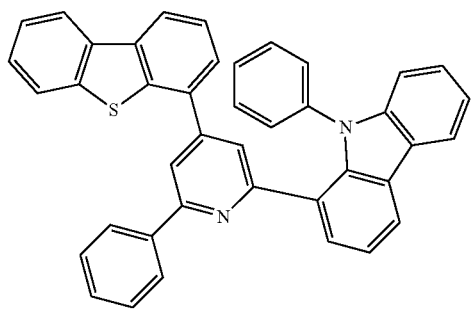
312
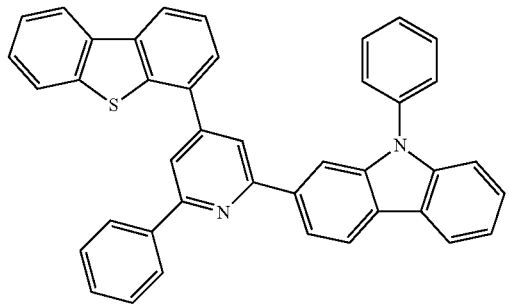
313
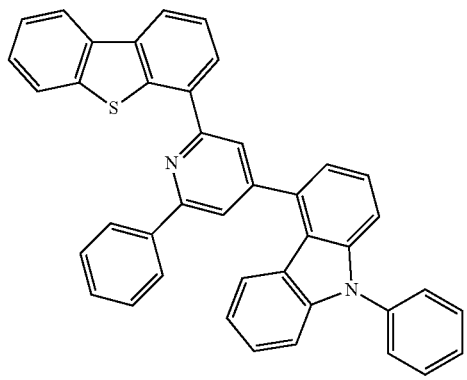

314
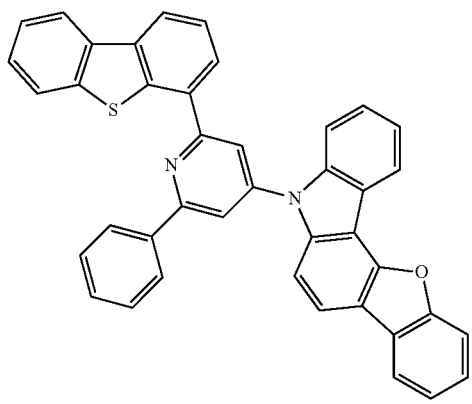
315
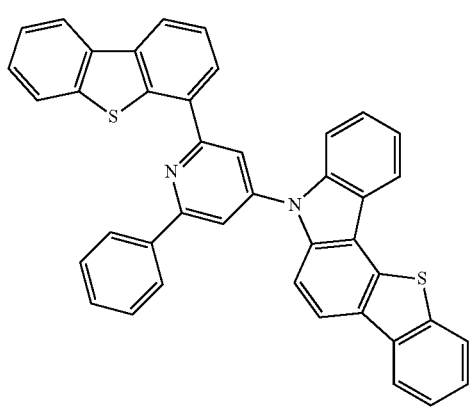
316
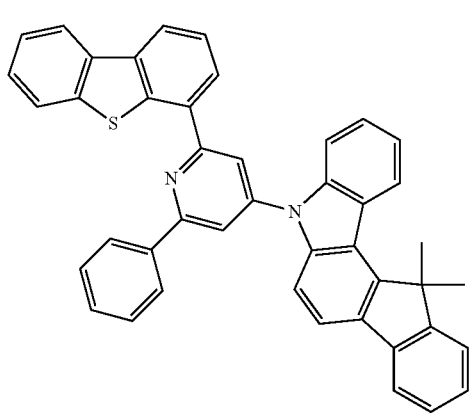
317
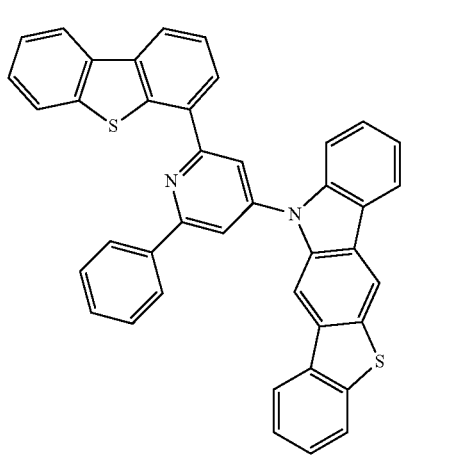
318
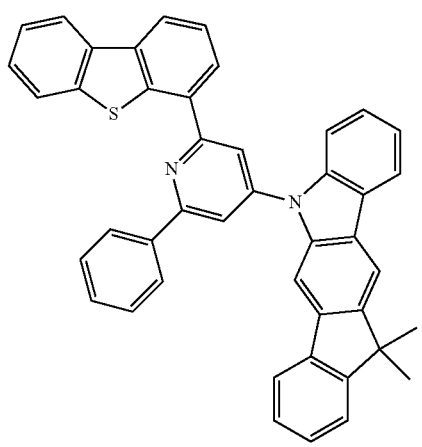
319
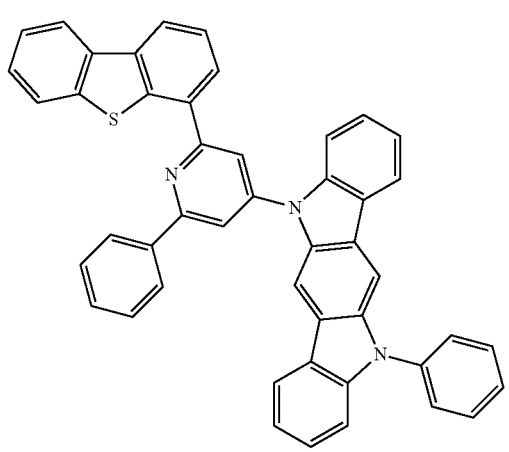
320
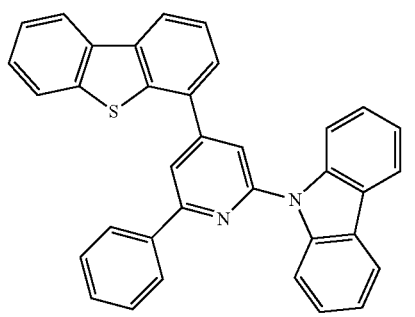
321
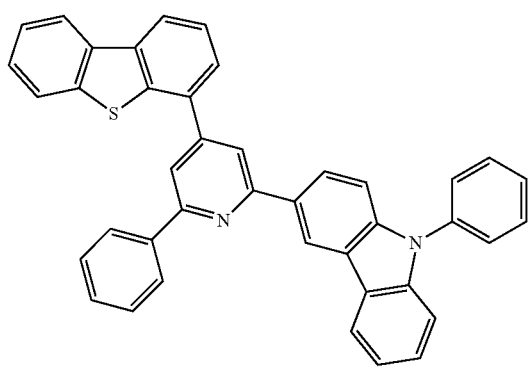

322
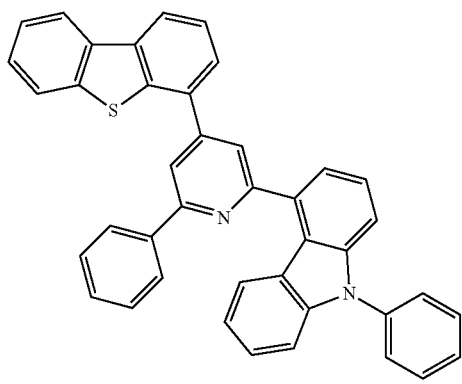
326
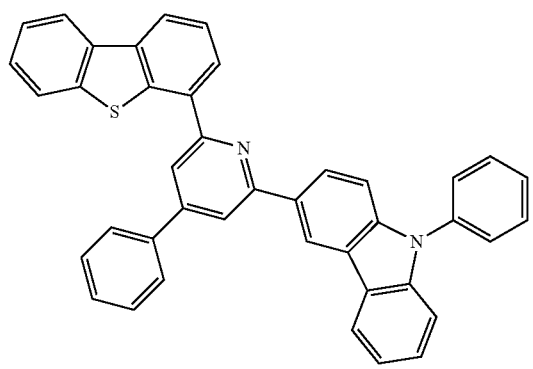
323
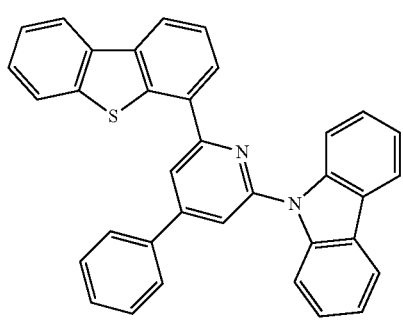
327
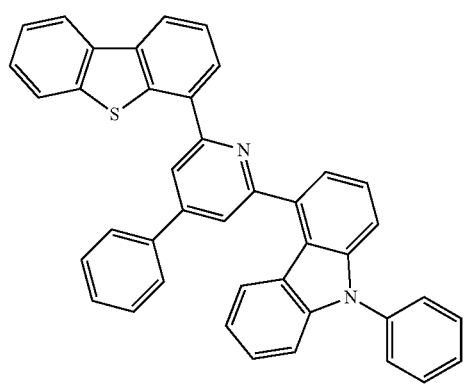
324
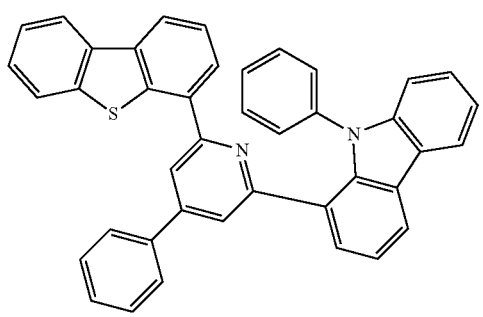
328
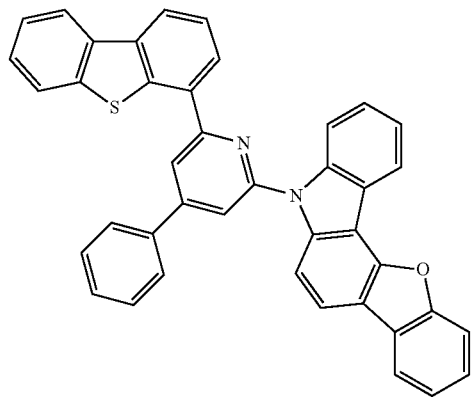
325
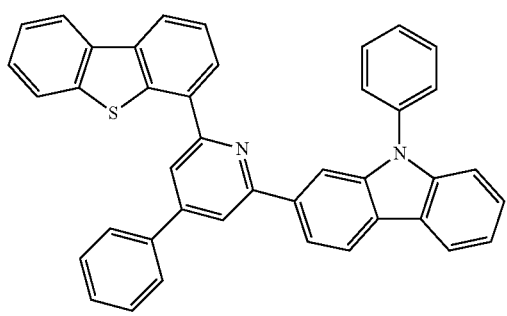
329
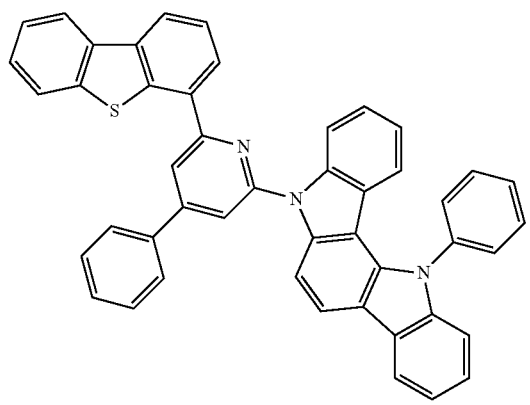

330
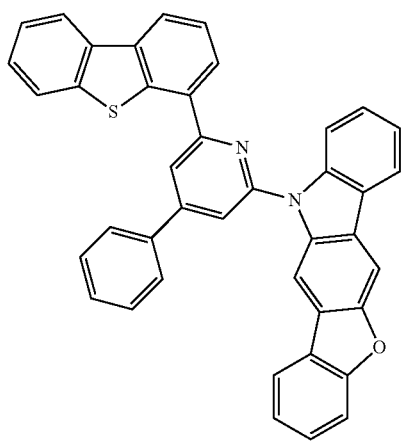
331
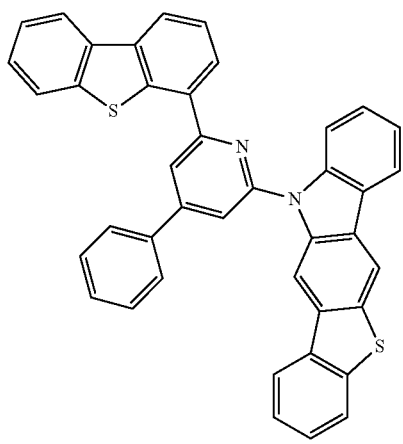
332
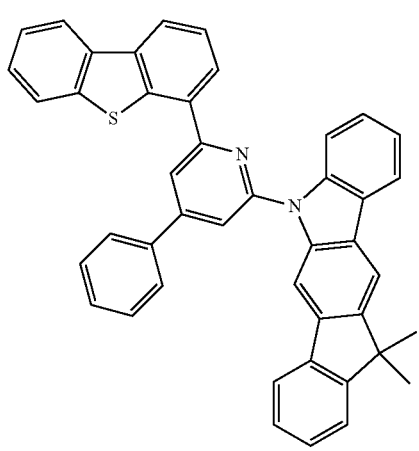
333
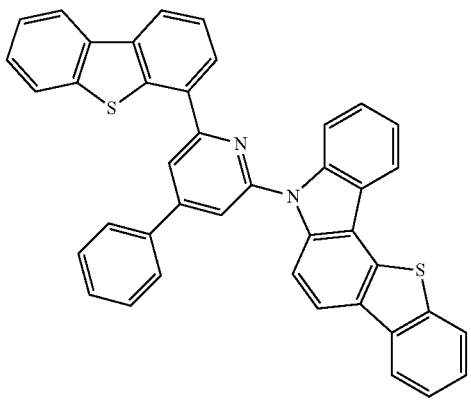
334
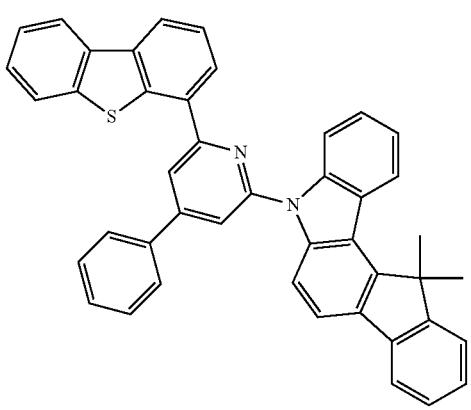
335
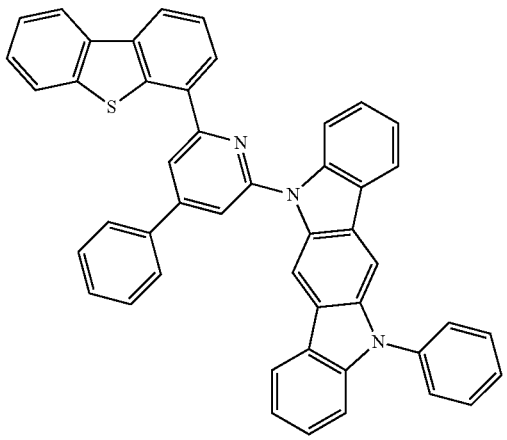
336
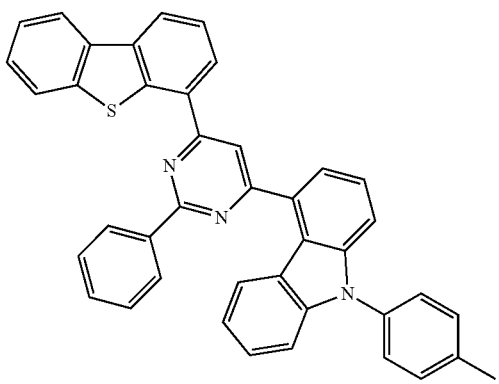

125
-continued
337
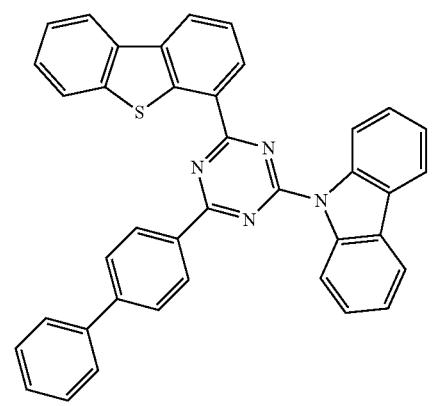
338
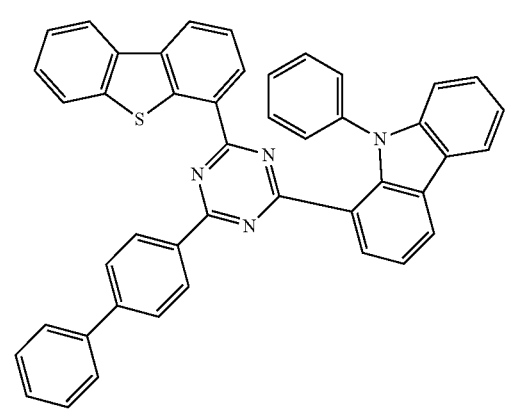
339
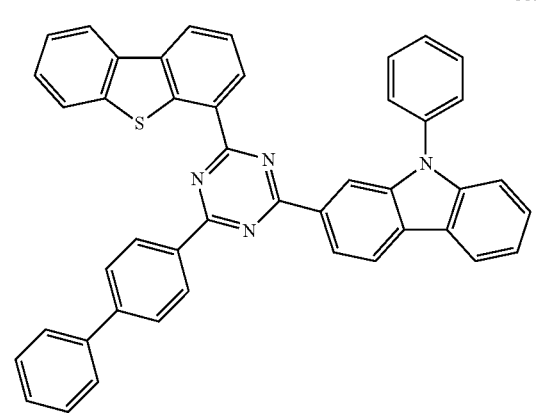
340
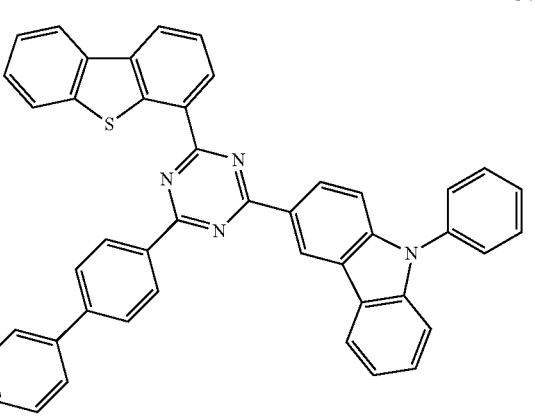
126
-continued
341
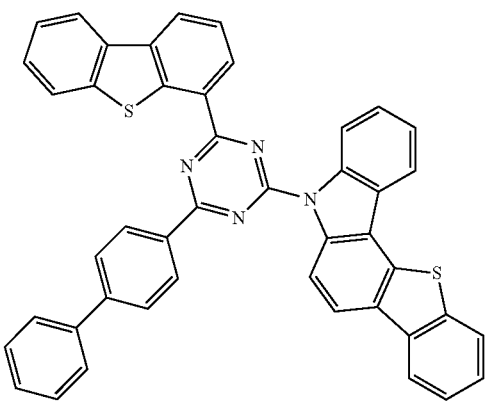
342
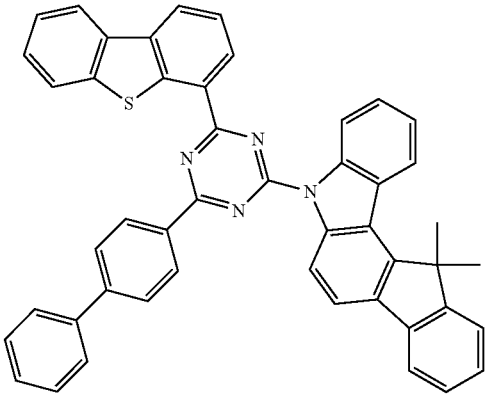
343
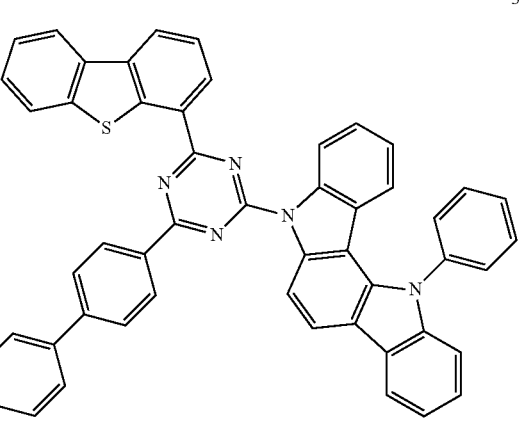
344
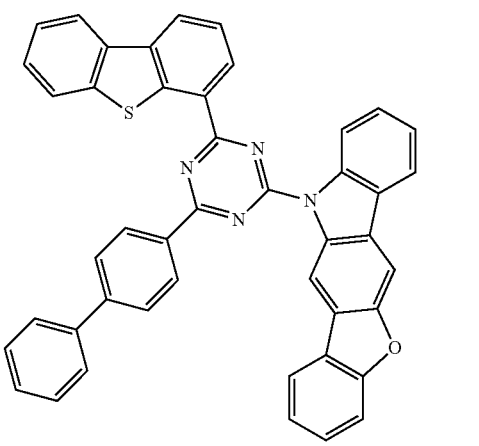

345
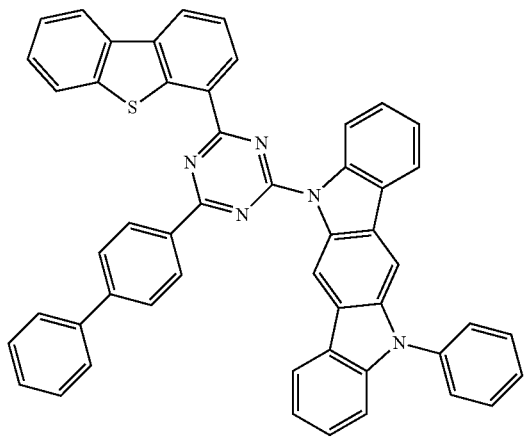
346
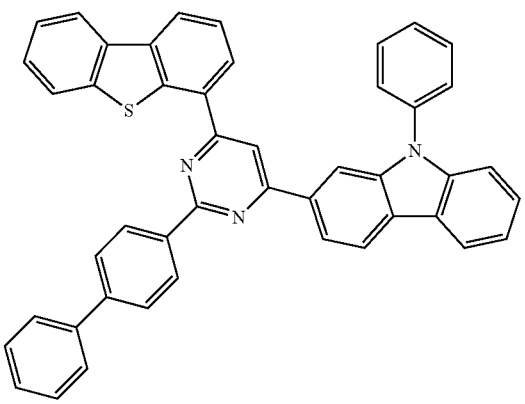
347
348
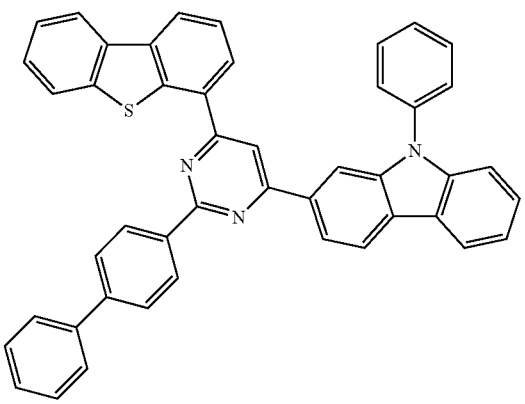
349
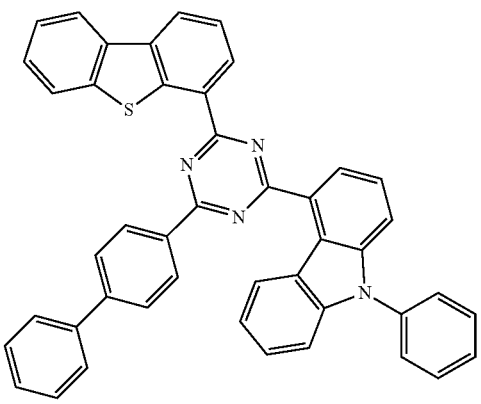
350
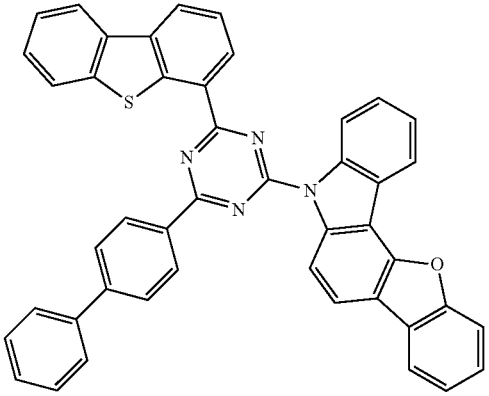
351
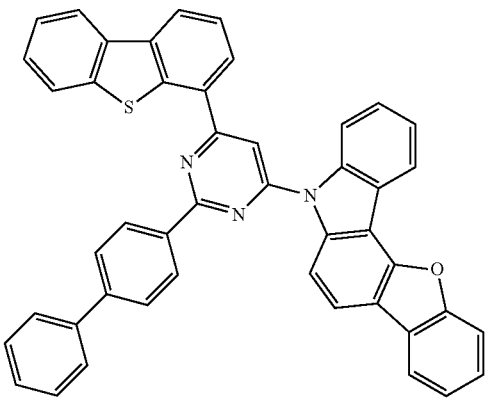

-continued
352
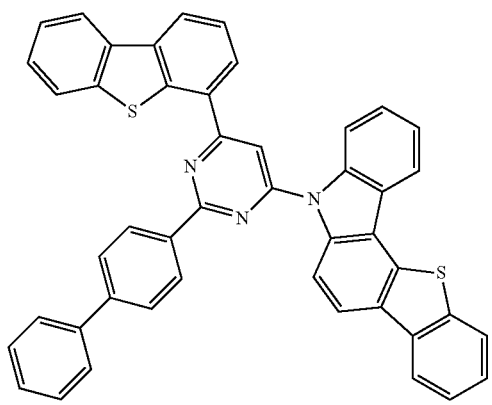
353
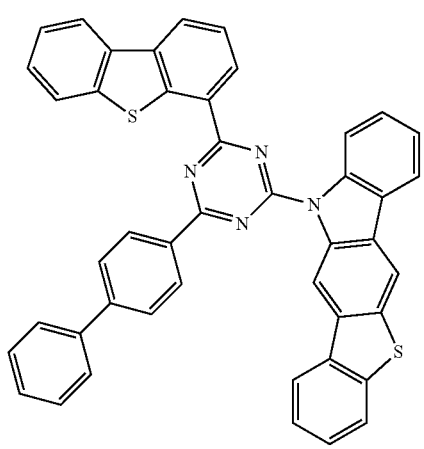
354
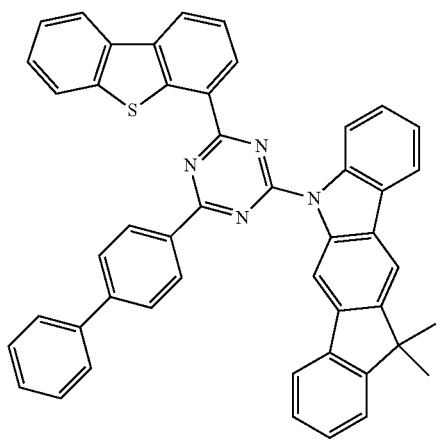
-continued
355
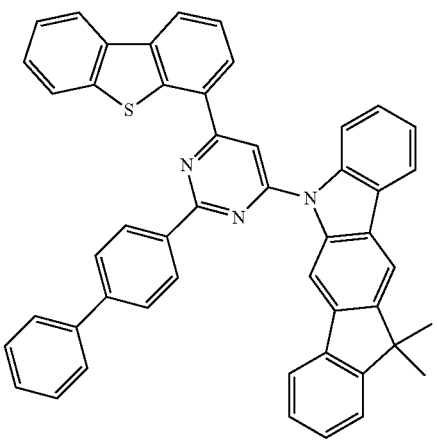
356
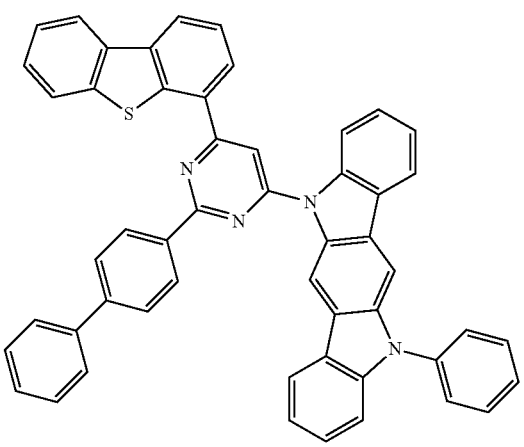
357
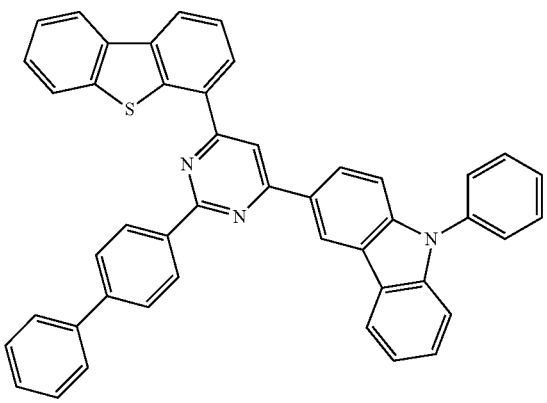

358
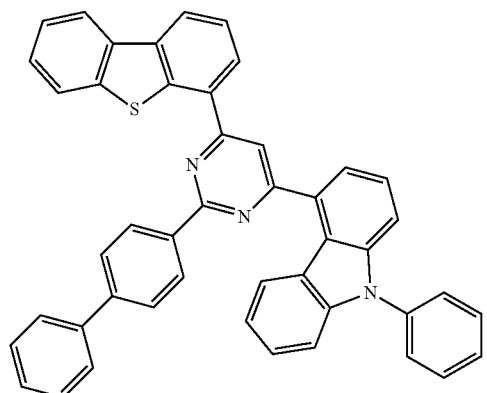
359
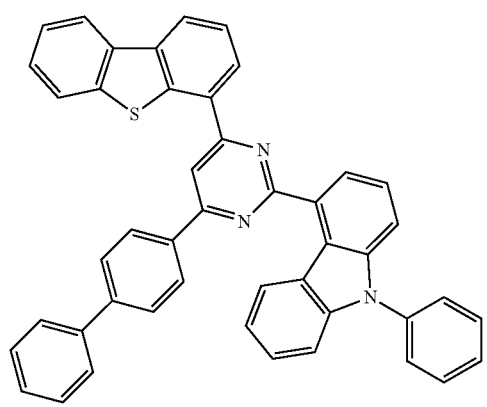
360
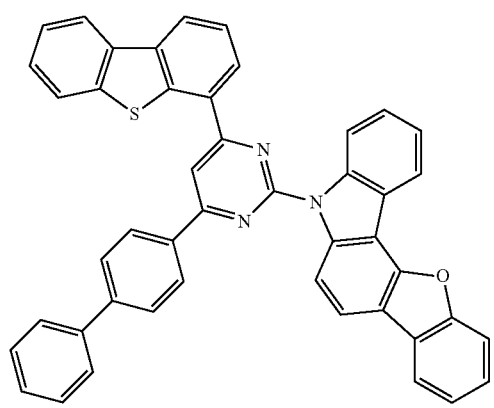
361
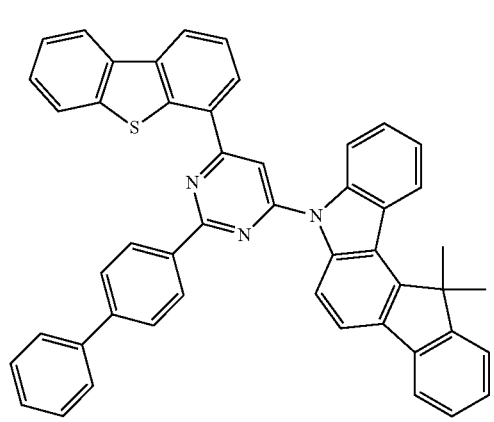
362
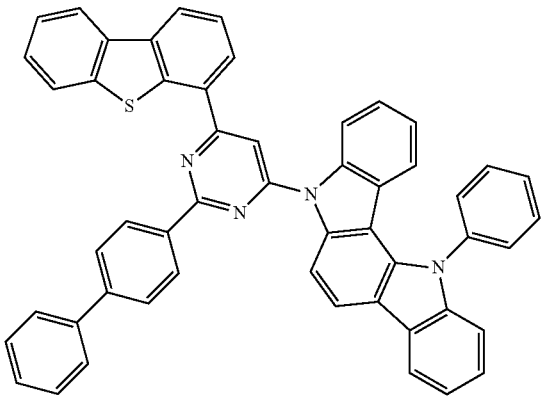
363
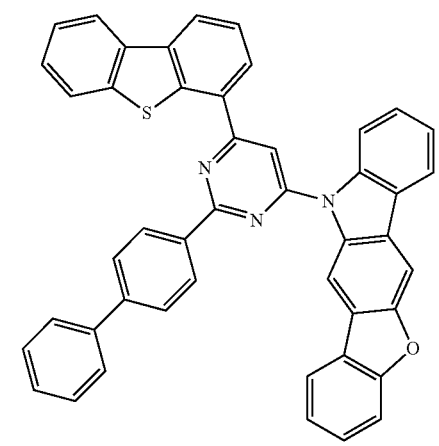
364
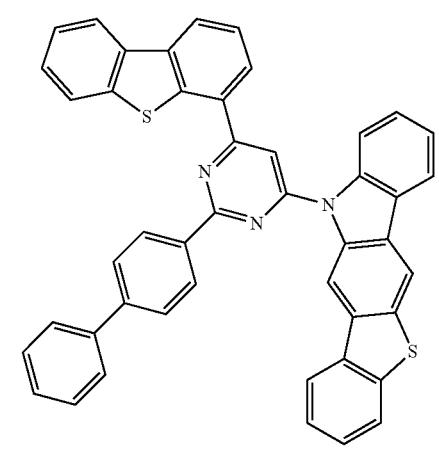

365
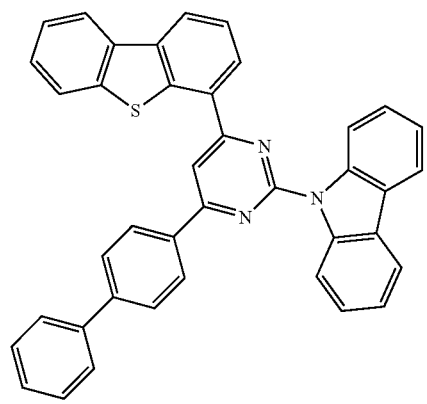
366
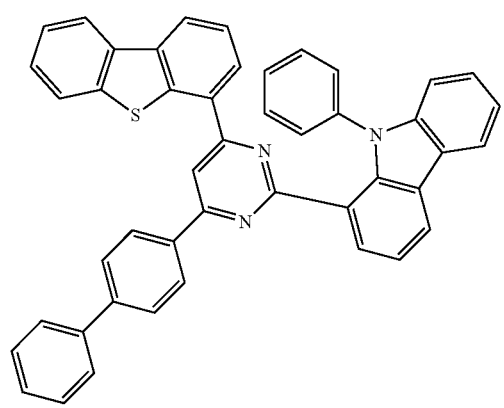
367
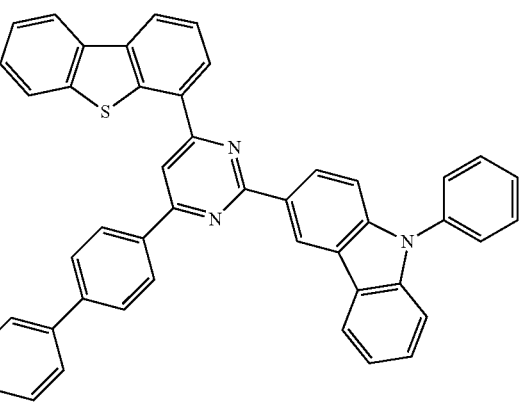
368
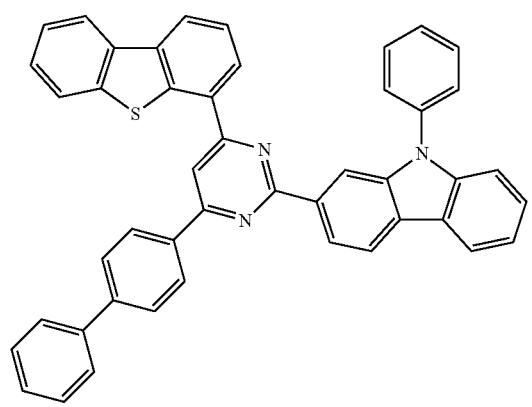
369
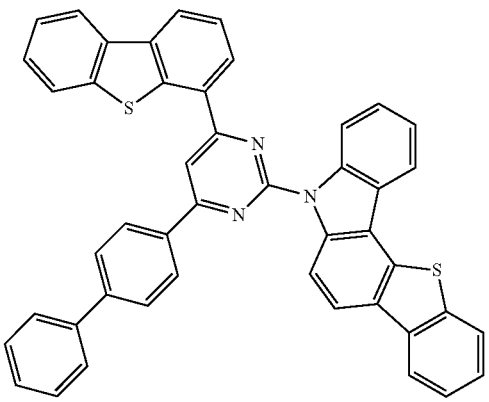
370
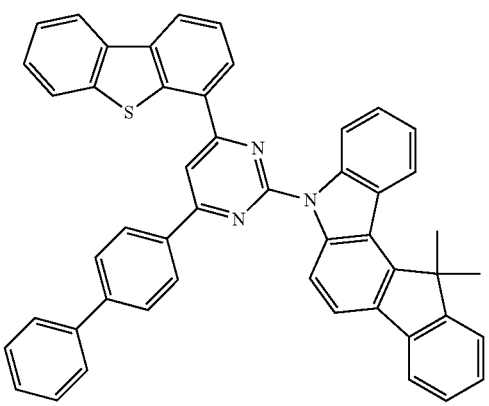
371
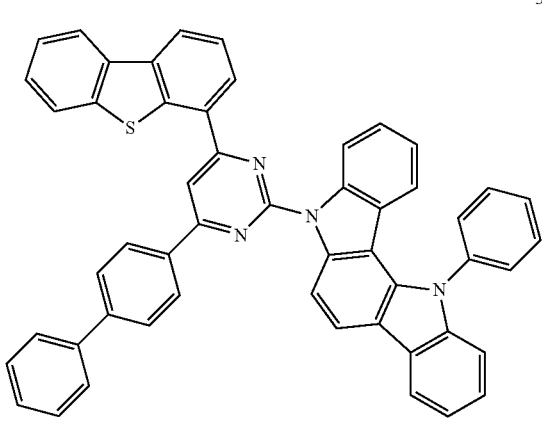
372
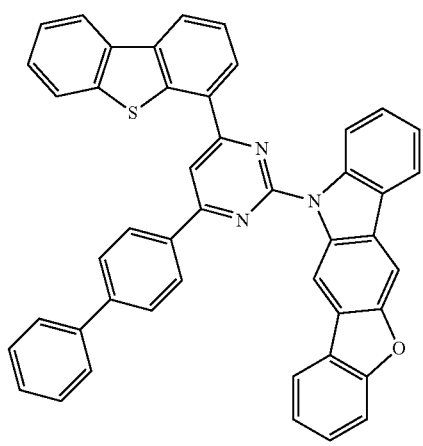

373
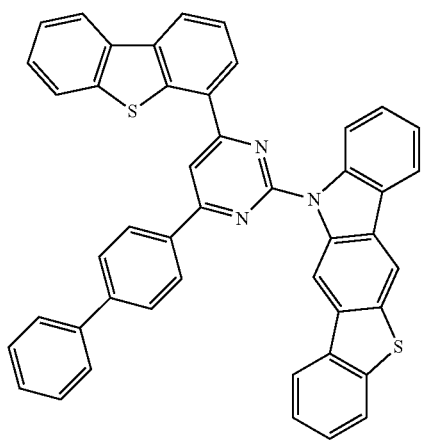
374
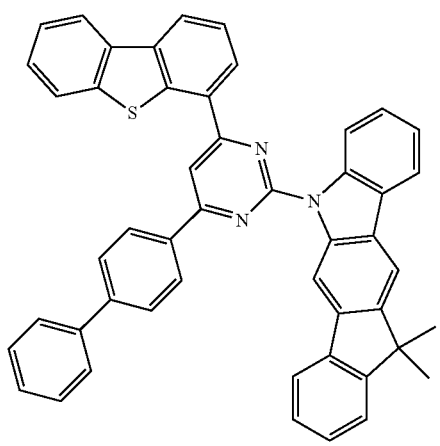
375
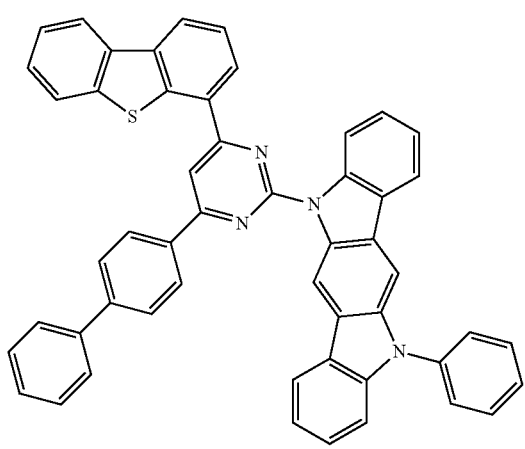
376
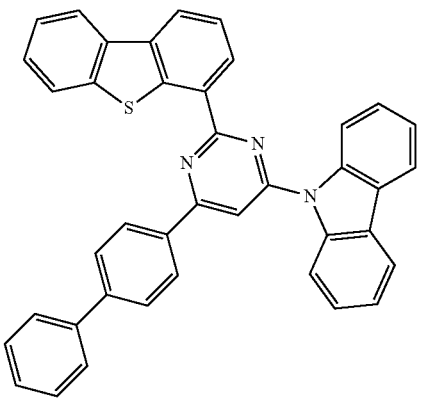
377
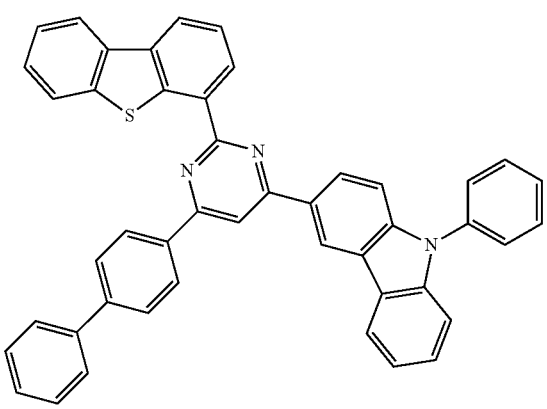
378
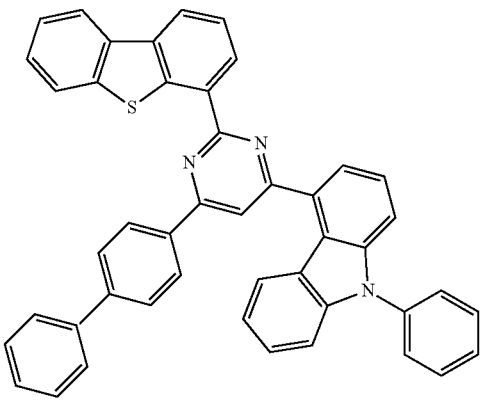
379
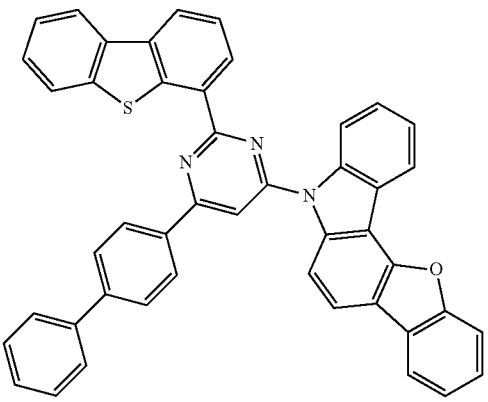

380
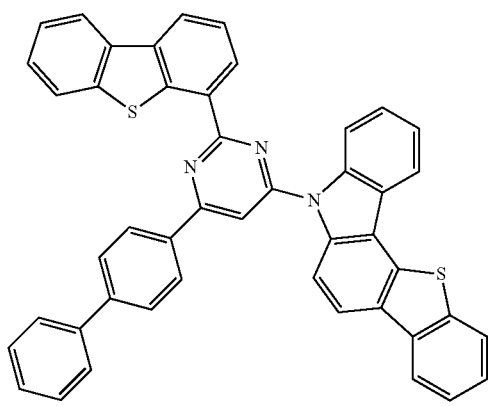
381
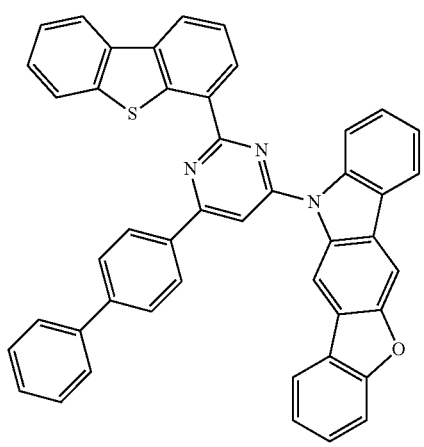
382
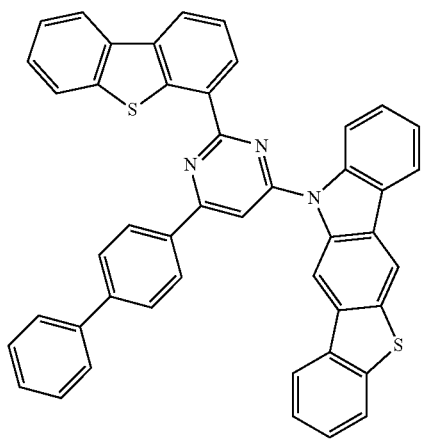
383
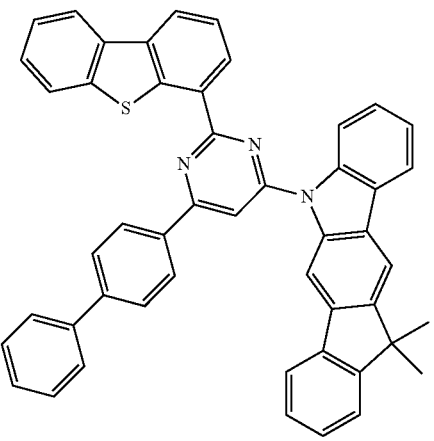
384
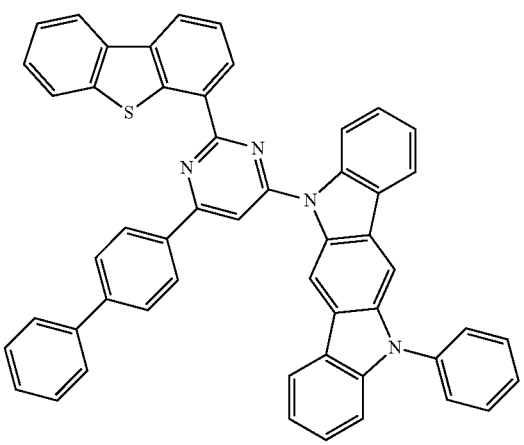
385
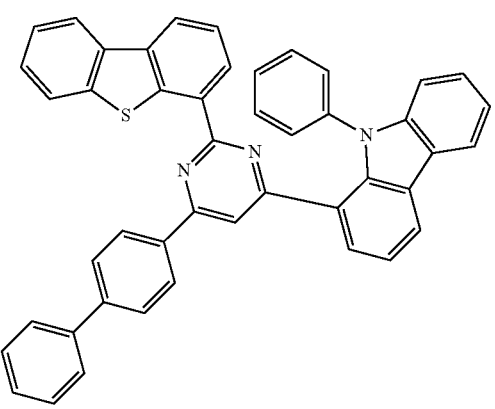

386
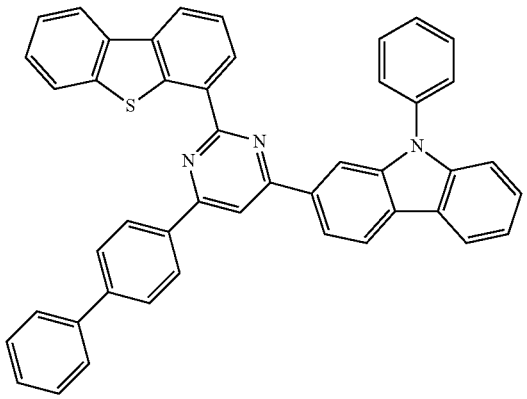
387
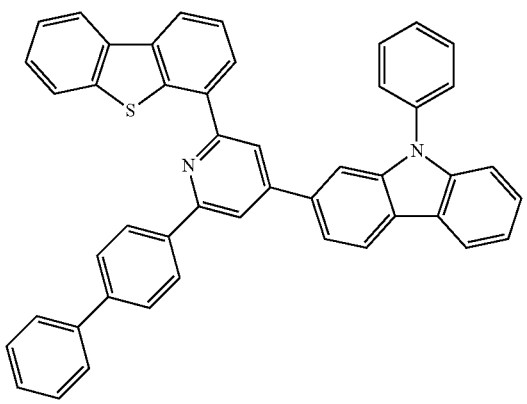
388
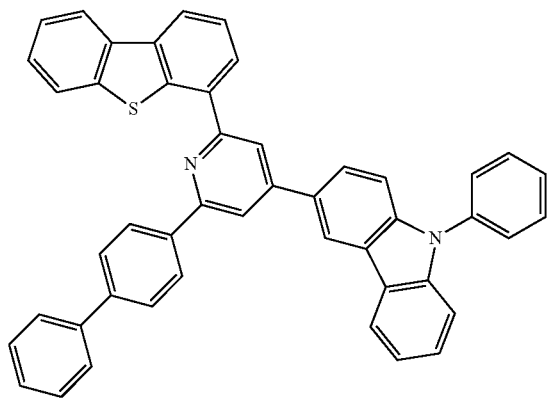
389
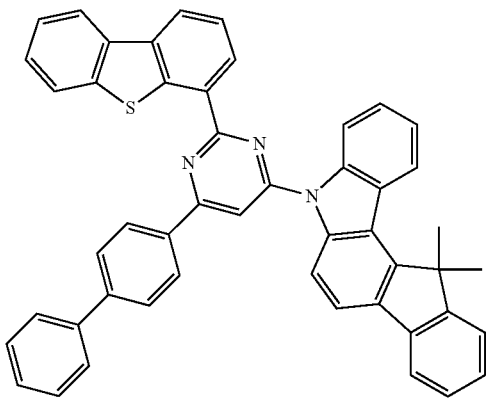
390
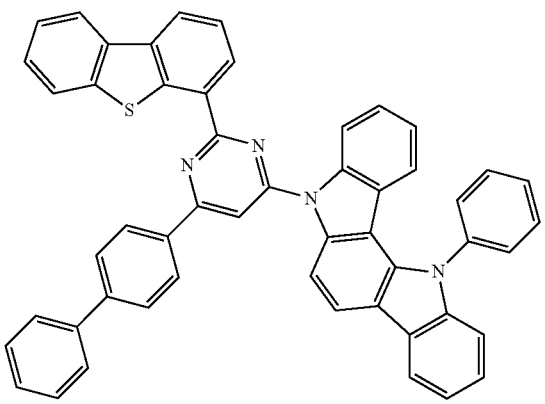
391
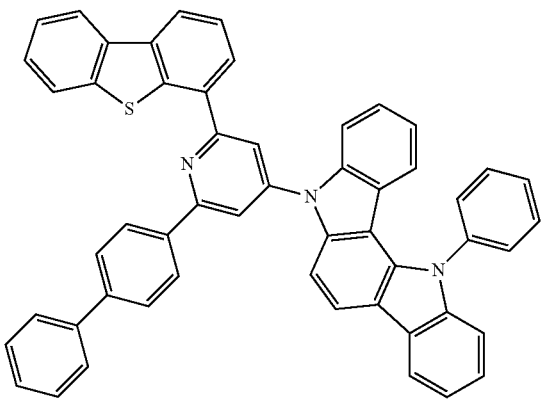
392
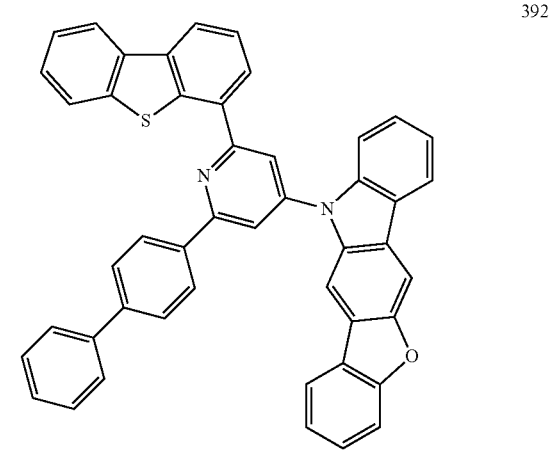

393
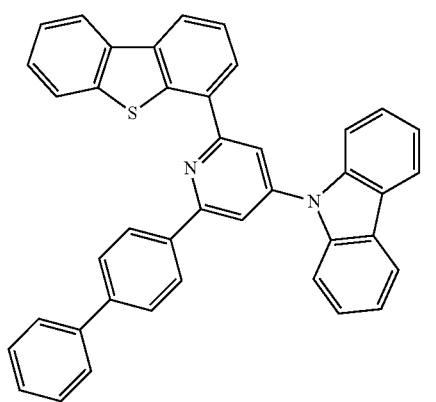
394
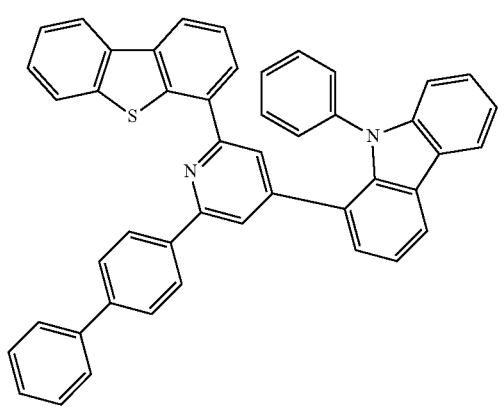
395
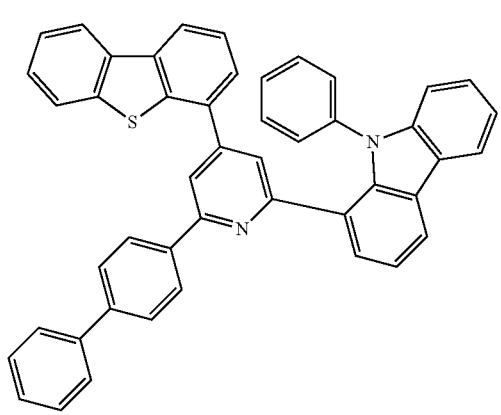
396
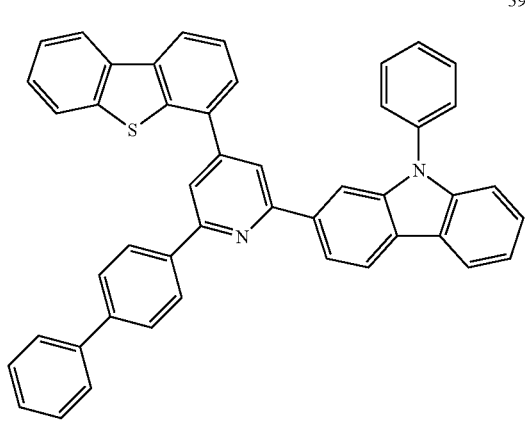
397
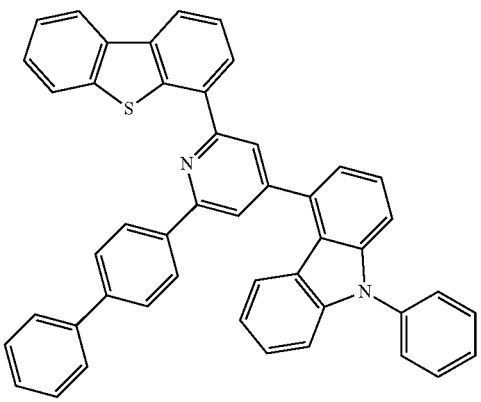
398
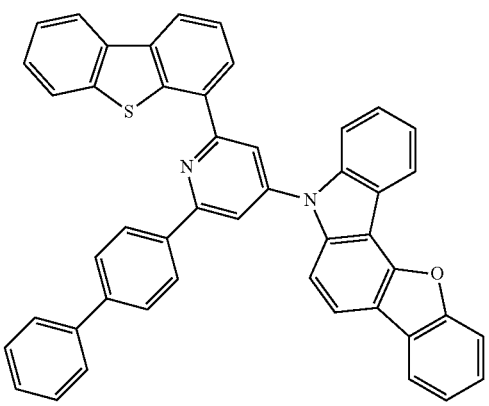
399
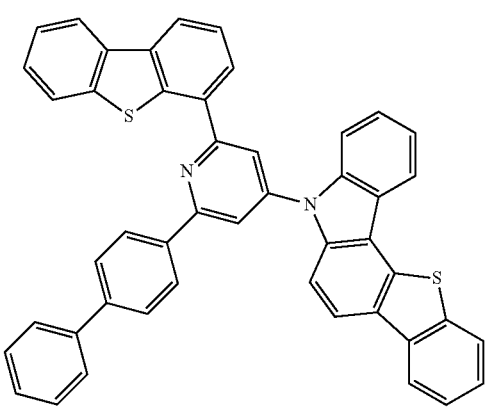
400
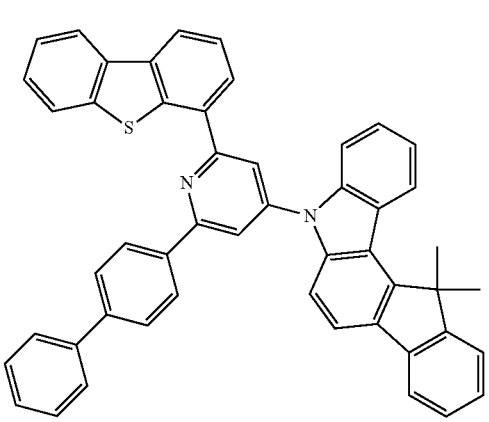

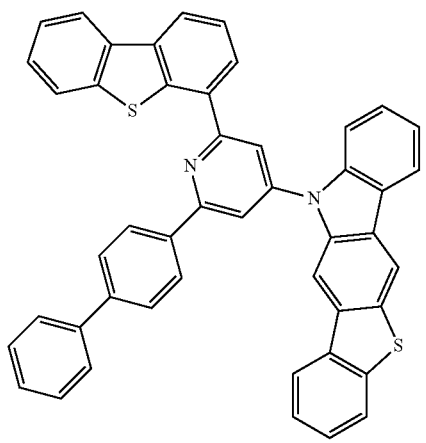
401
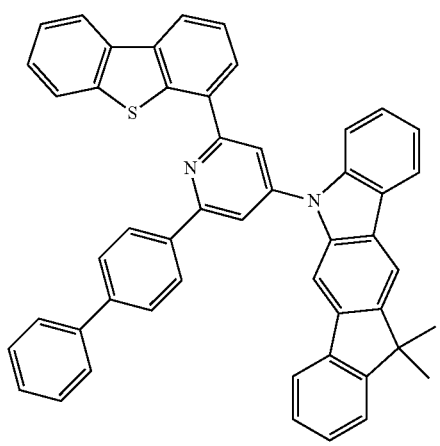
402
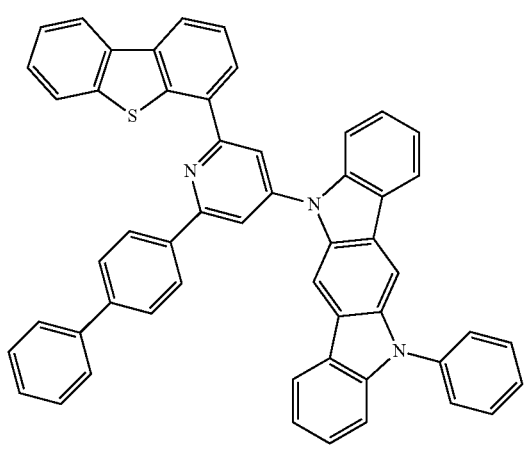
403
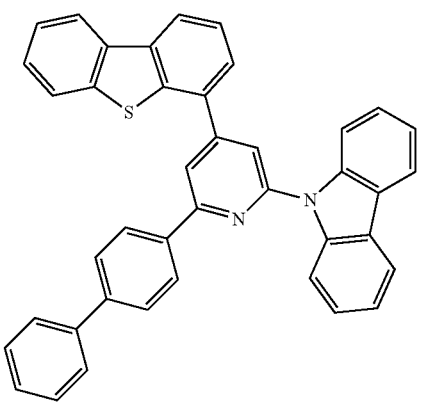
404
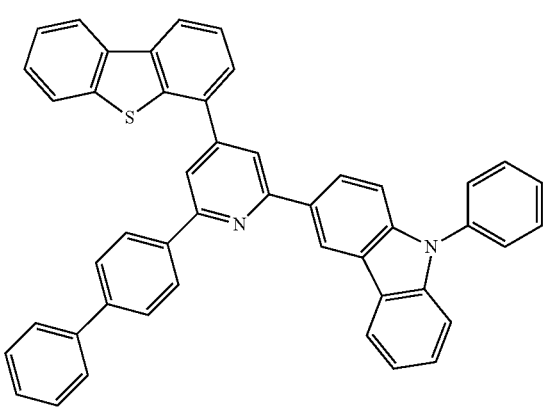
405
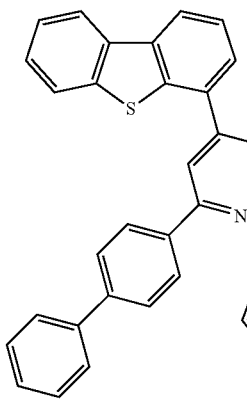
406
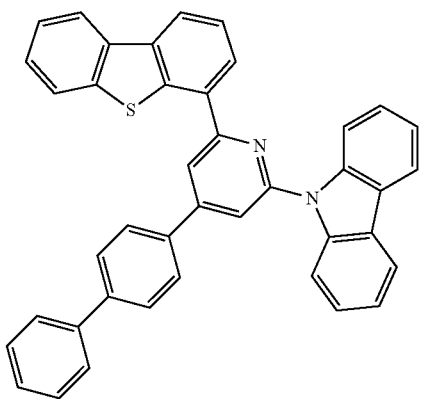
407

408
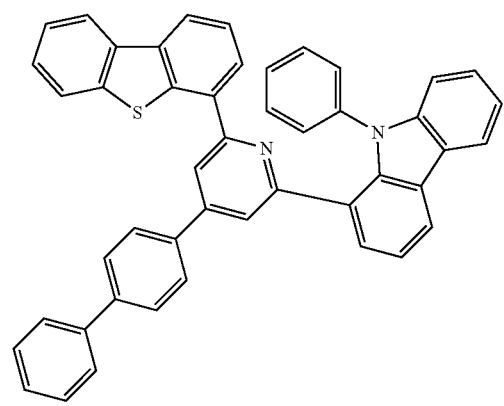
409
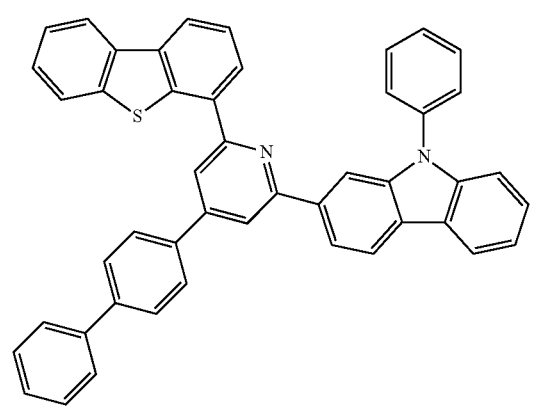
410
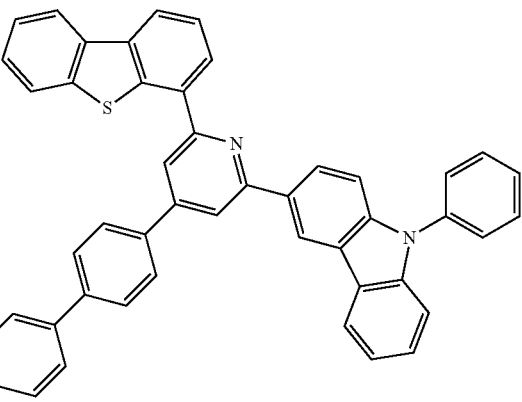
411
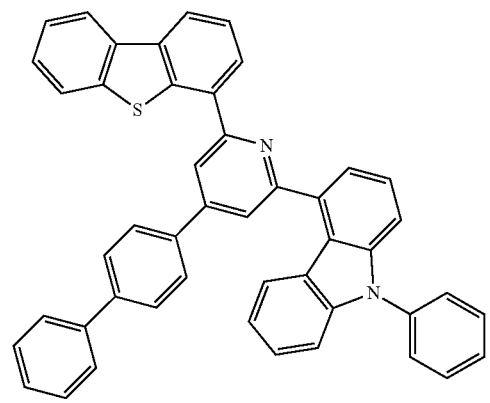
412
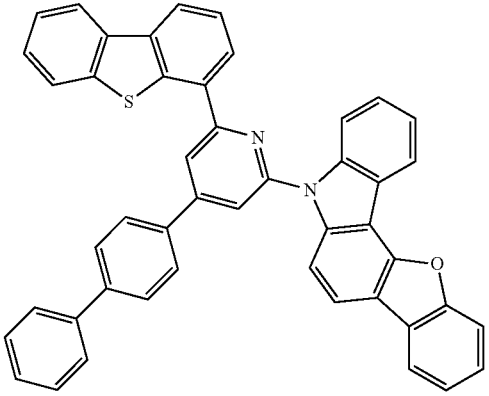
413
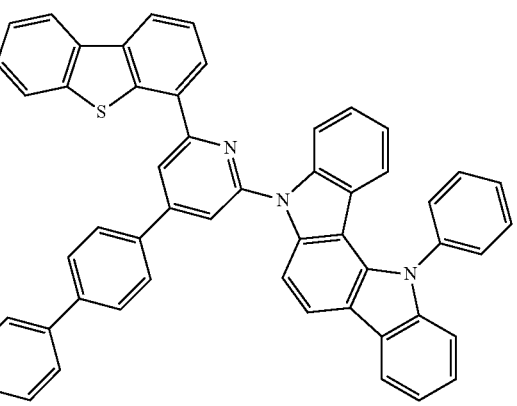
414
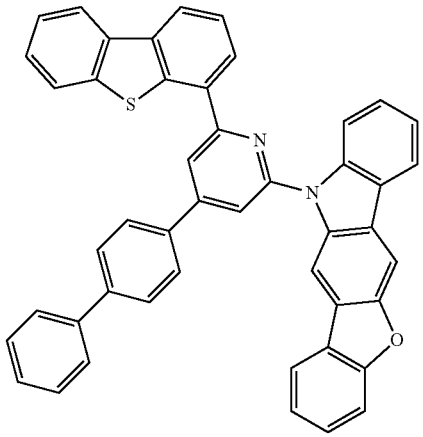

147
-continued
415
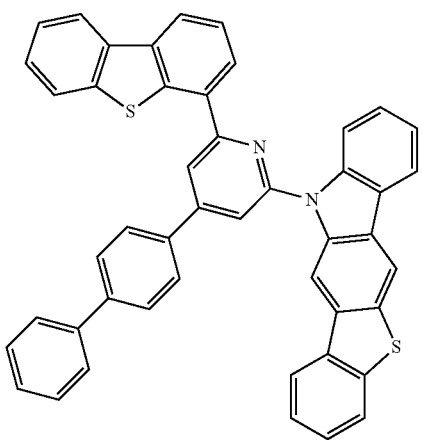
416
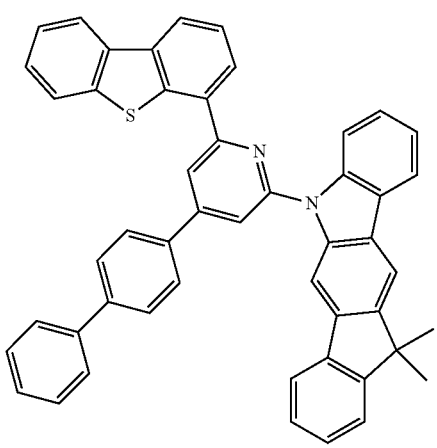
417
148
-continued
418
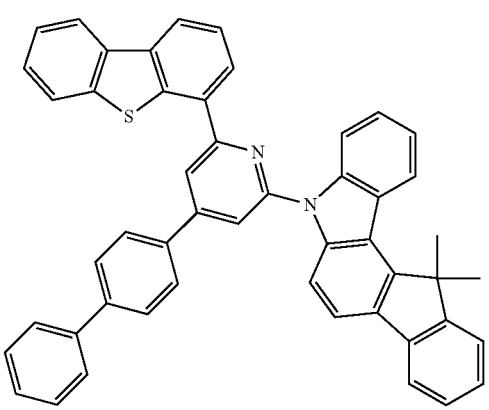
419
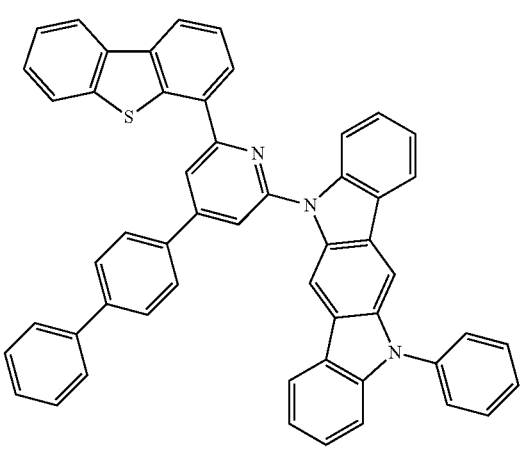
420
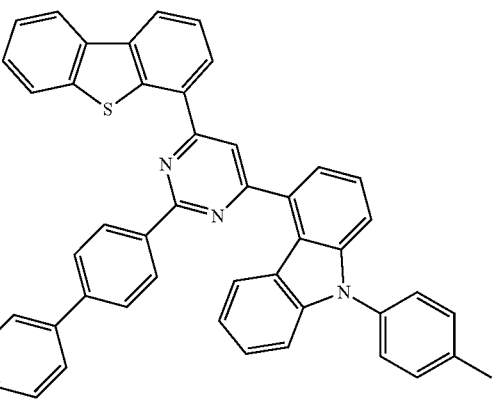
421
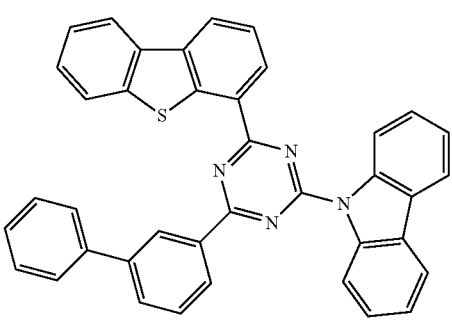

422
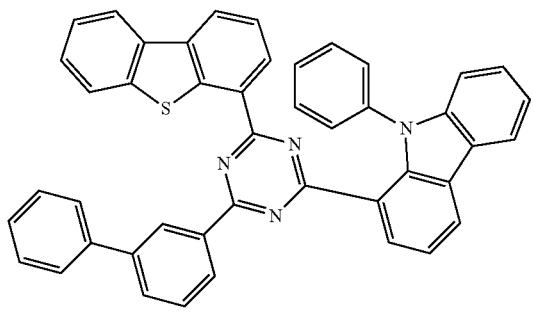
423
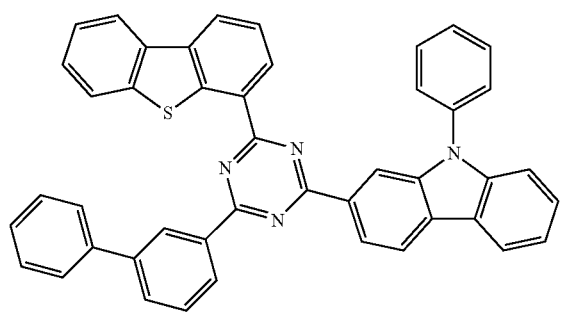
424
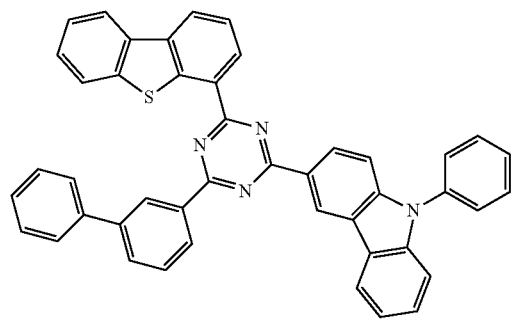
425
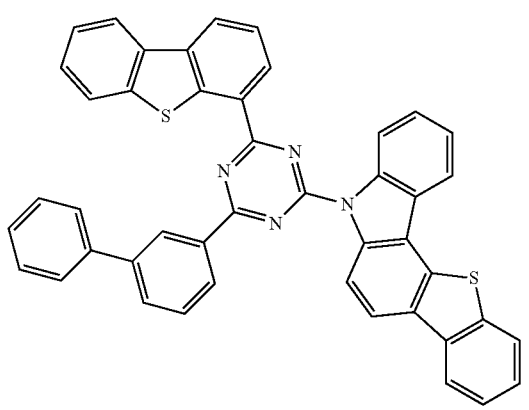
426
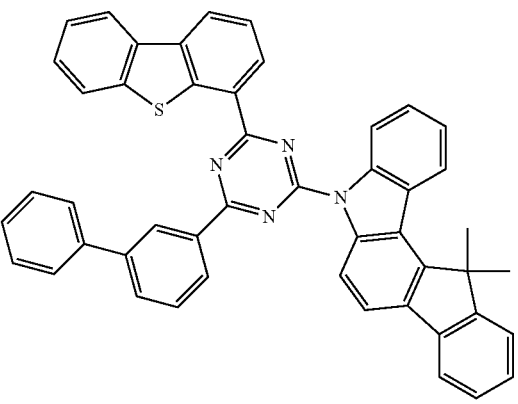
427
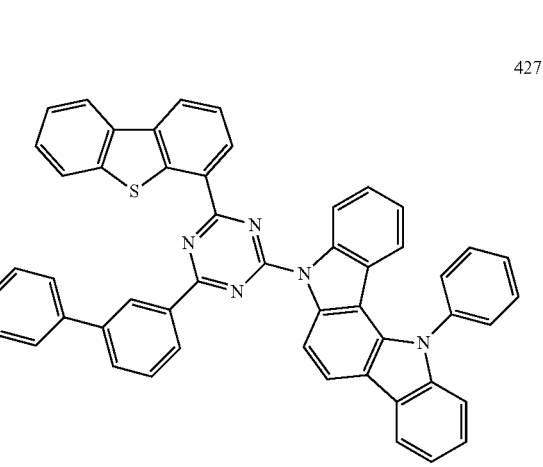
428
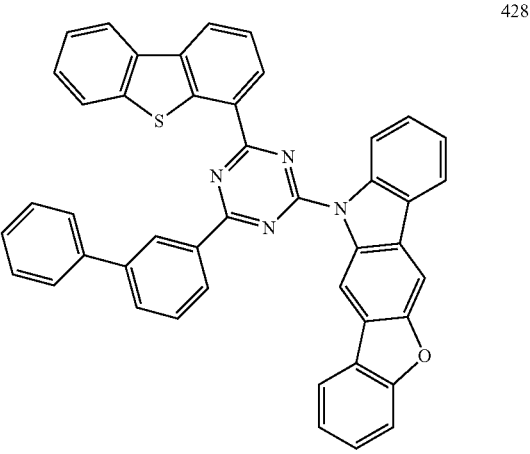

429
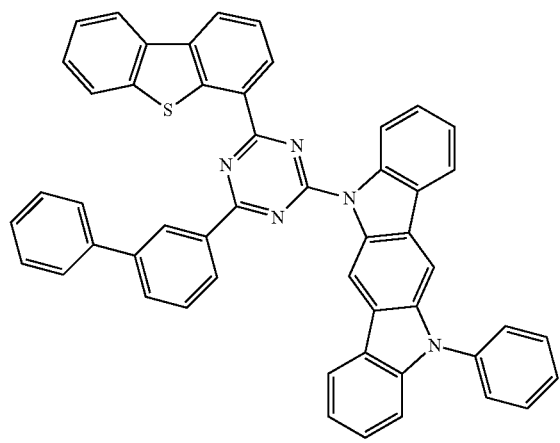
430
431
432
433
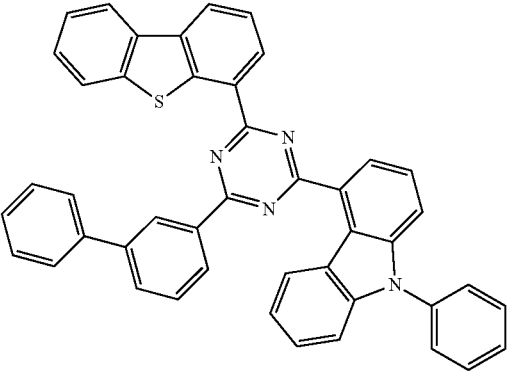
434
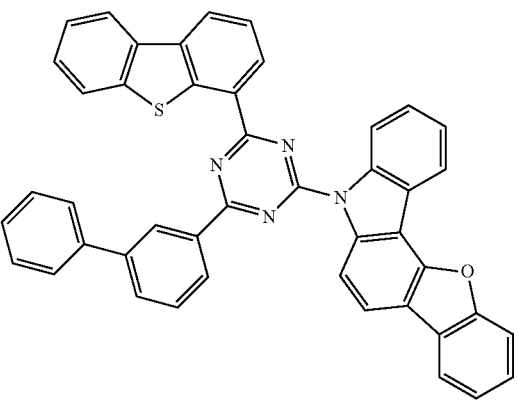
435
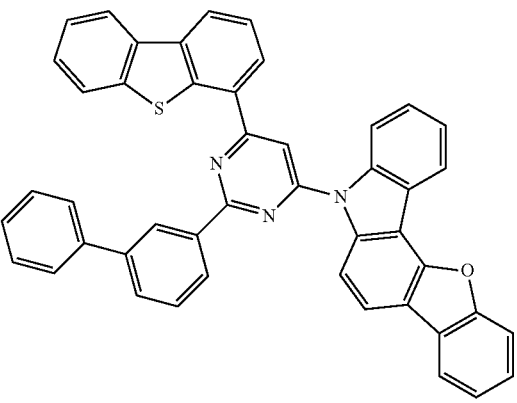
436
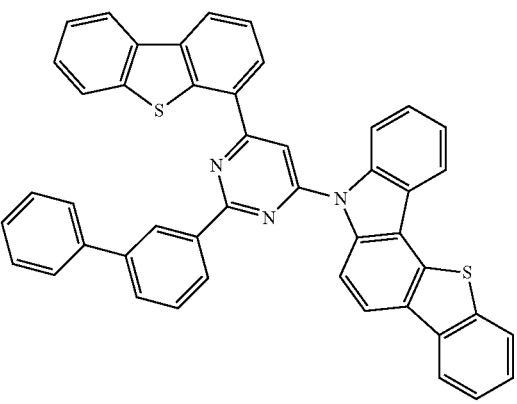

437
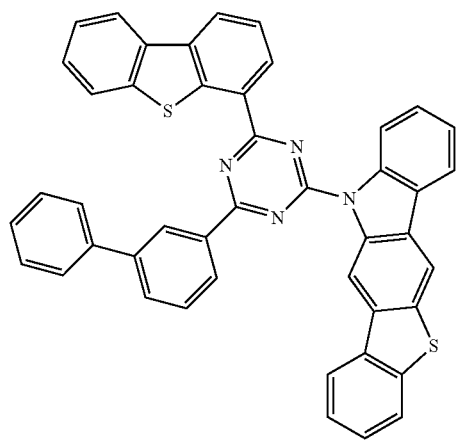
438
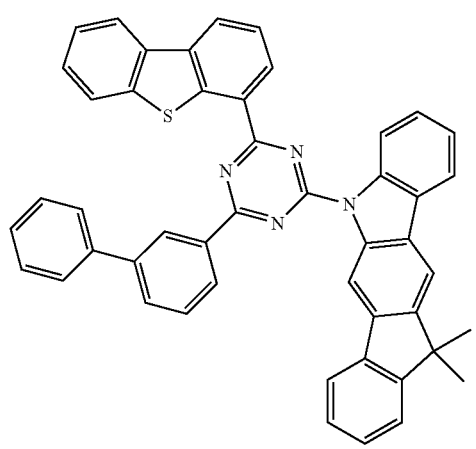
439
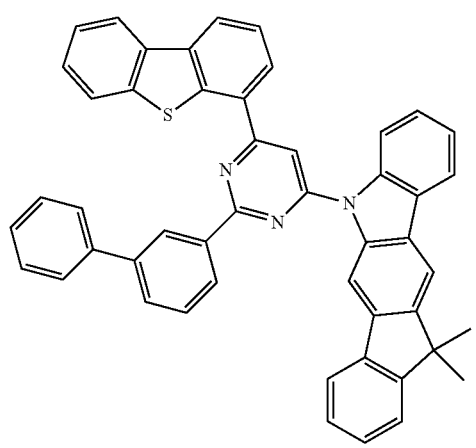
440
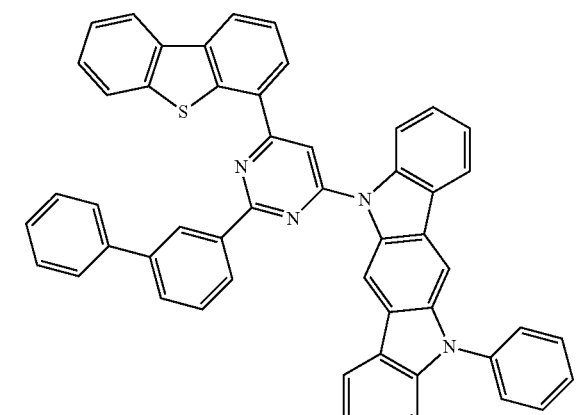
441
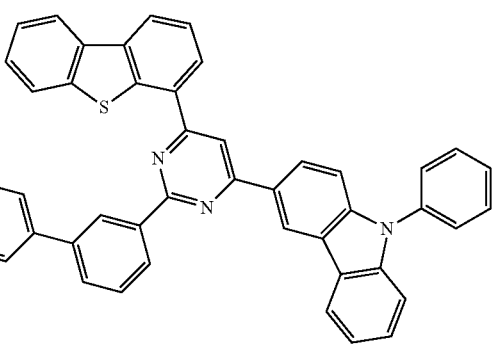
442
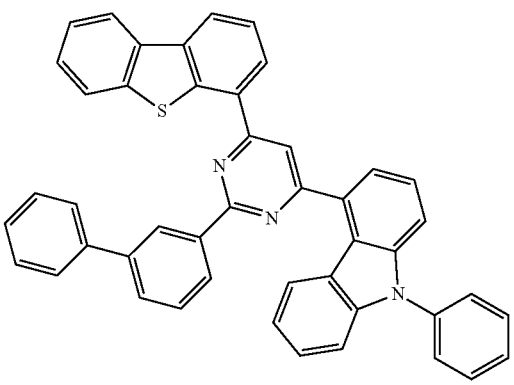
443
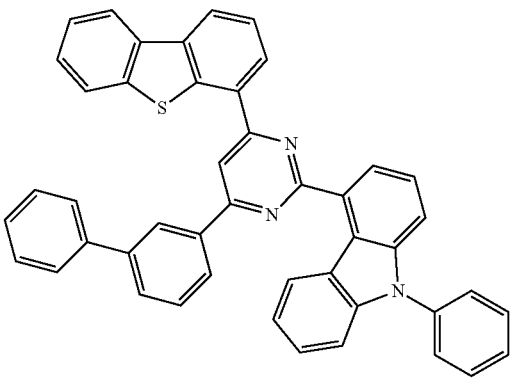

444
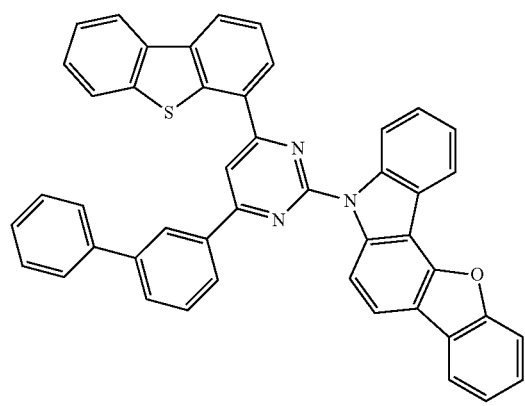
445
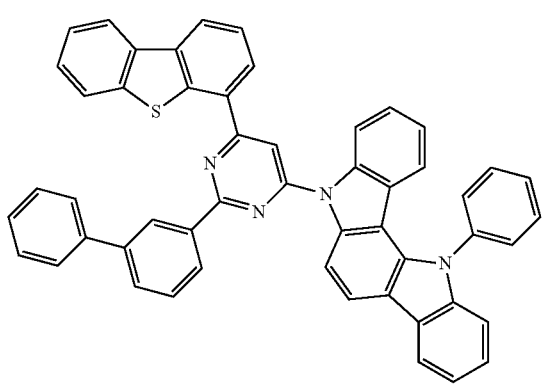
446
447
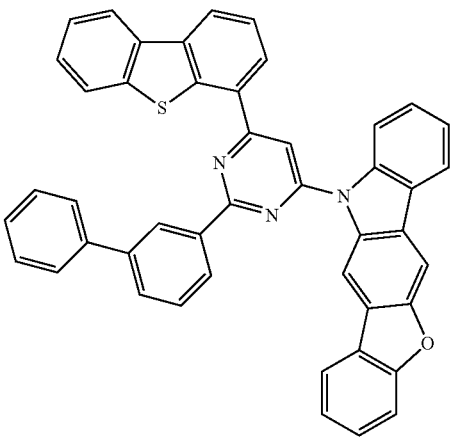
448
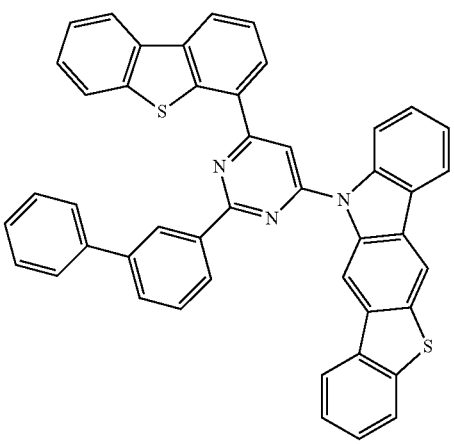
449
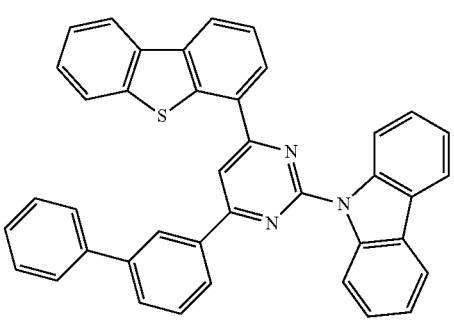
450
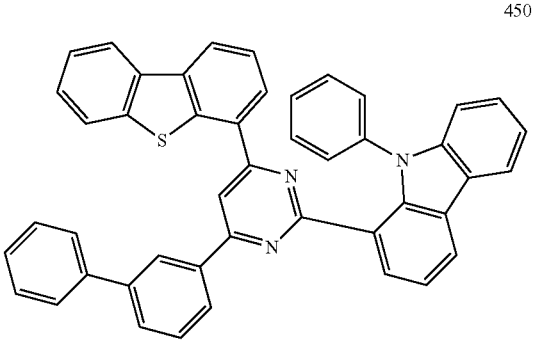

-continued
451
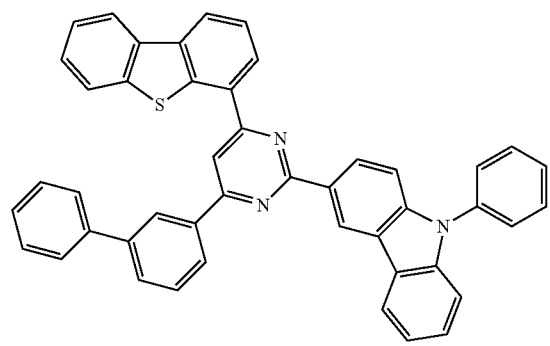
452
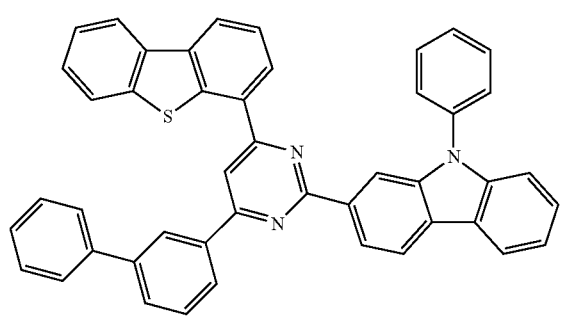
453
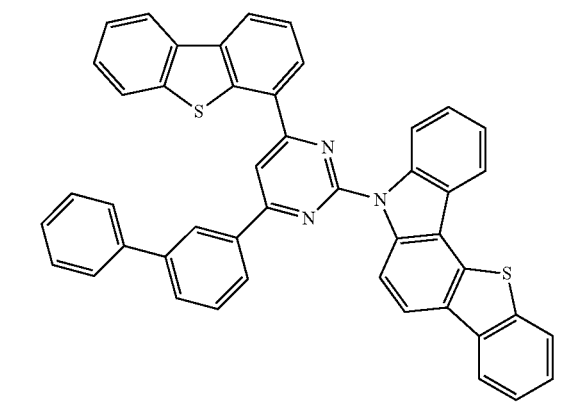
454
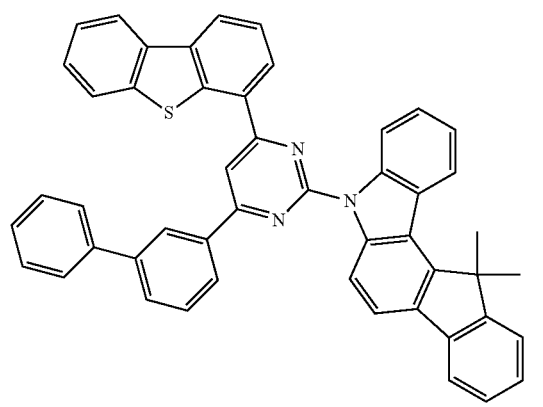
-continued
455
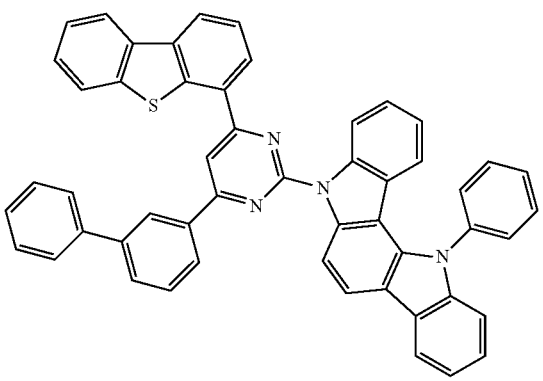
456
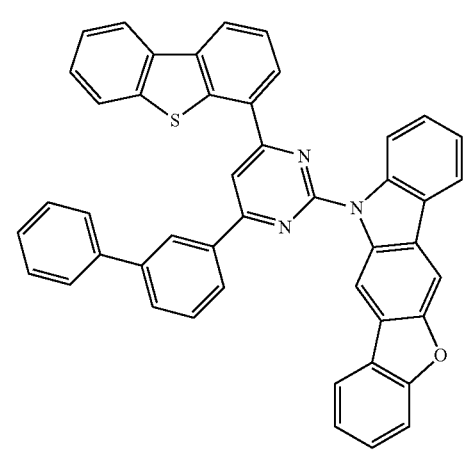
457
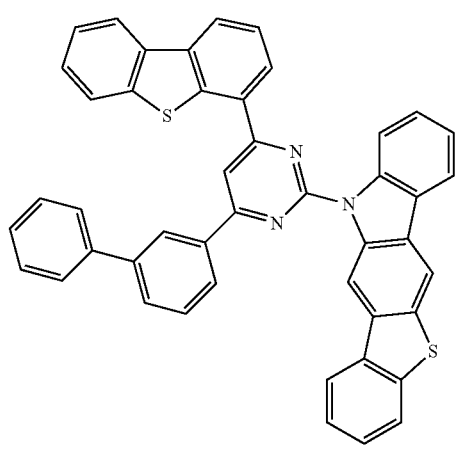

-continued
458
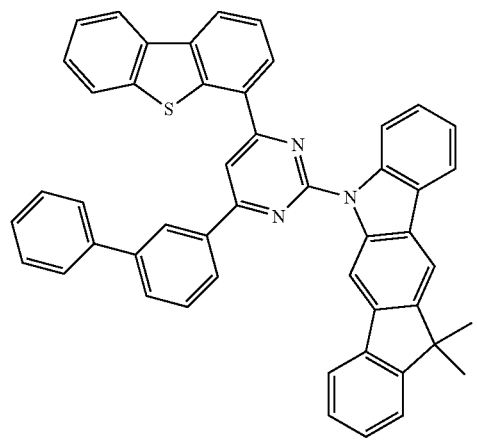
459
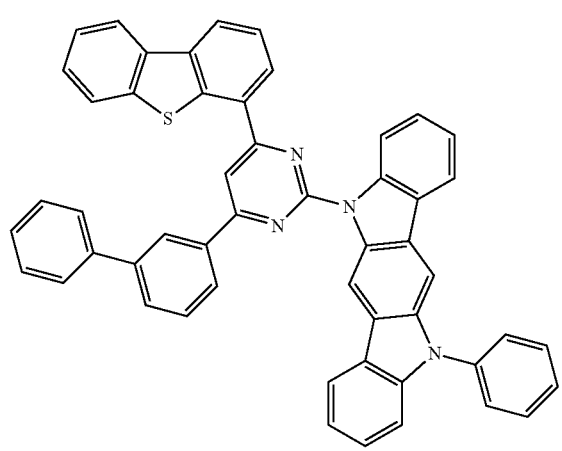
460
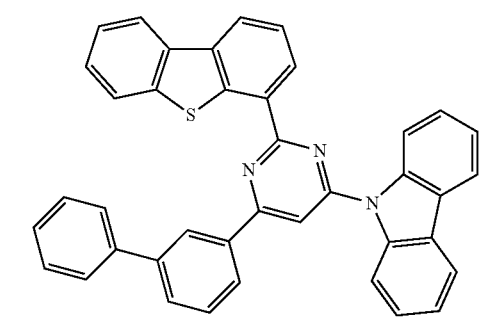
461
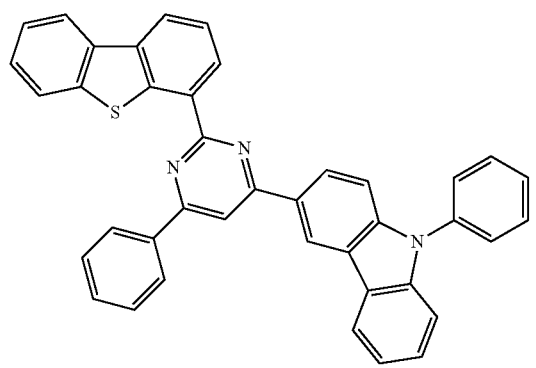
-continued
462
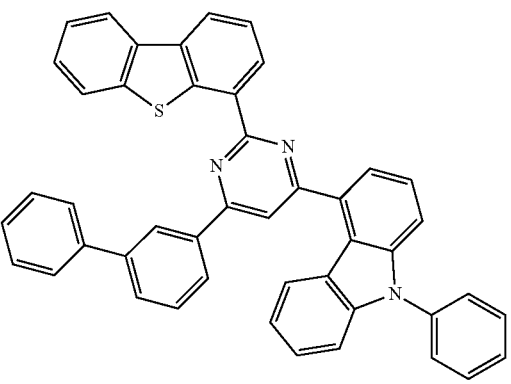
463
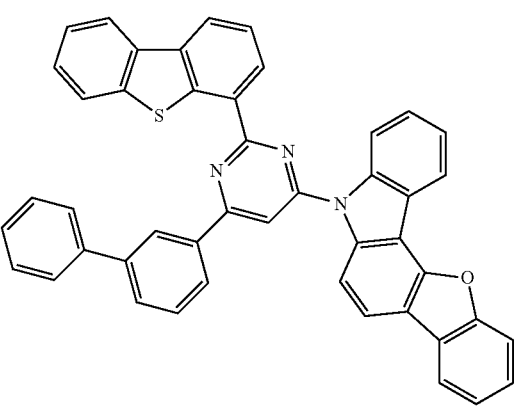
464
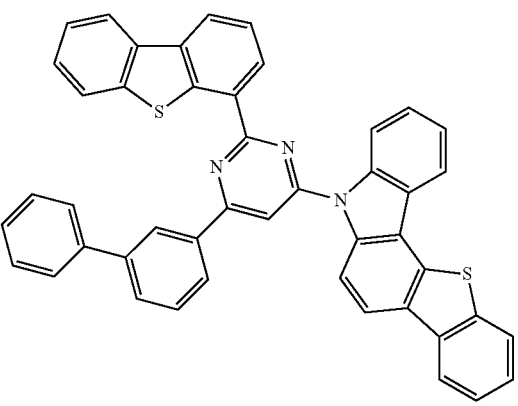

465
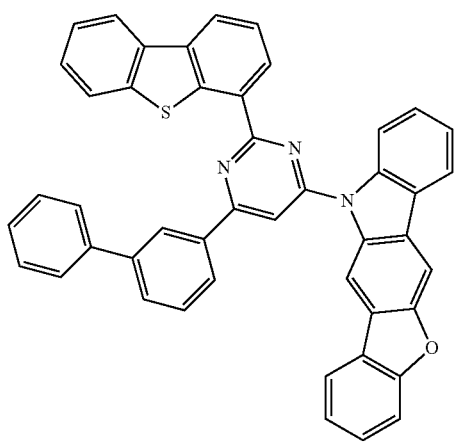
466
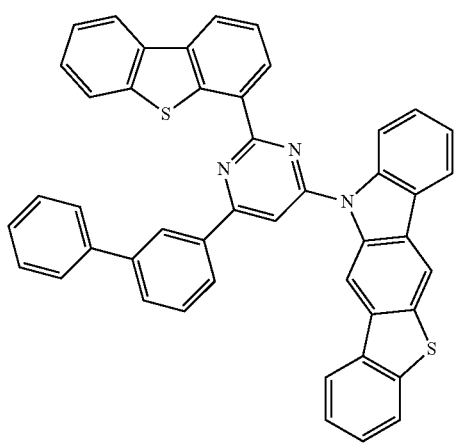
467
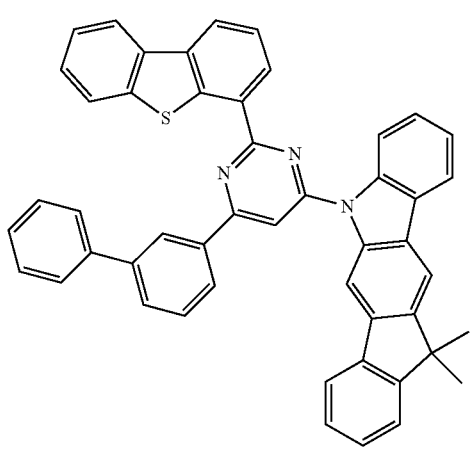
468
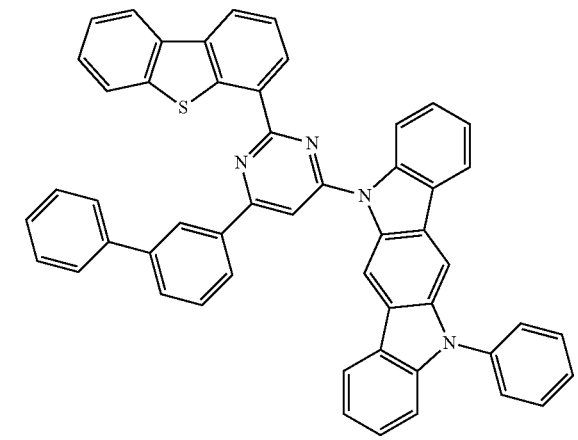
469
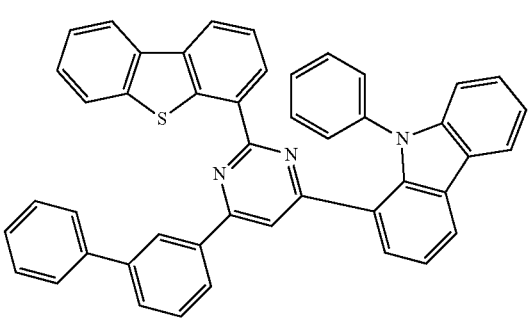
470
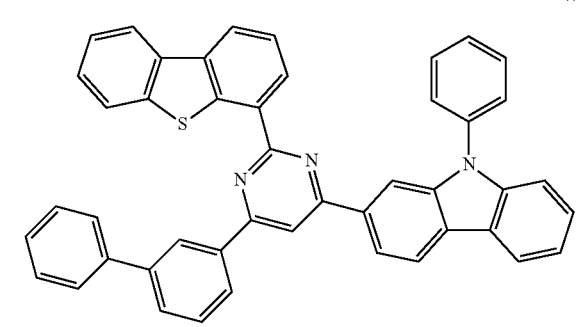
471
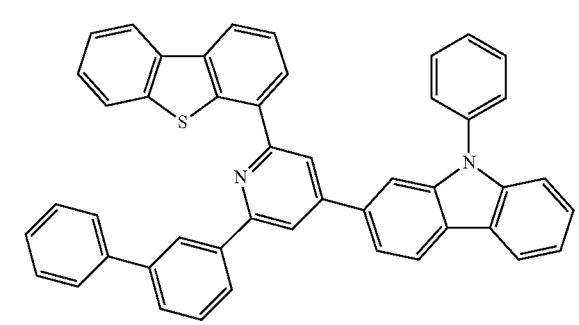

163
-continued
472
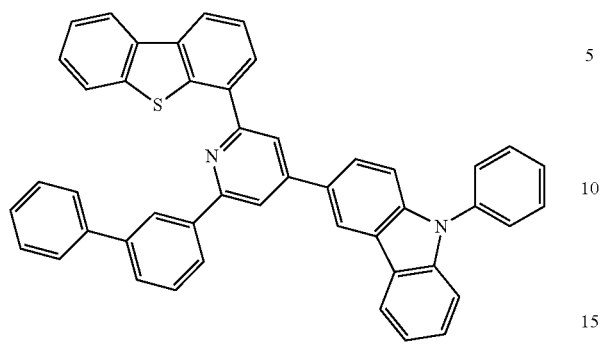
473
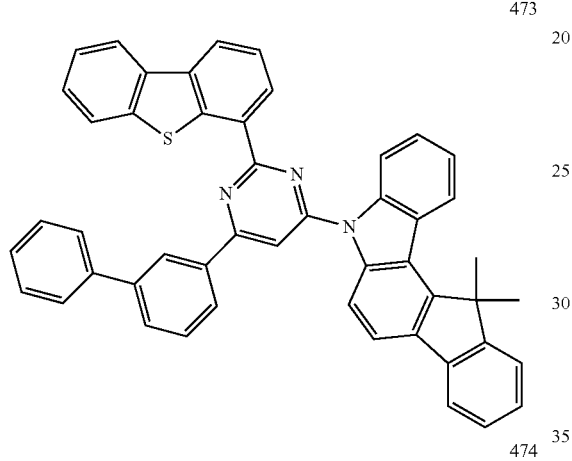
474
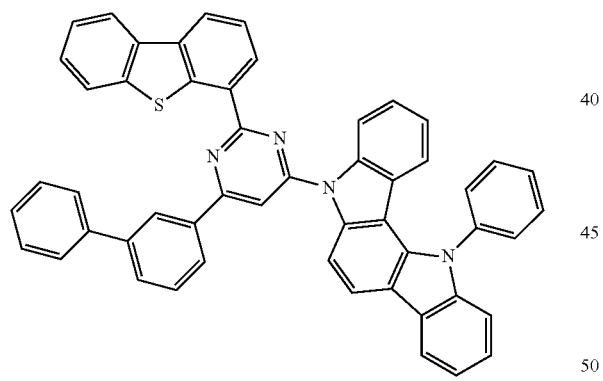
475
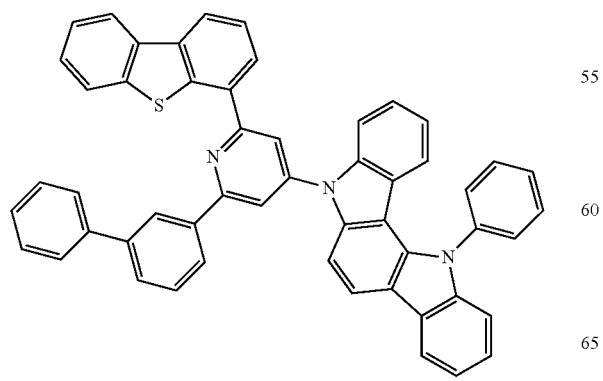
164
-continued
476
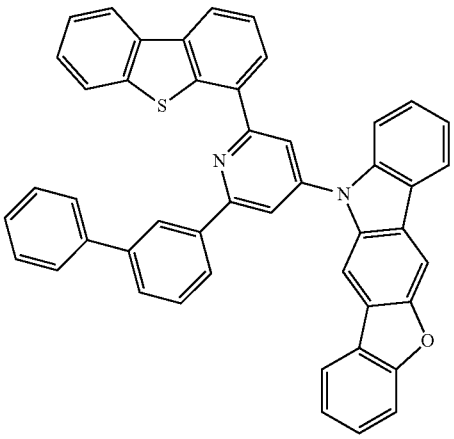
477
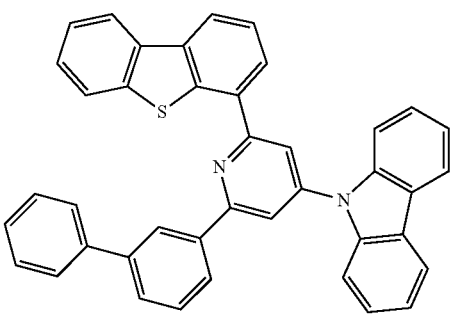
478
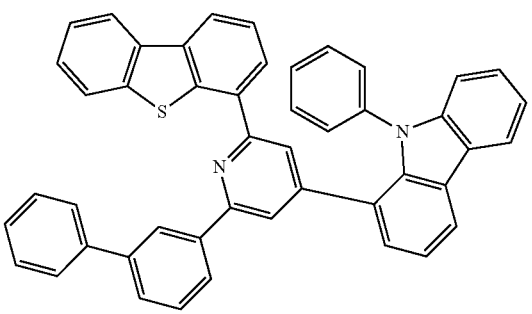
479
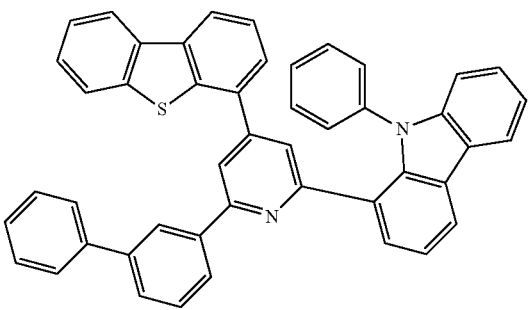

480
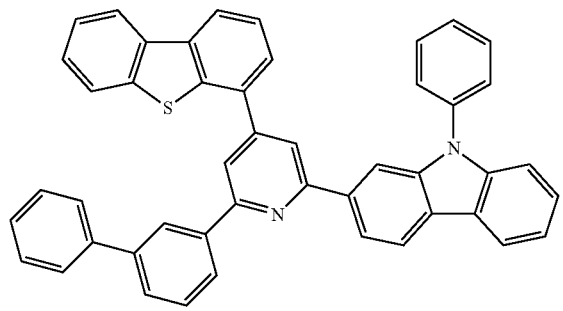
481
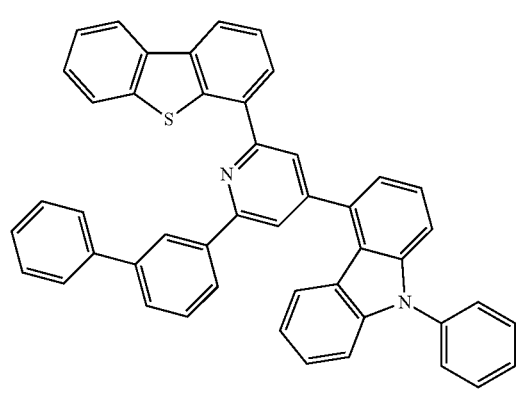
482
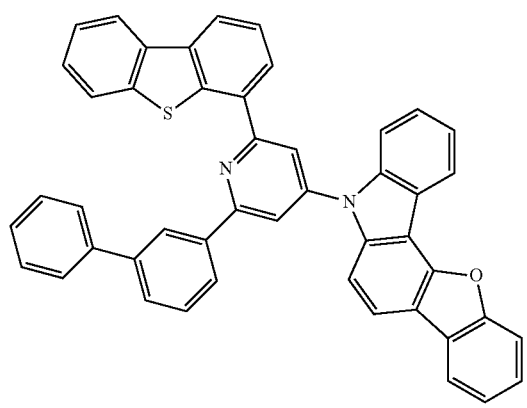
483
484
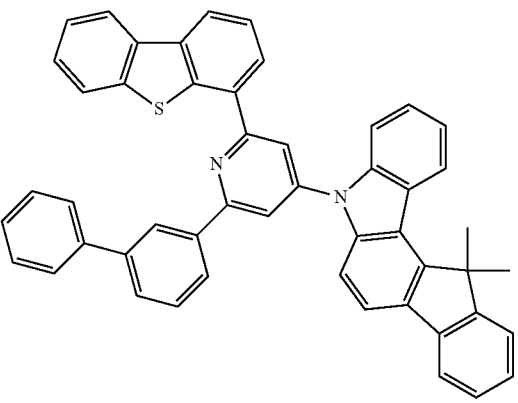
485
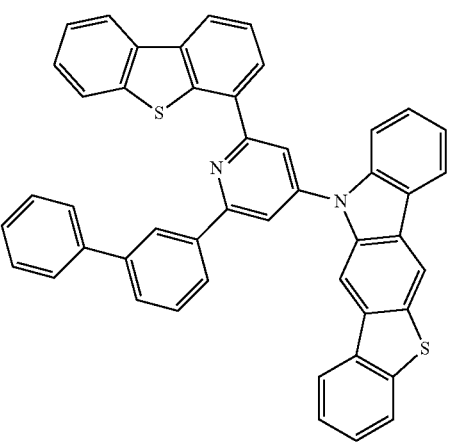
486
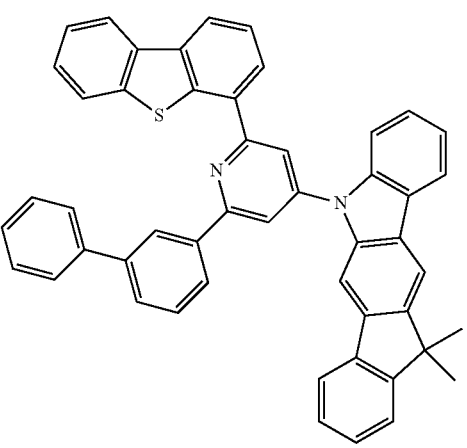

487
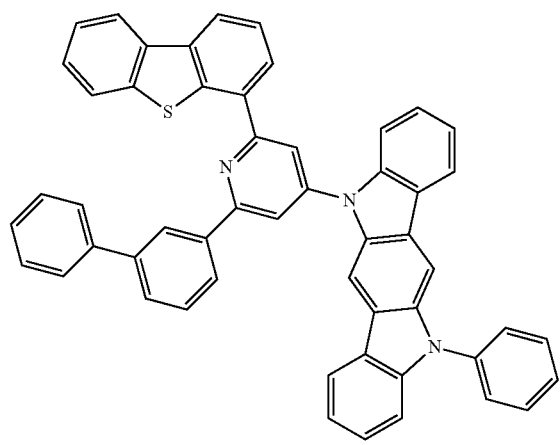
488
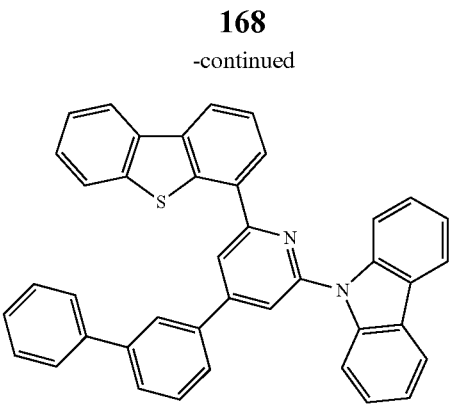
489
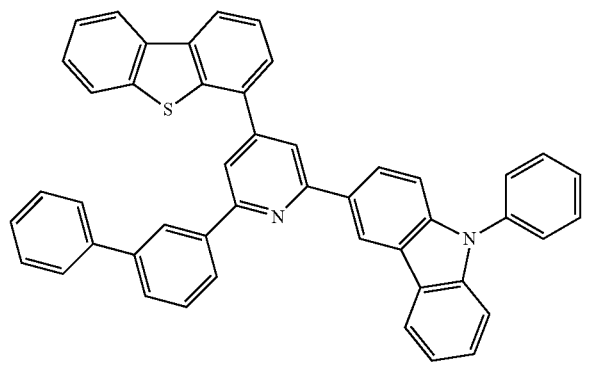
490
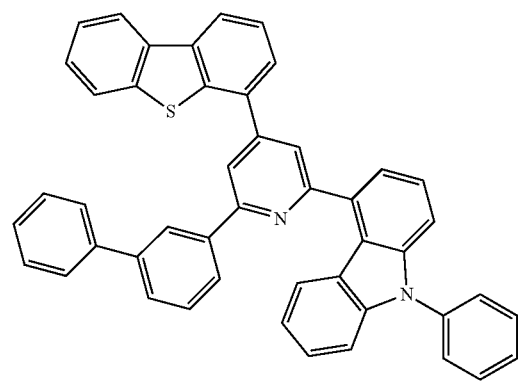
491
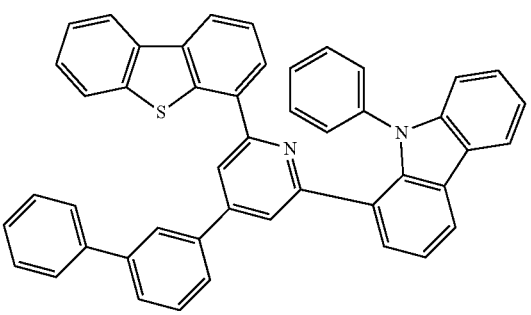
492
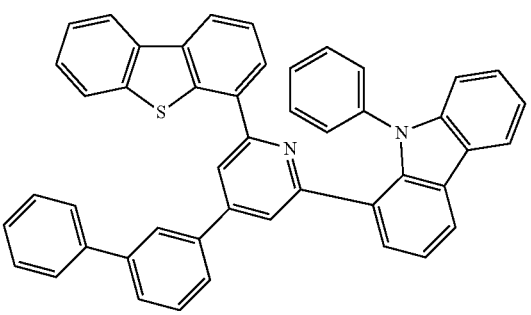
493
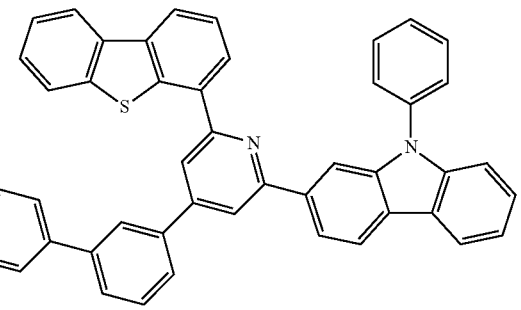
494
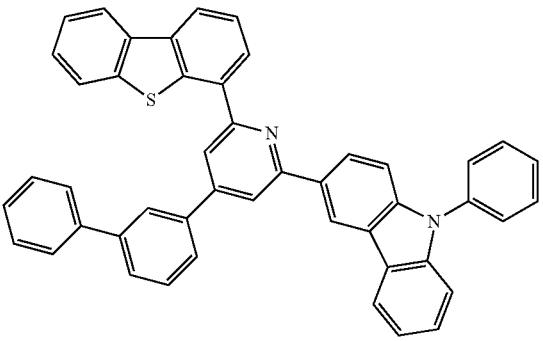

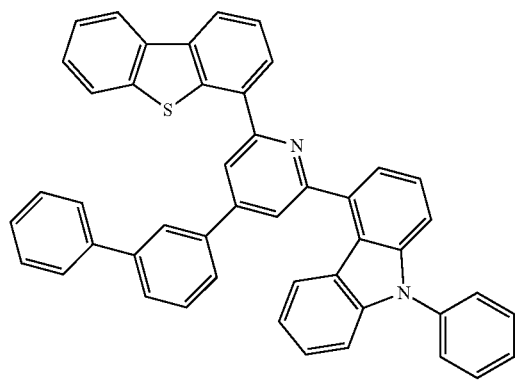
495
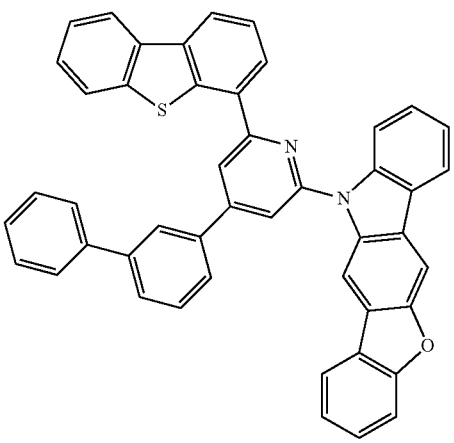
498
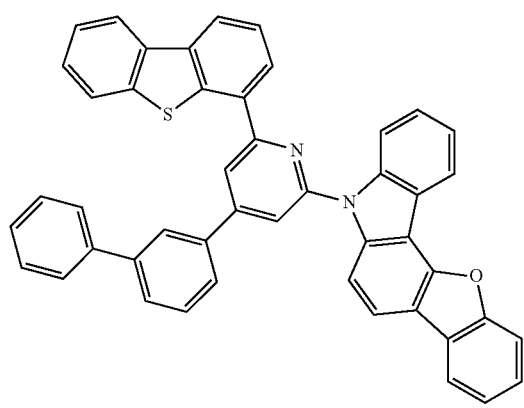
496
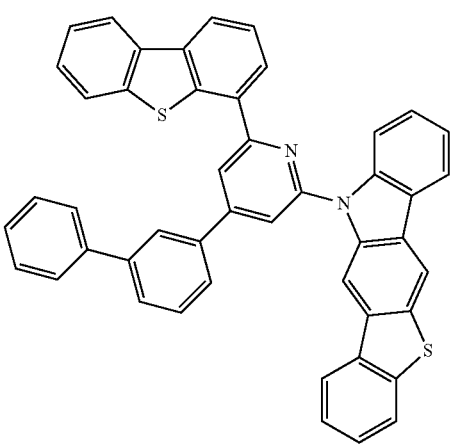
499
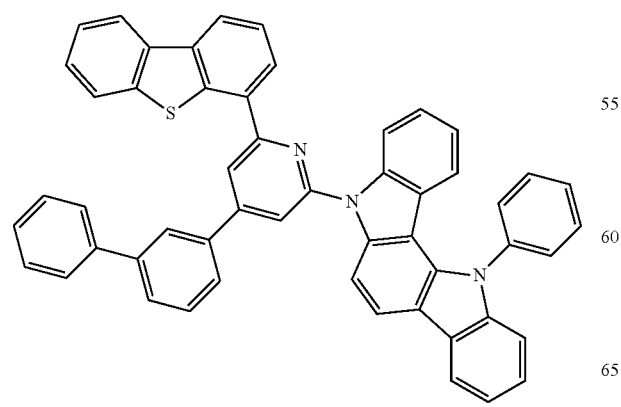
497
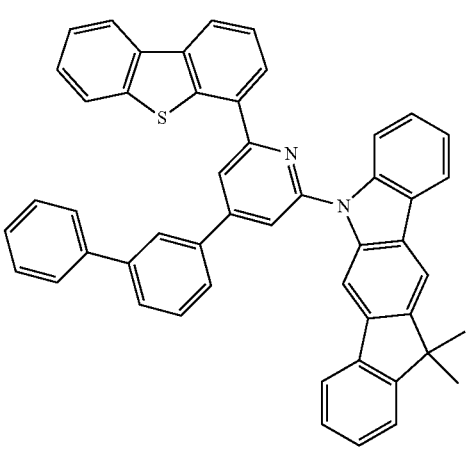
500

-continued
501
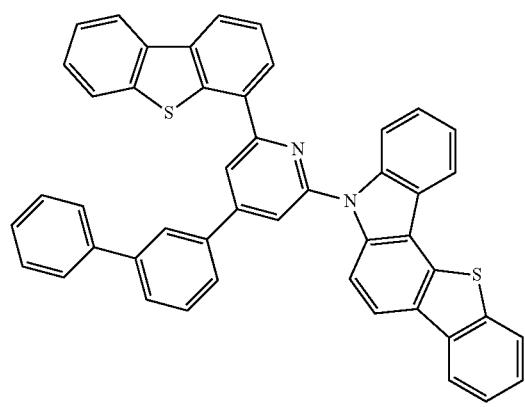
502
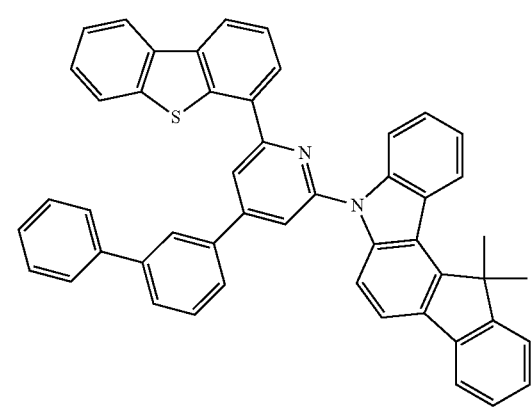
503
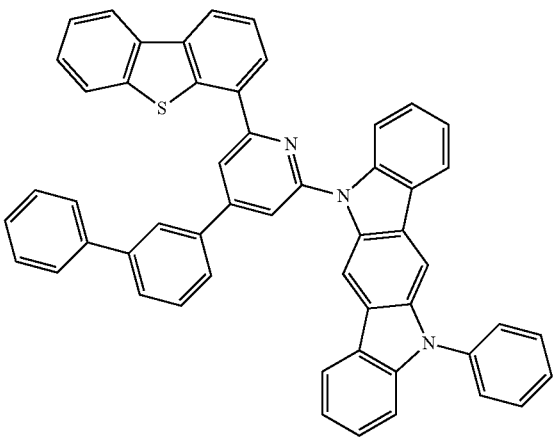
-continued
504
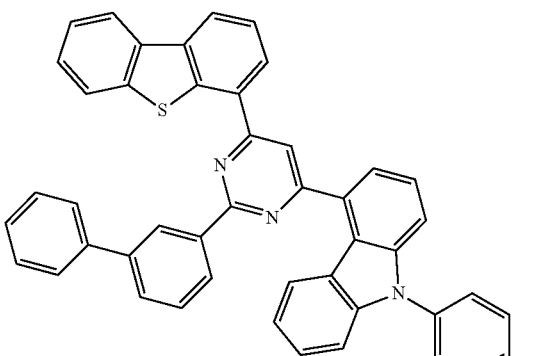
505
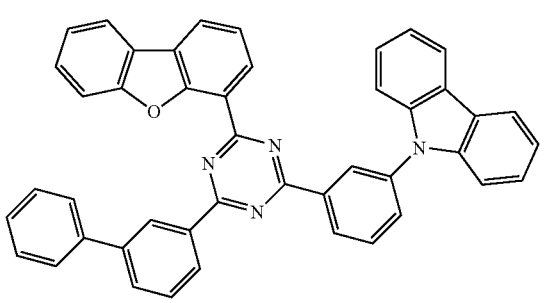
506
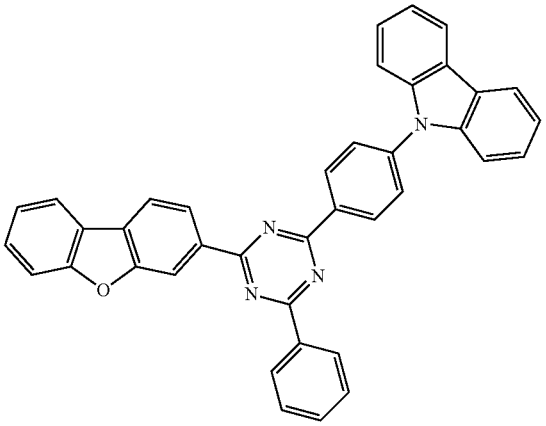
507
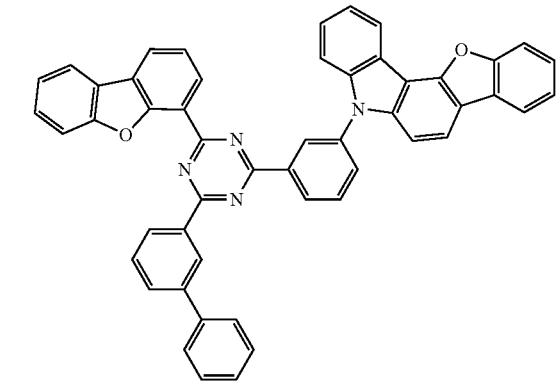

508
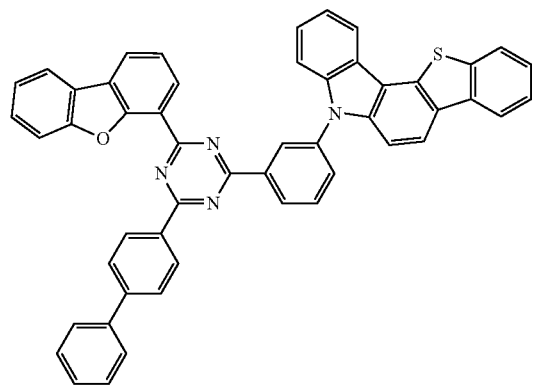
509
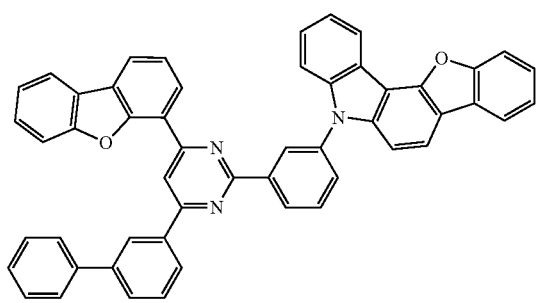
510
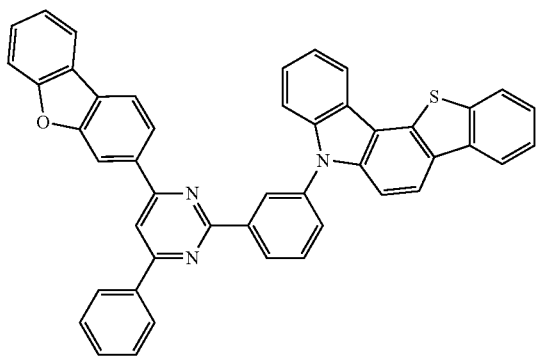
511
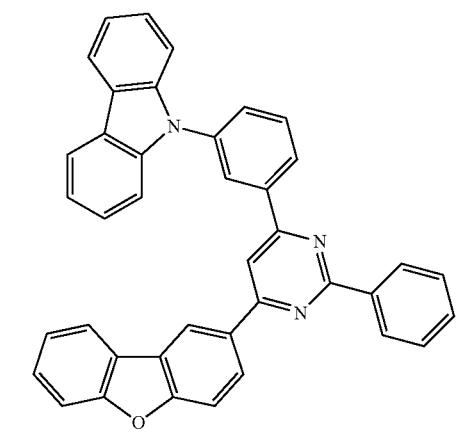
512
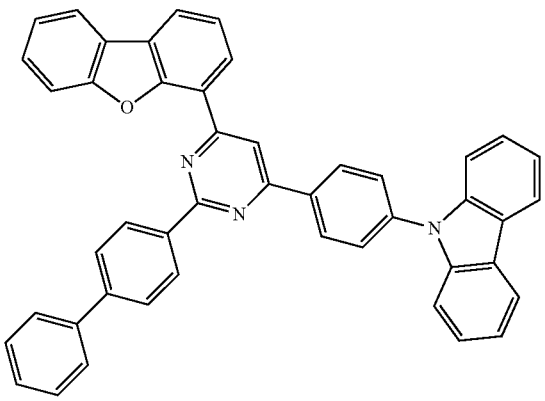
513
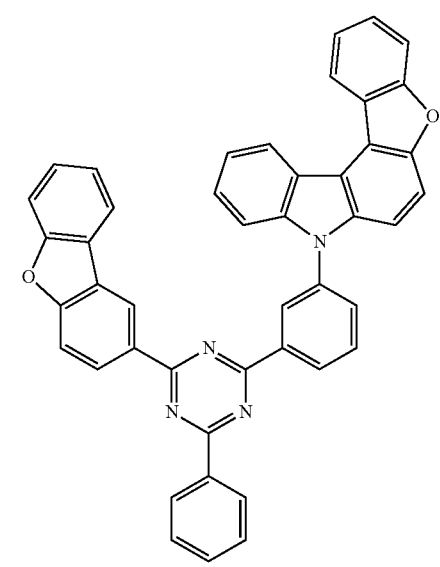
514
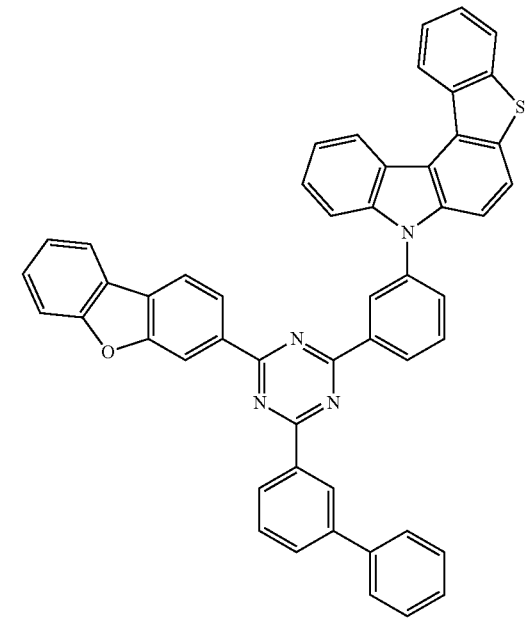

-continued
515
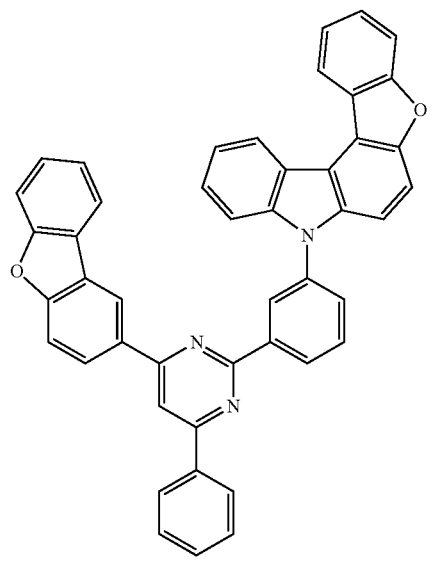
516
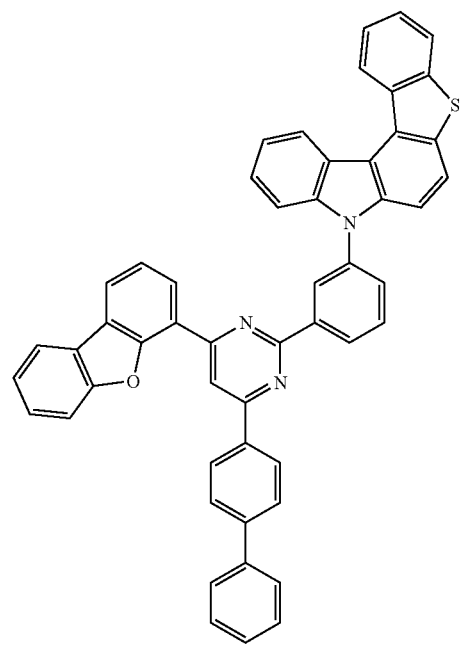
517
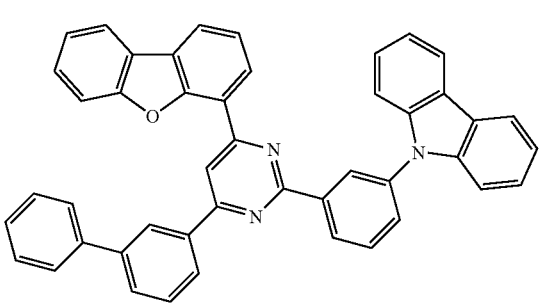
-continued
518
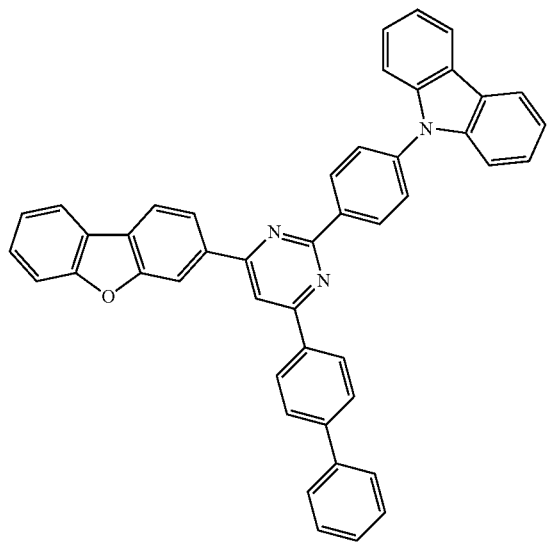
519
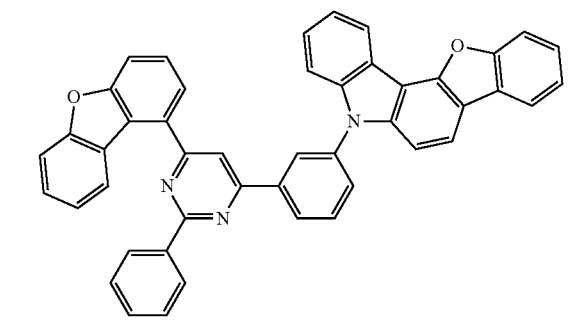
520
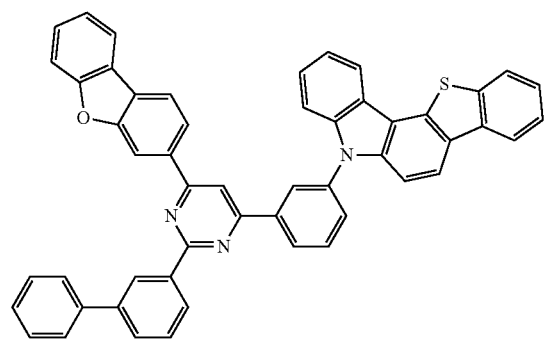
521
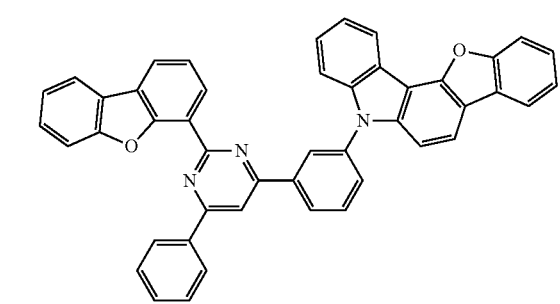

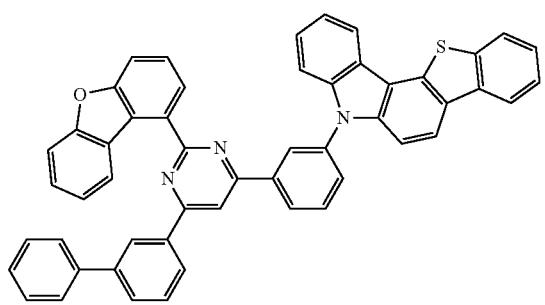
522
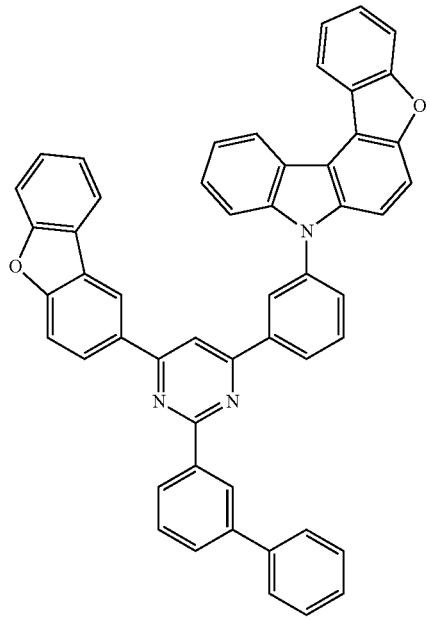
525
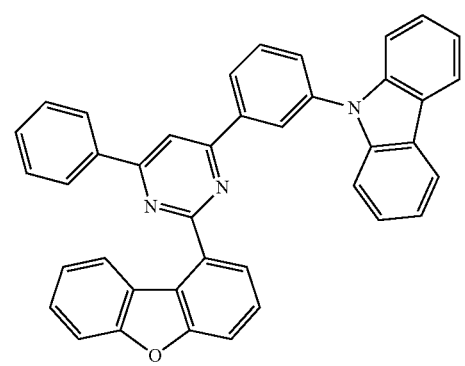
523
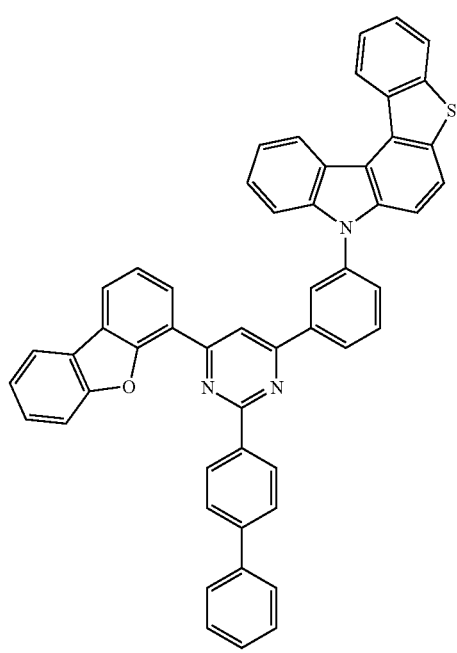
526
524

527
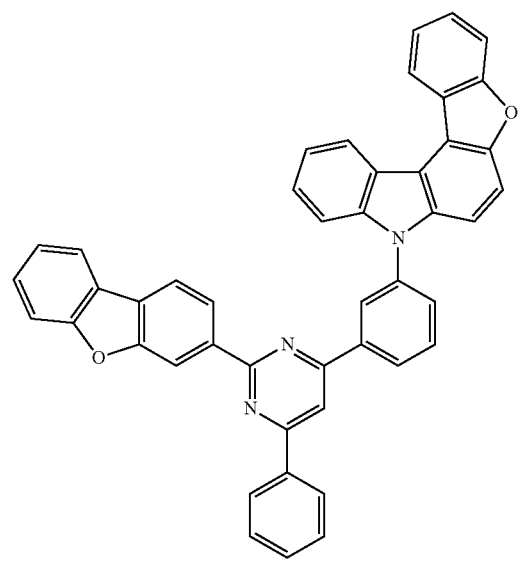
528
530
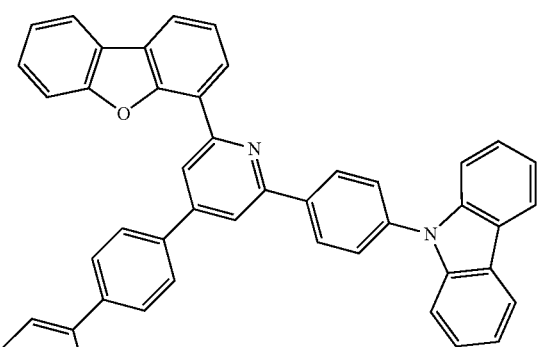
531
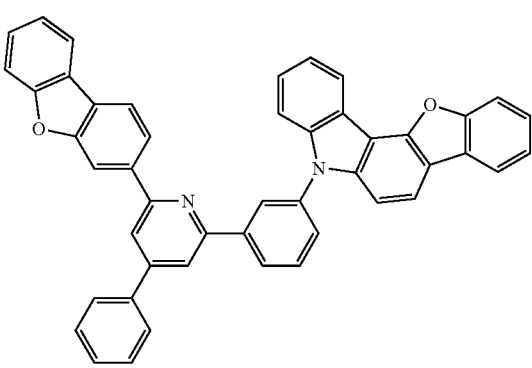
532
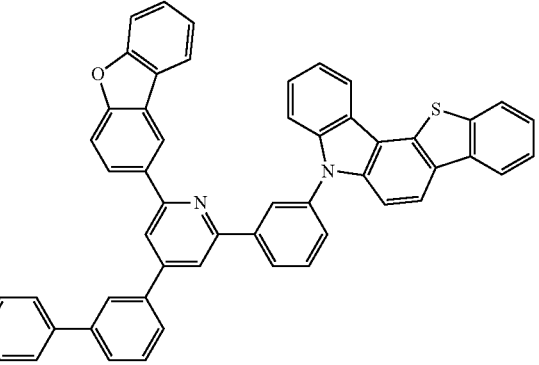
529
533
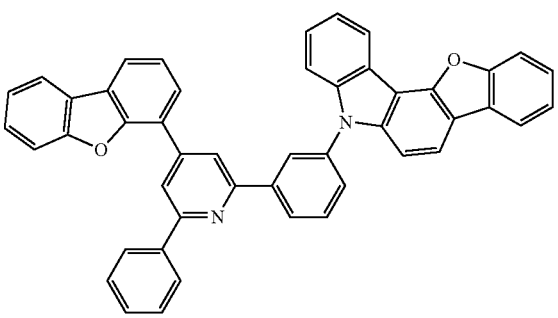

534
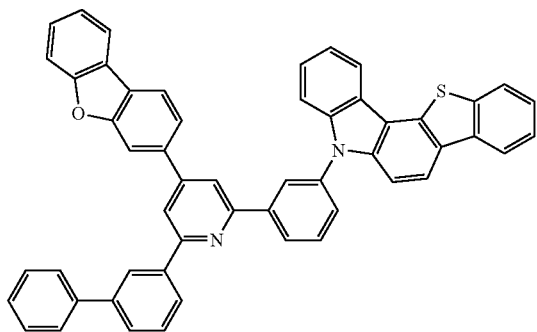
535
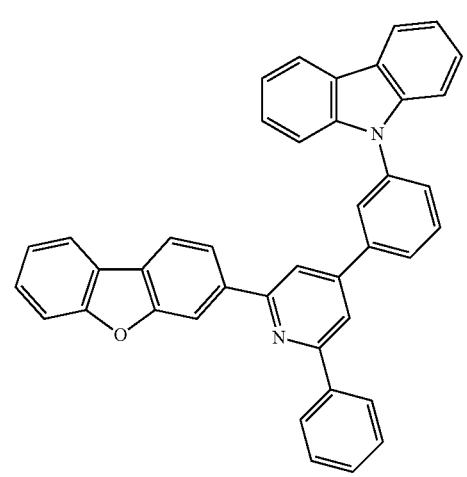
536
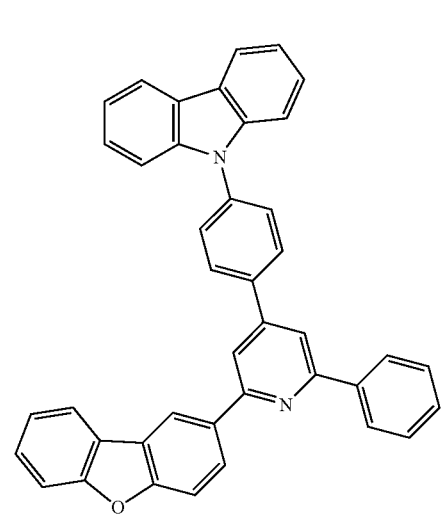
537
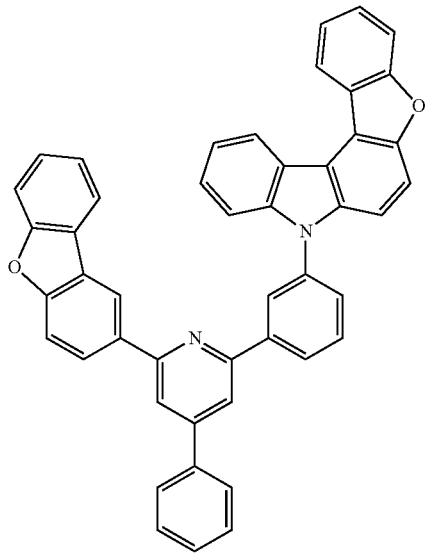
538
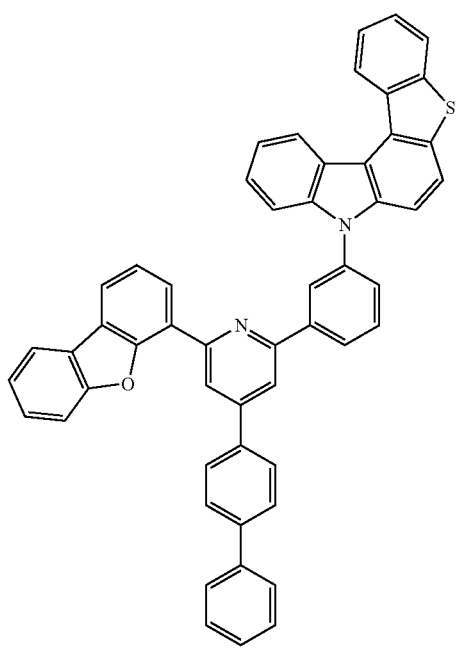

539
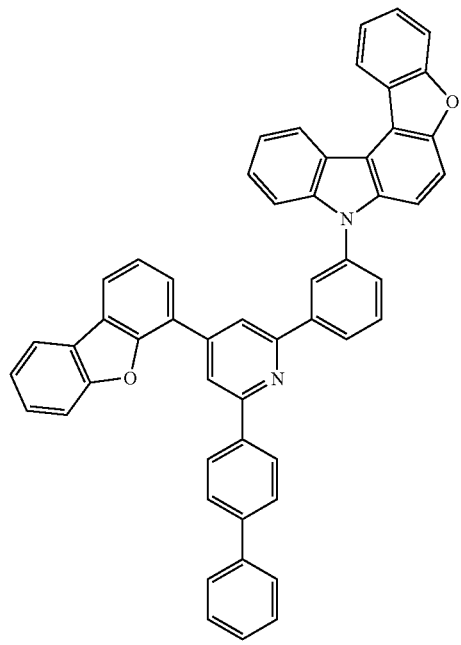
540
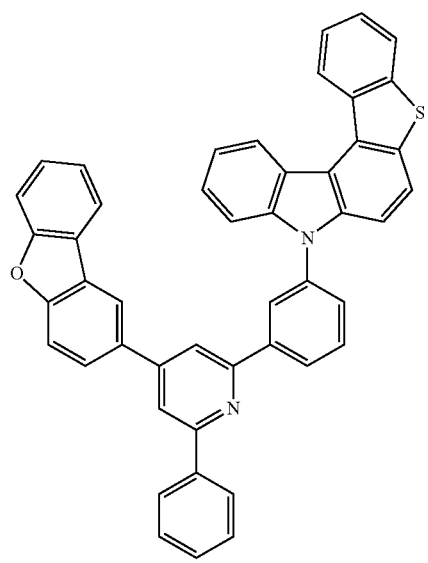
541
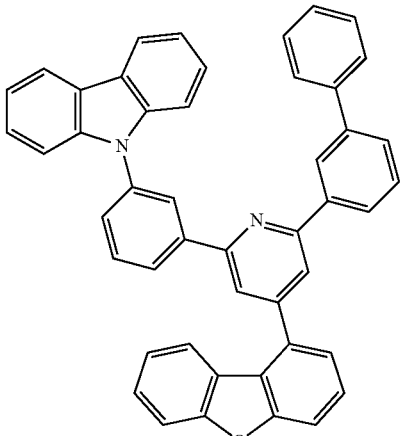
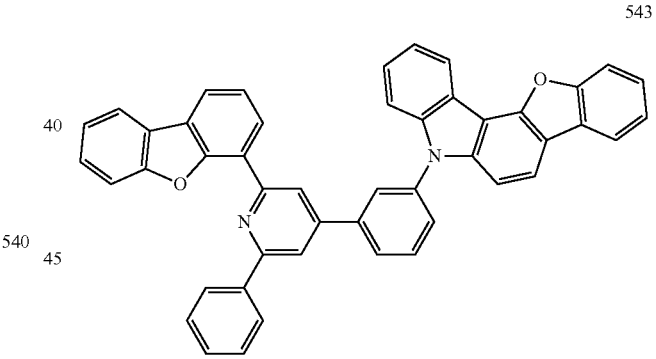
543
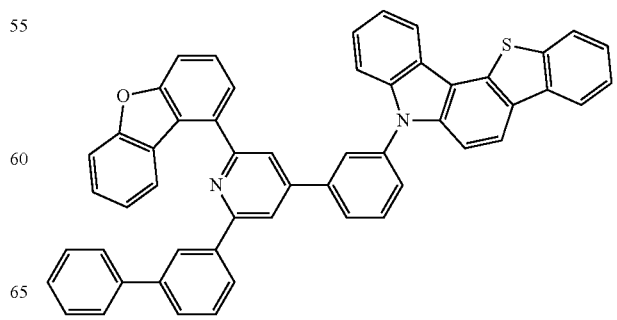
544

545
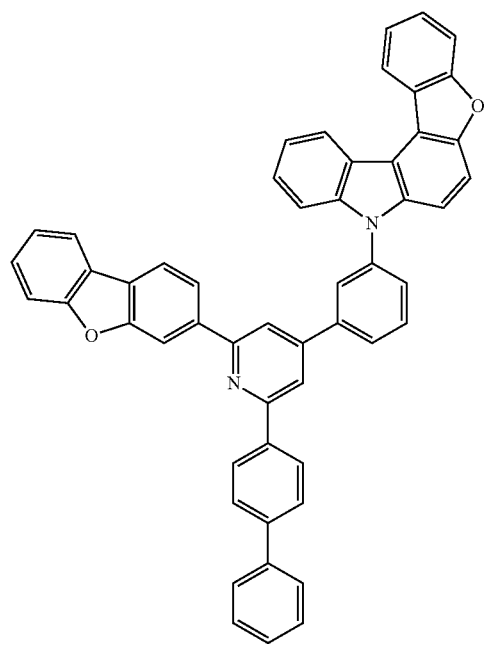
546
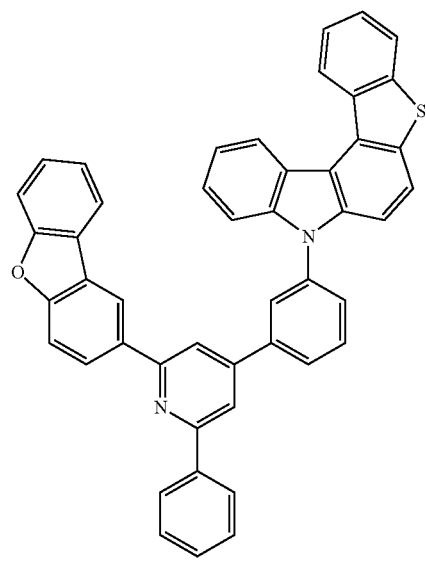
547
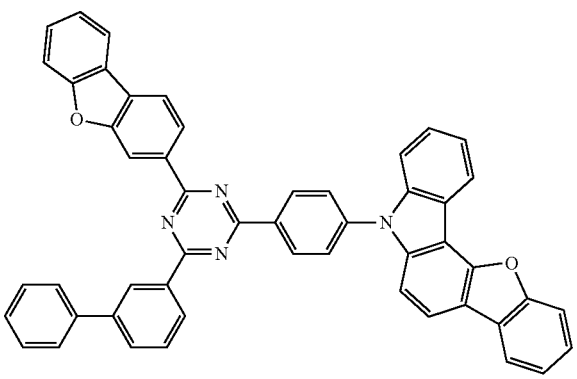
548
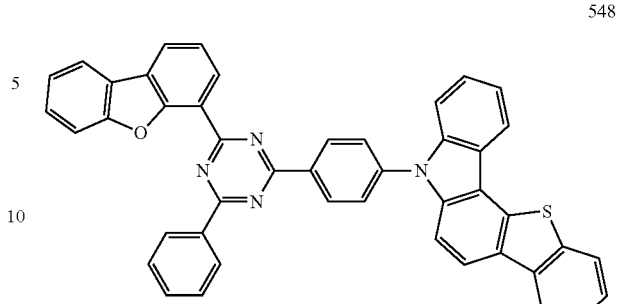
549
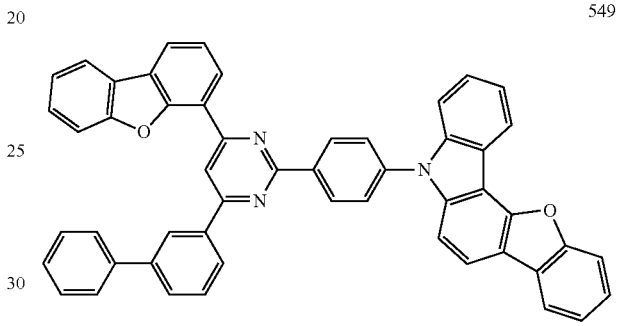
550
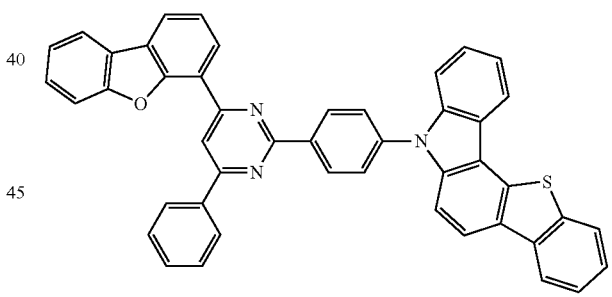
551
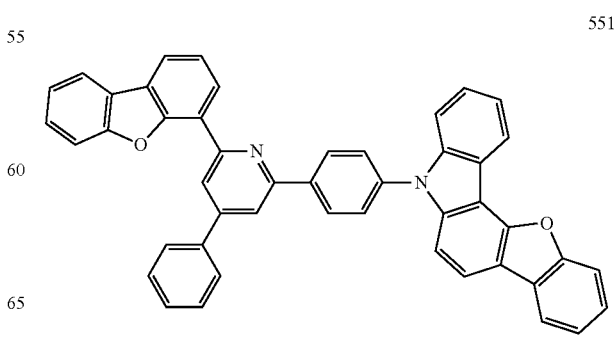

-continued
552
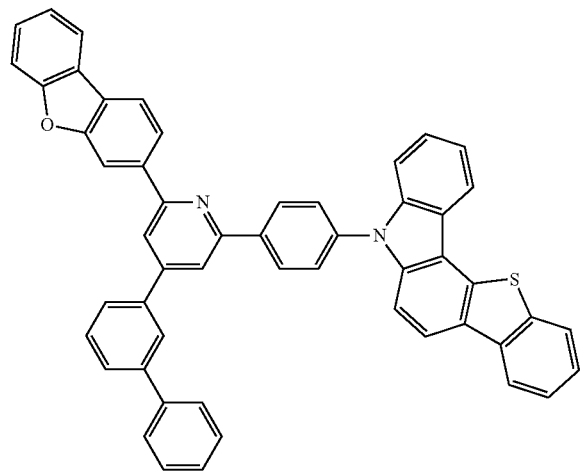
553
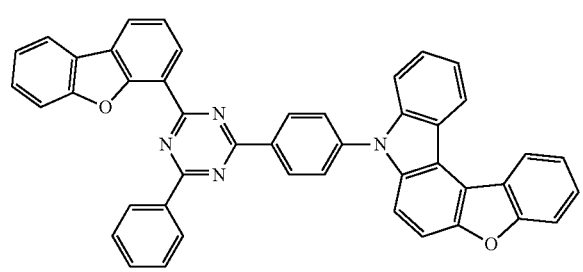
554
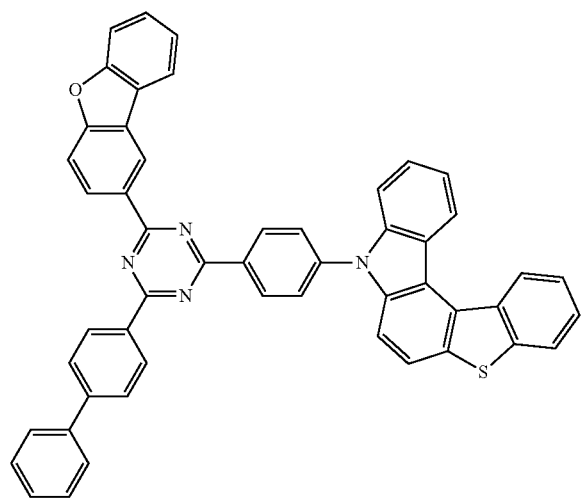
555
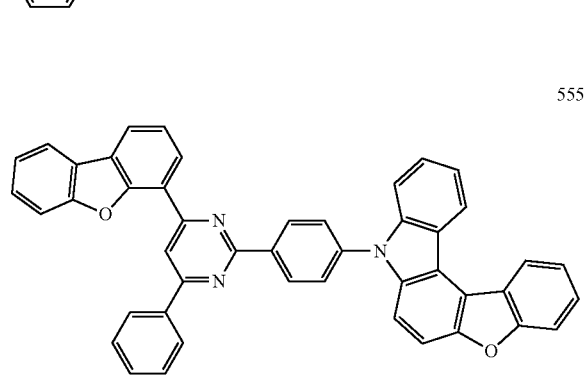
-continued
556
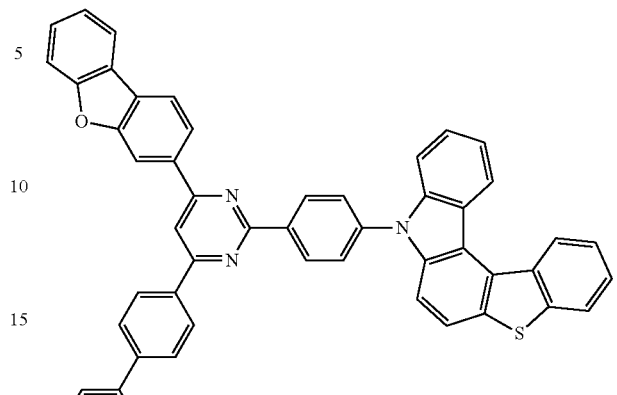
557
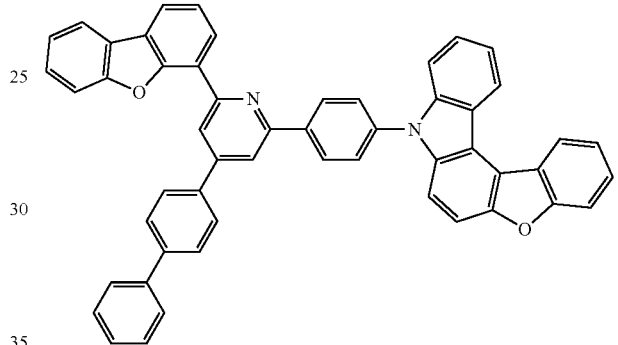
558
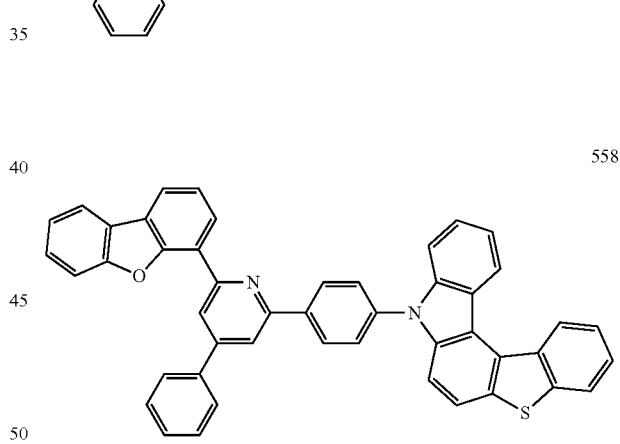
559
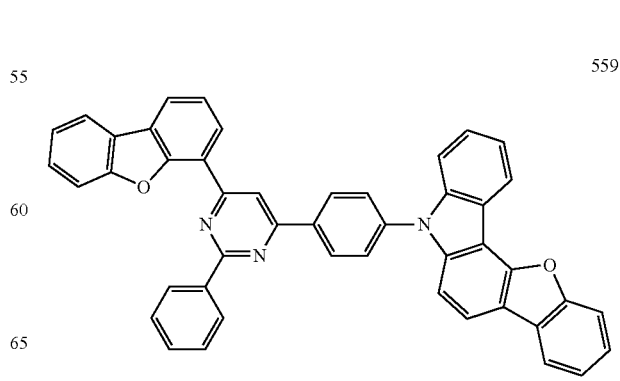

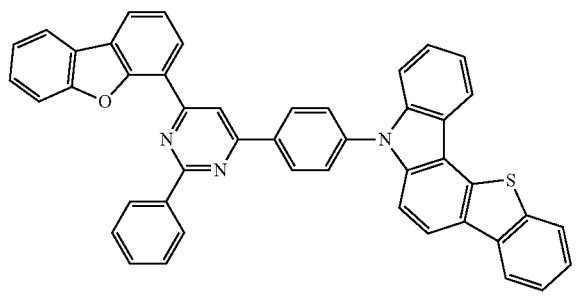
560
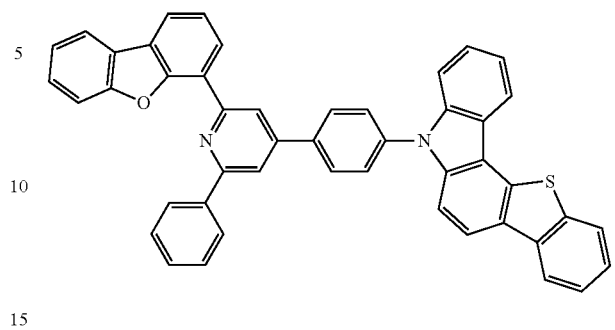
564
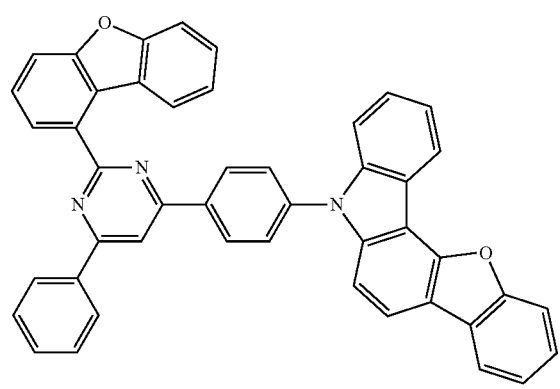
561
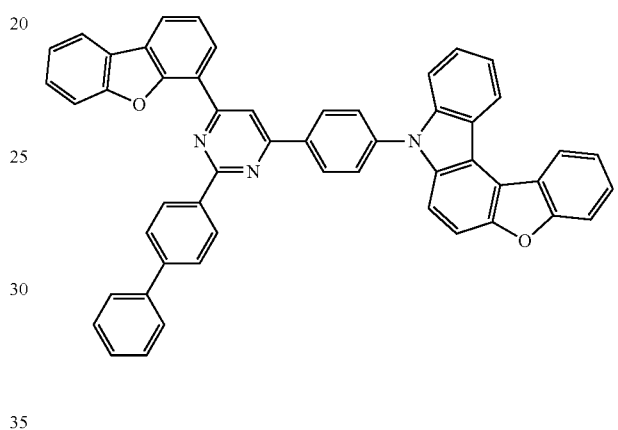
565
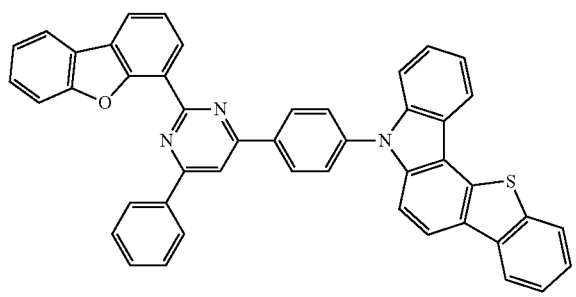
562
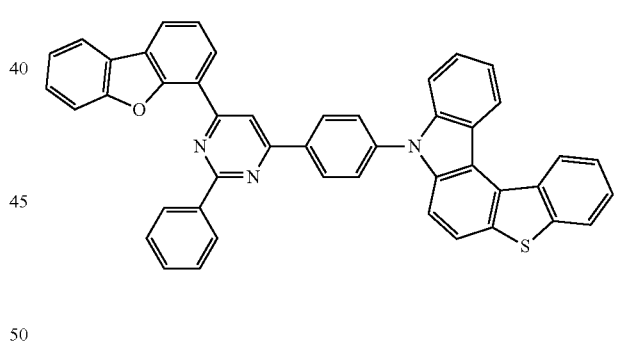
566
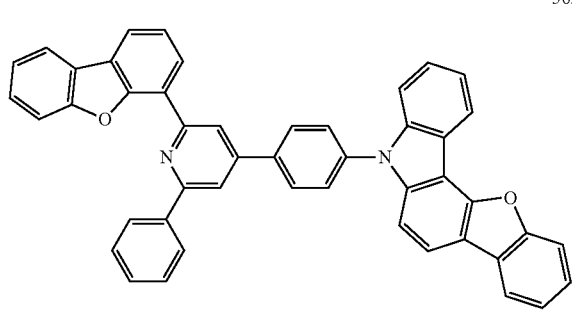
563
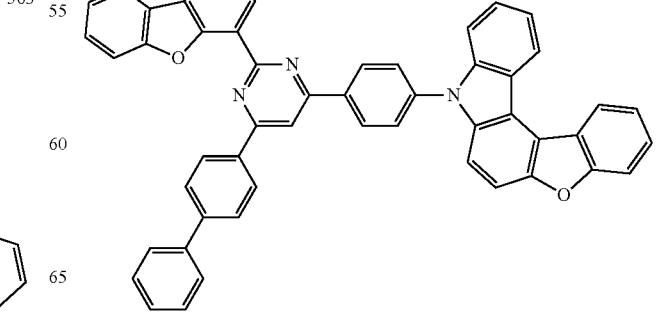
567

-continued
568
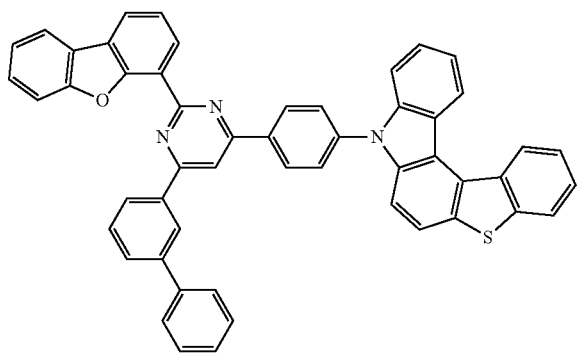
569
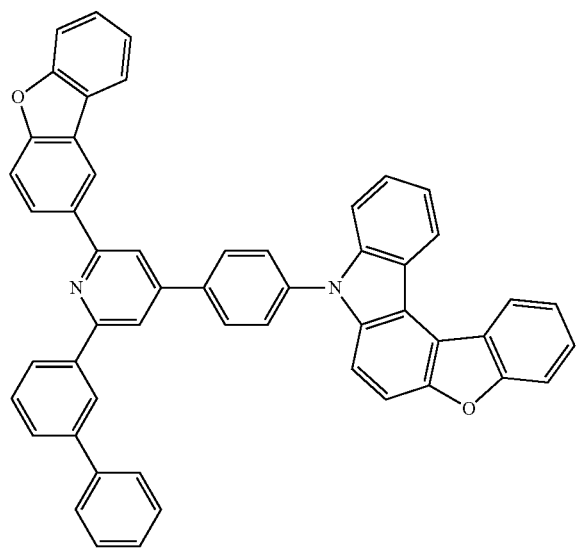
570
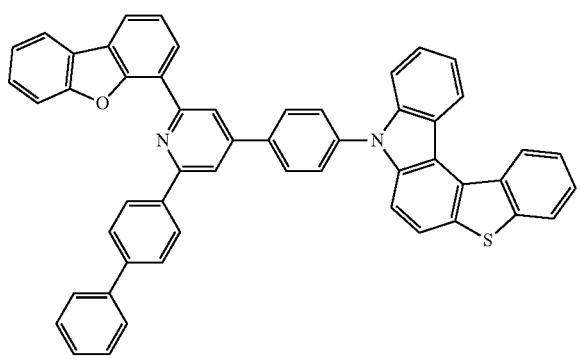
571
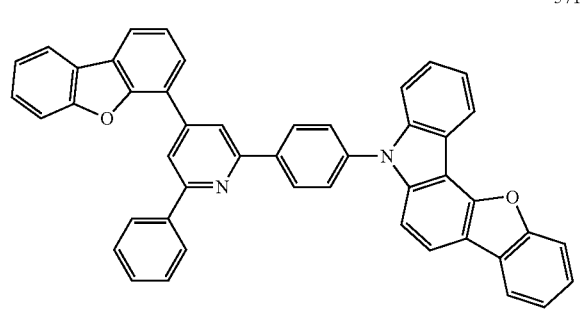
-continued
572
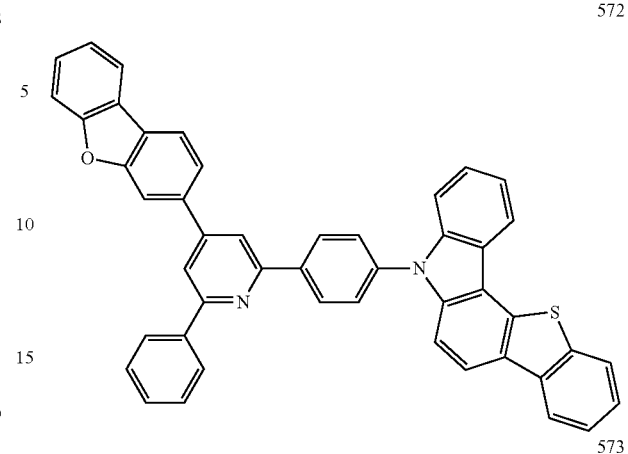
573
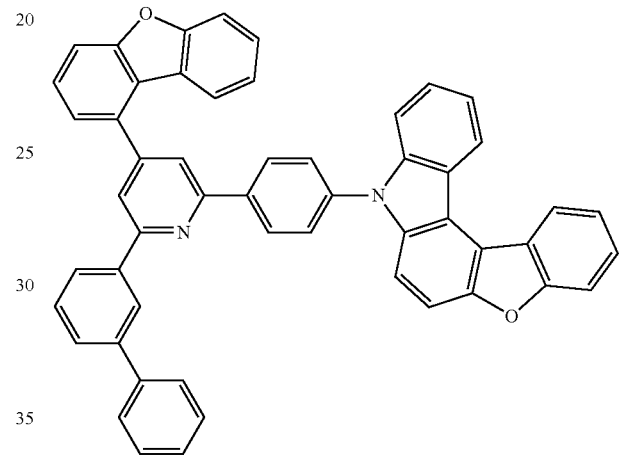
574
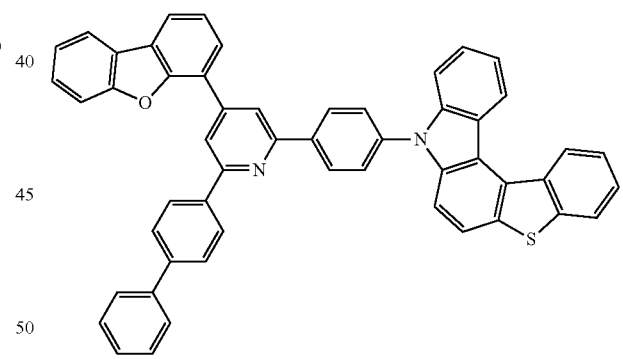
575
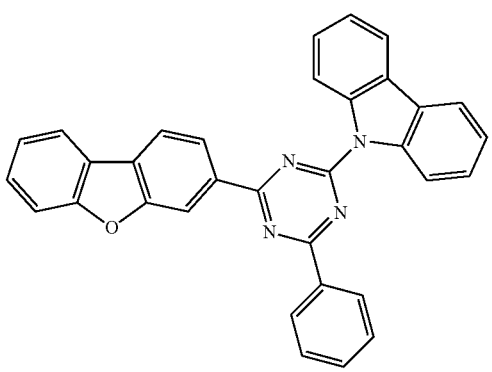

576
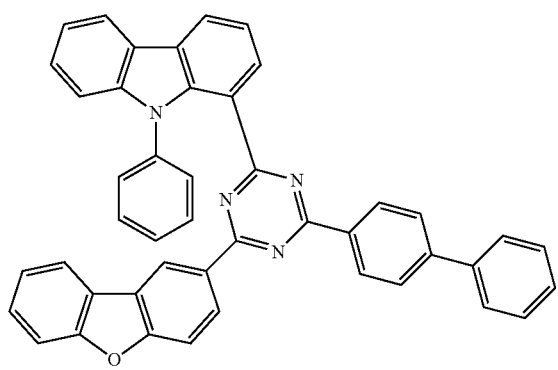
577
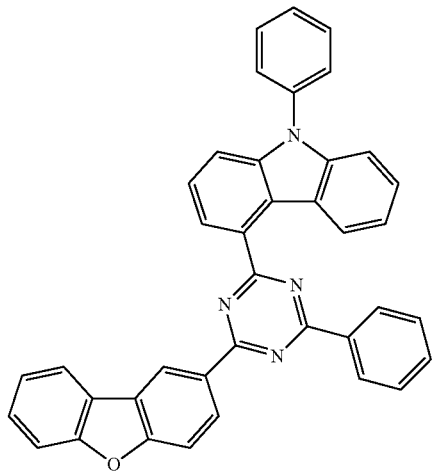
578
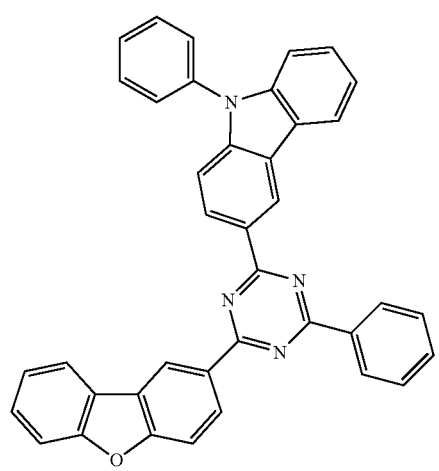
579
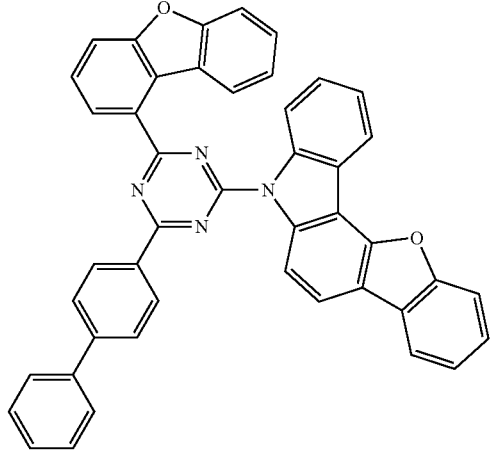
580
581
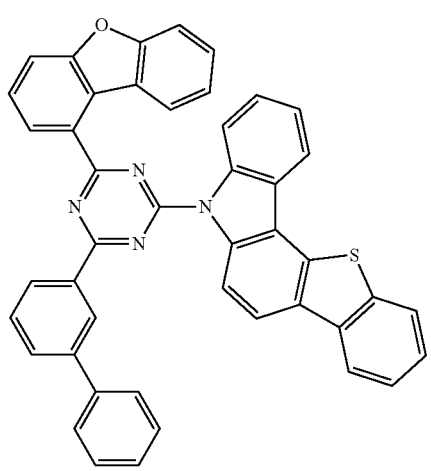

582
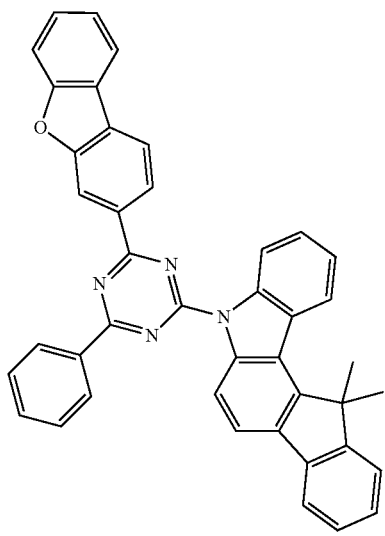
583
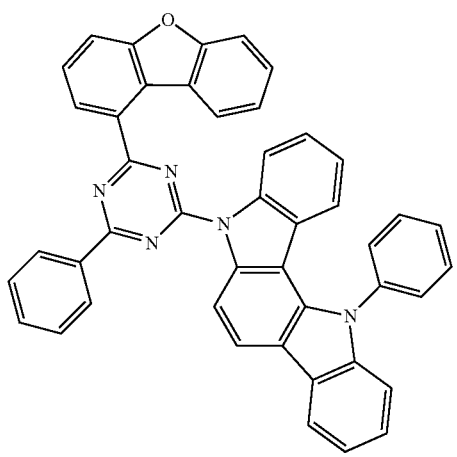
584
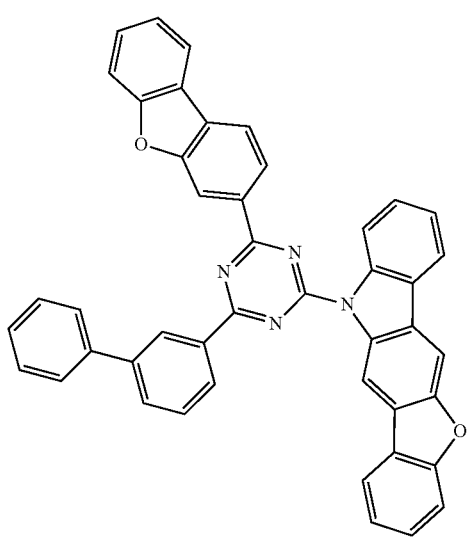
585
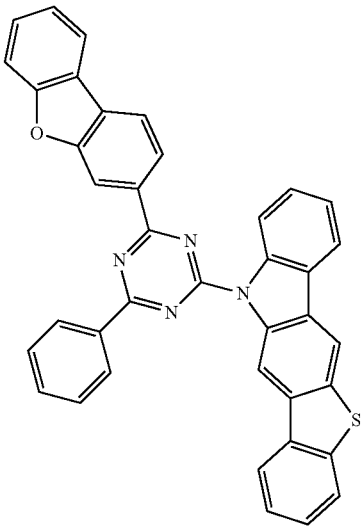
586
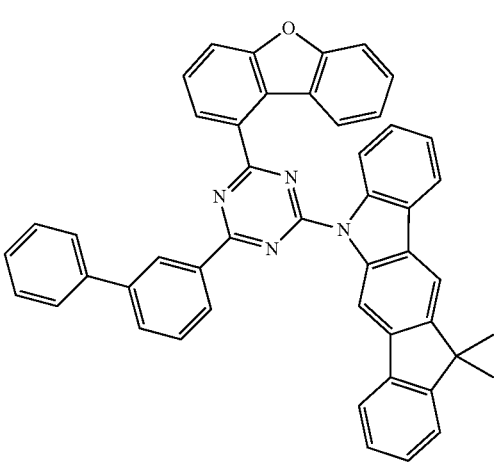
587
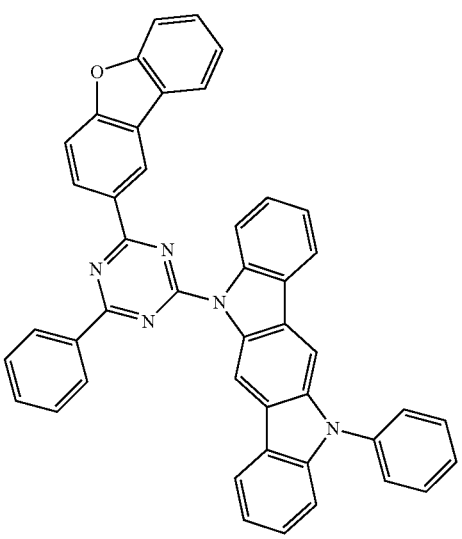

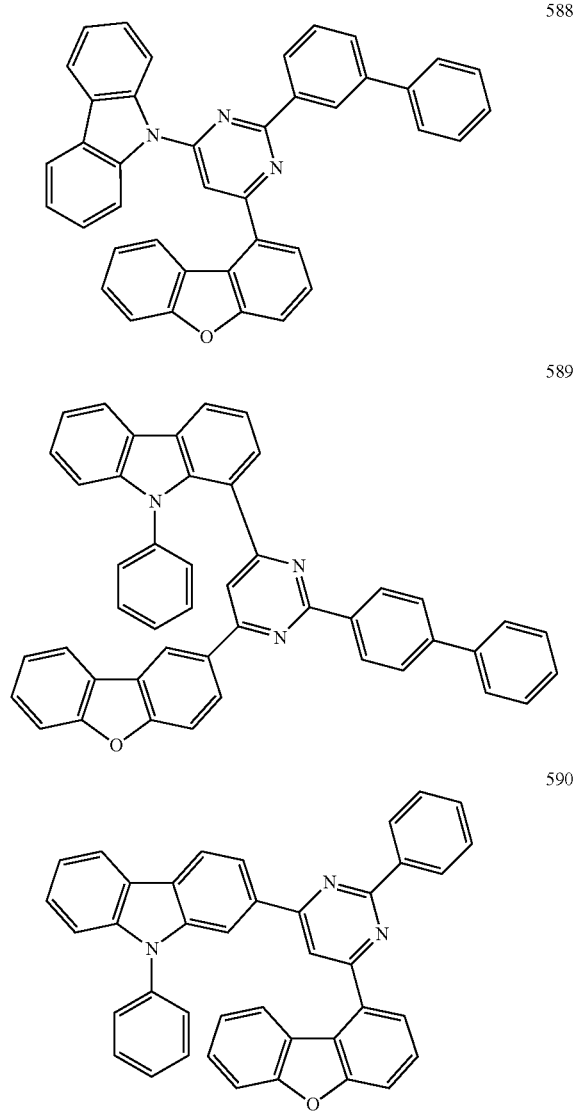
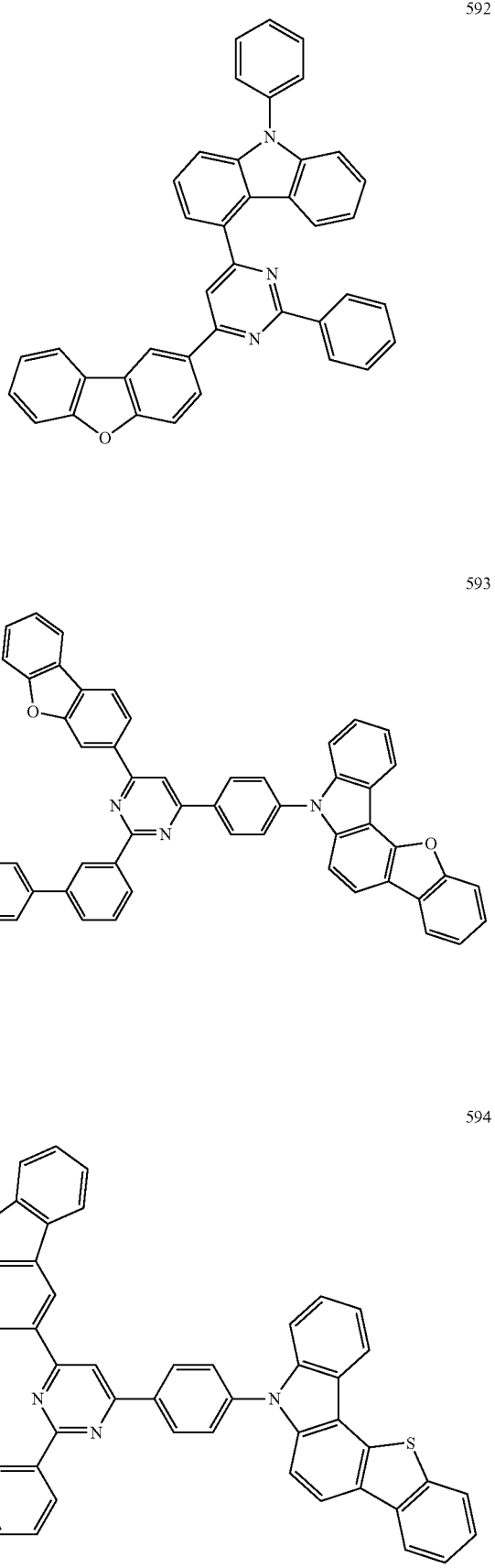

199
-continued
595
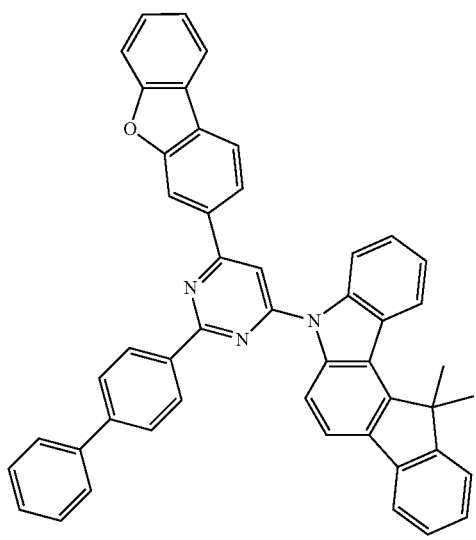
596
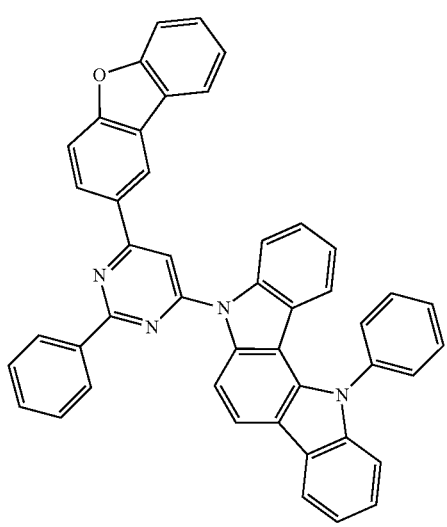
597
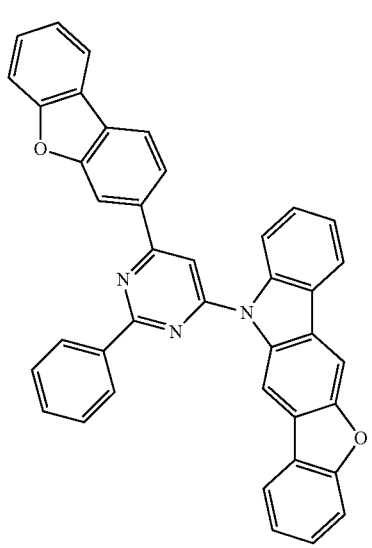
200
-continued
598
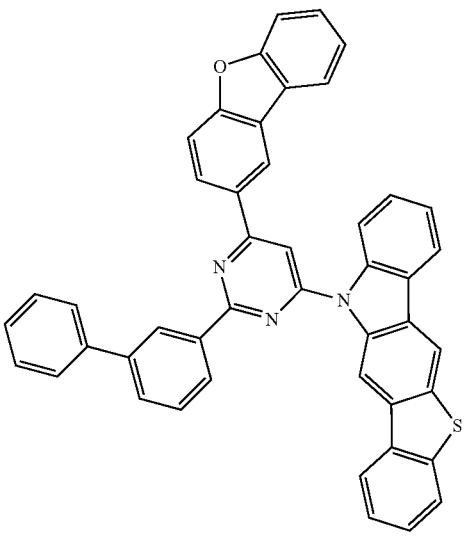
599
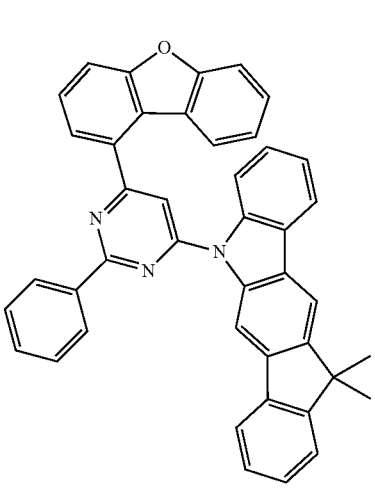
600
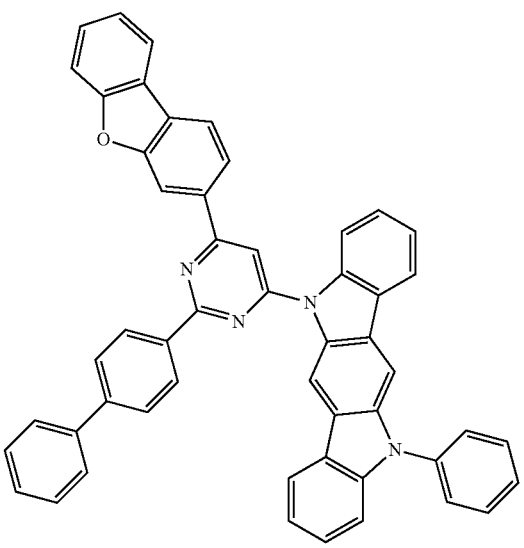

-continued
601
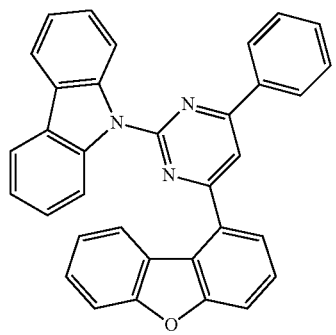
602
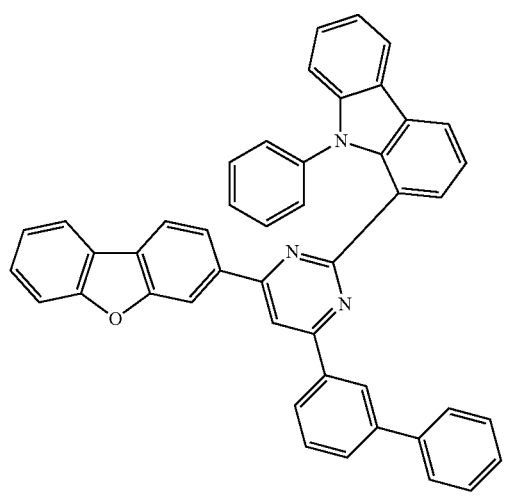
603
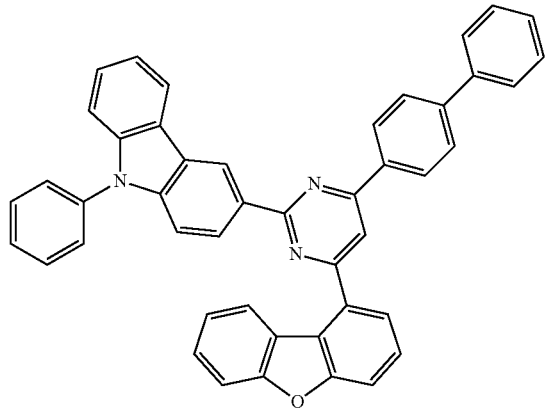
-continued
604
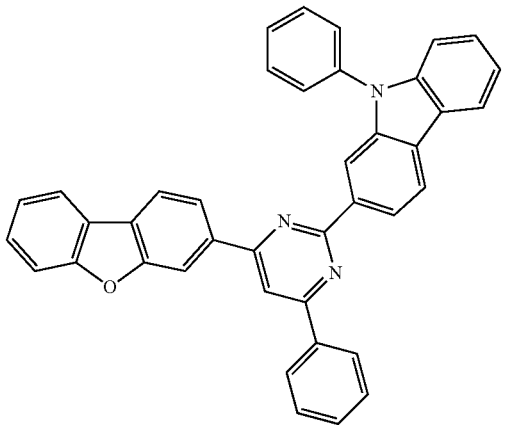
605
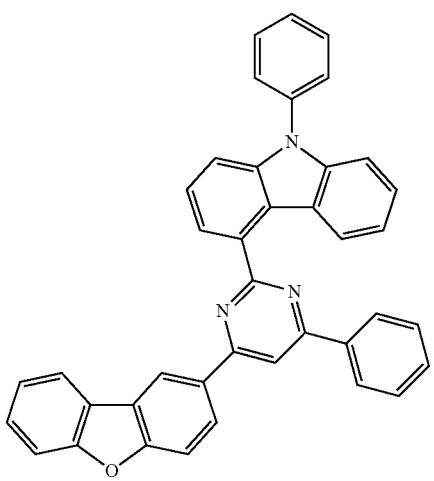
606
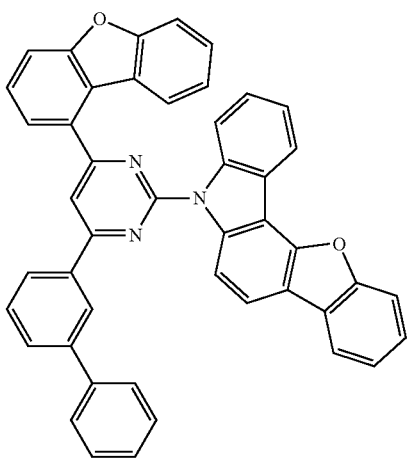

203
-continued
607
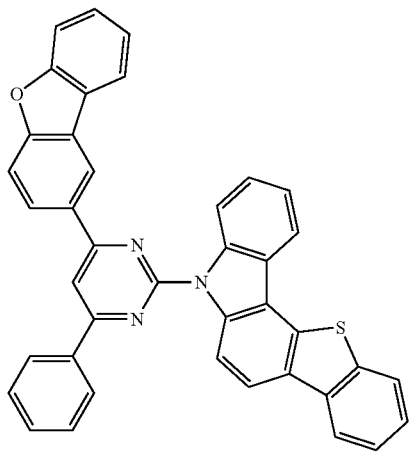
608
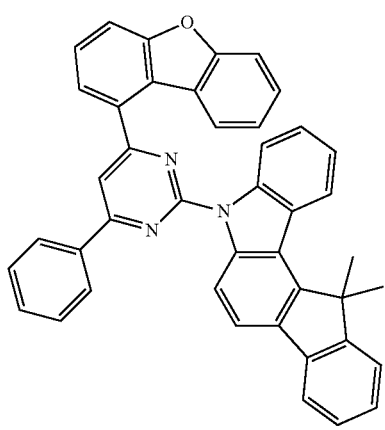
609
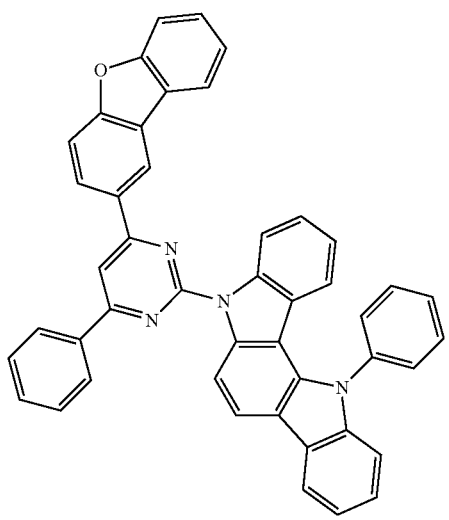
204
-continued
610
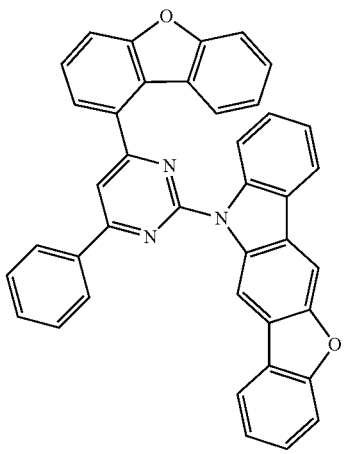
611
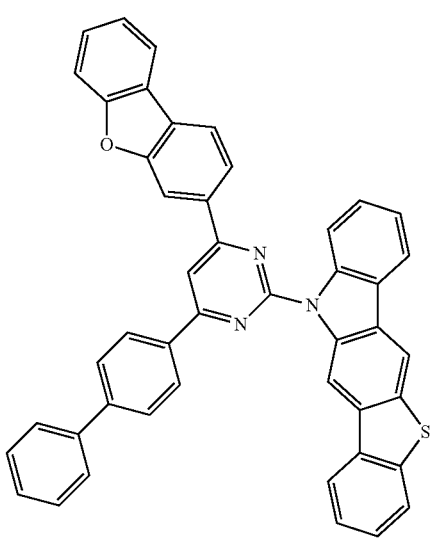
612
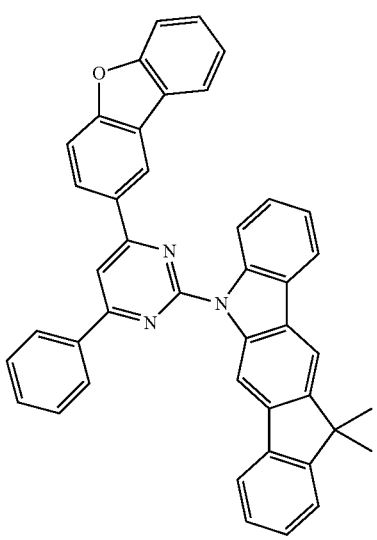

205
-continued
613
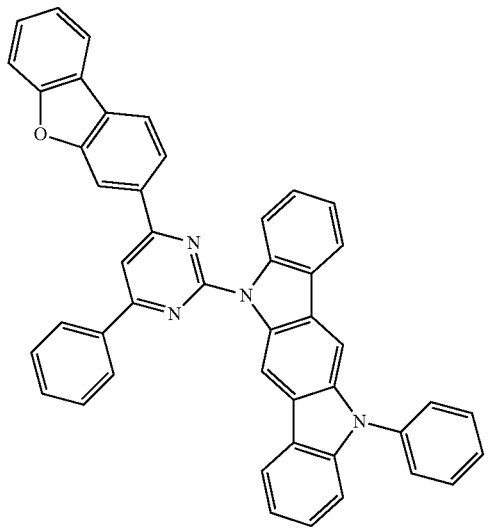
614
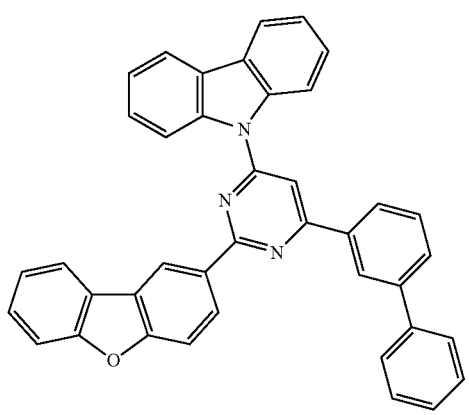
615
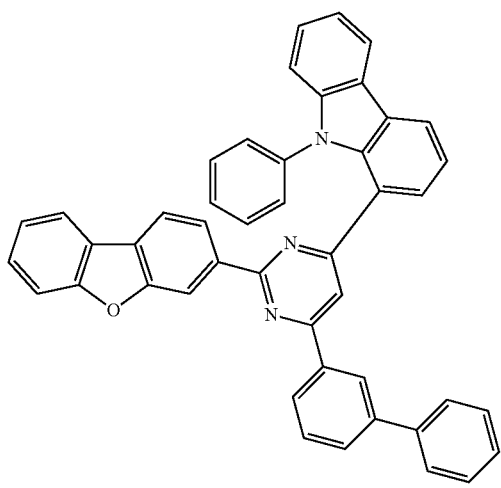
206
-continued
616
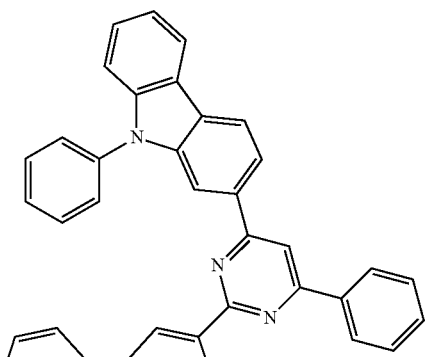
617
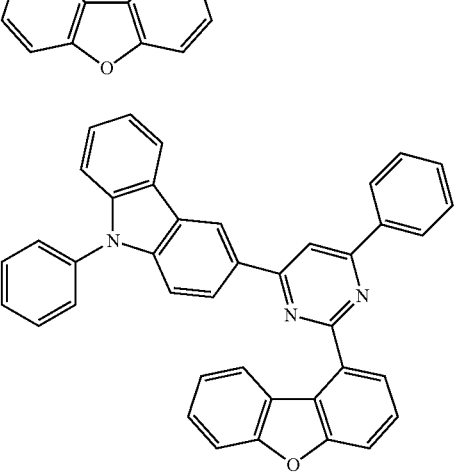
618
619
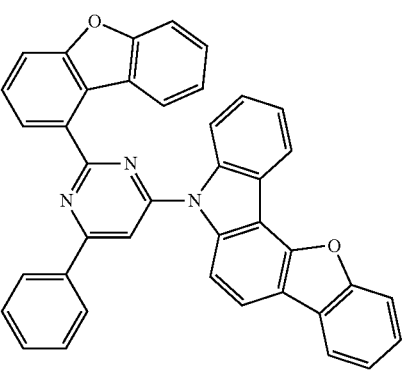

-continued
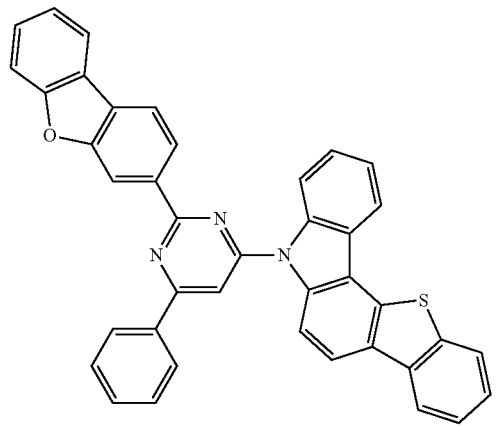
620
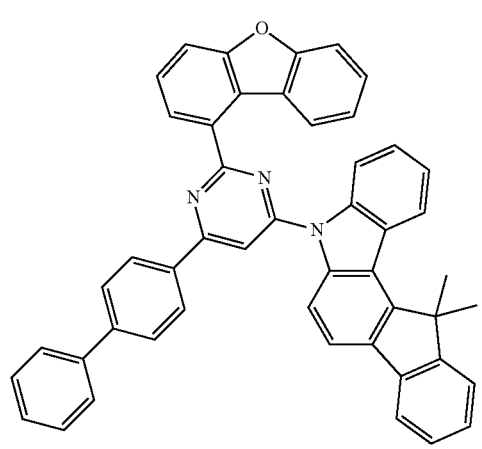
621
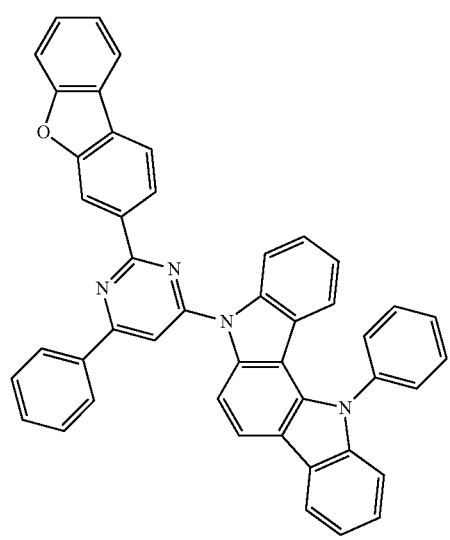
622
-continued
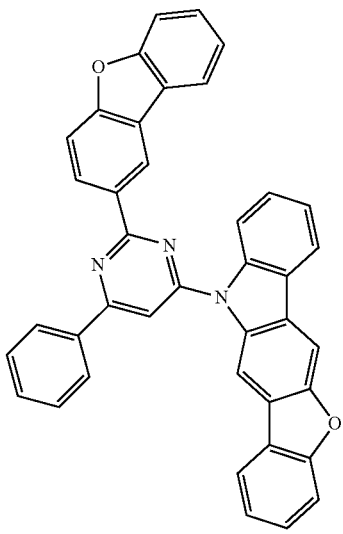
623
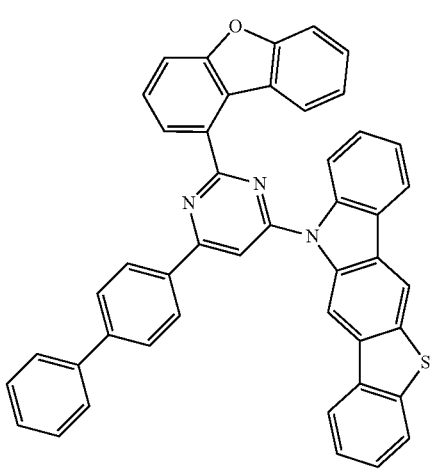
624
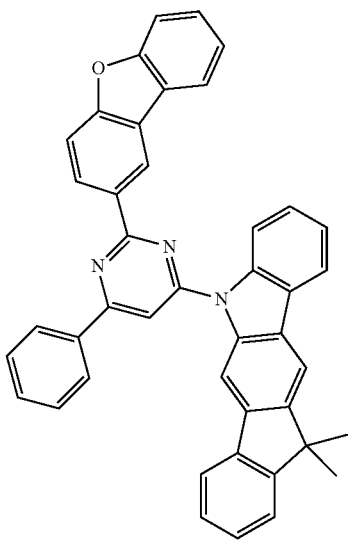
625

626
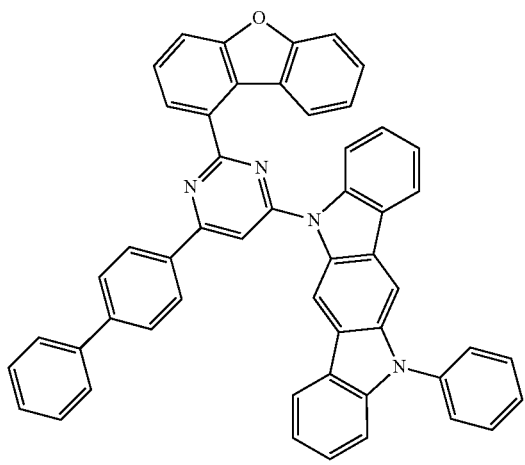
627
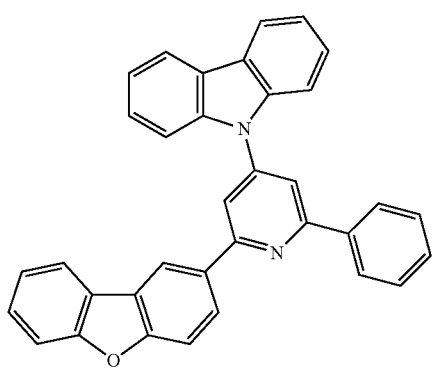
628
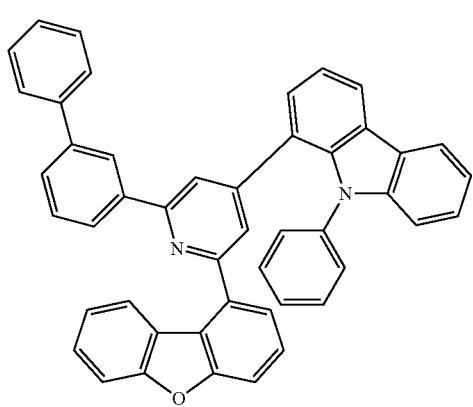
629
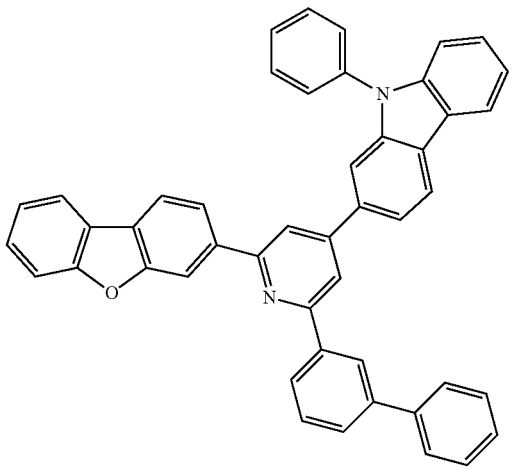
630
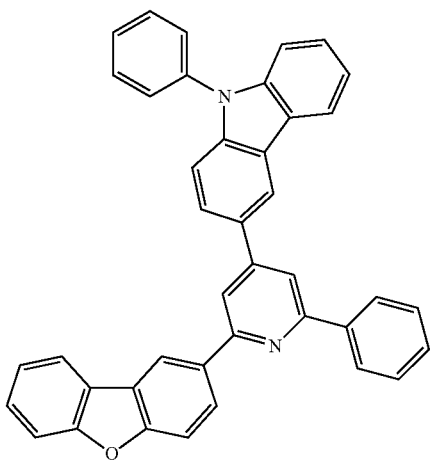
631
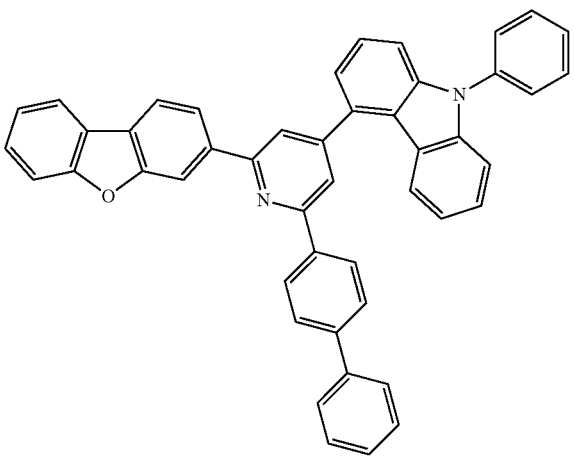

632
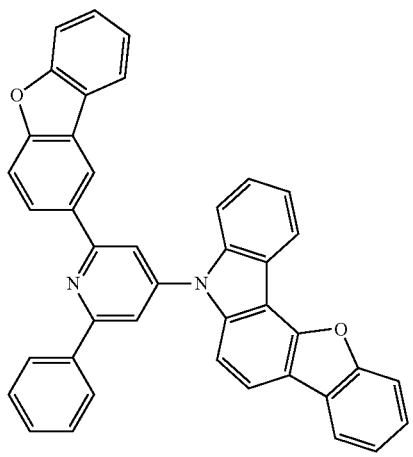
633
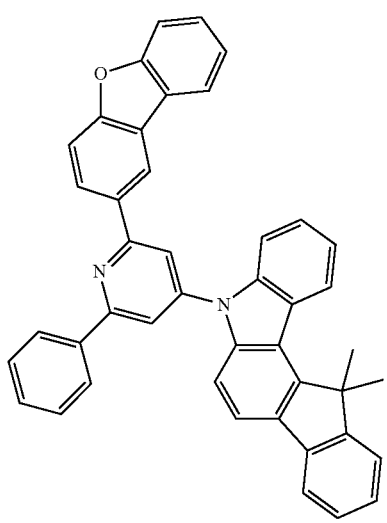
634
635
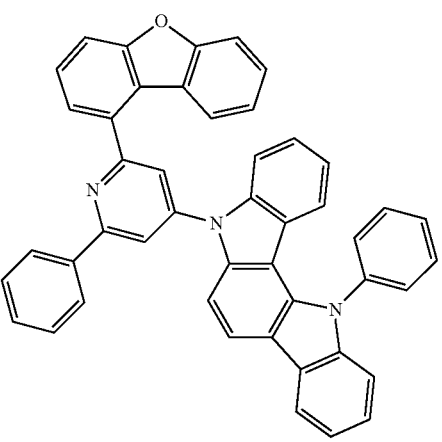
636
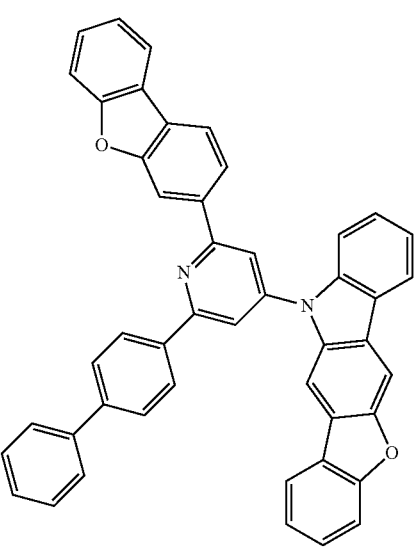
637
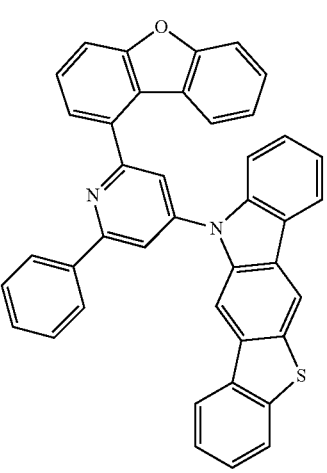

213
-continued
638
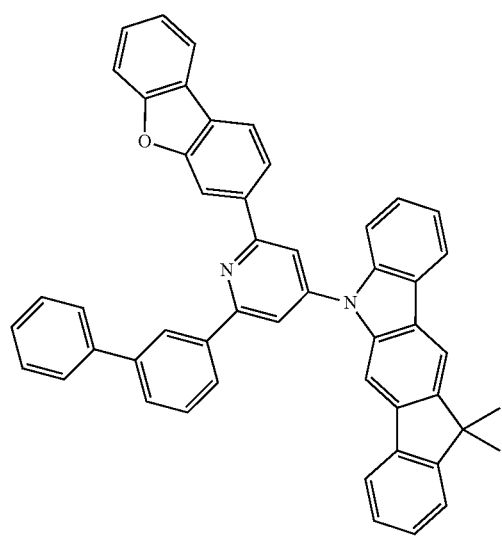
639
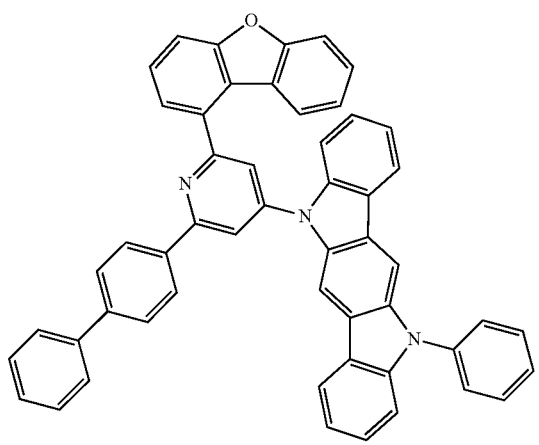
640
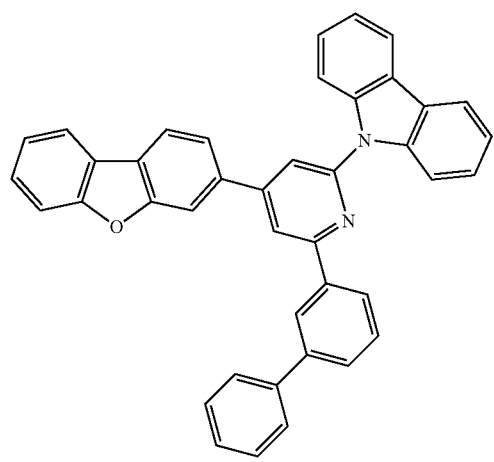
214
-continued
641
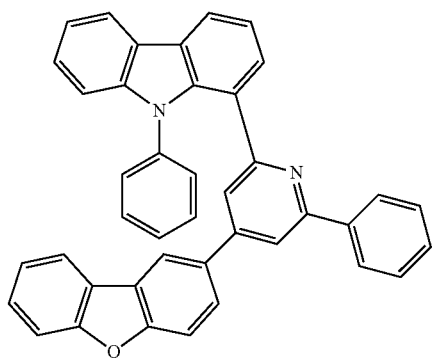
642
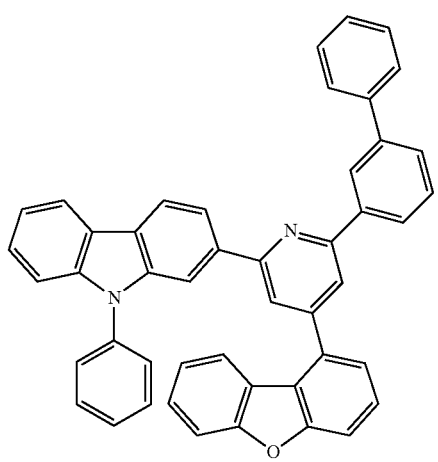
643
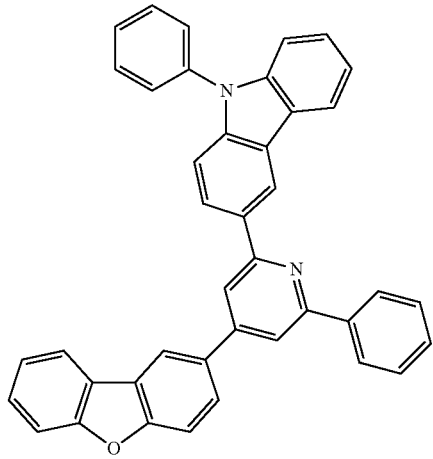

644
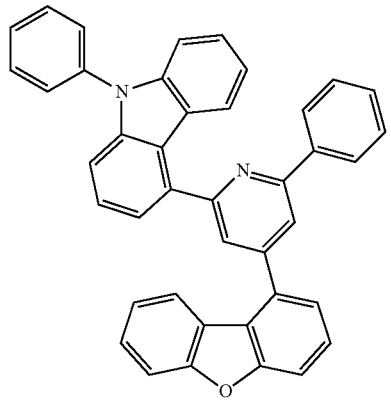
645
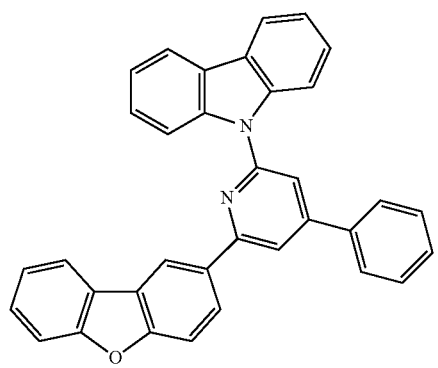
646
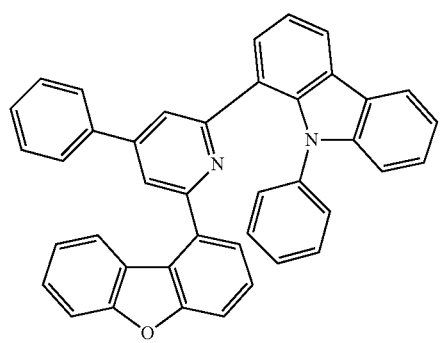
647
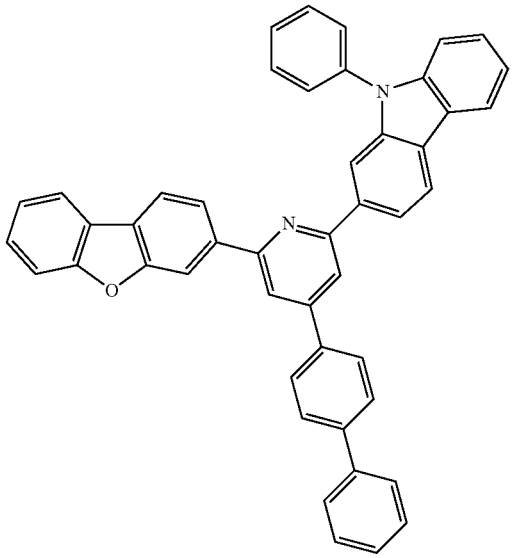
648
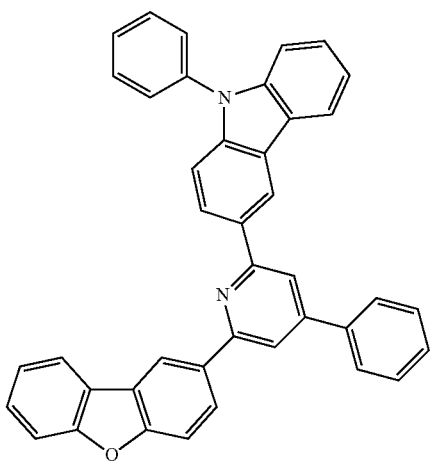
649
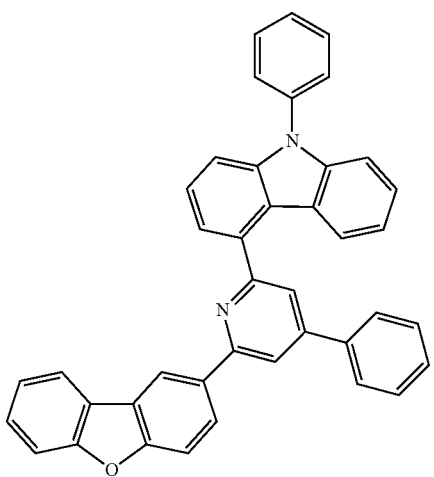

217
-continued
650
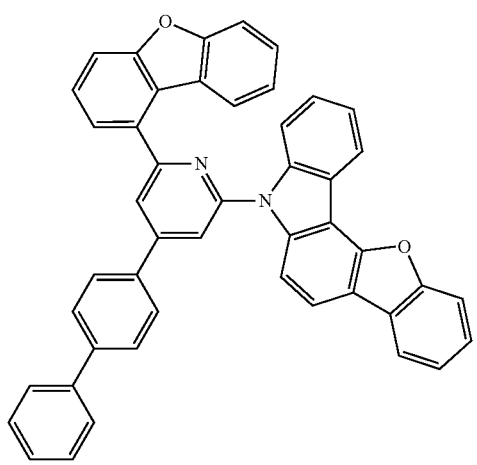
651
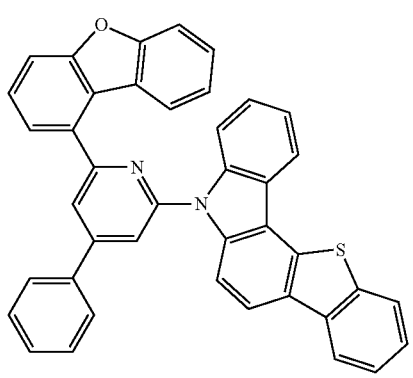
652
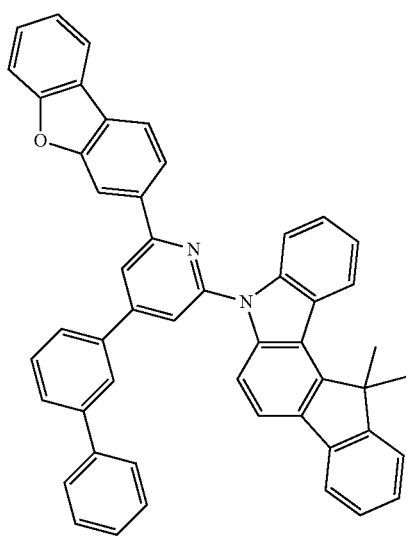
218
-continued
653
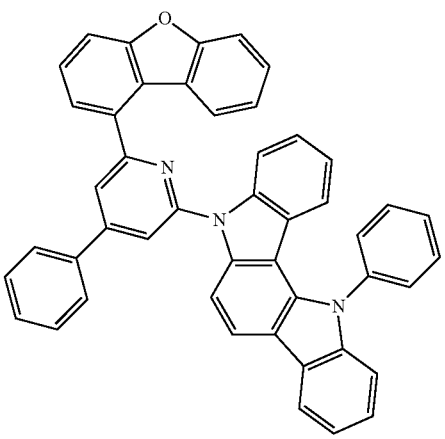
654
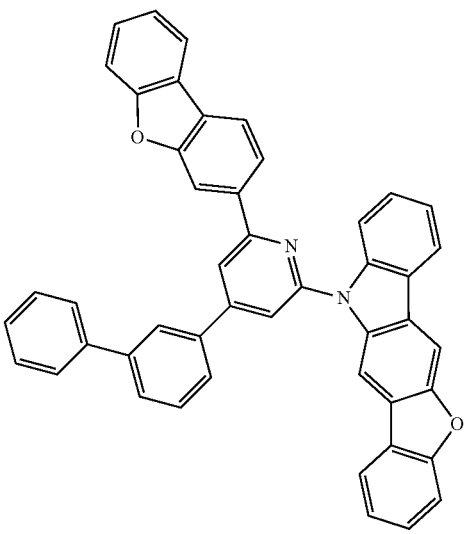
655
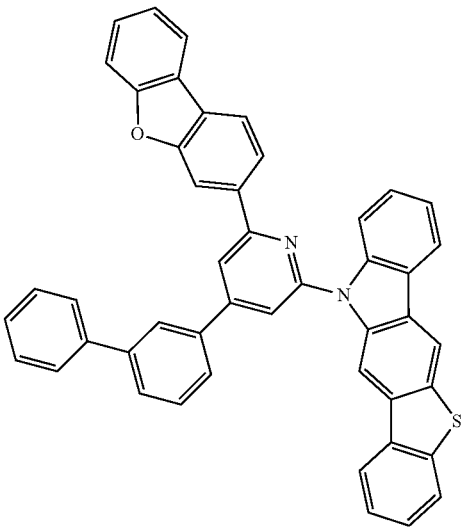

656
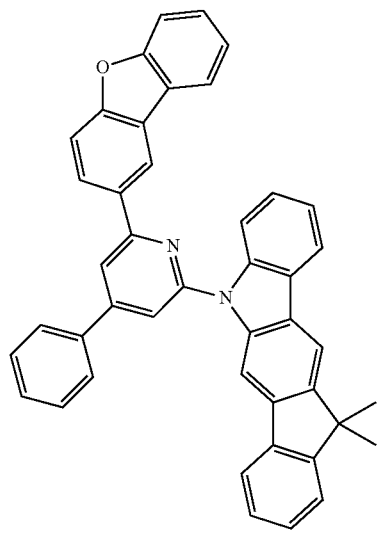
657
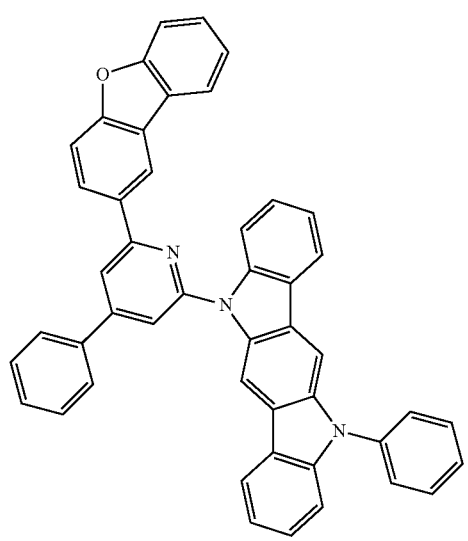
658
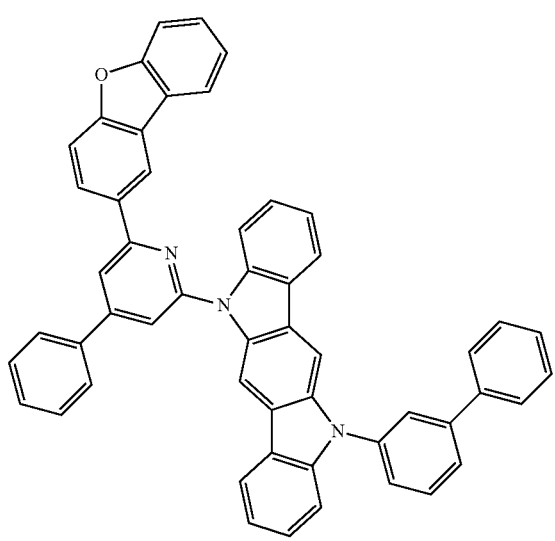
659
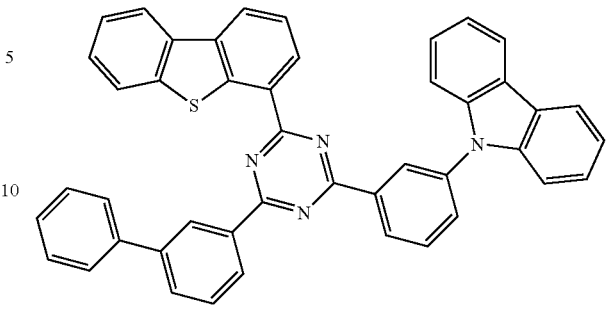
660
661
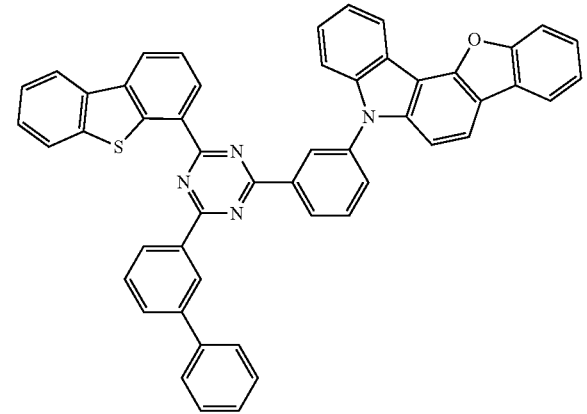

221
-continued
662
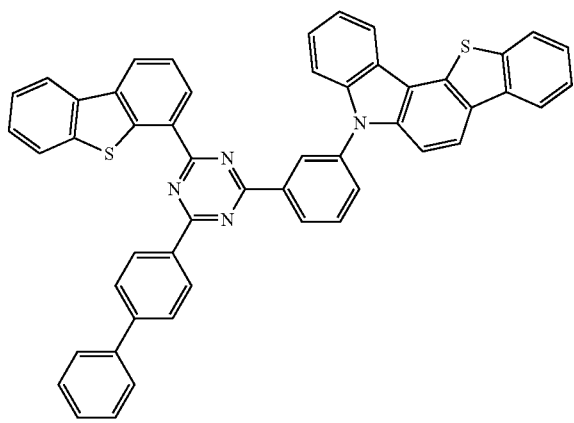
663
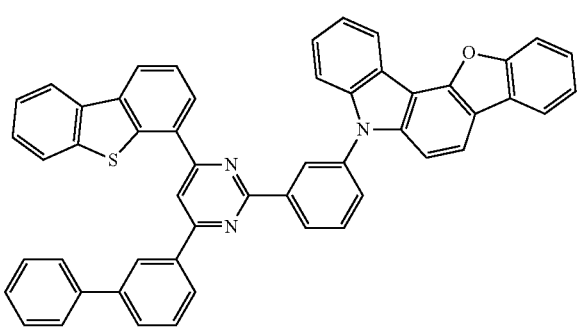
664
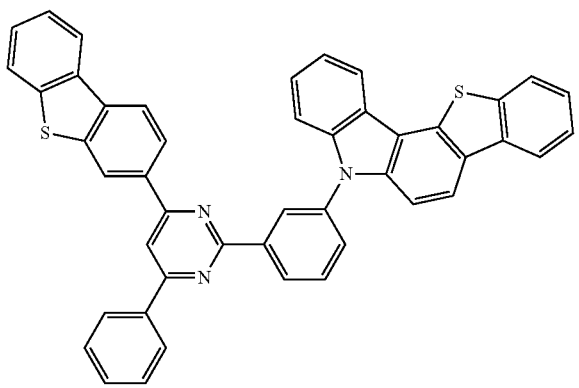
665
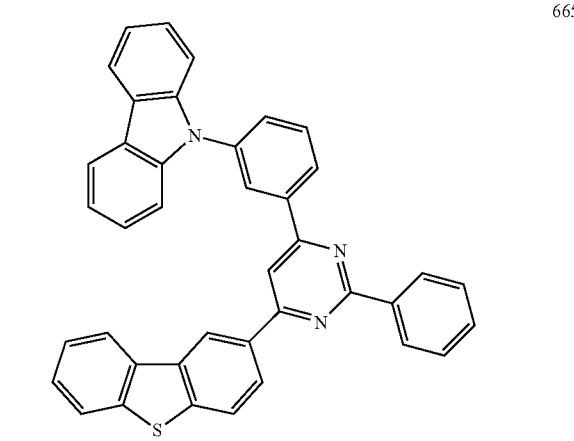
222
-continued
666
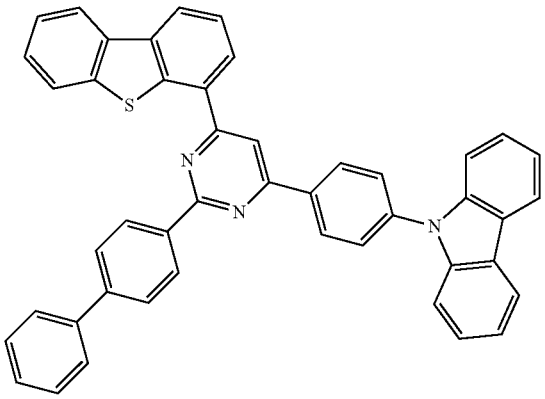
667
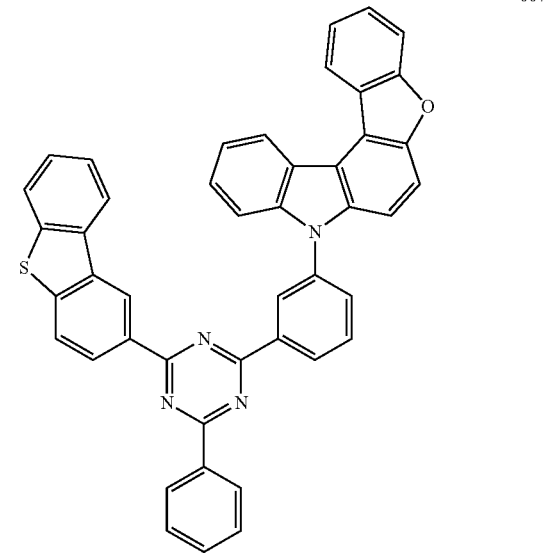
668
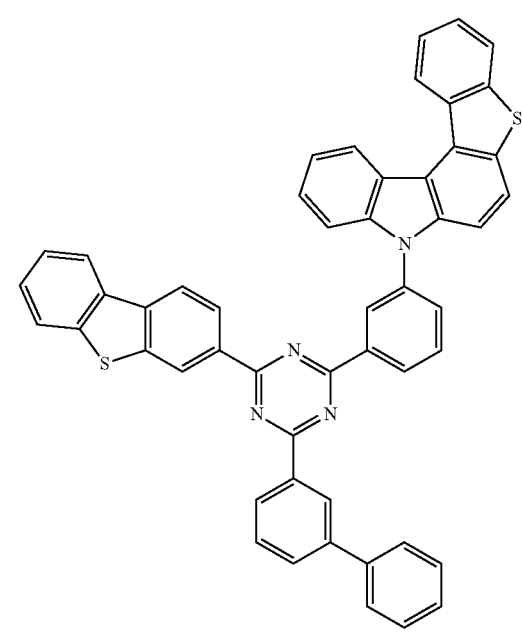

-continued
669
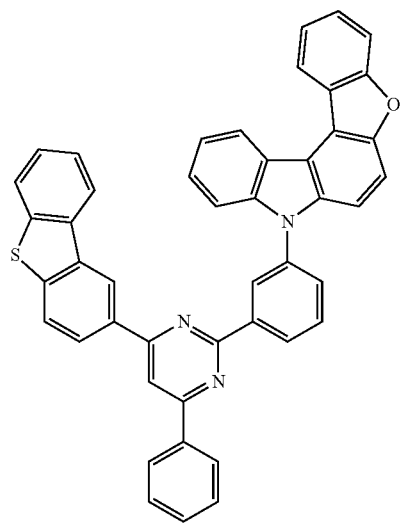
670
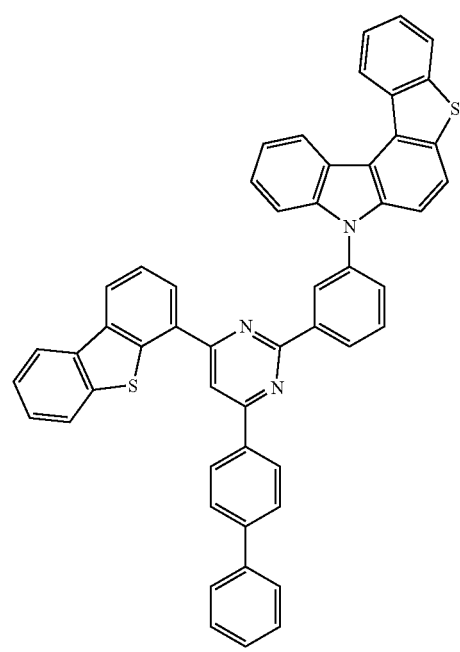
671
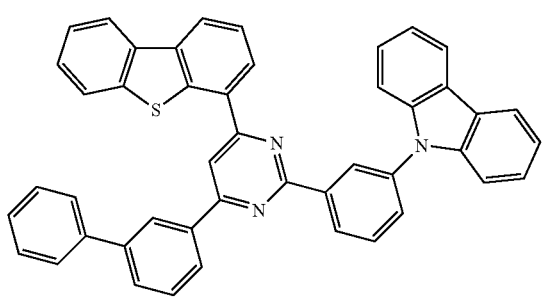
-continued
672
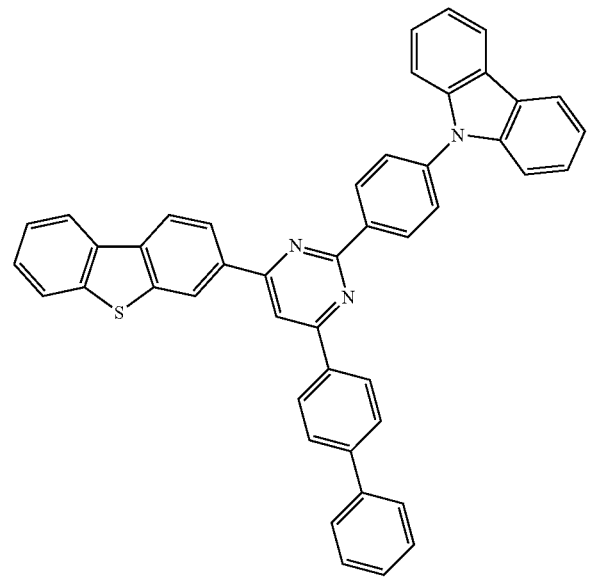
673
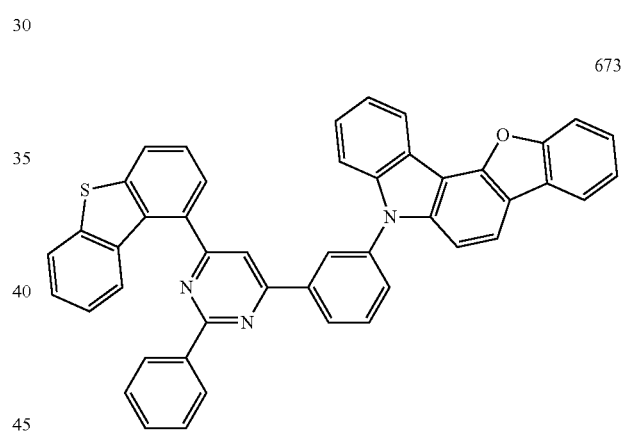
674
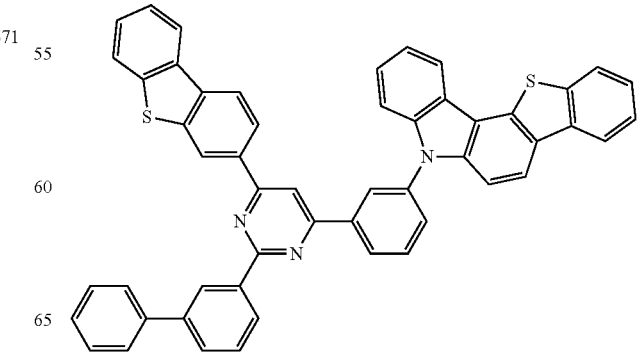

225
-continued
675
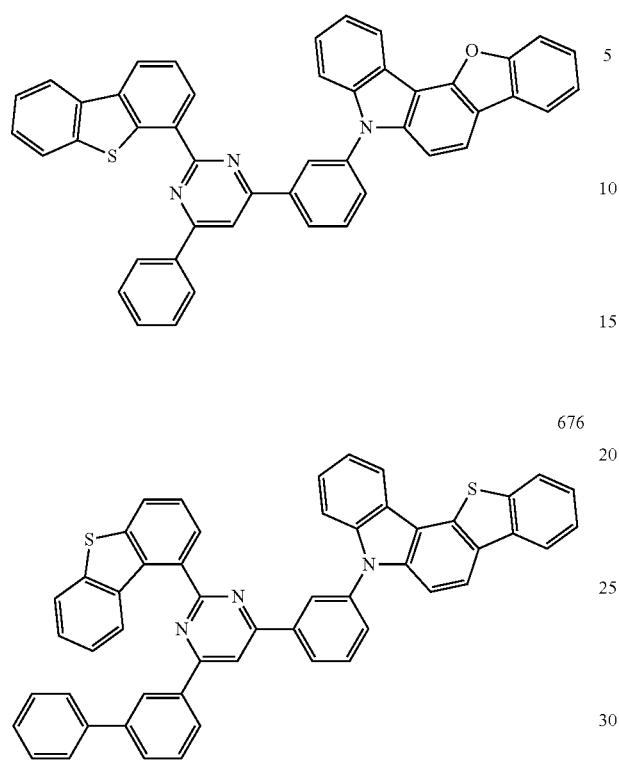
676
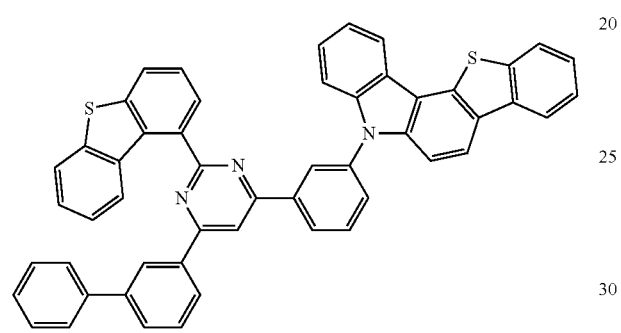
677
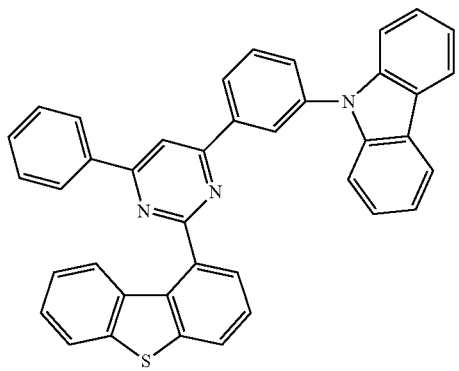
678
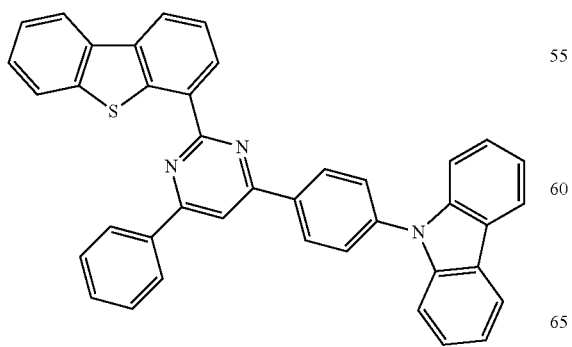
226
-continued
679
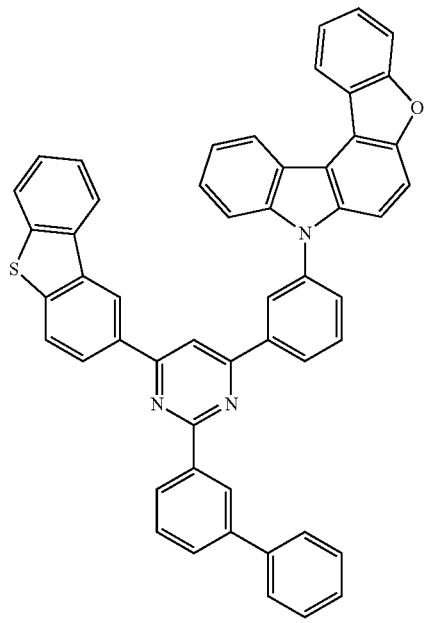
680
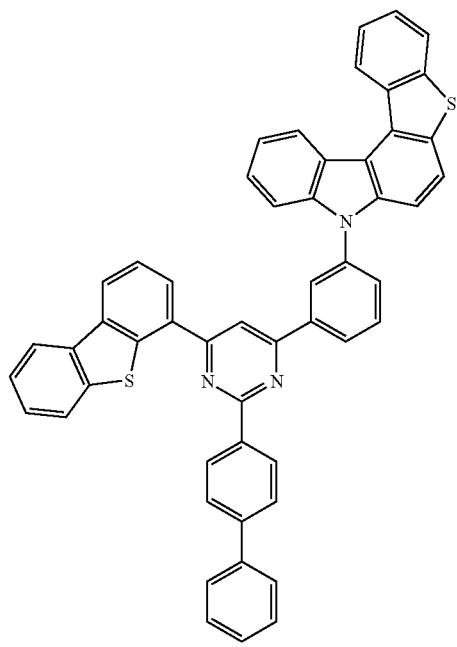

681
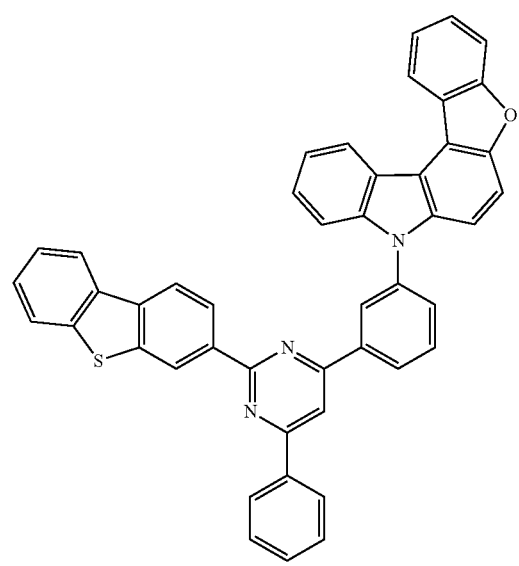
682
684
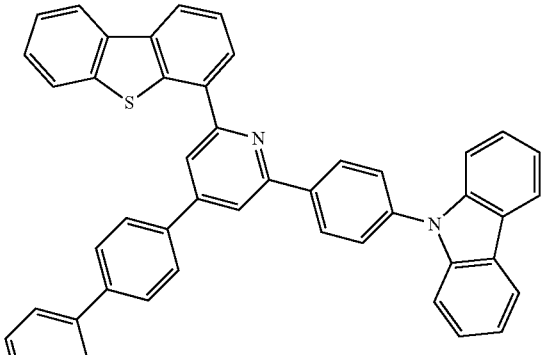
685
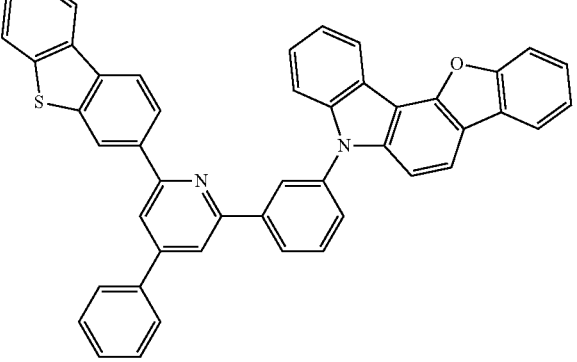
686
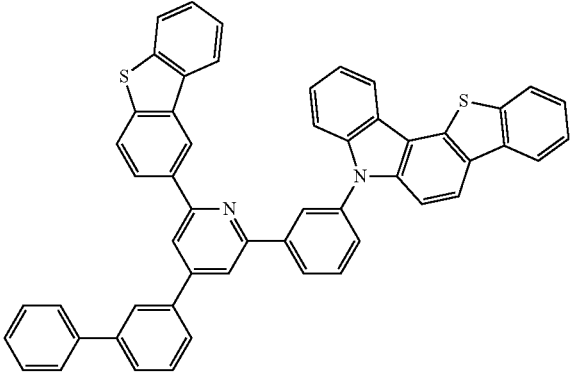
683
687
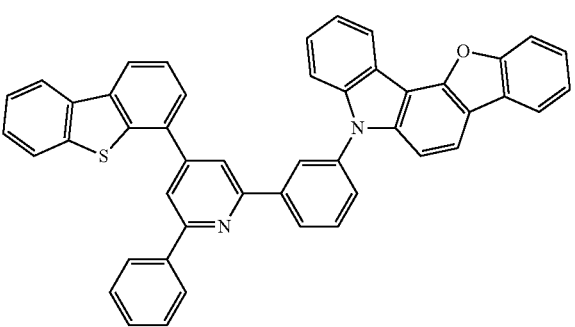

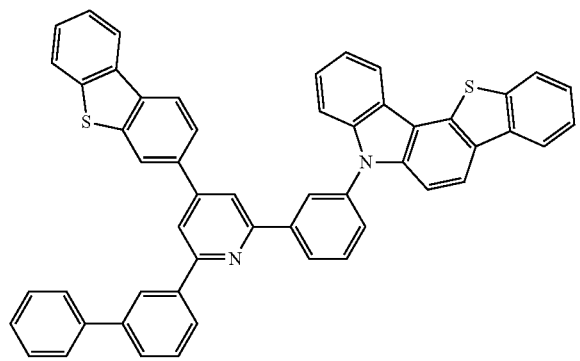
688
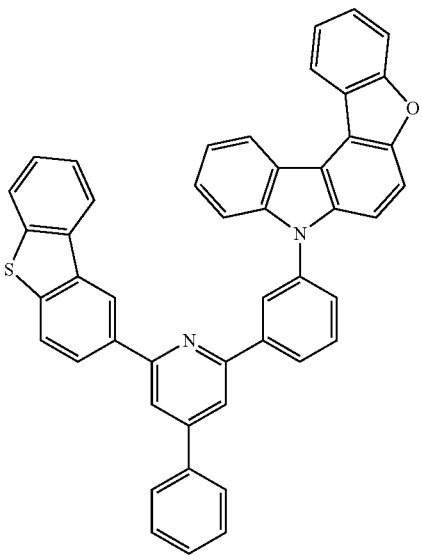
691
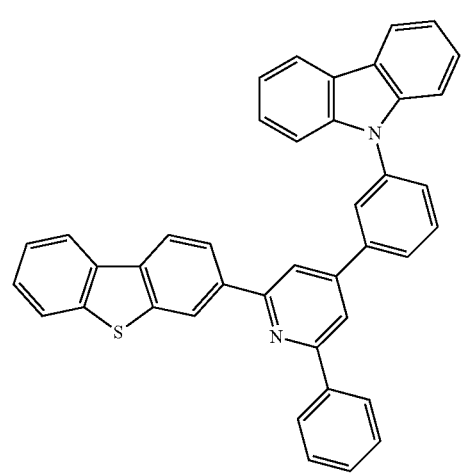
689
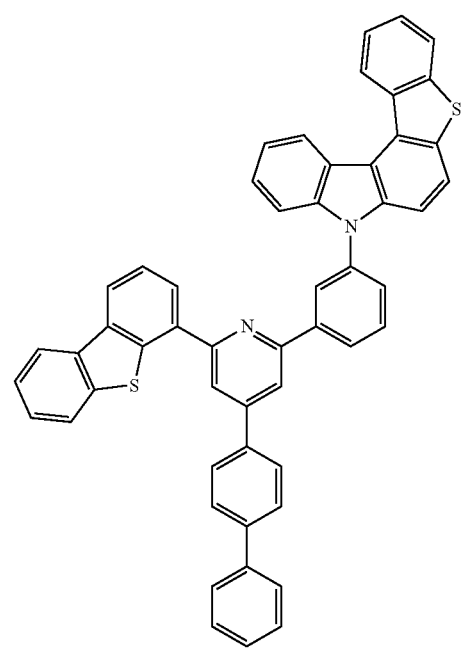
692
690

231
-continued
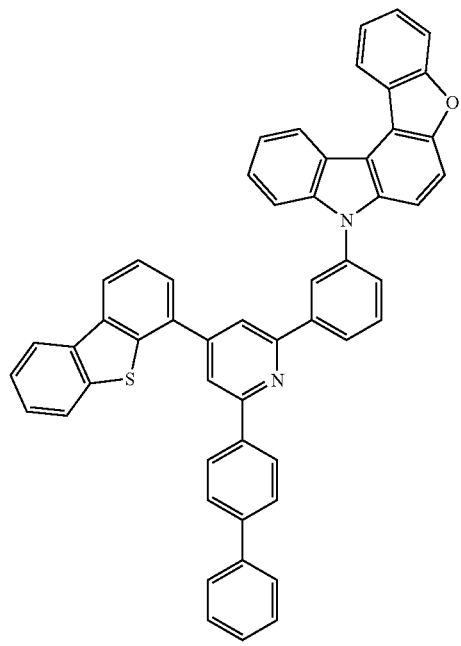
693
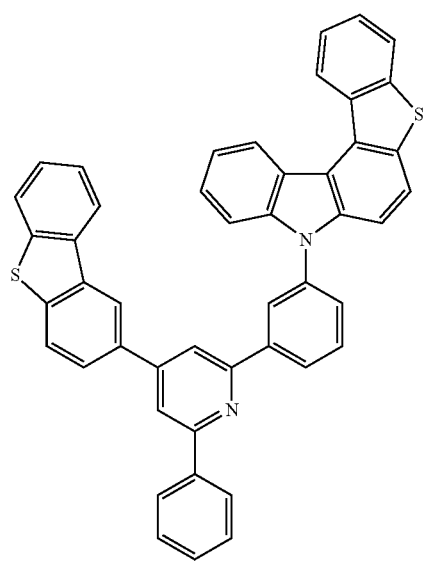
694
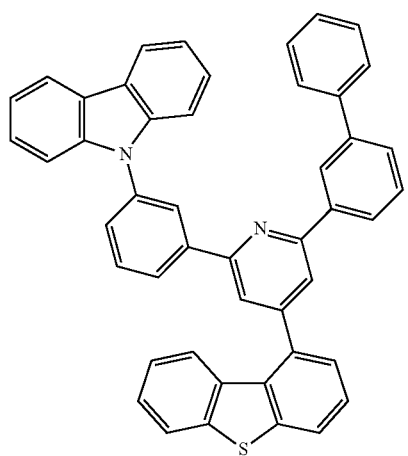
695
232
-continued
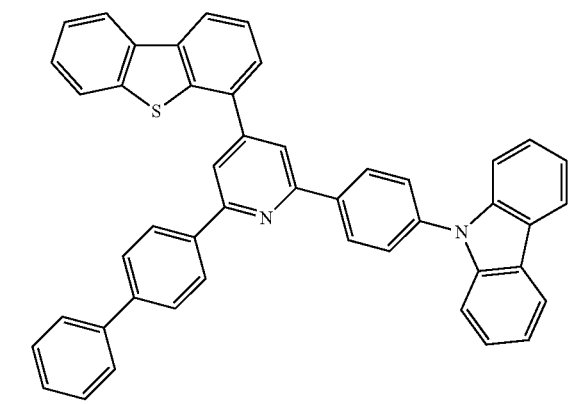
696
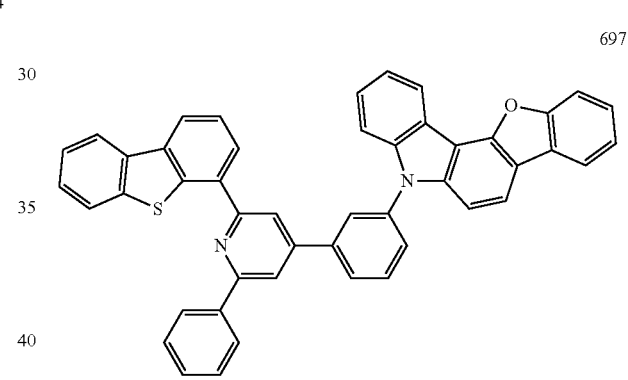
697
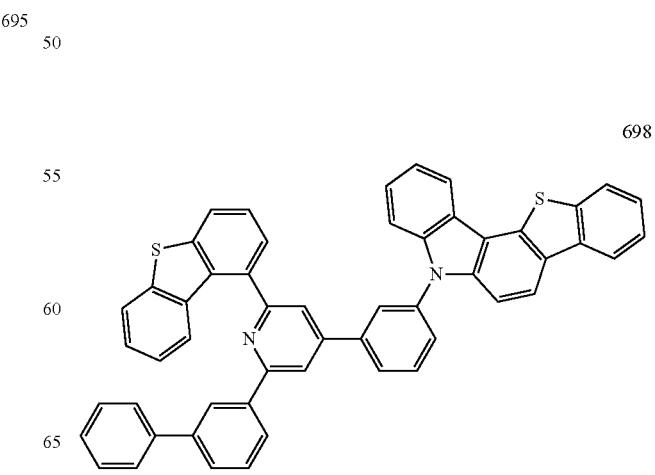
698

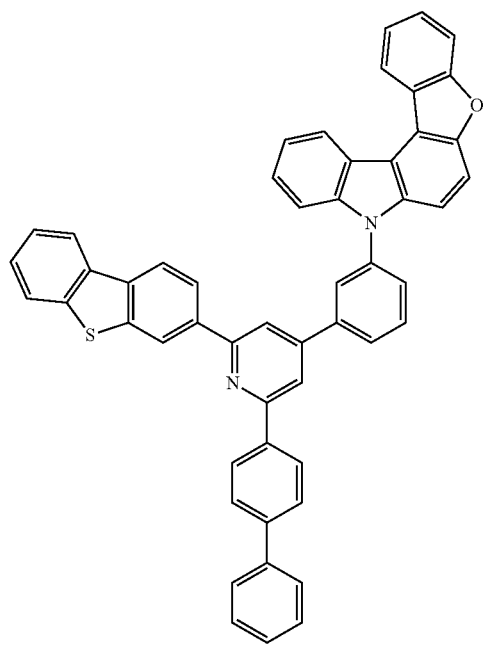
699
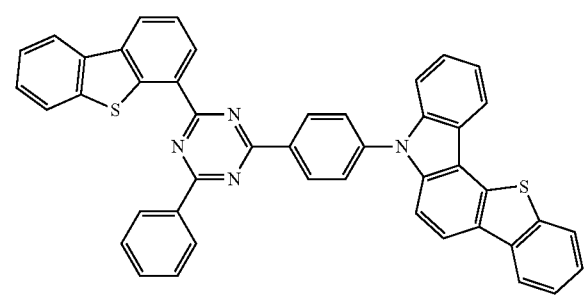
702
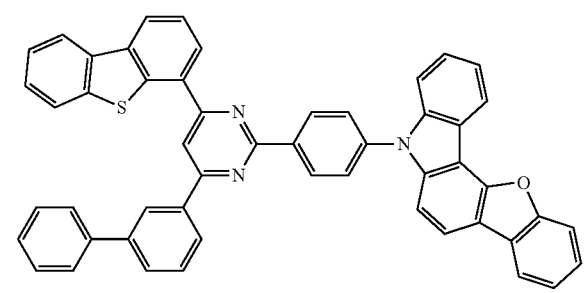
703
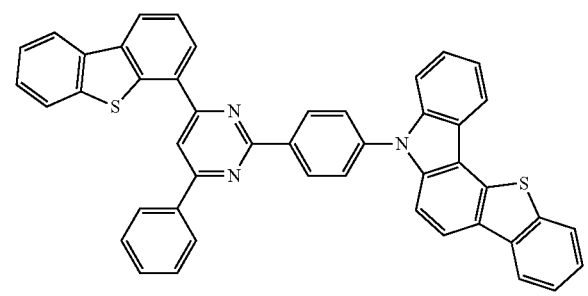
704
700
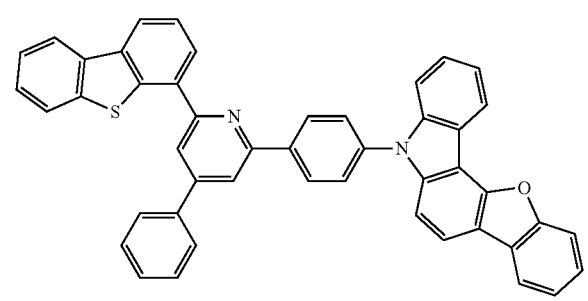
705
701

706
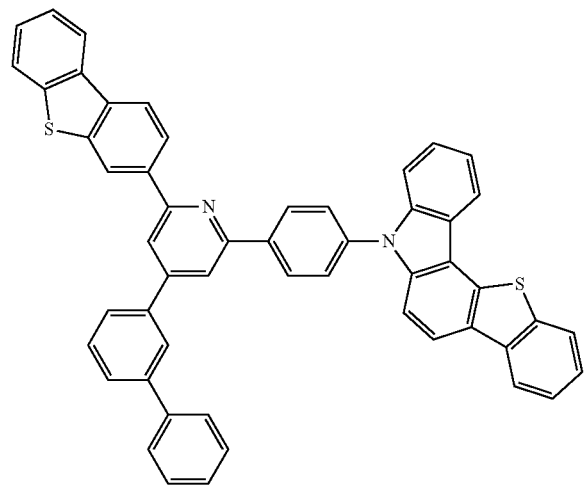
707
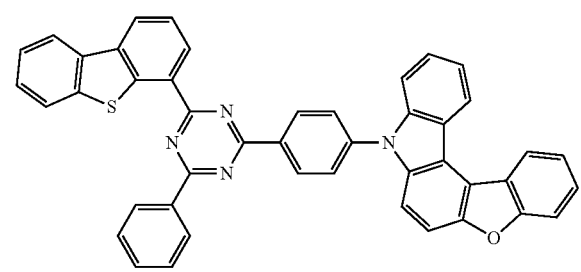
708
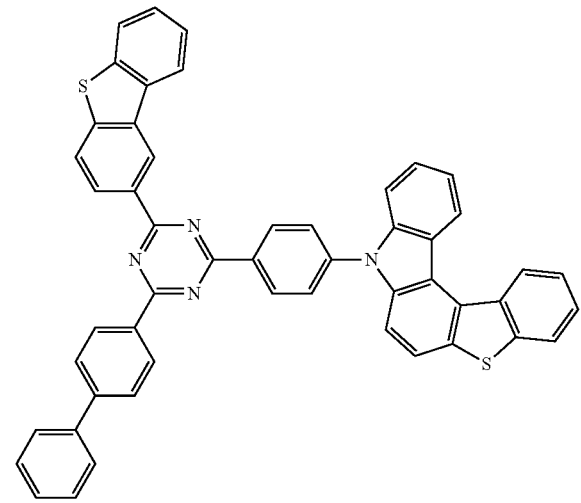
709
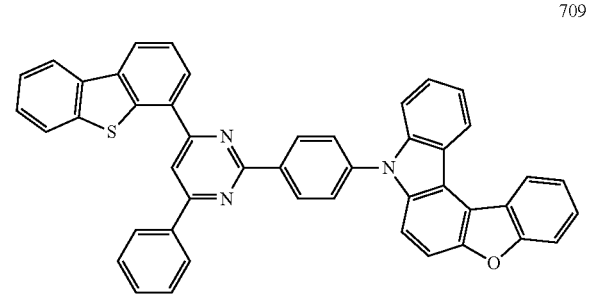
710
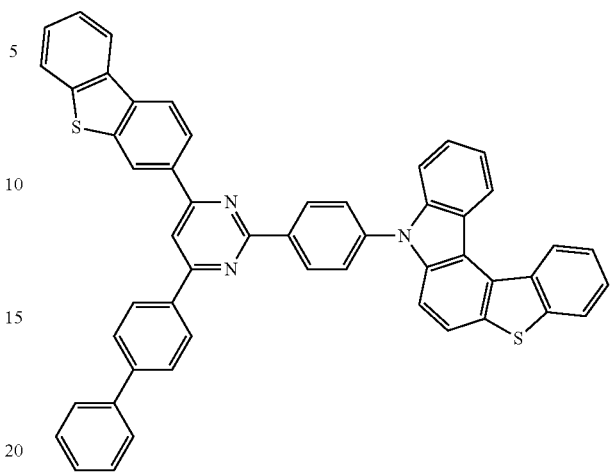
711
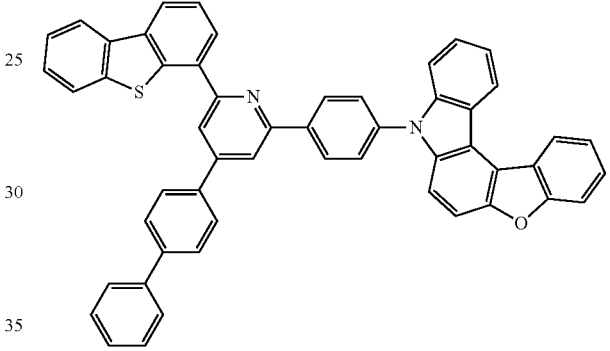
712
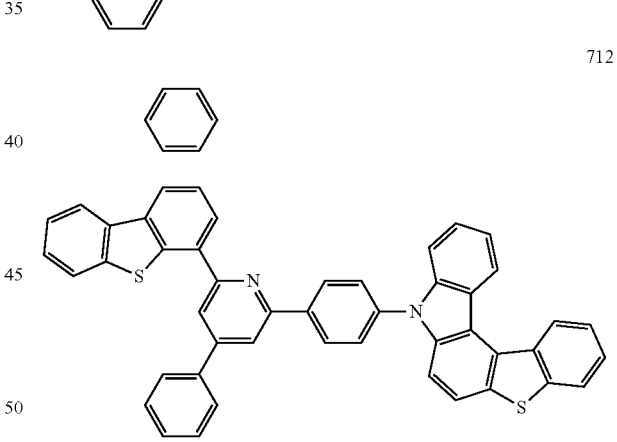
713
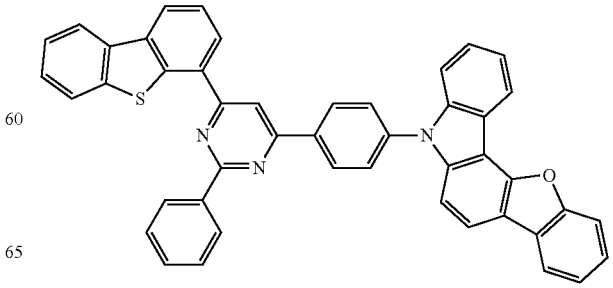

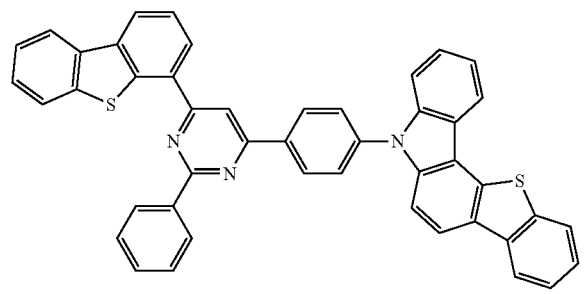
714
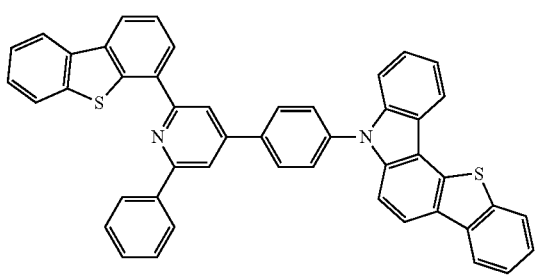
718
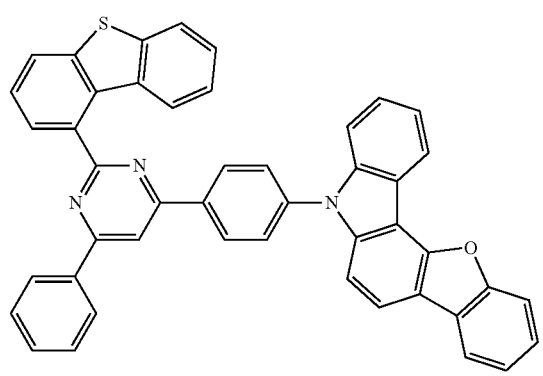
715
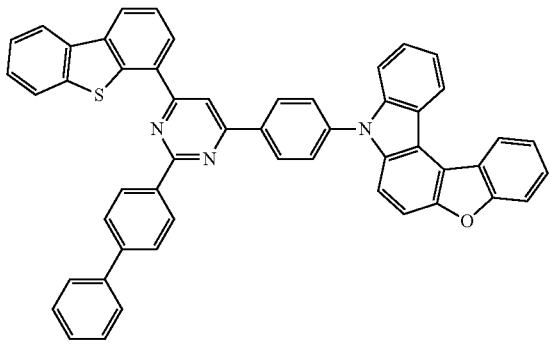
719
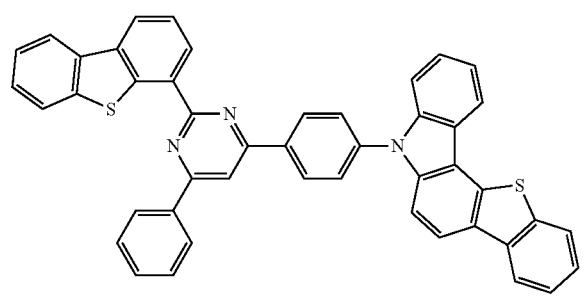
716
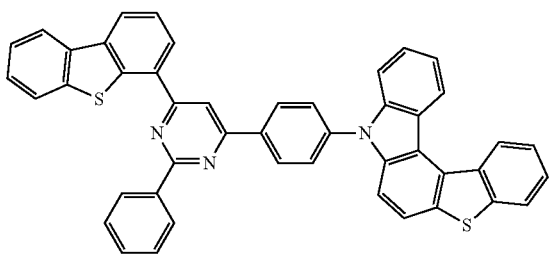
720
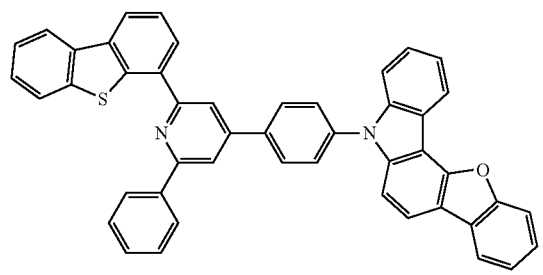
717
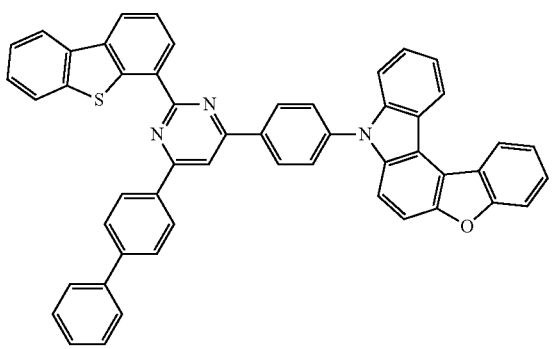
721

239
-continued
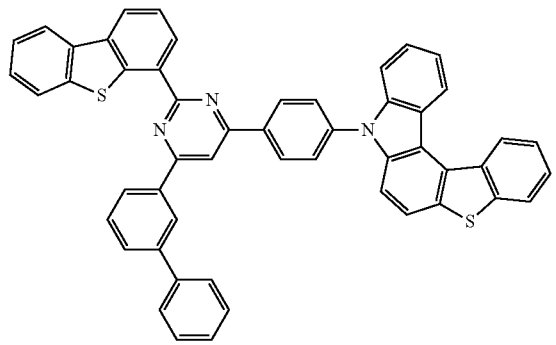
722
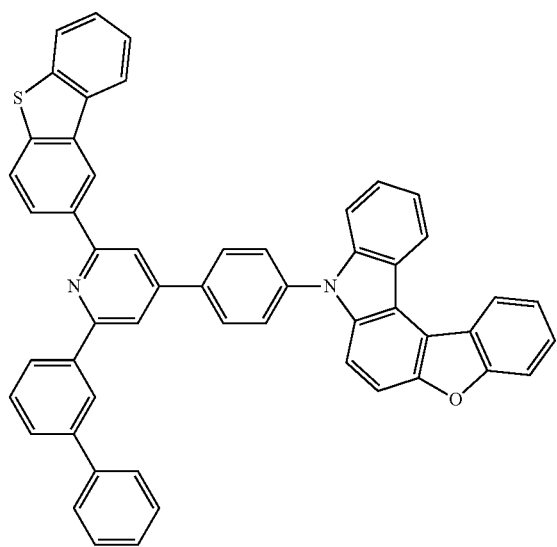
723
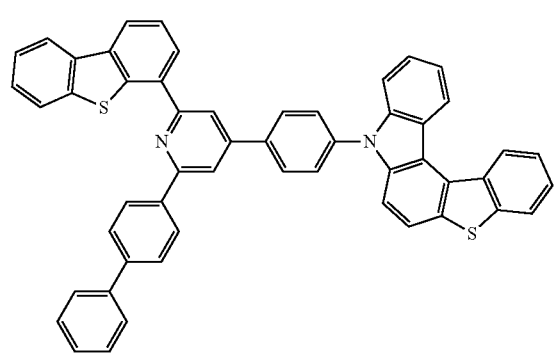
724
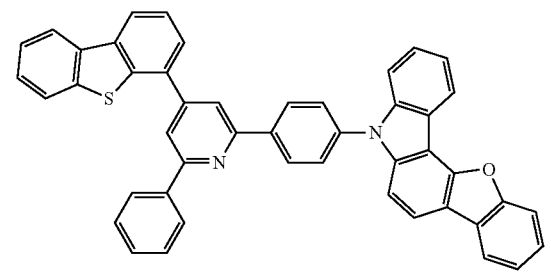
725
240
-continued
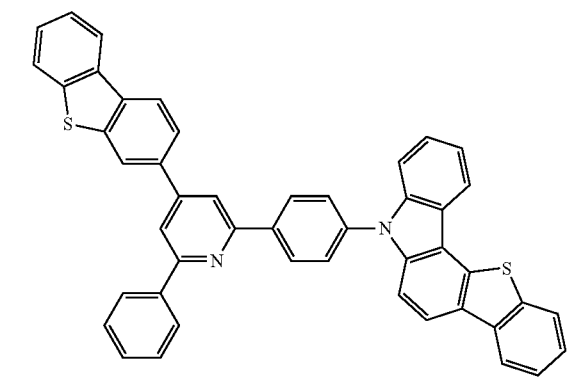
726
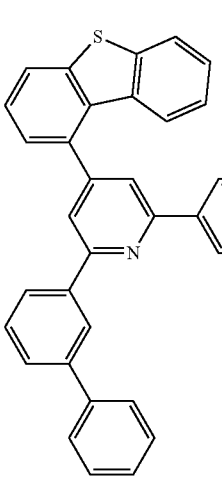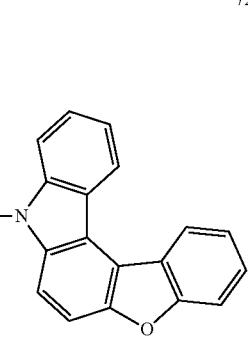
727
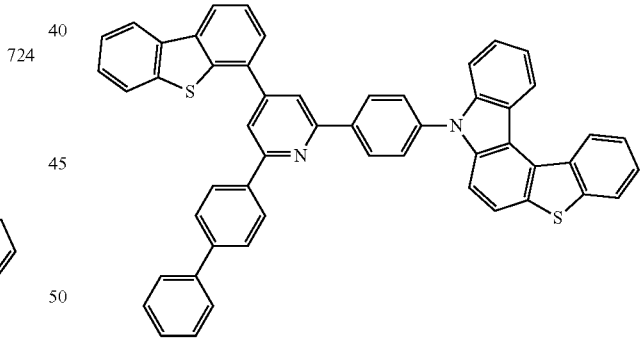
728
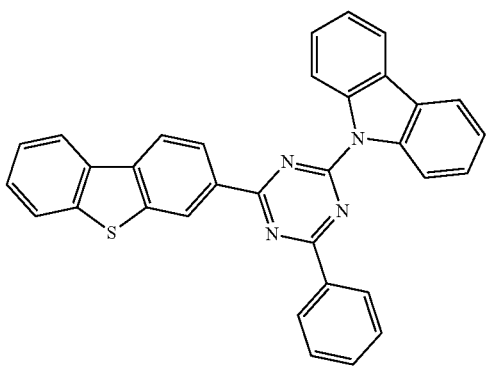
729

730
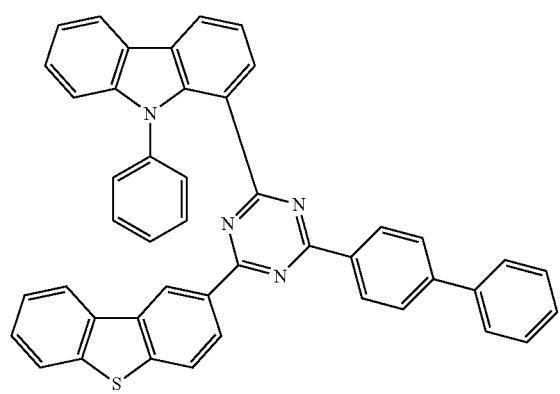
731
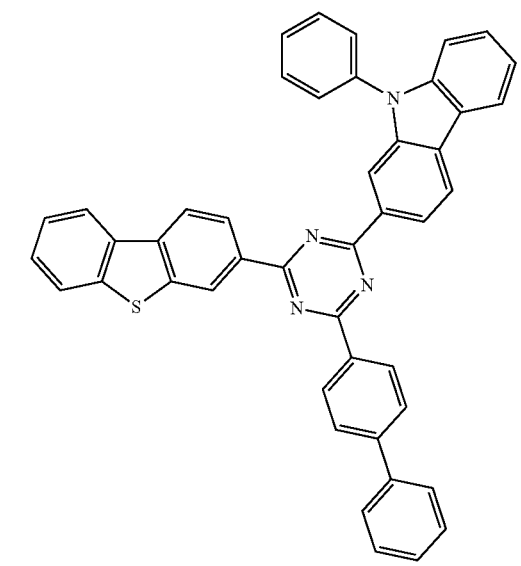
732
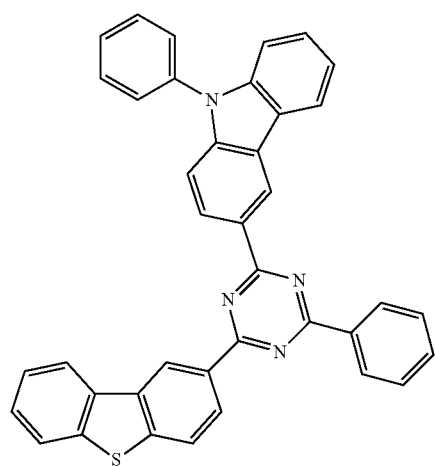
733
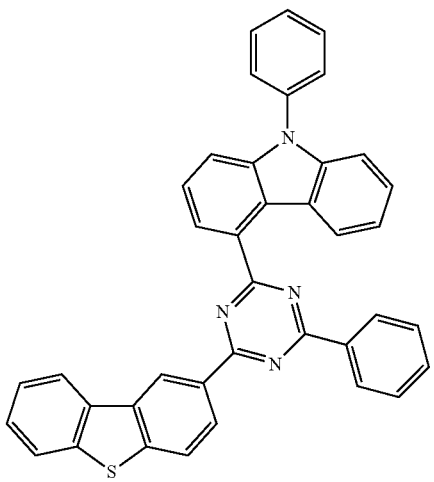
734
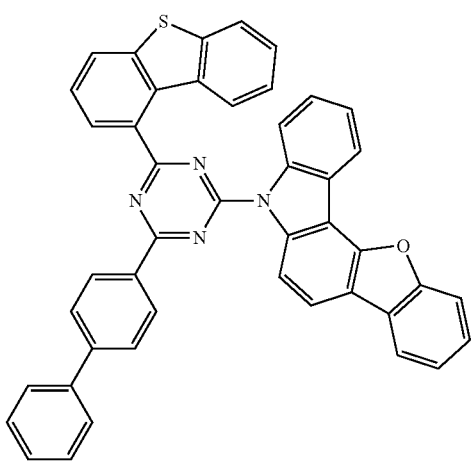
735
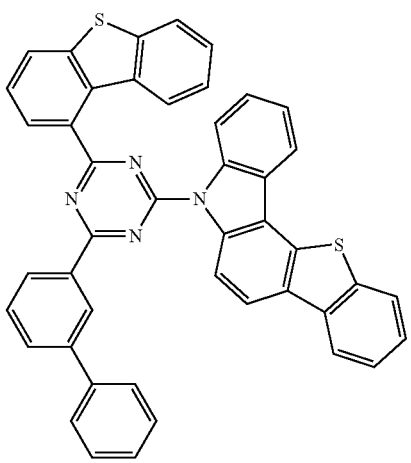

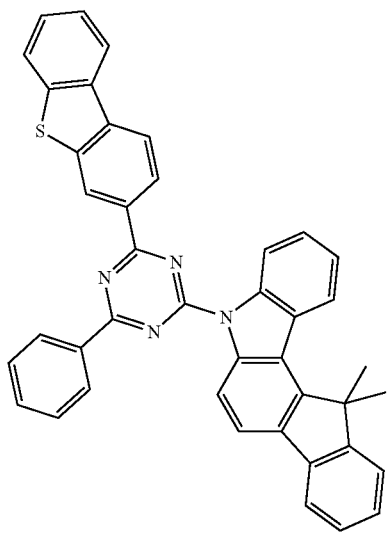
736
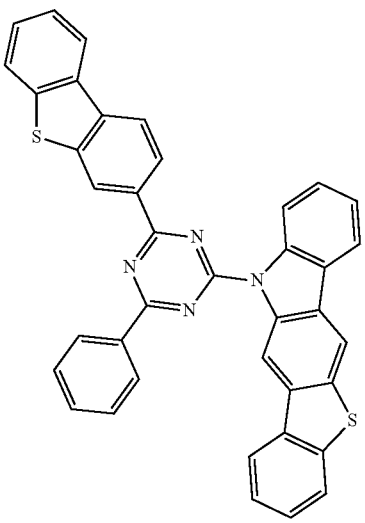
739
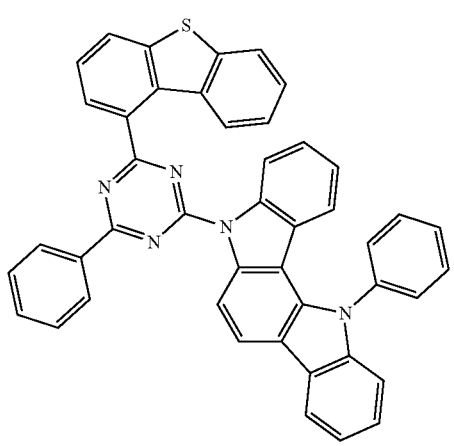
737
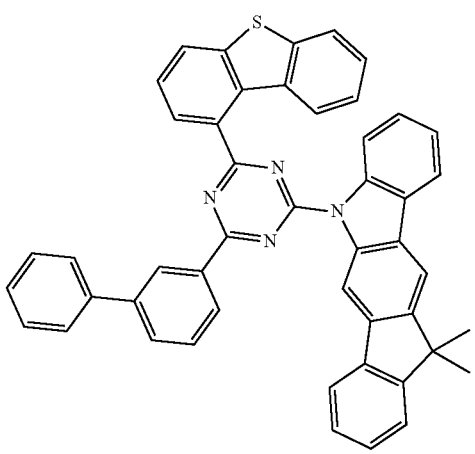
740
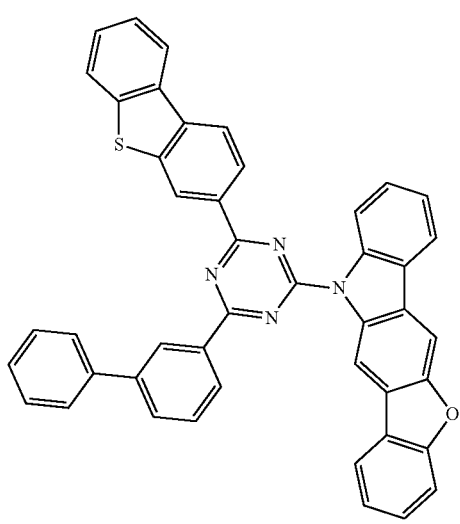
738
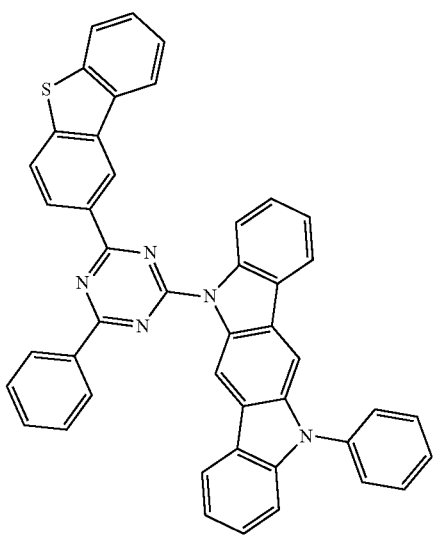
741

-continued
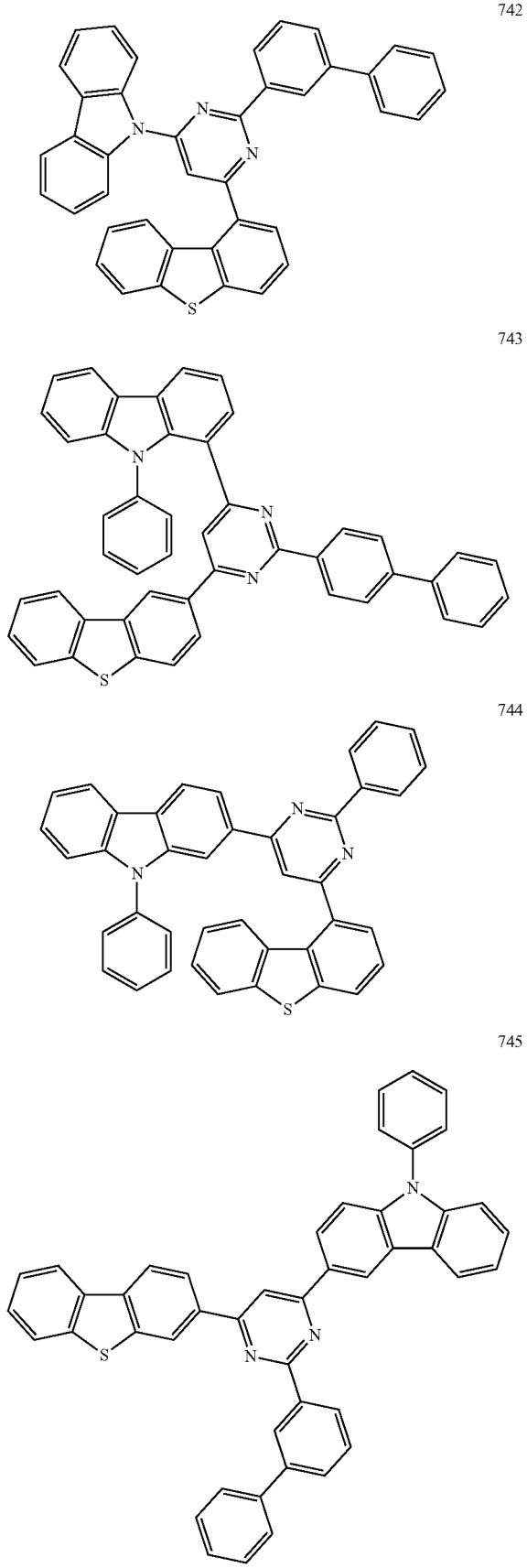
-continued
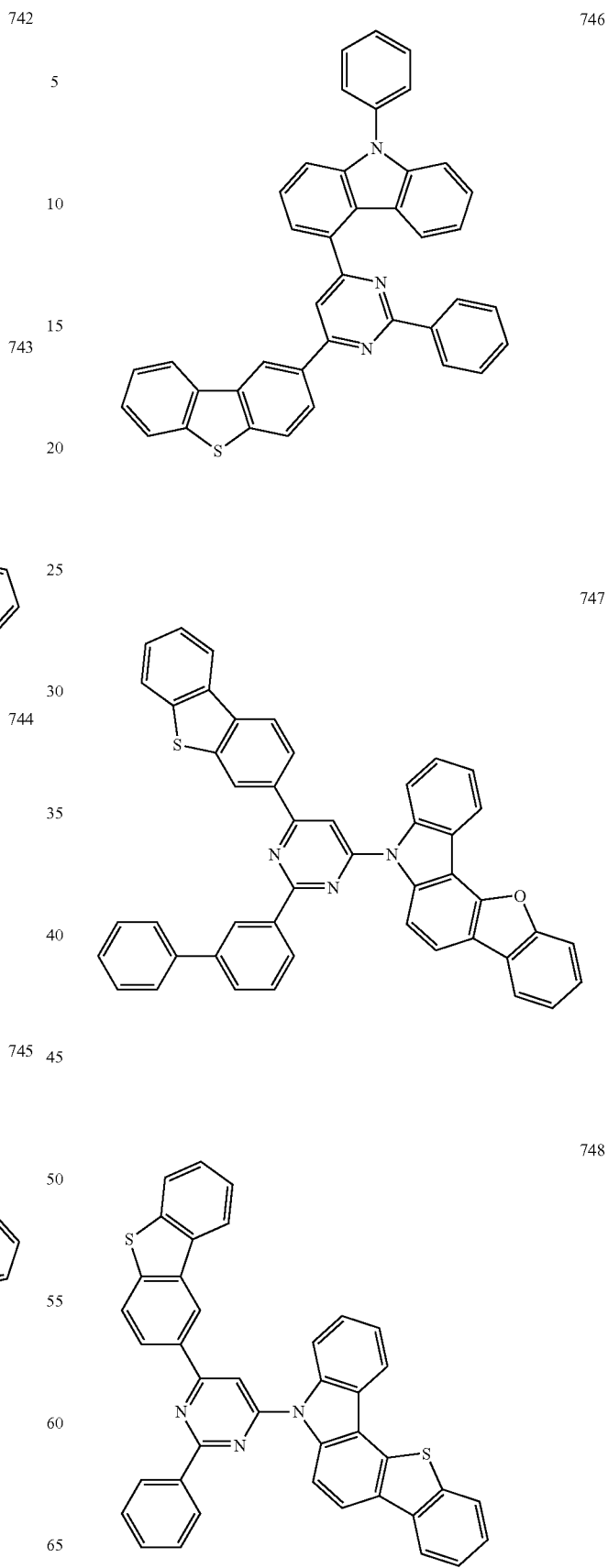

247
-continued
749
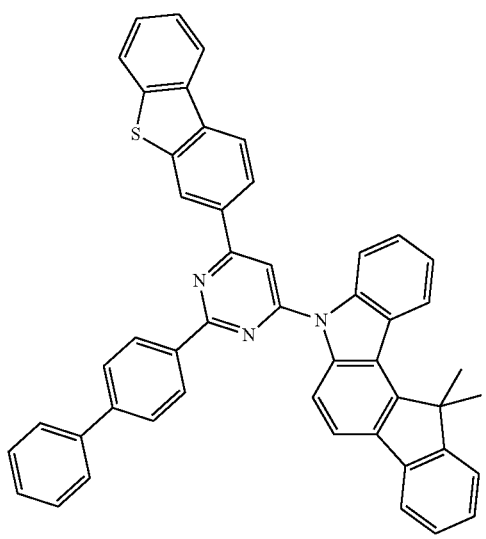
750
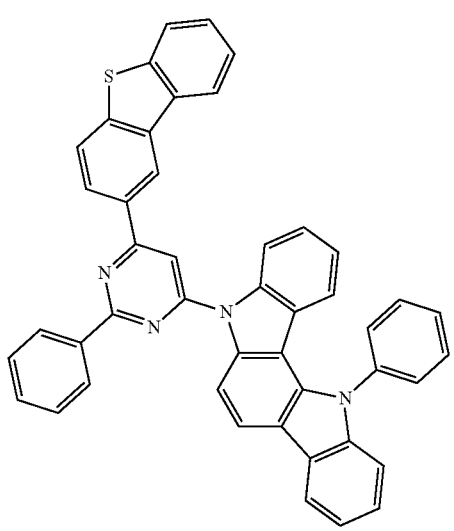
751
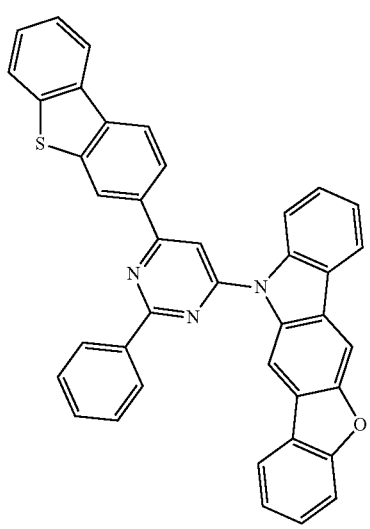
248
-continued
752
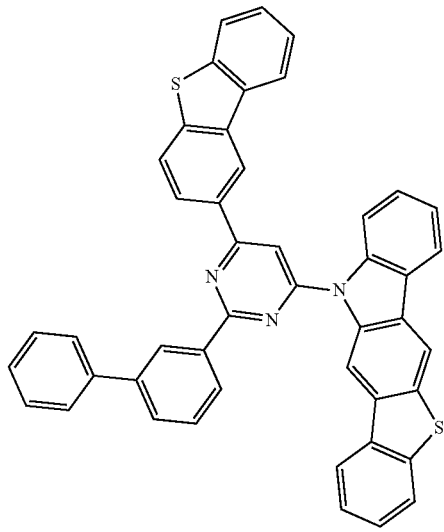
753
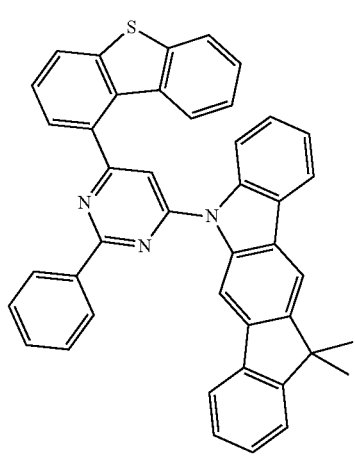
754
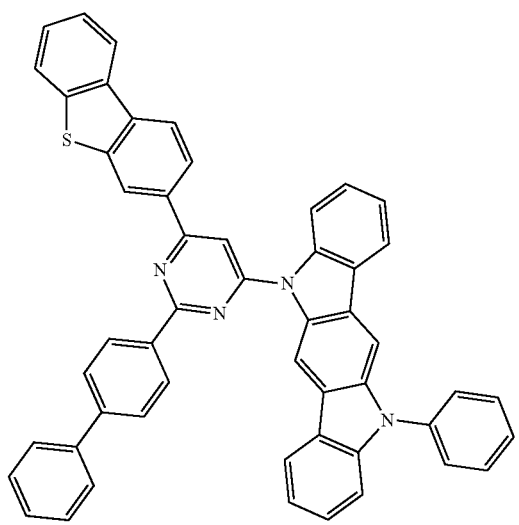

249
-continued
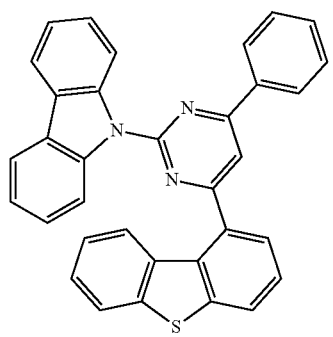
755
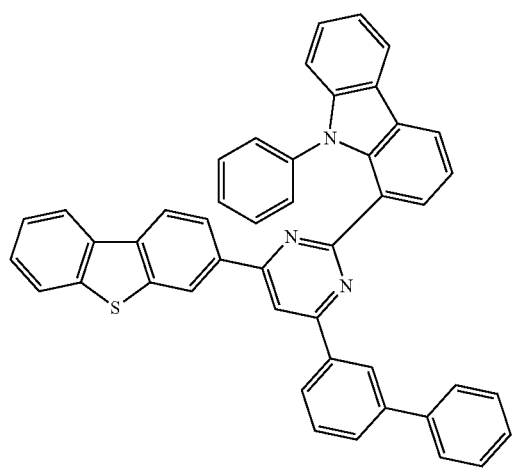
756
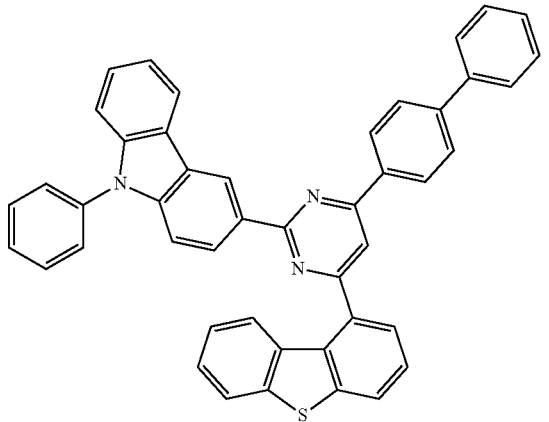
757
250
-continued
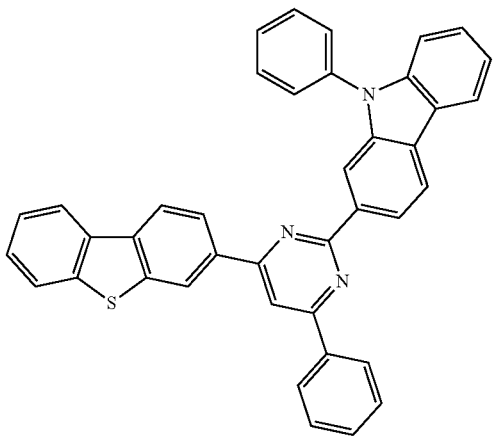
758
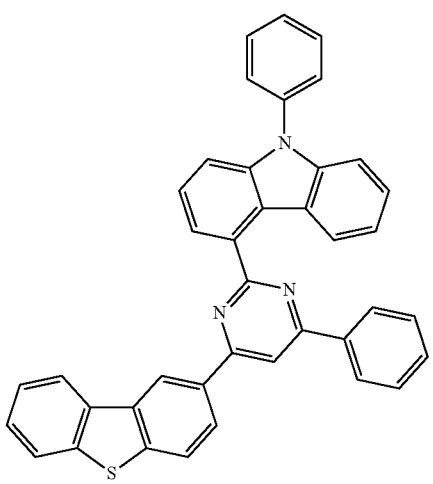
759
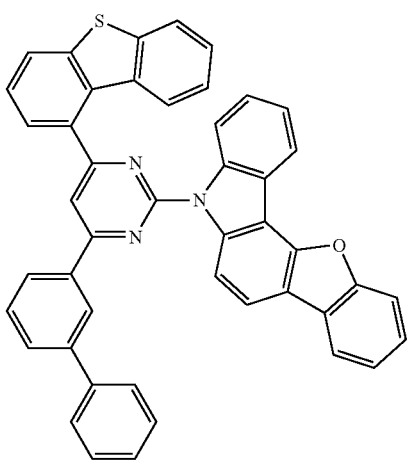
760

251
-continued
761
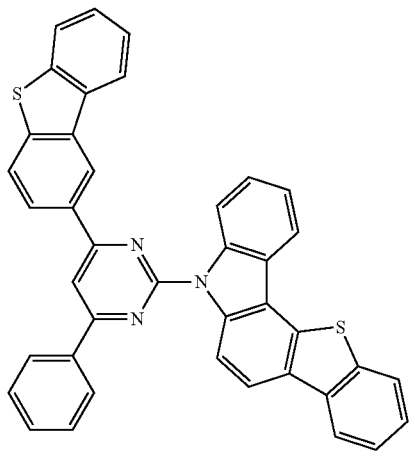
762
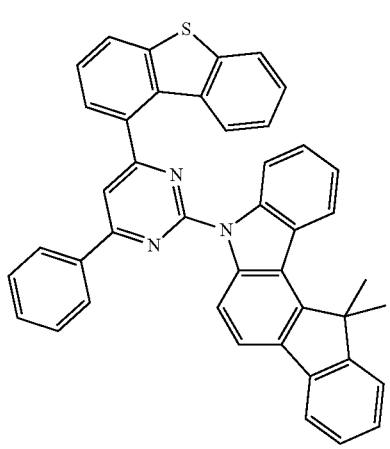
763
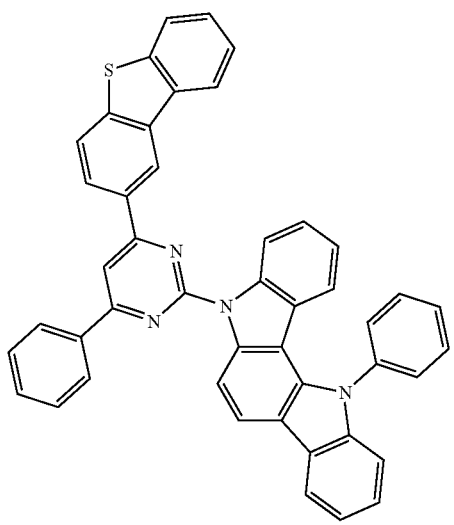
252
-continued
764
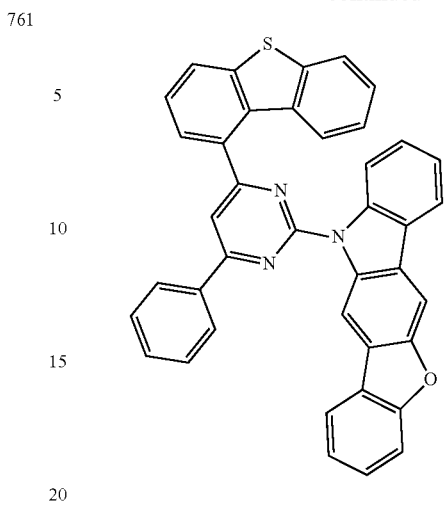
765
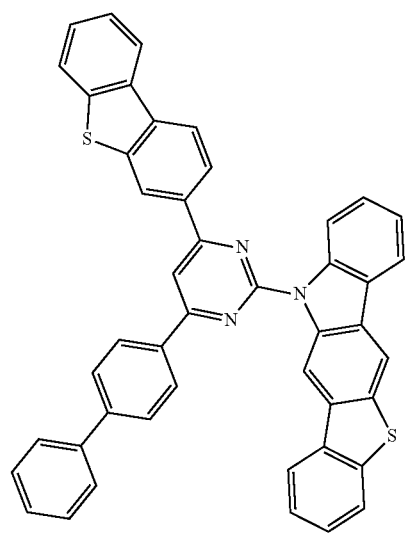
766
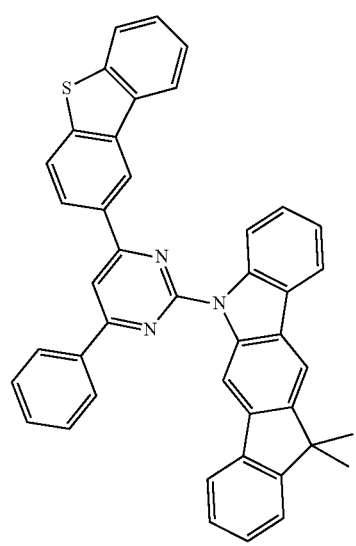

253
-continued
767
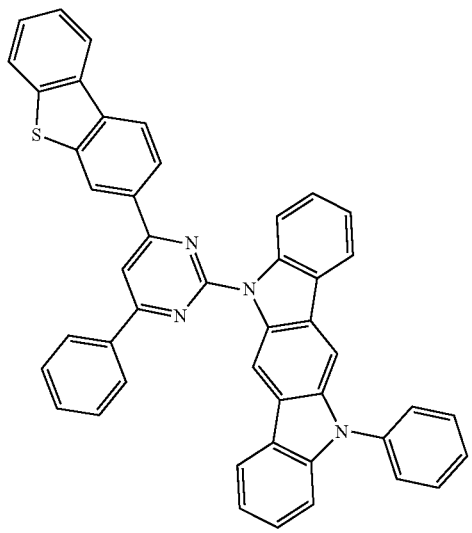
768
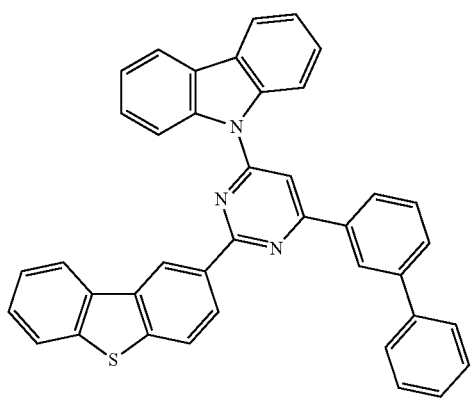
769
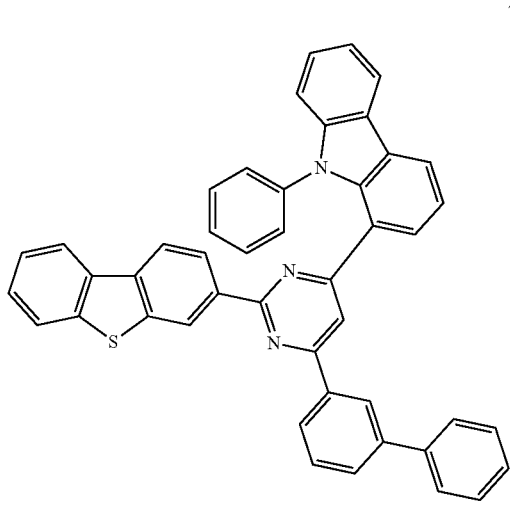
254
-continued
770
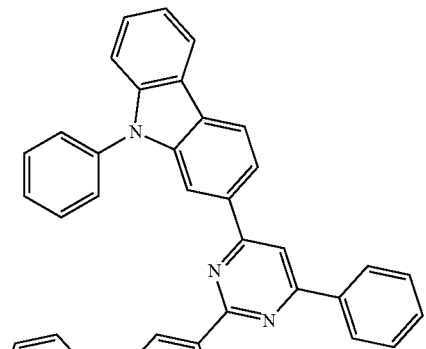
771
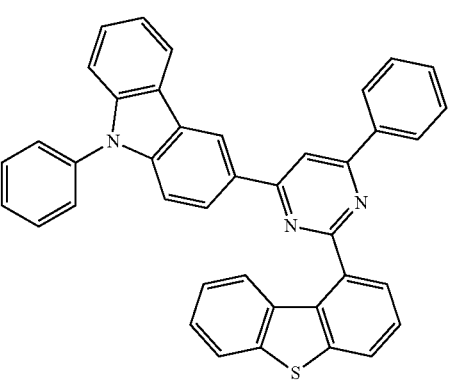
772
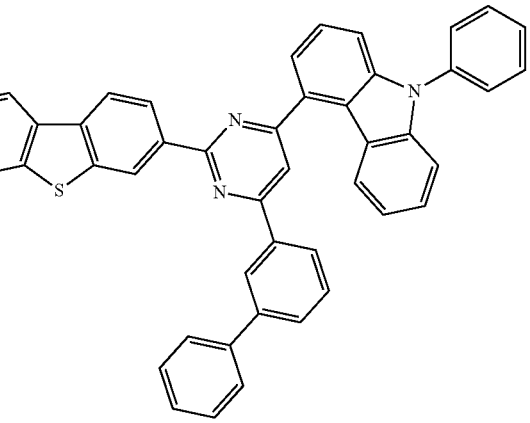
773
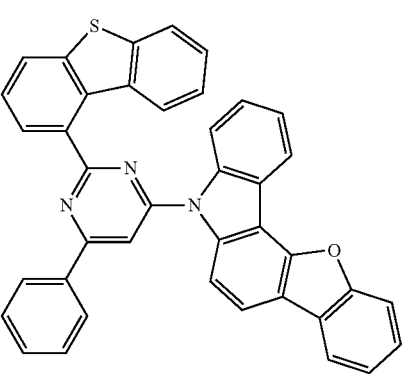

255
-continued
774
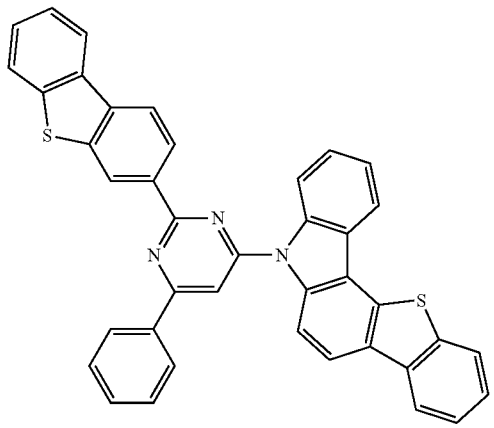
775
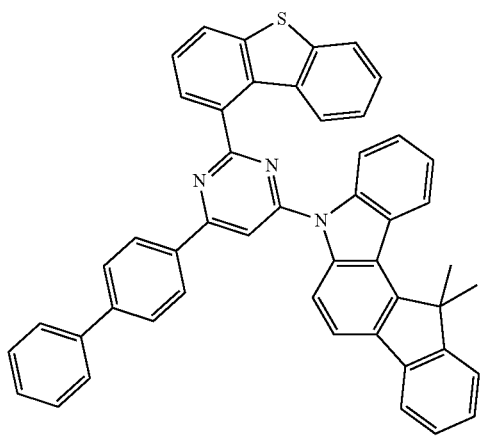
776
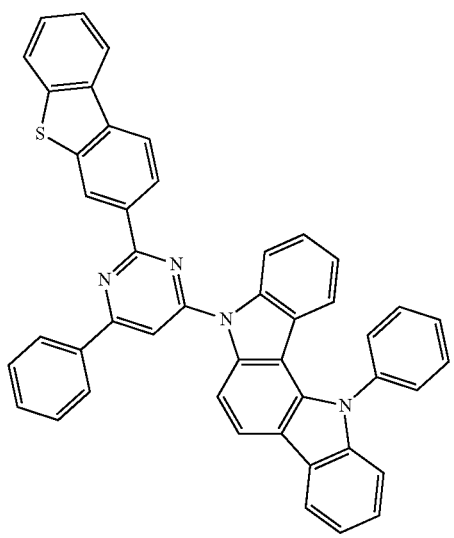
256
-continued
777
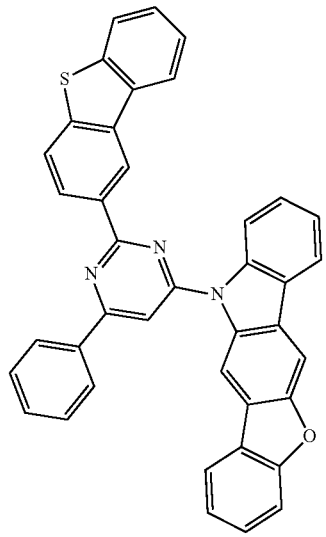
778
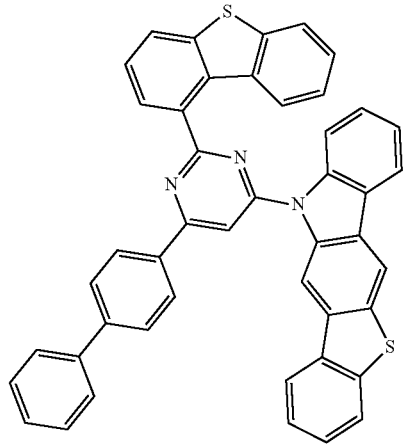
779
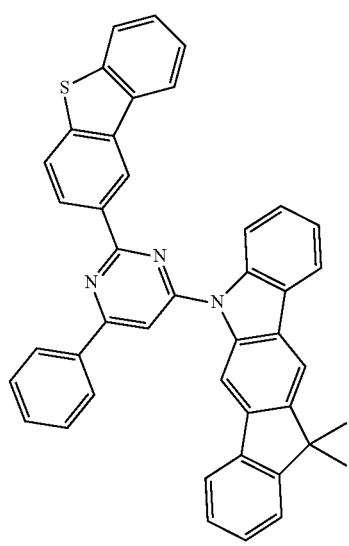

-continued
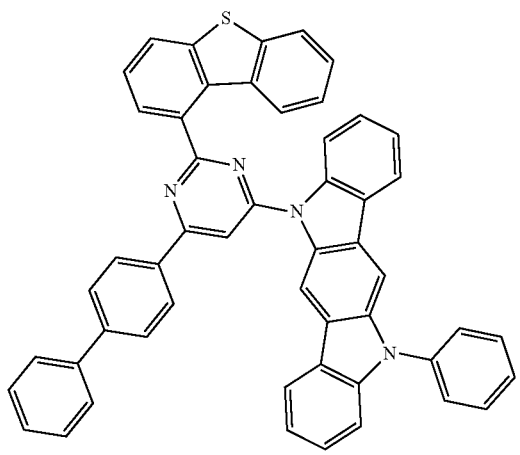
780
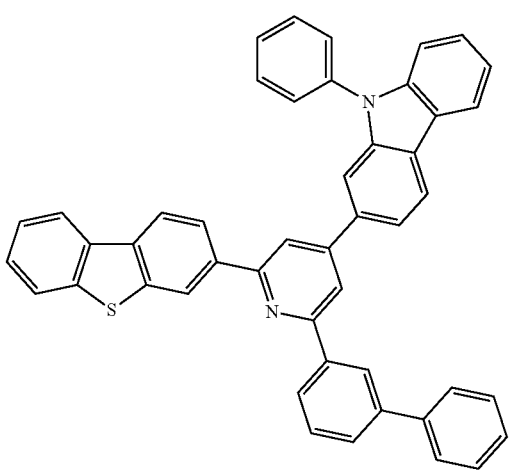
783
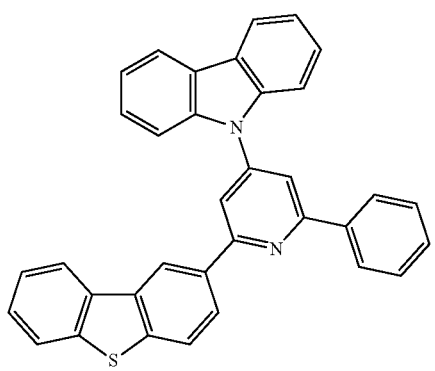
781
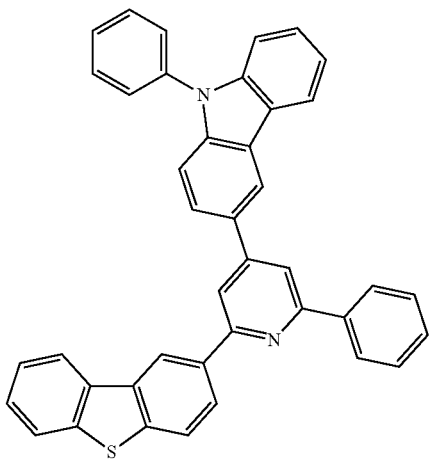
784
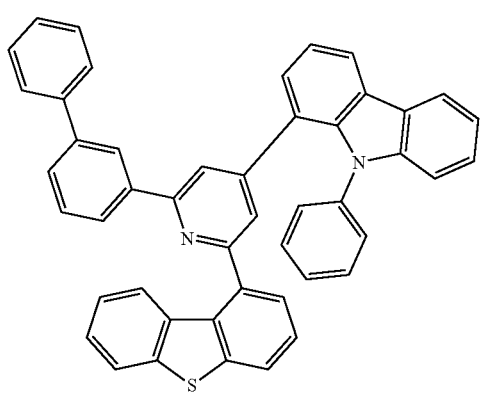
782
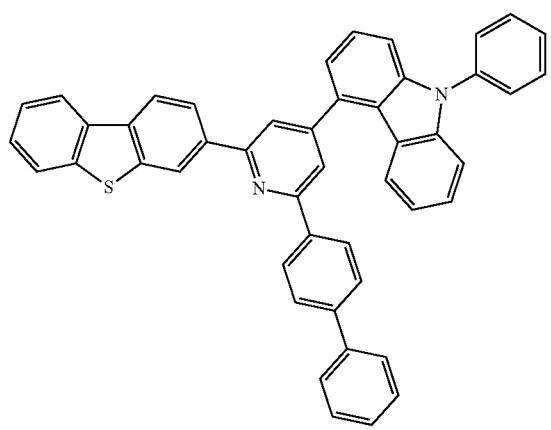
785

259
-continued
786
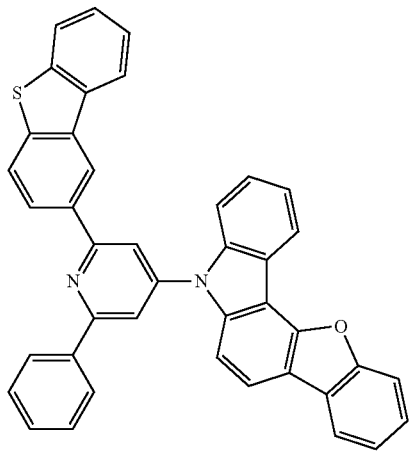
787
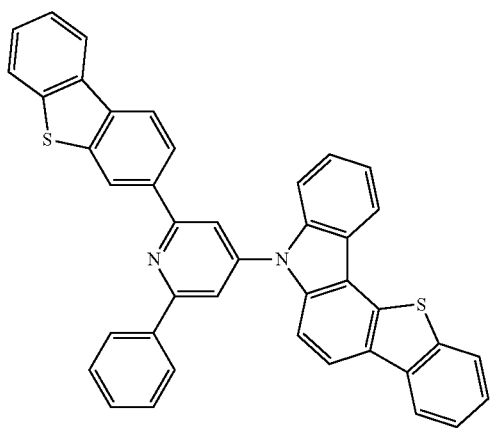
788
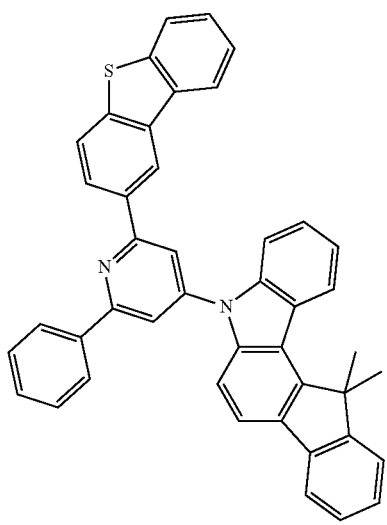
260
-continued
789
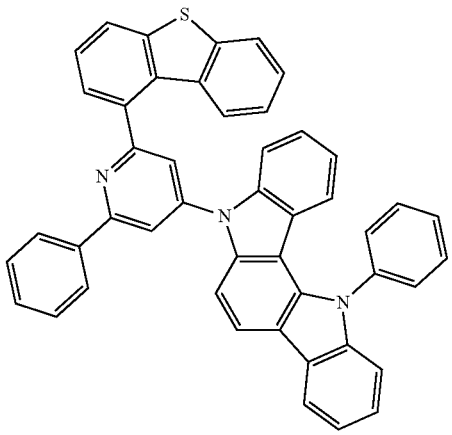
790
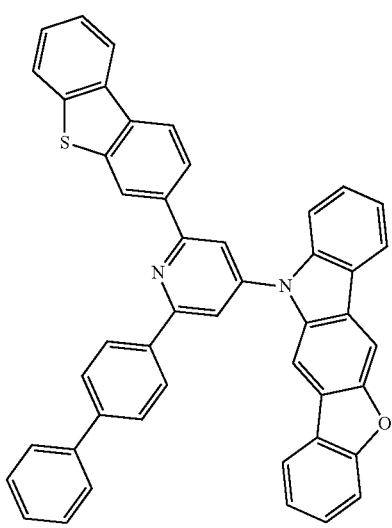
791
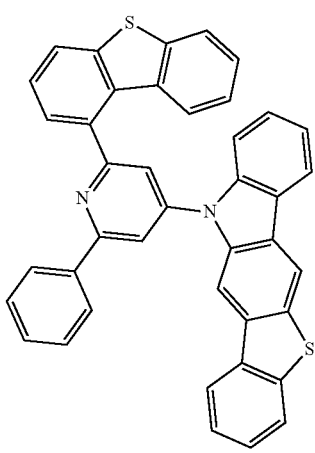

261
-continued
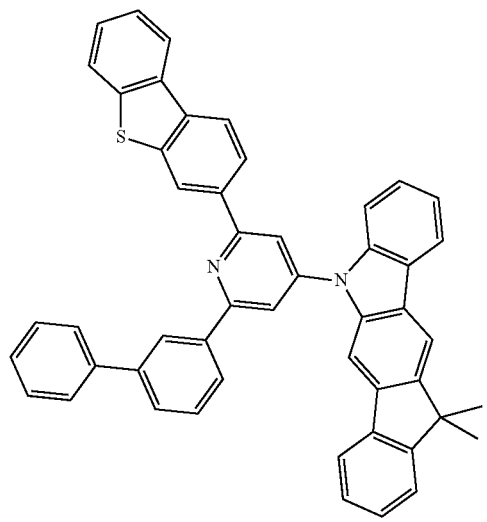
792
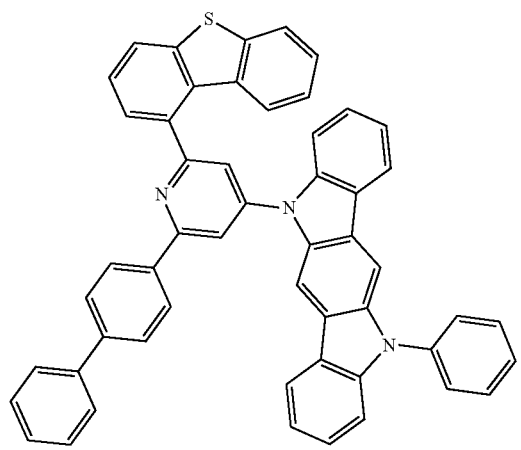
793
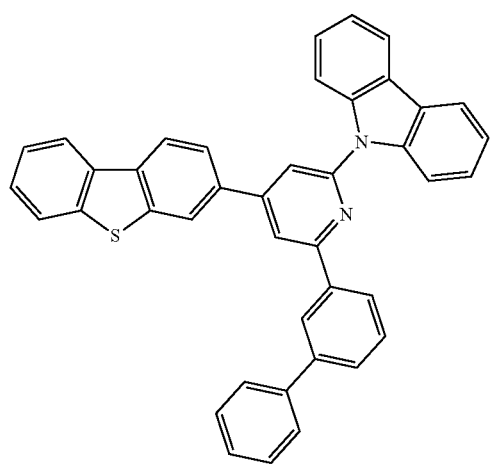
794
262
-continued
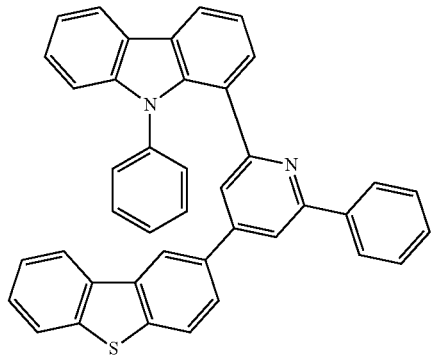
795
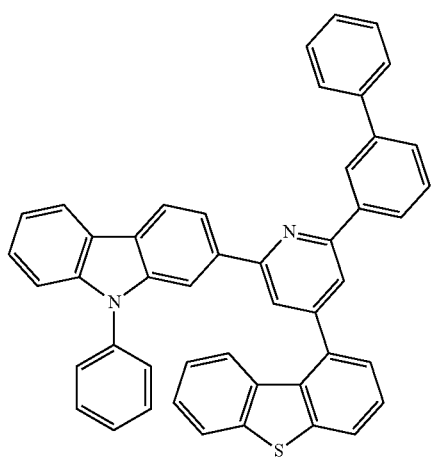
796
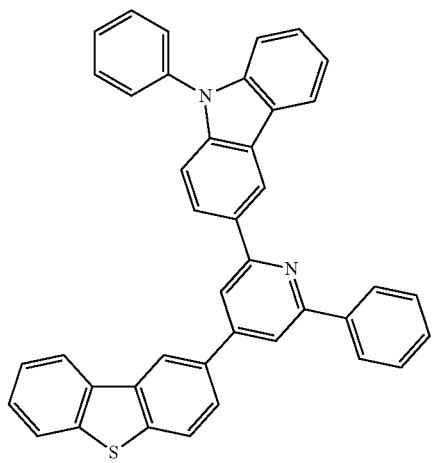
797

798
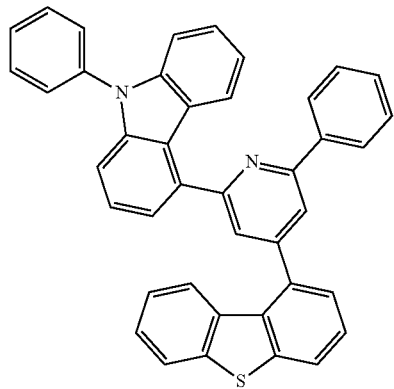
799
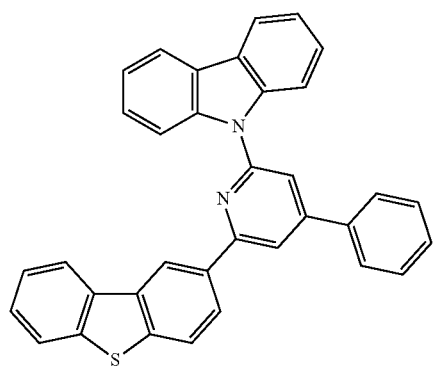
800
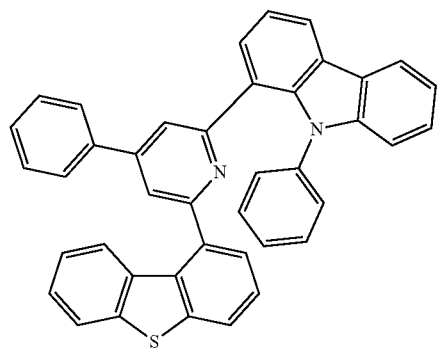
801
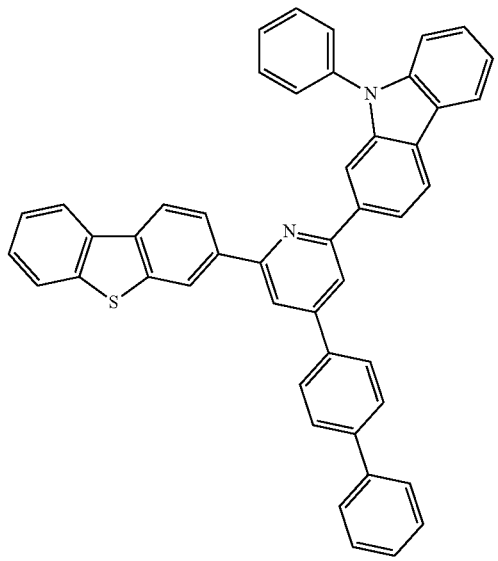
802
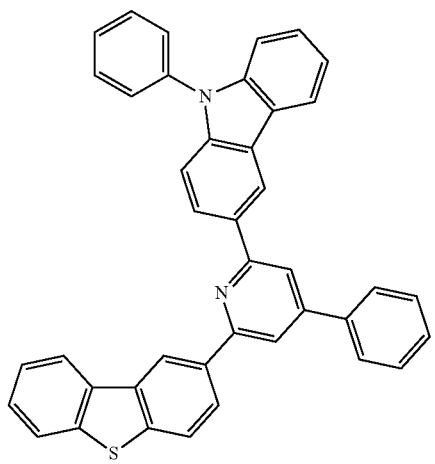
803
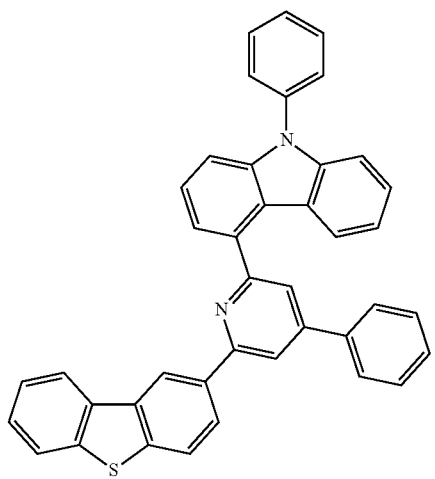

-continued
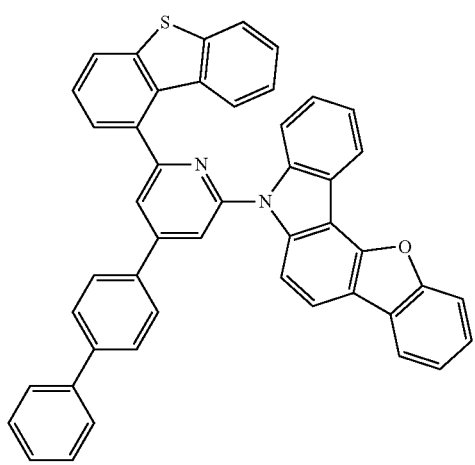
804
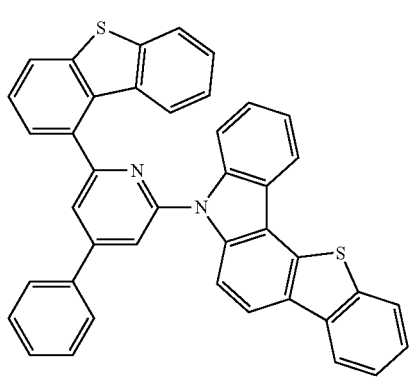
805
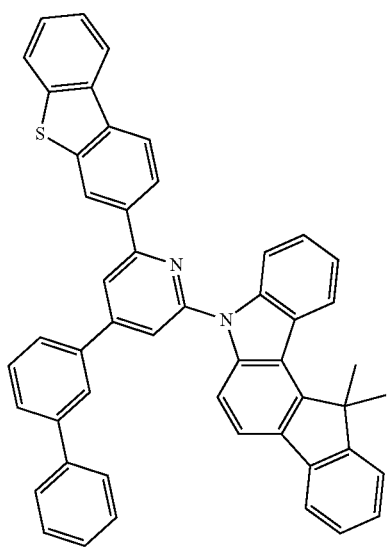
806
-continued
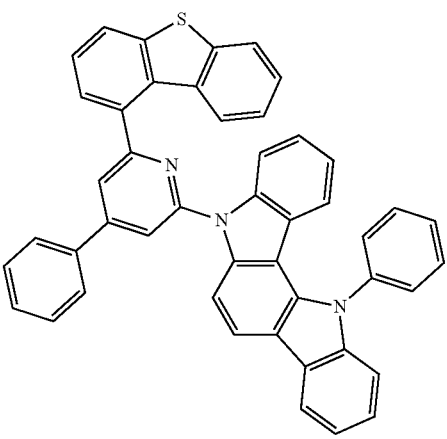
807
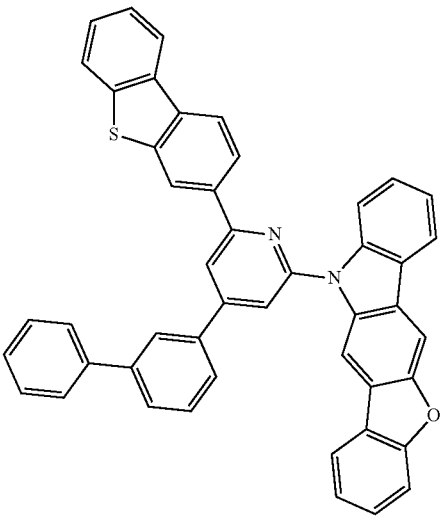
808
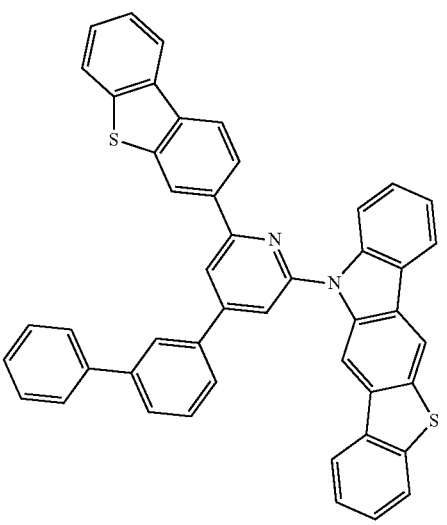
809

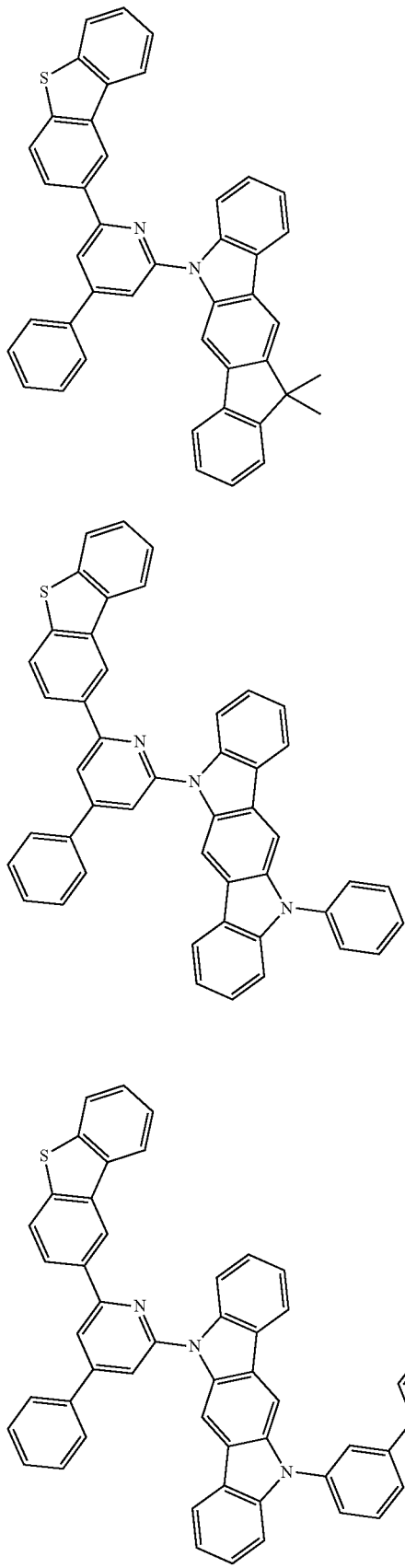
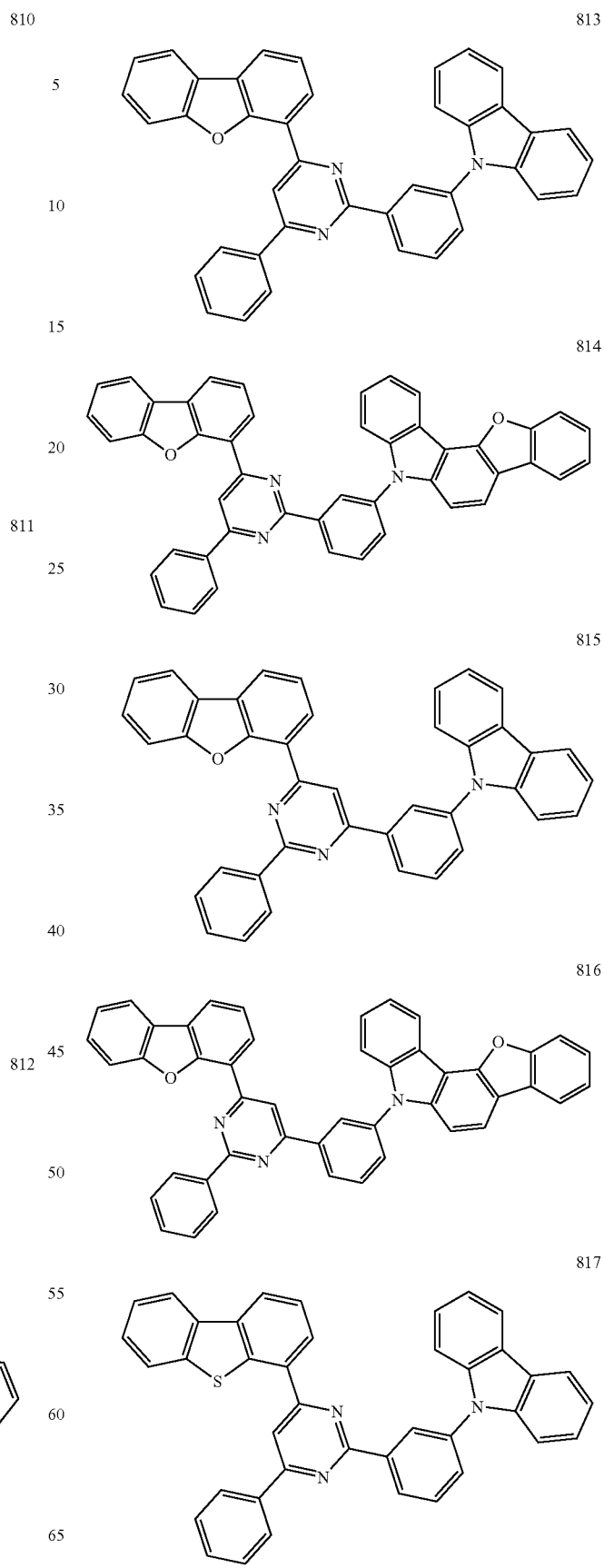

818
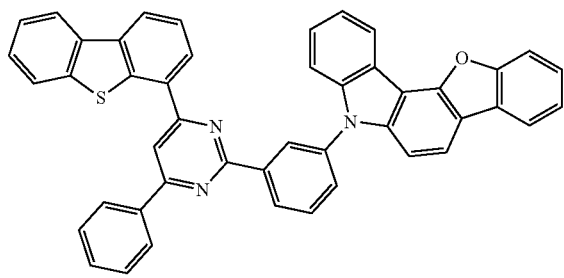
819
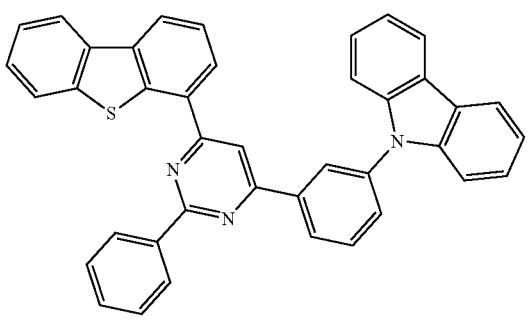
820
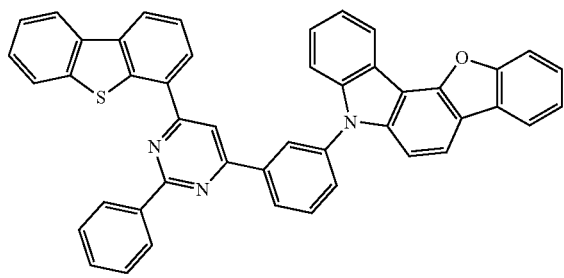
821
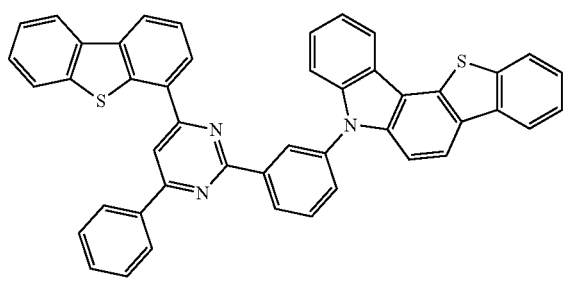
822
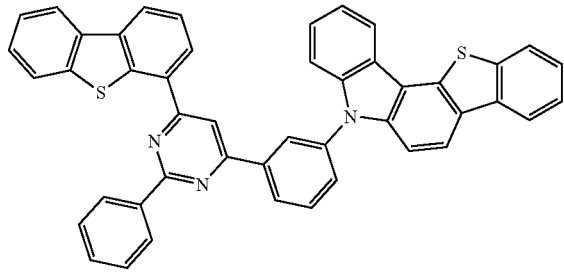
823
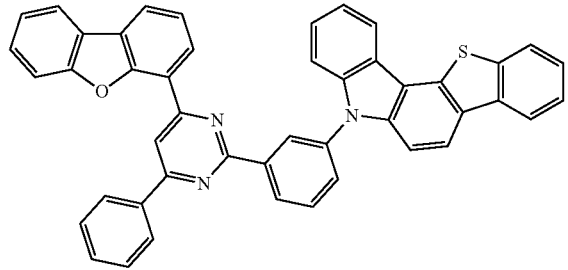
824
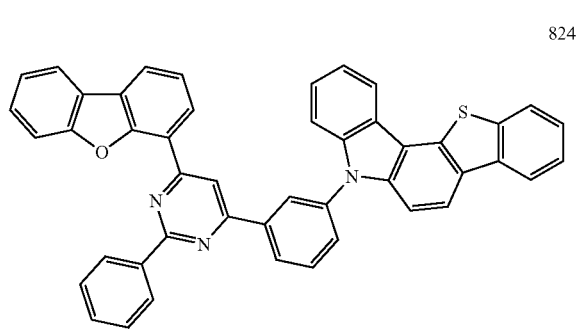
825
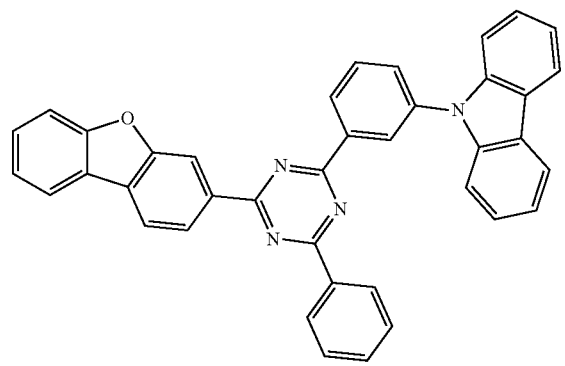
Alternatively, the condensed-cyclic compound may be any one of Compounds 1, 85, 169, 253, 337, 421, 505, 506, 575, 659, 660, 729 and 825, but it is not limited thereto:
1
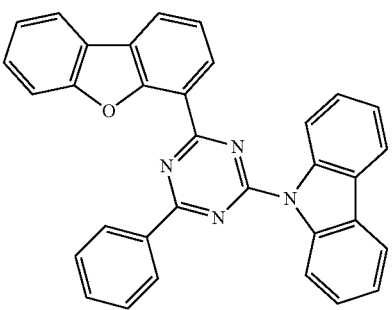

85
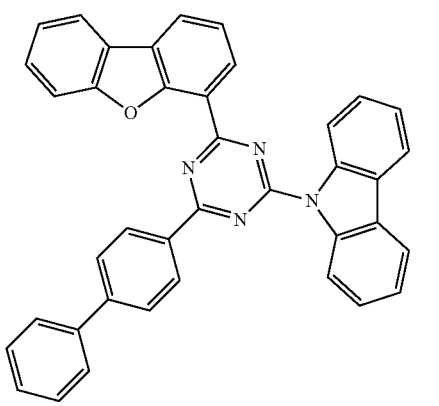
169
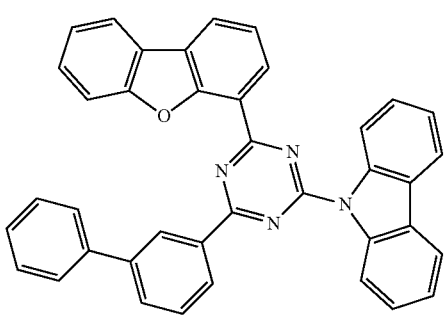
253
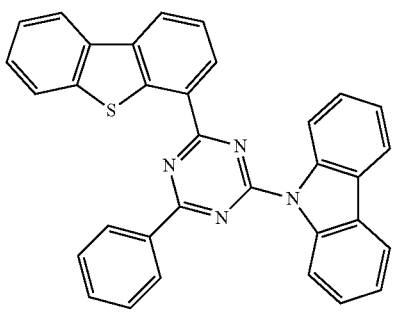
337
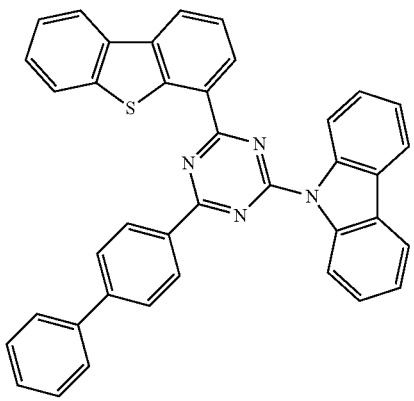
421
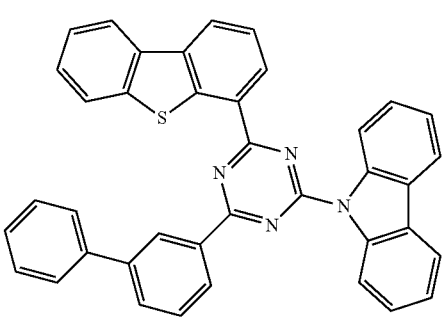
505
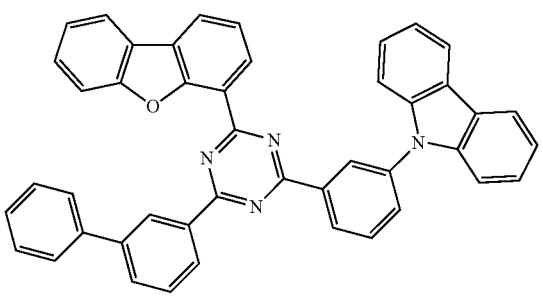
506
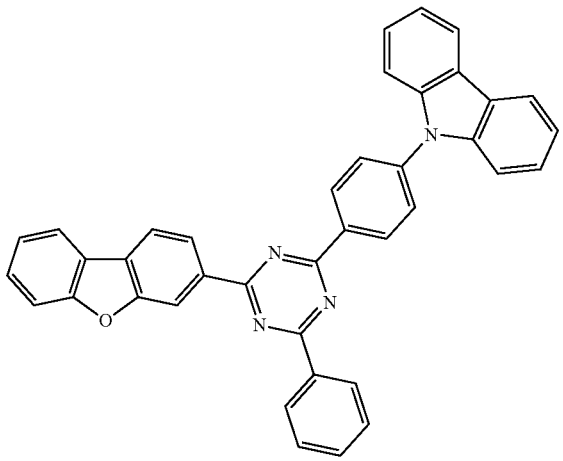
575
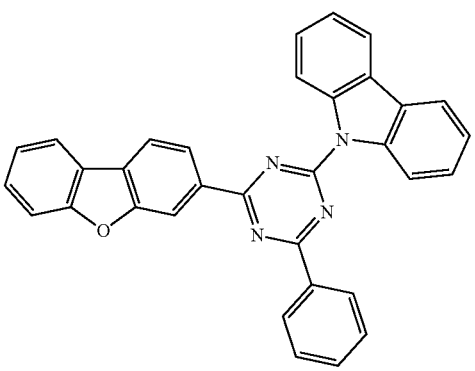

659
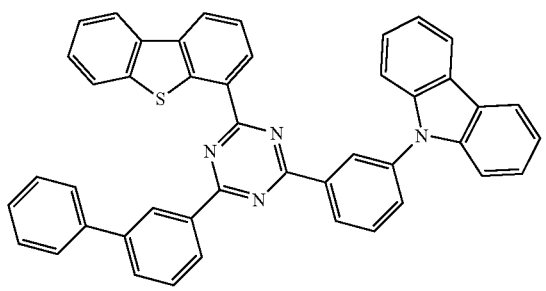

660
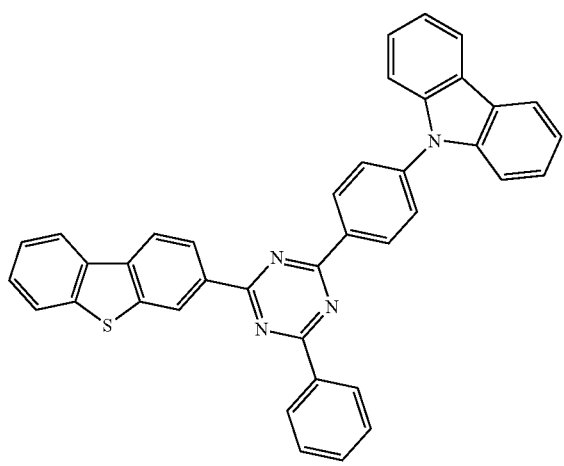

729
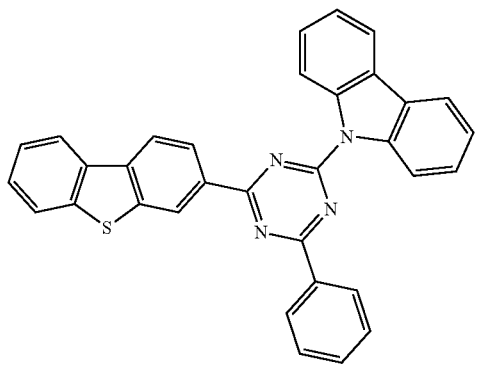

825
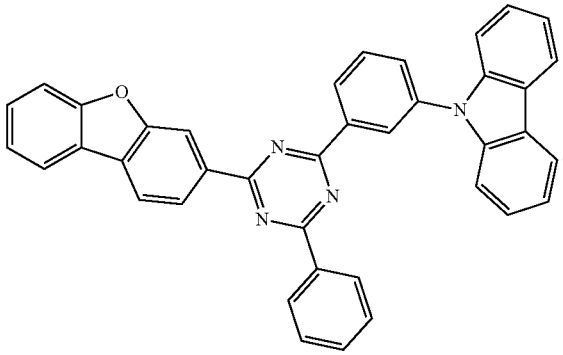

In the condensed-cyclic compound represented by Formula 1A or 1B, $R_4$ is selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, and a substituted or unsubstituted monovalent non-aromatic hetero-condensed polycyclic group.

In other words, in Formula 1A and 1B, $R_4$ necessarily includes a ring structure. As a result, the condensed-cyclic compound represented by Formula 1A or 1B is chemically and structurally stable and may actually have a spherical molecular structure. Accordingly, the condensed-cyclic compound represented by Formula 1A or 1B may have excellent thermal stability, which may increase deposition temperature. As a result, efficiency and lifespan of an organic light-emitting device including the condensed-cyclic compound may be improved to improve formability of the organic light-emitting device during the manufacturing process thereof.

Also, because both group "A" and the "carbazole-based" group in Formulae 1A and 1B are bound to a "nitrogen-containing 6-membered ring" (see Formulae 1A' and 1B'), hole injection and hole transport and electron injection and electron transport may occur thoroughly and Formulae 1A and 1B may each actually have a spherical molecular structure. Accordingly, the condensed-cyclic compound may simultaneously have excellent charge-transporting ability and thermal stability, such that the organic light-emitting device including the condensed-cyclic compound may have increased emission efficiency, reduced driving voltage, and a long lifespan.

Formula 1A'

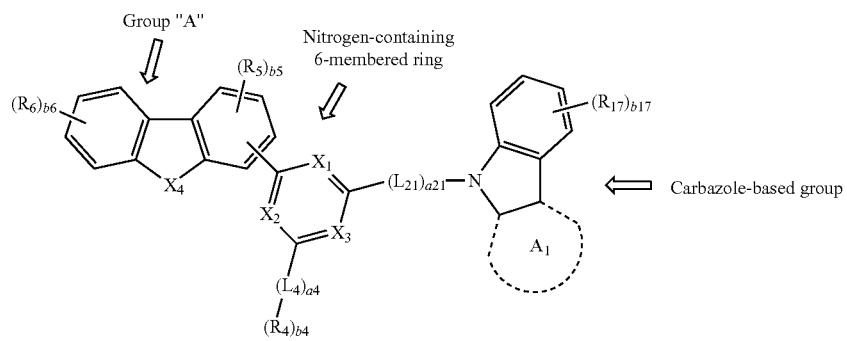

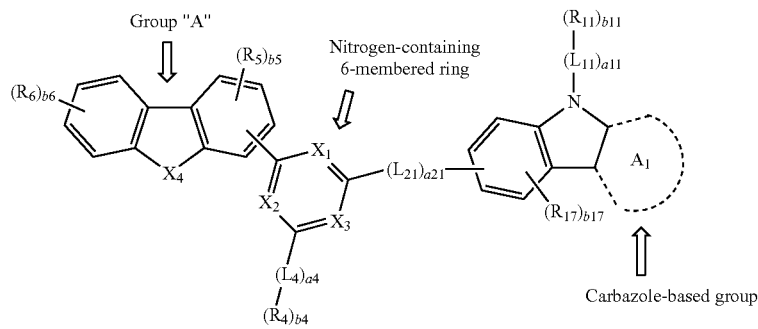

Formula 1B'

A method of synthesizing the condensed-cyclic compound represented by Formula 1A or 1B may be understood by one of ordinary skill in the art by referring to the embodiments described below.

Accordingly, the condensed-cyclic compound represented by Formula 1A or 1B may be suitable as a material for an organic layer (for example, a host of an EML) in an organic light-emitting device. According to another embodiment, provided is an organic light-emitting device including a first electrode;

a second electrode; and an organic layer disposed between the first electrode and the second electrode, wherein the organic layer includes the EML, which includes at least one condensed-cyclic compound represented by Formula 1A or 1B.

The organic light-emitting device including an organic layer including the condensed-cyclic compound represented by Formula 1A or 1B has low driving voltage, high efficiency, high brightness, and a long lifespan.

The condensed-cyclic compound represented by Formula 1A or 1B may be used between a pair of electrodes in the organic light-emitting device. For example, the condensed-cyclic compound may be included in at least one of an EML, a hole-transport region disposed between the first electrode and the EML (for example, the hole transport region may include at least one of a hole-injecting layer (HIL), a hole-transporting layer (HTL), and an electron-blocking layer (EBL)), and an electron-transport region disposed between the EML and the second electrode (for example, the electron transport region may include at least one of a hole-blocking layer (HBL), an electron-transporting layer (ETL), and an electron-injecting layer (EIL)). For example, the condensed-cyclic compound represented by Formula 1A or 1B may be included in the EML. In this regard, the EML further includes a dopant and the condensed-cyclic compound included in the EML may act as a host. The EML may be a green EML emitting green light and the dopant may be a phosphorescent dopant.

As used herein, the term "(the organic layer) includes at least one condensed-cyclic compound" may be understood as "(the organic layer) may include at least one condensed-cyclic compound belonging to the group of Formula 1A or 1B or two different condensed-cyclic compounds belonging to the group of Formula 1A or 1B".

For example, the organic layer may only include Compound 1 as the condensed-cyclic compound. In this regard, Compound 1 may be situated in the EML of the organic light-emitting device. Alternatively, the organic layer may include Compound 1 and Compound 2 as the condensed-cyclic compound. In this regard, Compound 1 and Compound 2 may be present on the same layer (for example, Compound 1 and Compound 2 may all be present on the EML) or on different layers.

The organic layer includes i) a hole transport region that is disposed between the first electrode and the EML and includes at least one of an HIL, an HTL, a buffer layer, and an EBL, and ii) an electron transport region that is disposed between the EML and the second electrode and includes at least one layer selected from a HBL, an ETL, and an EIL.

The expression "organic layer", as used herein refers to a single layer and/or a plurality of layers disposed between the first and second electrodes of an organic light-emitting device. A material of the "organic layer" is not limited to an organic material and may include an organic metal complex including a metal.

The FIGURE is a schematic view of an organic light-emitting device 10 according to an embodiment. Hereinafter, a structure and a method of manufacturing the organic light-emitting device according to an embodiment will be described with reference to the FIGURE. The organic light-emitting device 10 includes a first electrode 11, an organic layer 15, and a second electrode 19, which are sequentially stacked in the stated order.

A substrate may be additionally disposed under the first electrode 11 or on the second electrode 19. The substrate may be a conventional glass substrate or a transparent plastic substrate, each with excellent mechanical strength, thermal stability, transparency, surface smoothness, ease of handling, and water repellency.

The first electrode 11 may be formed by depositing or sputtering a material for forming the first electrode 11 on the substrate. When the first electrode 11 is an anode, the material for the first electrode 11 may be selected from materials with a high work function for an easy hole injection. The first electrode 11 may be a reflective electrode, a semi-transmissive electrode, or a transmissive electrode. The material for the first electrode 110 may be selected from indium tin oxide (ITO), indium zinc oxide (IZO), tin oxide ($SnO_2$), and zinc oxide (ZnO). Alternatively, a metal such as magnesium (Mg), aluminum (Al), aluminum-lithium (Al—Li), calcium (Ca), magnesium-indium (Mg—In), and magnesium-silver (Mg—Ag).

The first electrode 11 may have a single-layer structure or a multi-layer structure including two or more layers.

The organic layer 15 is disposed on the first electrode 11.

The organic layer 15 may include a hole transport region; an EML; and an electron transport region.

The hole transport region may be disposed between the first electrode 11 and the EML.

The hole transport region may include at least one of the HIL, HTL, EBL, and buffer layer.

The hole transport region may only include the HIL or HTL. Alternatively, the hole transport region may have an HIL/HTL structure or an HIL/HTL/EBL structure, wherein layers of each structure are sequentially stacked on the first electrode 11 in this stated order, but it is not limited thereto.

When the hole transport region includes an HIL, the HIL may be formed on the first electrode 11 by using various methods, such as vacuum deposition, spin coating, casting, a Langmuir-Blodgett (LB) method, or the like.

When an HIL is formed by vacuum deposition, for example, the vacuum deposition may be performed at a deposition temperature of about 100 to about 500° C., at a vacuum degree of about $10^{-8}$ to about $10^{-3}$ torr, and at a deposition rate of about 0.01 Angstrom per second (Å/sec) to about 100 Å/sec in consideration of a compound for an HIL to be deposited, and the structure of an HIL to be formed, but the conditions are not limited thereto.

When an HIL is formed by spin coating, the spin coating may be performed at a coating rate of about 2,000 revolutions per minute (rpm) to about 5,000 rpm, and at a temperature of about 80° C. to 200° C. for removing a solvent after the spin coating, in consideration of a compound for an HIL to be deposited, and the structure of an HIL to be formed, but the conditions are not limited thereto.

The conditions for forming the HTL and EBL may be inferred based on the conditions for forming the HIL.

The hole transport region may include at least one compound selected from m-MTDATA, TDATA, 2-TNATA, NPB, 8-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

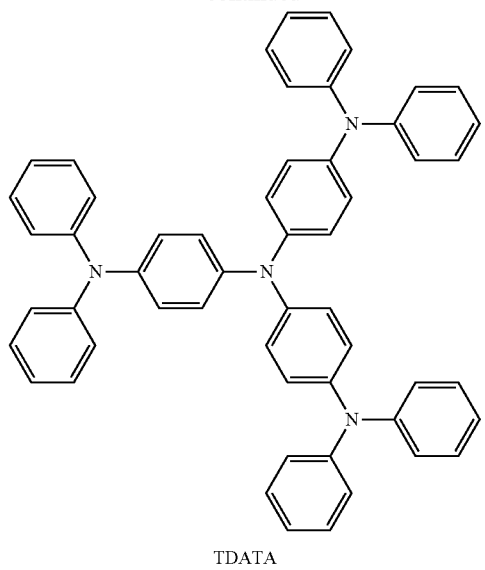

TDATA

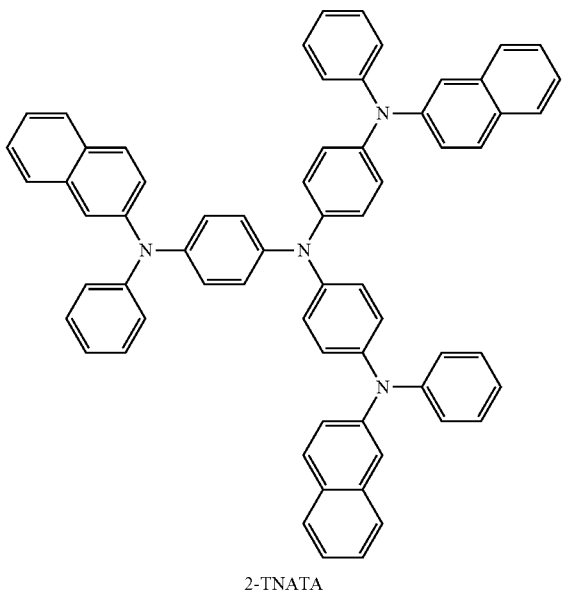

2-TNATA

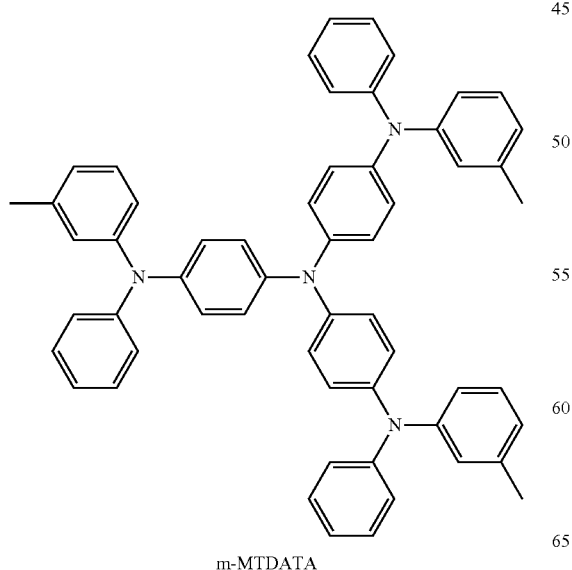

m-MTDATA

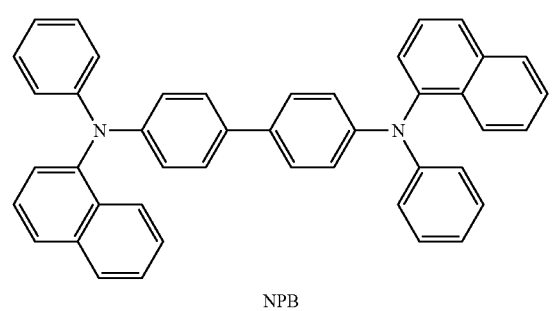

NPB

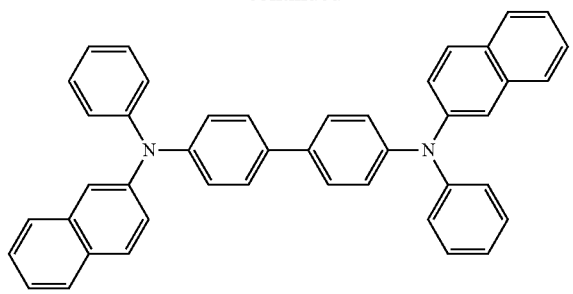

β-NPB

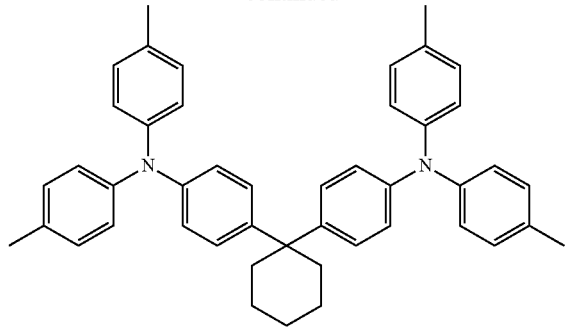

TAPC

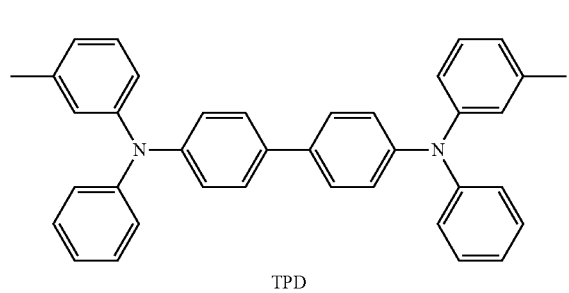

TPD

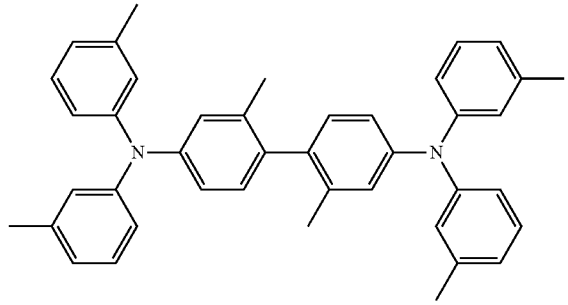

HMTPD

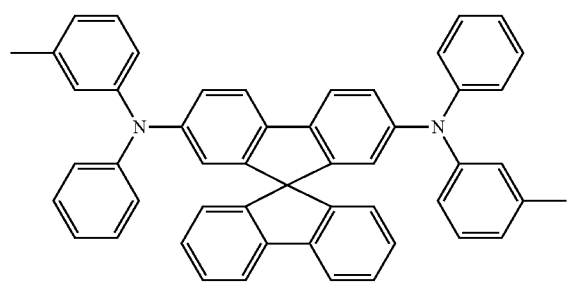

Spiro-TPD

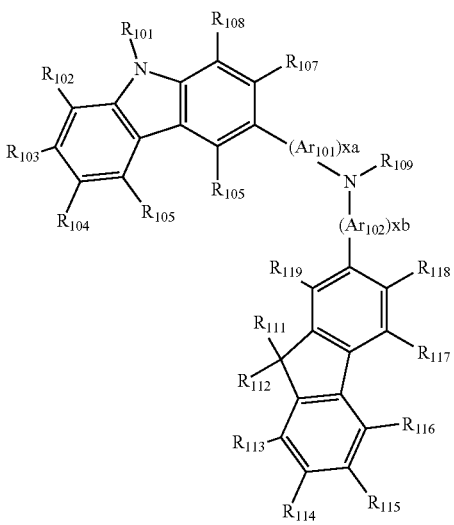

Formula 201

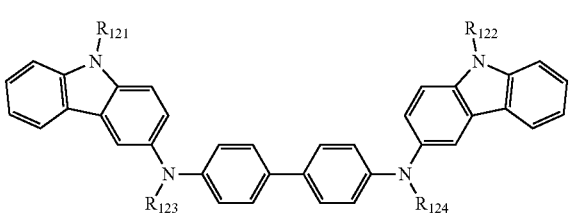

Spiro-NPB methylated NPB

Formula 202

In Formula 201, $Ar_{101}$ and $Ar_{102}$ may be each independently selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group.

In Formula 201, xa and xb may be each independently integers of 0 to 5, or 0, 1, or 2. For example, xa may be 1 and xb may be 0, but they are not limited thereto.

In Formulae 201 and 202, $R_{101}$ to $R_{108}$, $R_{111}$ to $R_{119}$, and $R_{121}$ to $R_{124}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, and a hexyl group) and a $C_1$-$C_{10}$ alkoxy group (for example, a methoxy group, an ethoxy group, a propoxy group, a butoxy group, and a pentoxy group);

a $C_1$-$C_{10}$ alkyl group and a $C_1$-$C_{10}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but they are not limited thereto.

In Formula 201, $R_{109}$ may be any one of a phenyl group, a naphthyl group, an anthracenyl group and a pyridinyl group; a phenyl group, a naphthyl group, an anthracenyl group, and a pyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group and a $C_1$-$C_{20}$ alkoxy group.

According to an embodiment, the compound represented by Formula 201 may be represented by Formula 201A, but it is not limited thereto:

Formula 201A

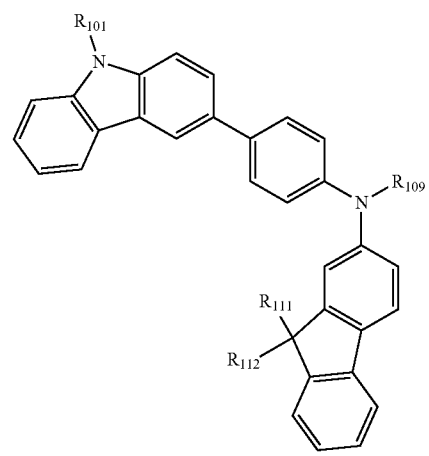

In Formula 201A, detailed descriptions of $R_{101}$, $R_{111}$, $R_{112}$, and $R_{109}$ may be the same as described herein.

For example, the compound represented by Formula 201 and the compound represented by Formula 202 may include Compounds HT1 to HT20, but the compound is not limited thereto:

HT1

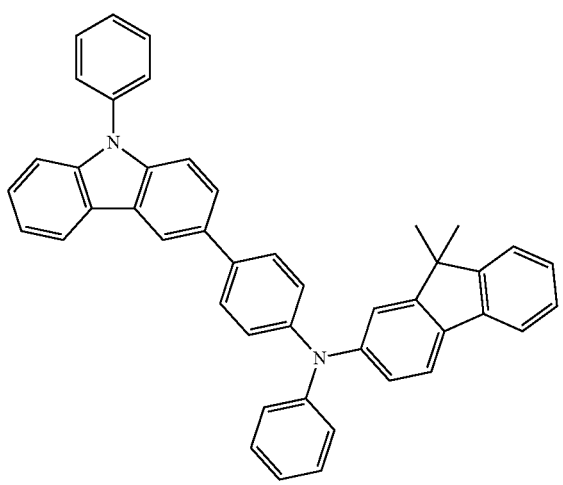

283
-continued
HT2
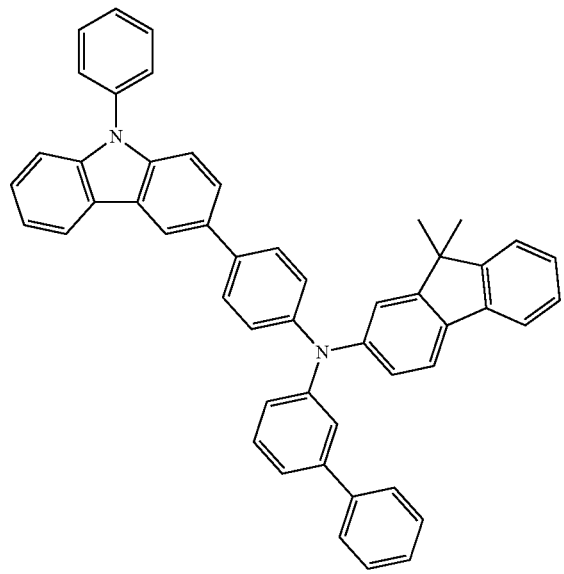
HT3
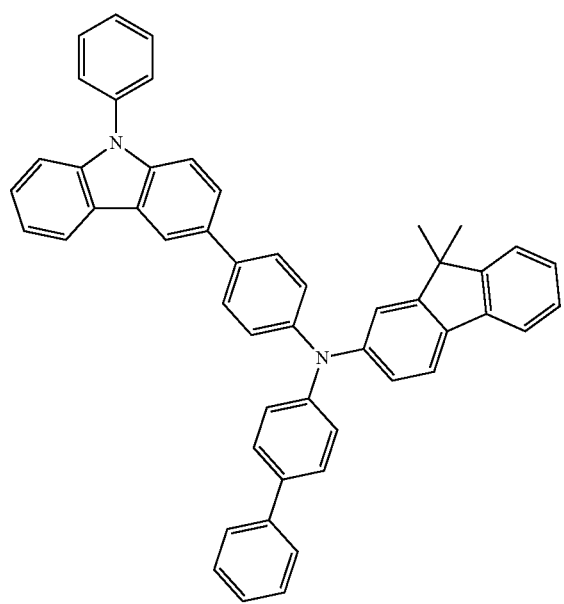
284
-continued
HT4
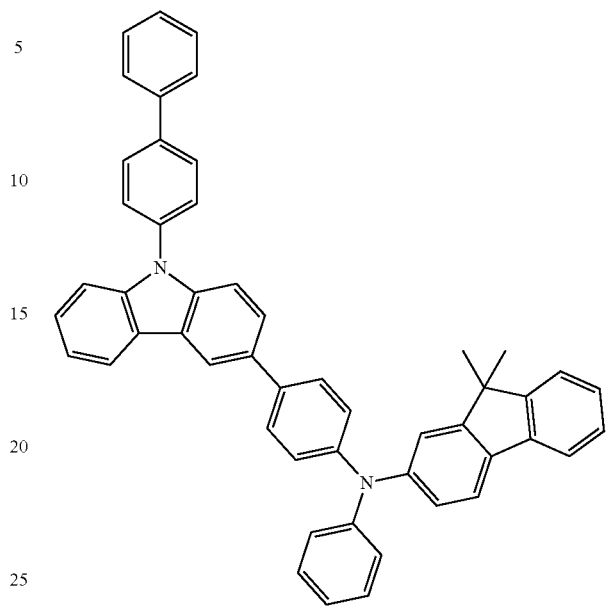
HT5
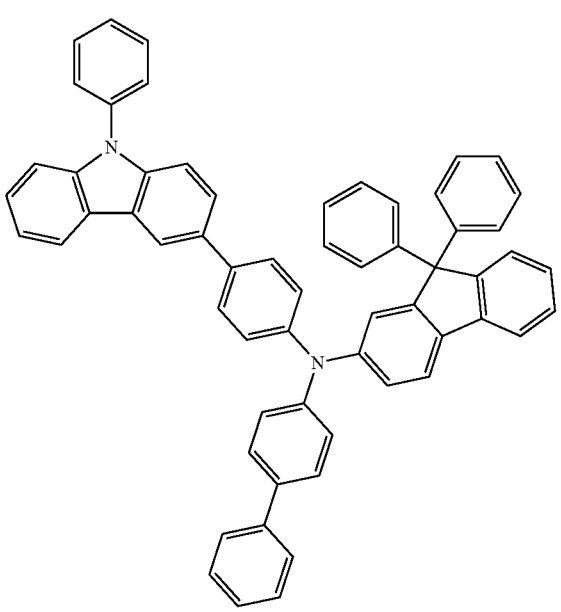

HT6
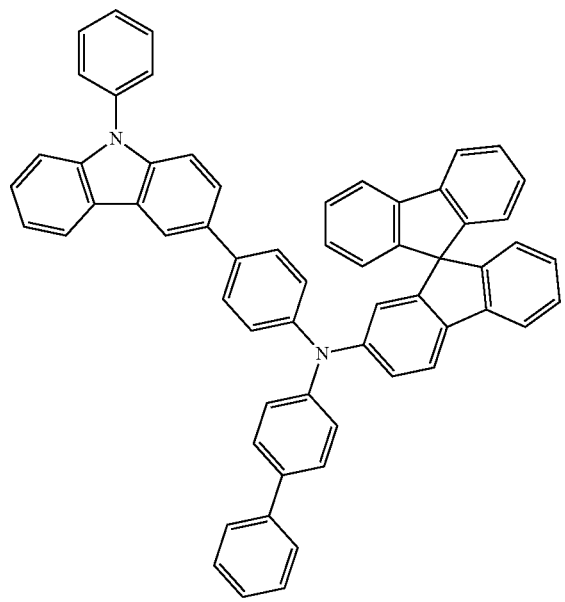
HT7
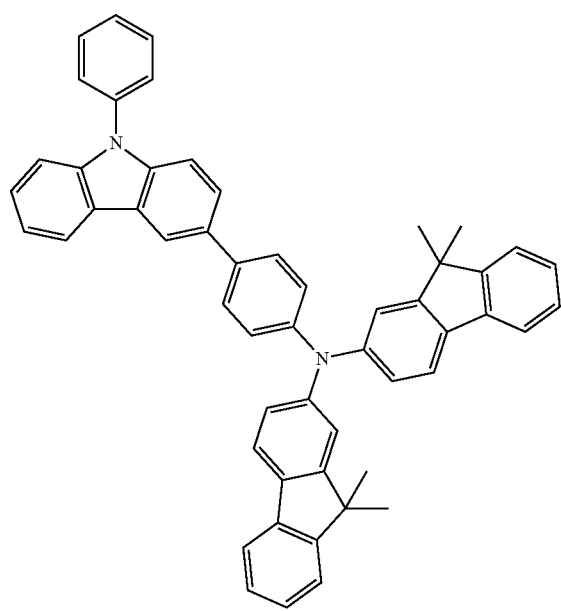
HT8
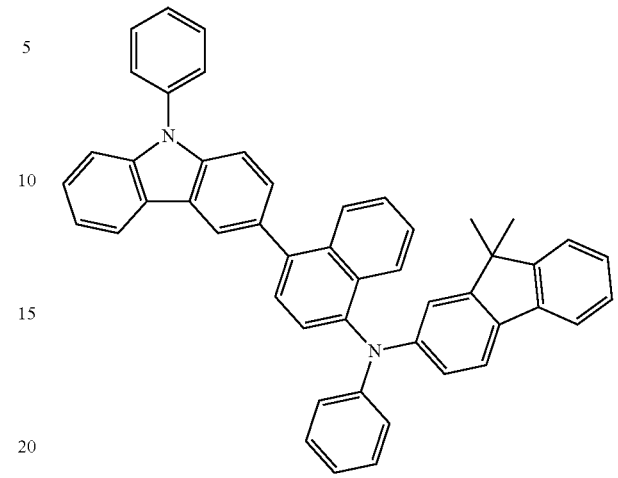
HT9
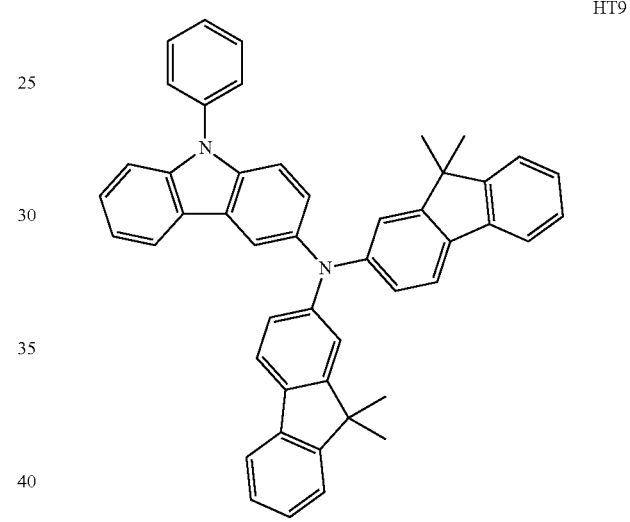
HT10
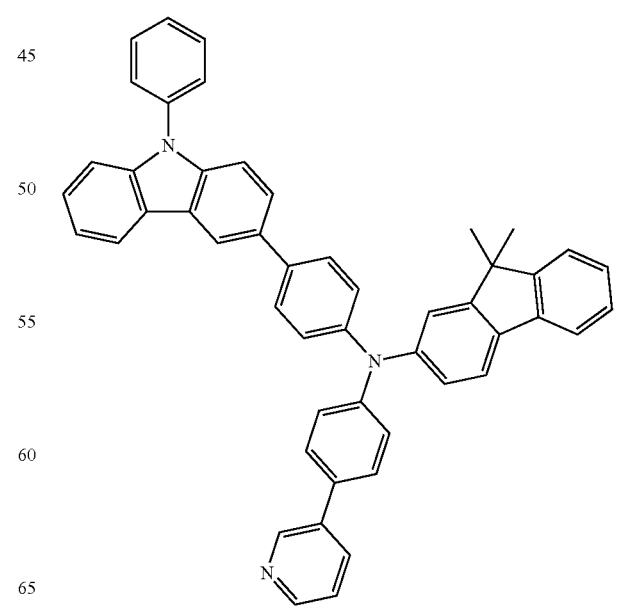

HT11
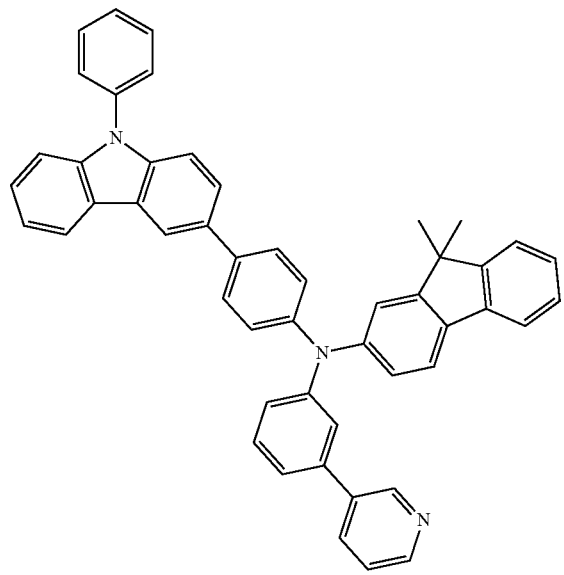
HT12
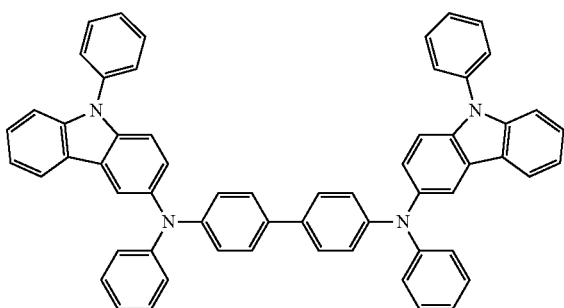
HT14
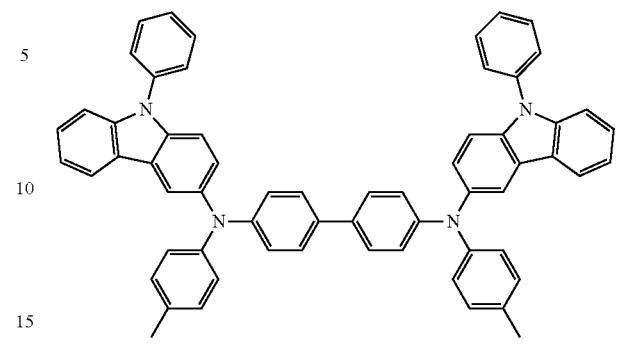
HT15
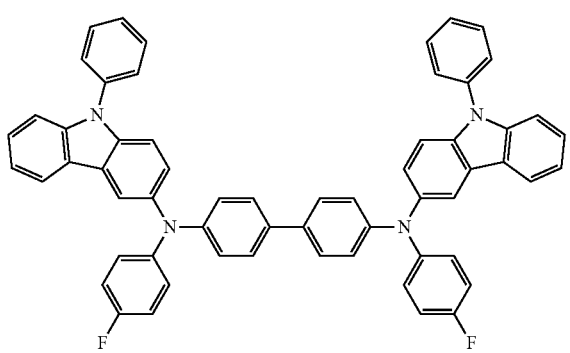
HT16
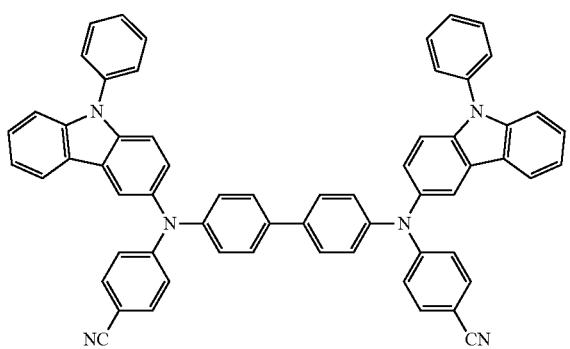
HT13
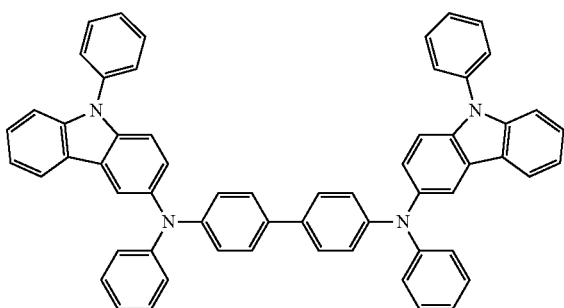
HT17
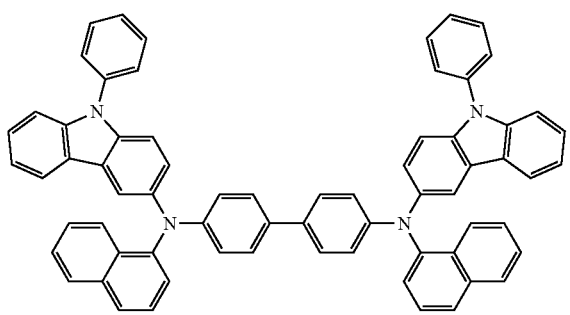

HT18

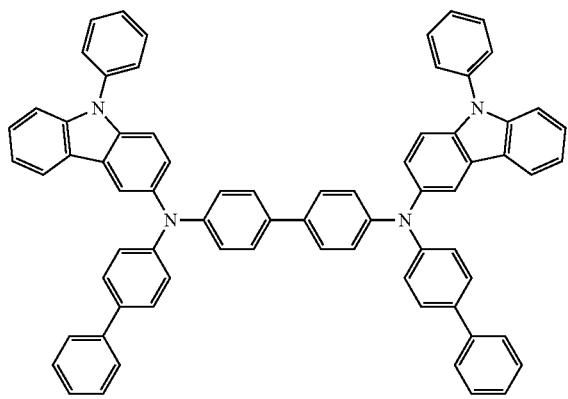

HT19

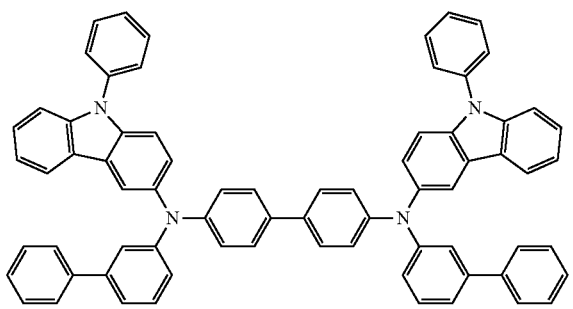

HT20

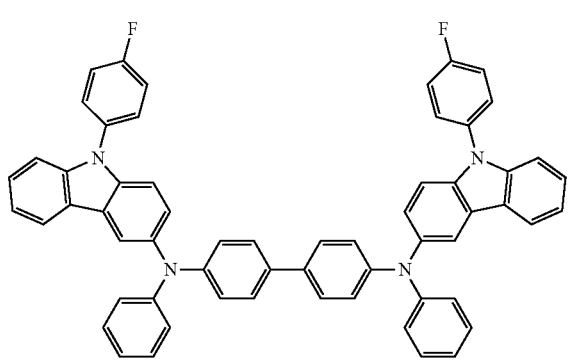

A thickness of the hole transport region may be in a range of about 100 Angstrom (Å) to about 10,000 Å, for example, about 100 Å to about 1,000 Å. When the hole transport region includes an HIL and a HTL, a thickness of the HIL may be in a range of about 100 Å to about 10,000 Å, for example, about 100 Å to about 1,000 Å, and a thickness of the HTL may be in a range of about 50 Å to about 2,000 Å, for example, about 100 Å to about 1,500 Å. When the thicknesses of the hole transport region, the HIL, and the HTL are within these ranges, satisfactory hole transporting characteristics may be obtained without a substantial increase in driving voltage.

The hole transport region may further include, in addition to the abovementioned materials, a charge-generating material for the improvement of conductive properties. The charge-generating material may be homogeneously or non-homogeneously dispersed throughout the hole transport region.

The charge-generating material may be, for example, a p-dopant. The p-dopant may be one of a quinone derivative, a metal oxide, and a cyano group-containing compound, but is not limited thereto. For example, non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and Compound HT-D1 illustrated below, but are not limited thereto.

Compound HT-D1

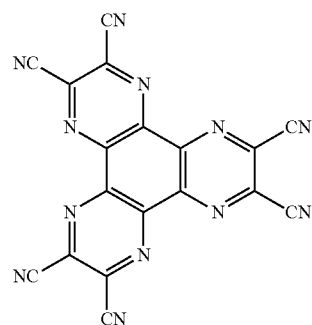

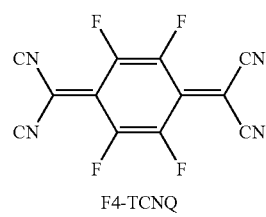

F4-TCNQ

The hole transport region may further include a buffer layer.

The buffer layer may compensate for an optical resonance distance according to a wavelength of light emitted from the EML, and thus, efficiency of an organic light-emitting device may be improved.

An EML may be formed on the hole transport region by using various methods, such as vacuum deposition, spin coating, casting, or an LB method. When the EML is formed by vacuum deposition or spin coating, deposition and coating conditions for the EML may be determined by referring to the deposition and coating conditions for the HIL.

The EML may include a host and a dopant. The host may include at least one condensed-cyclic compound represented by Formula 1A or 1B.

The host may include at least one compound selected from TPBi, TBADN, ADN (also referred to as "DNA"), CBP, CDBP, and TCP:

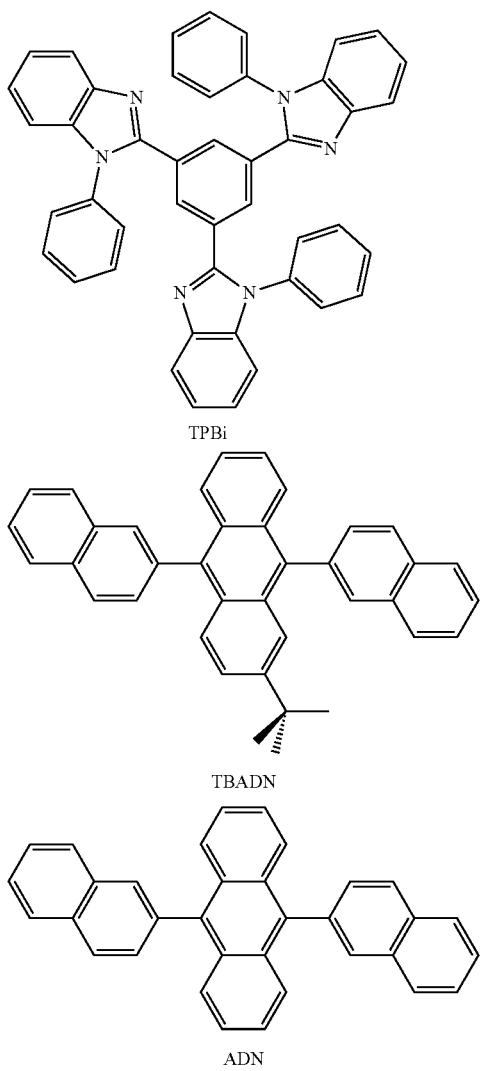

TPBi

TBADN

ADN

CBP

CDBP

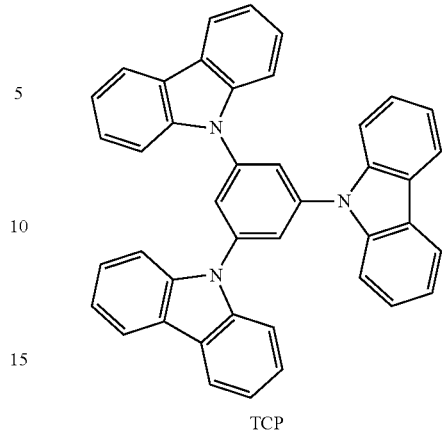

TCP

When the organic light-emitting device 10 is a full color organic light-emitting device, the EML may be patterned into a red EML, a green EML, and a blue EML. In some embodiments, the EML may have a stacked structure of a red EML, a green EML, and/or a blue EML to emit white light. The host in the red EML, green EML, and blue EML may include the condensed-cyclic compound represented by Formula 1. According to an embodiment, the host in the green EML may include the condensed-cyclic compound represented by Formula 1A or 1B.

The EML may include a fluorescent dopant that emits light according to a fluorescent light emission mechanism or a phosphorescent dopant that emits light according to a phosphorescent light emission mechanism.

According to an embodiment, the EML may include a fluorescent and a phosphorescent dopant including the condensed-cyclic compound represented by Formula 1A or 1B. The phosphorescent dopant may include an organic metal complex including a transition metal (for example, iridium (Ir), platinum (Pt), osmium (Os), rhodium (Rh), or the like).

The phosphorescent compound may include an organometallic compound represented by Formula 81:

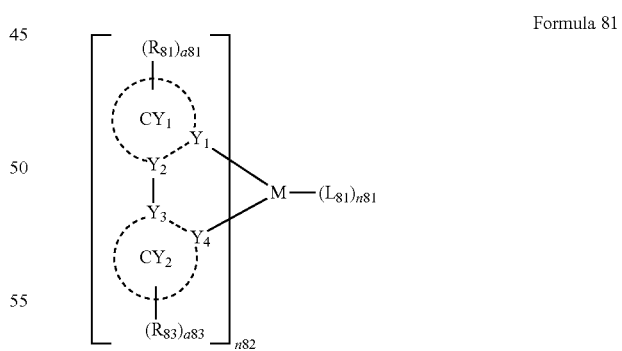

Formula 81

In Formula 81,

M may be selected from Iridium (Ir), platinum (Pt), osmium (Os), titanium (Ti), zirconium (Zr), hafnium (Hf), europium (Eu), terbium (Tb), and thulium (Tm);

$Y_1$ to $Y_4$ may be each independently carbon (C) or nitrogen (N);

$Y_1$ and $Y_2$ may be connected by a single bond or a double bond, and $Y_3$ and $Y_4$ may be connected by a single bond or a double bond;

CY$_1$ and CY$_2$ may be each independently selected from a benzene, a naphthalene, a fluorene, a spiro-fluorene, an indene, a pyrrole, a thiophene, a furan, an imidazole, a pyrazole, a thiazole, an isothiazole, an oxazole, an isooxazole, a pyridine, a pyrazine, a pyrimidine, a pyridazine, a quinoline, an isoquinoline, a benzoquinoline, a quinoxaline, a quinazoline, a carbazole, a benzoimidazole, benzofuran, a benzothiopene, an isobenzothiopene, a benzooxazole, an isobenzooxazole, a triazole, a tetrazole, an oxadiazole, a triazine, a dibenzofuran, and a dibenzothiopene, wherein CY$_1$ and CY$_2$ are optionally bound to each other via a single bond or an organic linking group;

R$_{81}$ and R$_{82}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, —SF$_5$, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_2$-C$_{10}$ heterocycloalkyl group, a substituted or unsubstituted C$_3$-C$_{10}$ cycloalkenyl group, a substituted or unsubstituted C$_2$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_2$-C$_{60}$ heteroaryl group, a substituted or unsubstituted monovalent non-aromatic condensed polycyclic group, a substituted or unsubstituted monovalent non-aromatic hetero-condensed polycyclic group, —N(Q$_1$)(Q$_2$), —Si(Q$_3$)(Q$_4$)(Q$_5$), and —B(Q$_6$)(Q$_7$);

a81 and a82 are each independently selected from integers of 1 to 5;

n81 is selected from integers of 0 to 4;

n82 is 1, 2, or 3; and

L$_{81}$ is selected from a monovalent organic ligand, a divalent organic ligand, and a trivalent organic ligand.

Descriptions of R$_{81}$ and R$_{82}$ may be the same as the description of R$_5$.

The phosphorescent dopant may include at least one of Compounds PD1 to PD74, but it is not limited thereto:

PD1

PD2

PD3

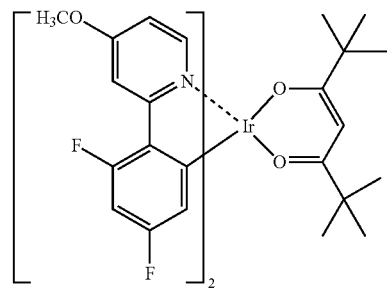

PD4

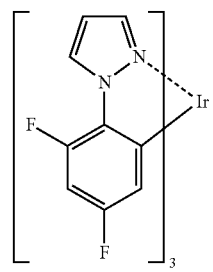

PD5

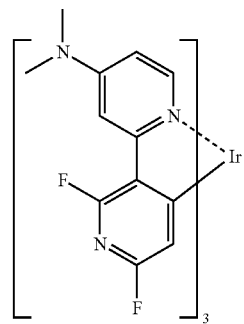

PD6

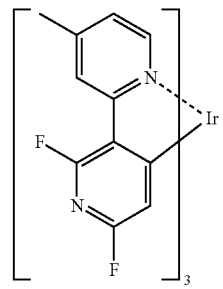

PD7

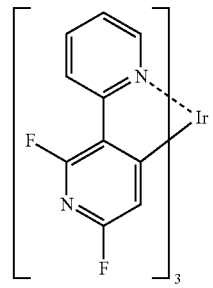

PD8
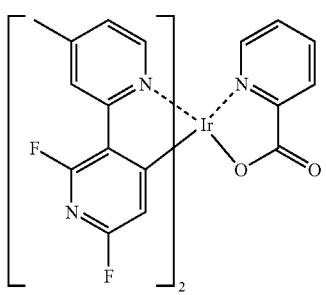
PD9
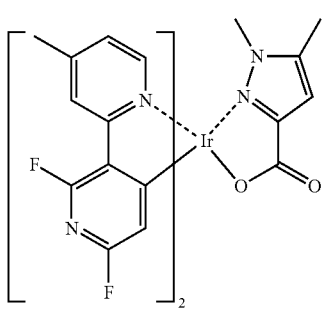
PD10
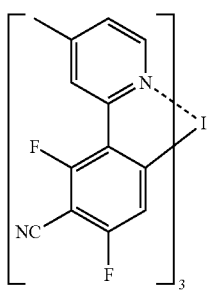
PD11
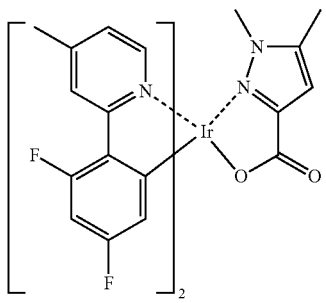
PD12
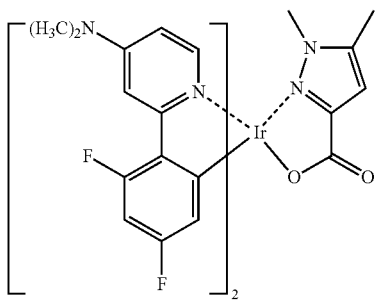
PD13
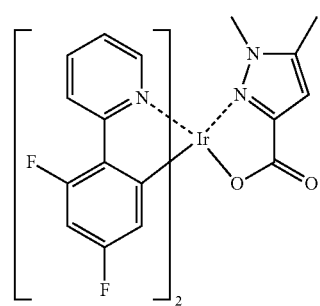
PD14
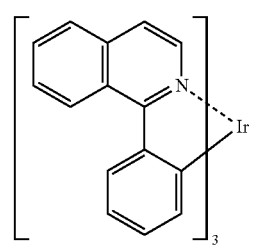
PD15
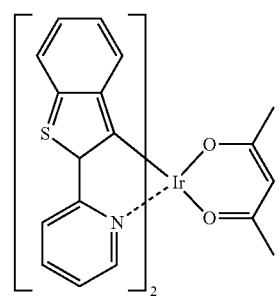
PD16
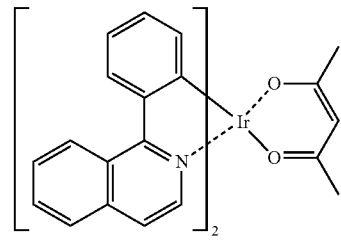
PD17
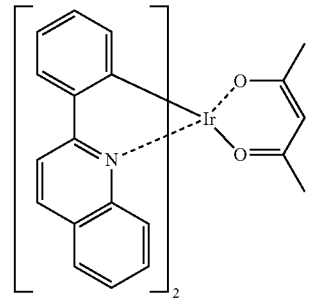

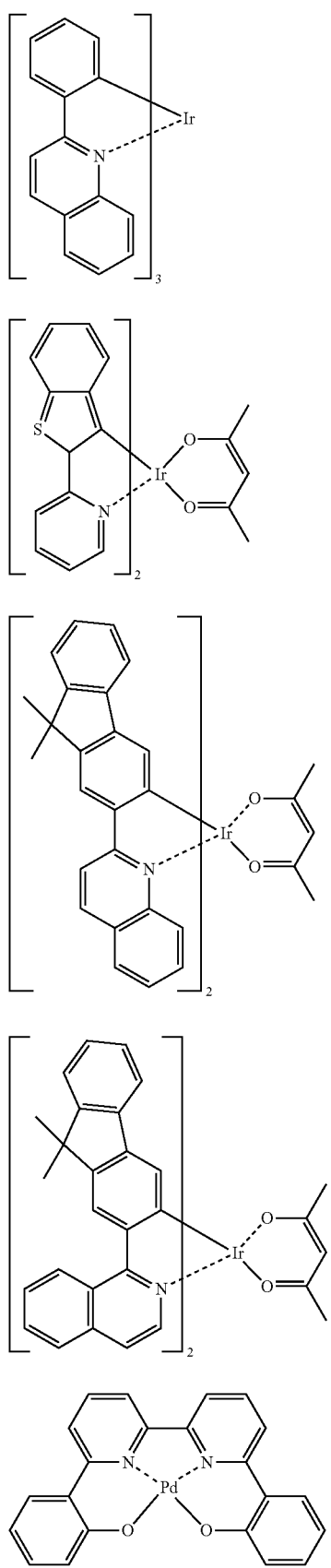
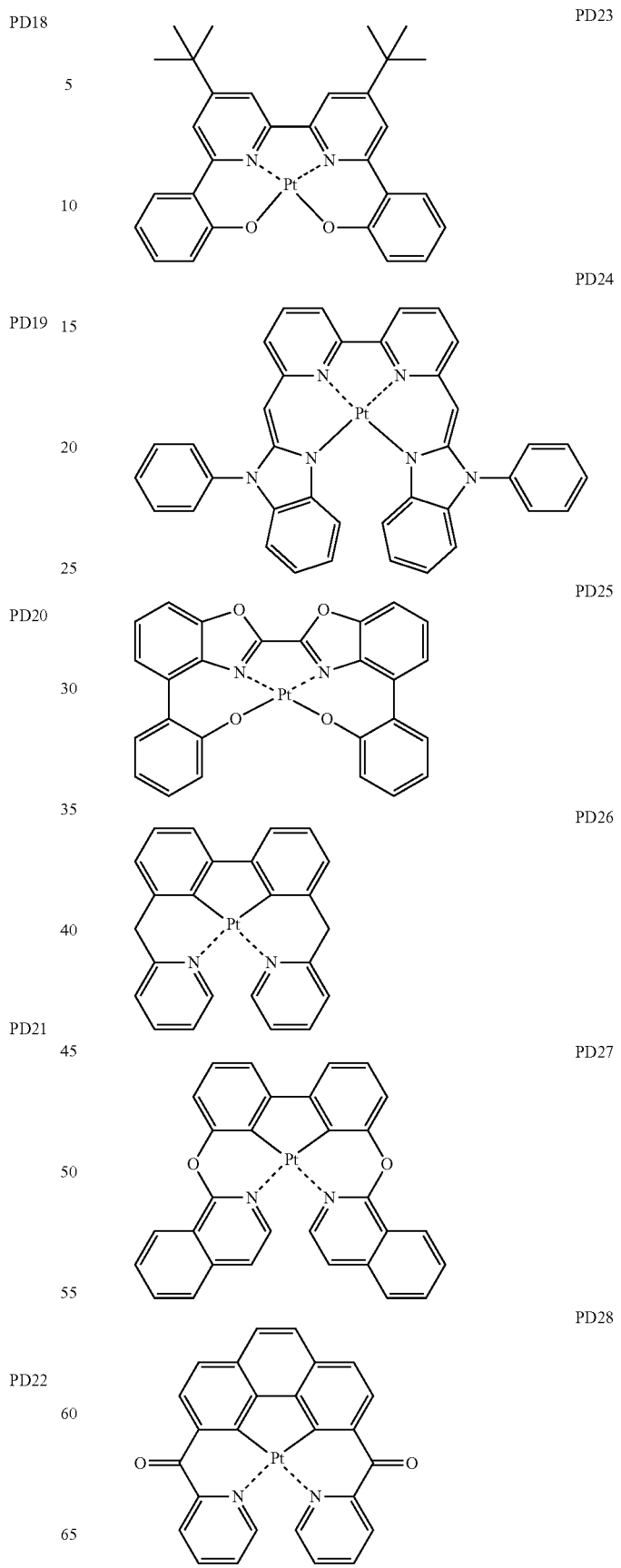

-continued
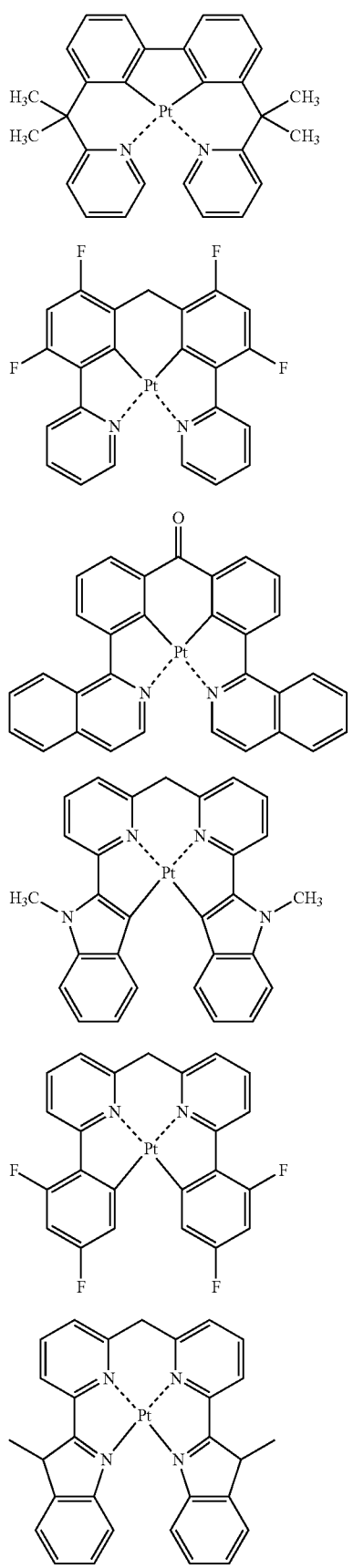
-continued
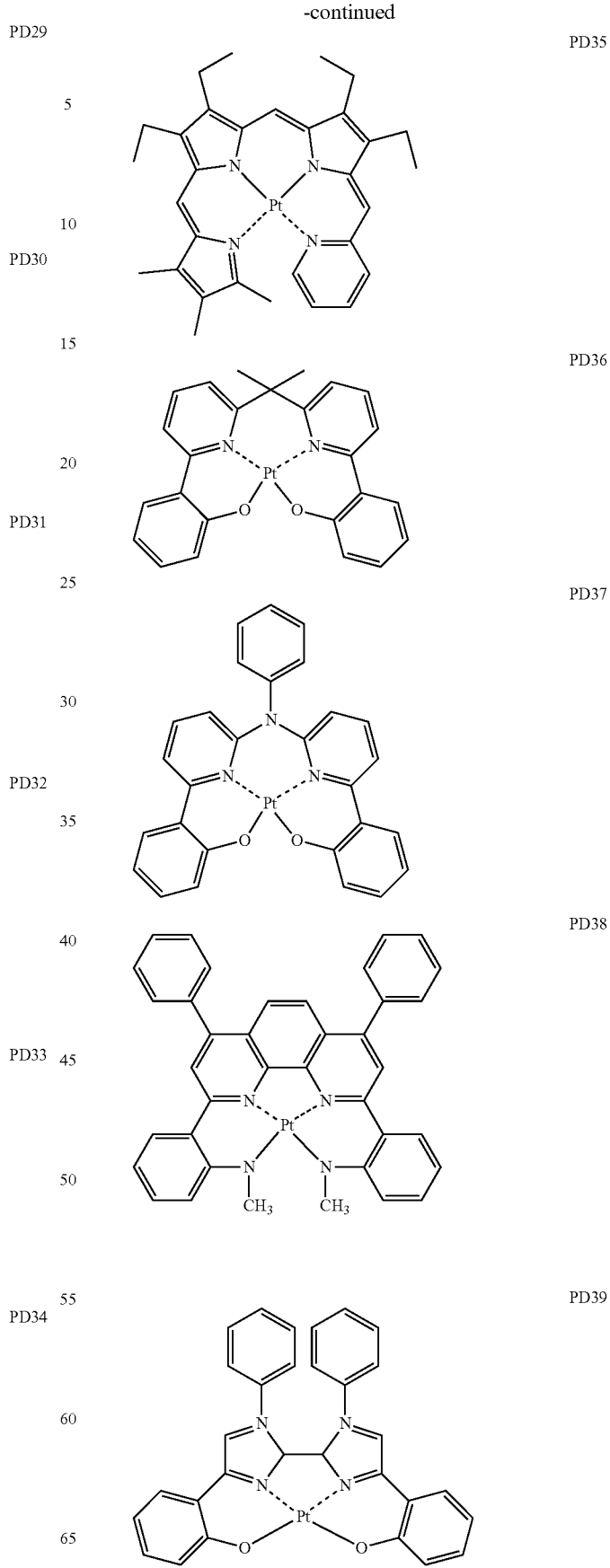

PD40 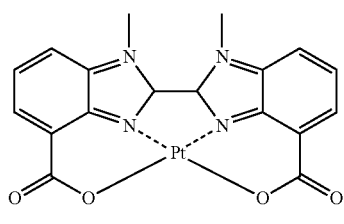
PD41 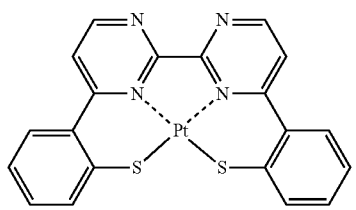
PD42 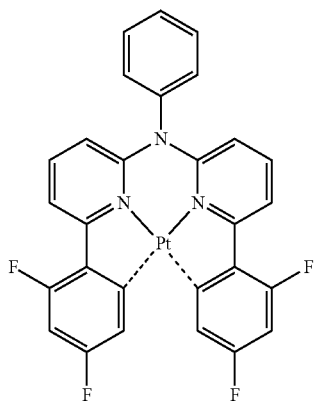
PD43 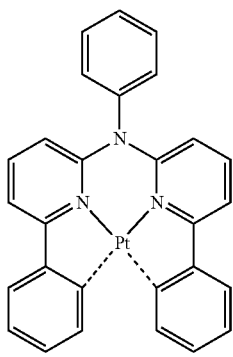
PD44 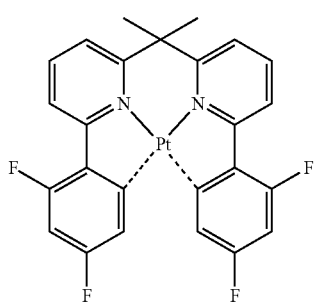
PD45 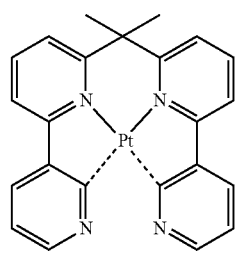
PD46 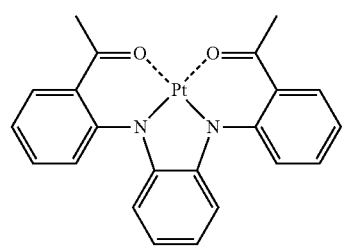
PD47 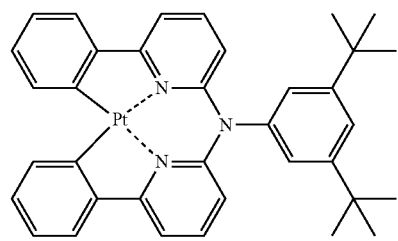
PD48 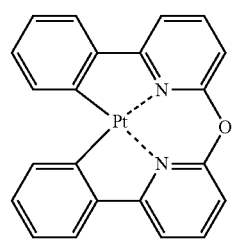
PD49 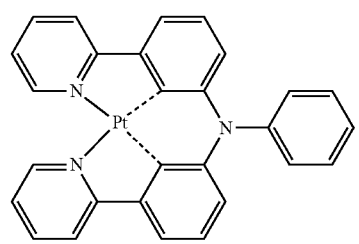
PD50 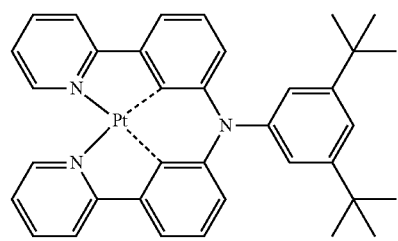

PD51 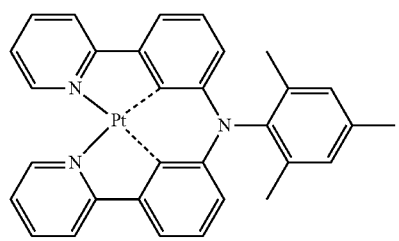
PD57 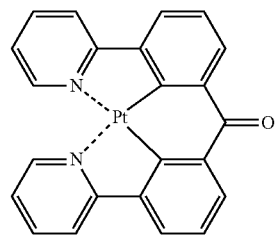
PD52 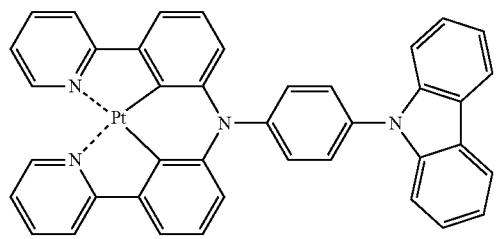
PD58 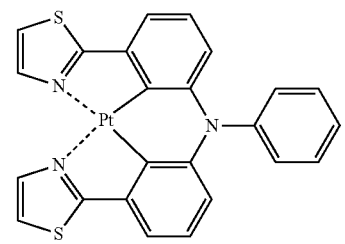
PD53 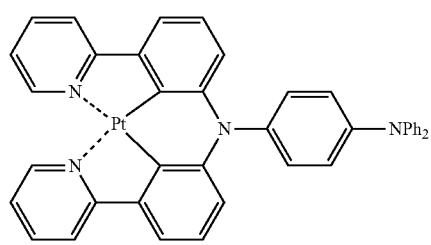
PD54 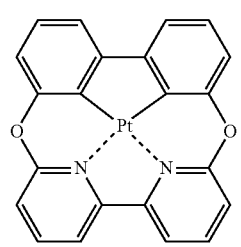
PD59 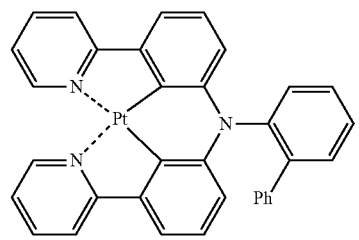
PD55 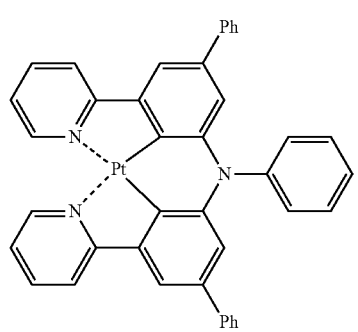
PD60 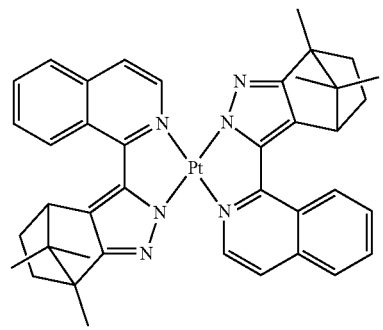
PD56 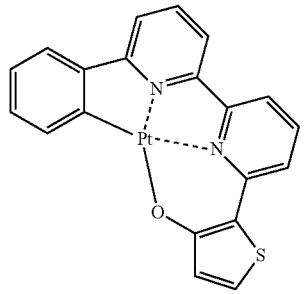
PD61

-continued
PD62
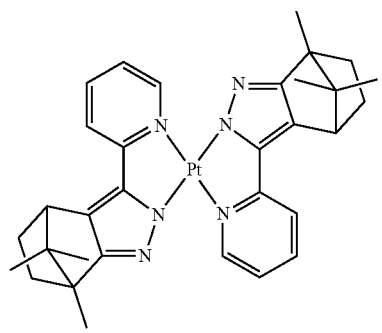
PD63
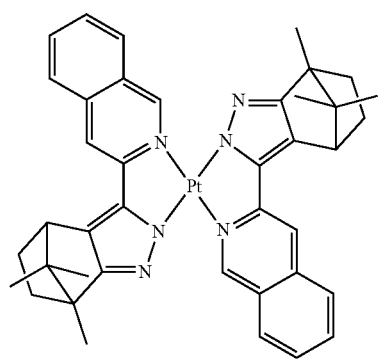
PD64
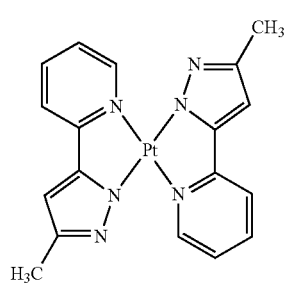
PD65
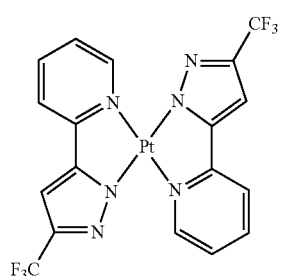
PD66
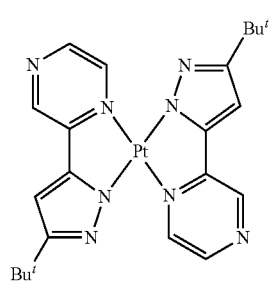
-continued
PD67
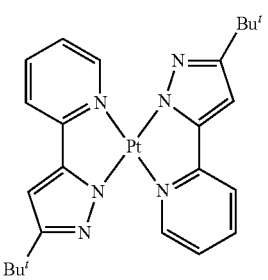
PD68
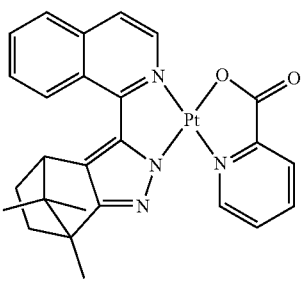
PD69
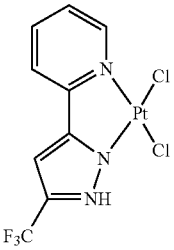
PD70
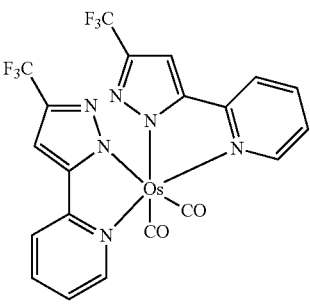
PD71
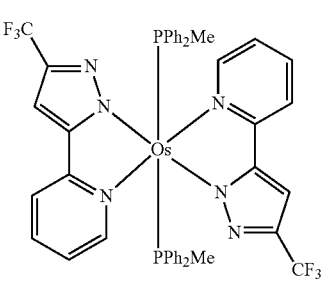

-continued
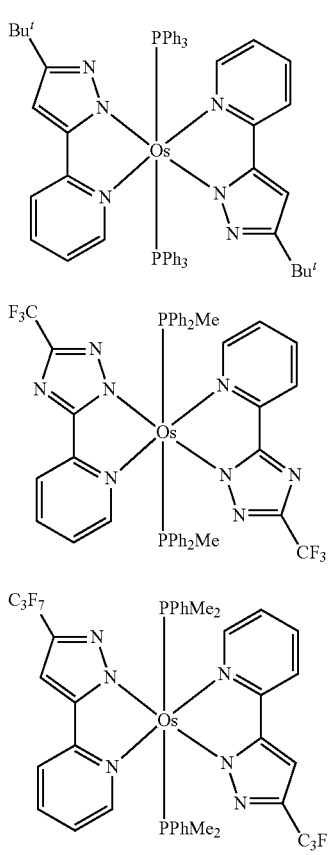
Alternatively, the phosphorescent dopant may include PtOEP or compound PhGD:
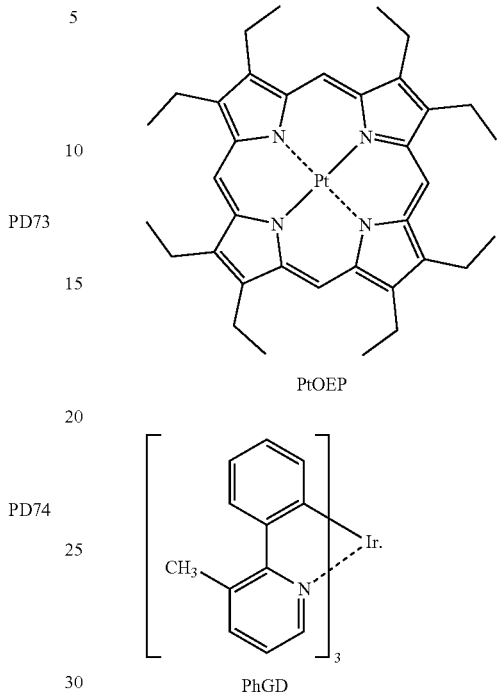
The fluorescent dopant may include at least one of DPVBi, DPAVBi, TBPe, DCM, DCJTB, Coumarin 6, and C545T.
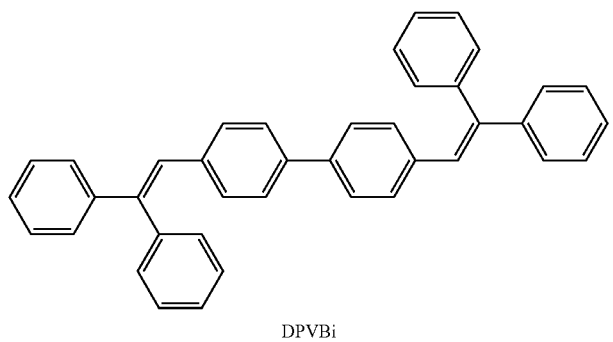
DPVBi
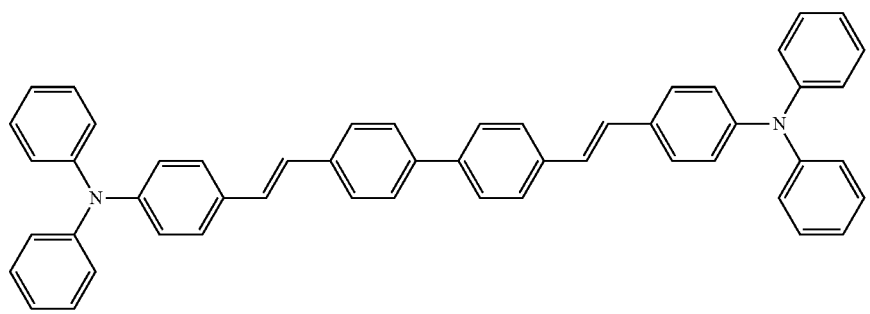
DPAVBi

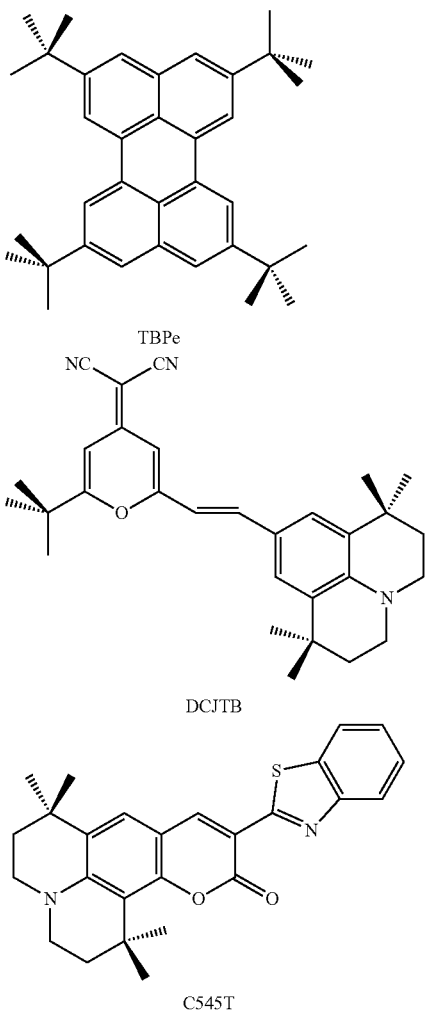
TBPe

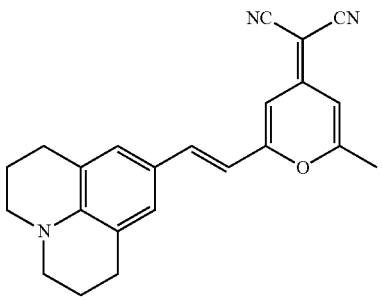
DCM

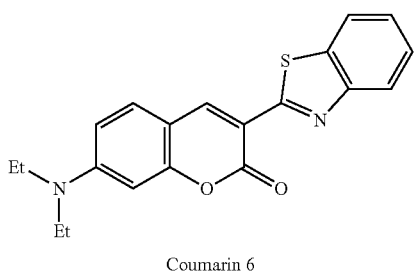
Coumarin 6

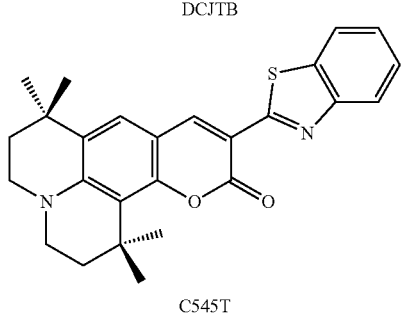
DCJTB

C545T

When the EML includes the host and the dopant, an amount of the dopant may be selected from a range of about 0.01 parts by weight to about 15 parts by weight based on 100 parts by weight of the host, but the amount is not limited thereto.

A thickness of the EML may be about 100 Å to about 1,000 Å, for example, about 200 Å to about 600 Å. When the thickness of the EML is within this range, excellent light-emission characteristics may be obtained without a substantial increase in driving voltage.

Then, an electron transport region may be disposed on the EML.

The electron transport region may include at least one layer selected from a HBL, an ETL, and an EIL, but is not limited thereto.

For example, the electron transport region may have an HBL/ETL/EIL structure or an ETL/EIL structure, wherein layers of each structure are sequentially stacked from the EML in the stated order, but is not limited thereto. The ETL may have a single layer or a multi-layer structure including two or more different materials.

The conditions for forming the HBL, ETL, and EIL may be understood by referring to the conditions for forming the HIL.

When the electron transport region includes the HBL, the HBL may include, for example, at least one of BCP and Bphen, but it is not limited thereto.

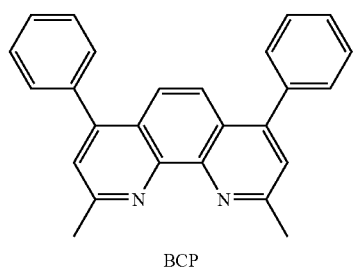
BCP

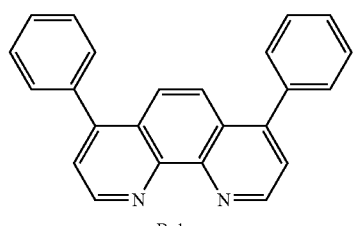
Bphen

A thickness of the HBL may be in a range of about 20 Å to about 1,000 Å, for example, about 30 Å to about 300 Å. When the thickness of the HBL is within the range described above, the HBL may have excellent hole blocking characteristics without a substantial increase in driving voltage.

The ETL may include at least one of BCP and Bphen, and may further include at least one of Alq₃, Balq, TAZ, and NTAZ.

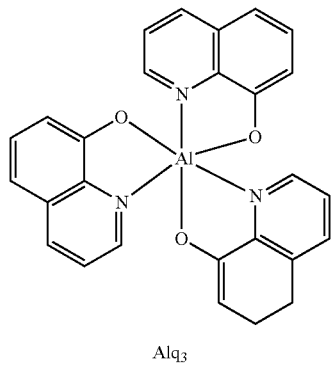

Alq₃

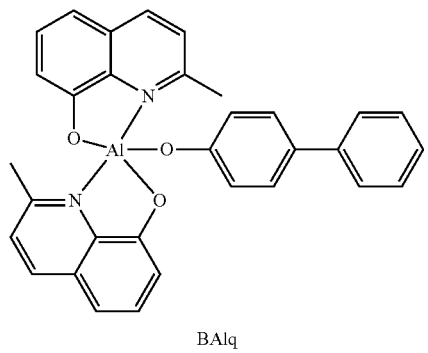

BAlq

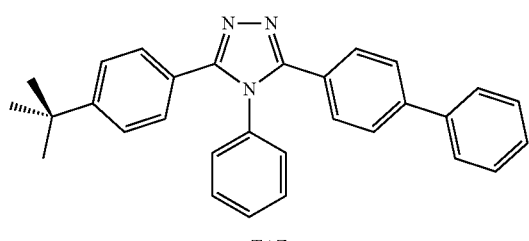

TAZ

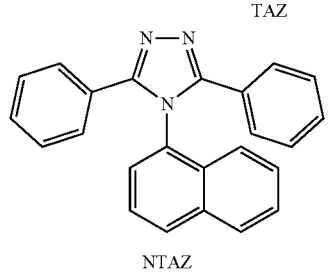

NTAZ

Alternatively, the ETL may include at least one of Compound ET1 and ET2, but it is not limited thereto.

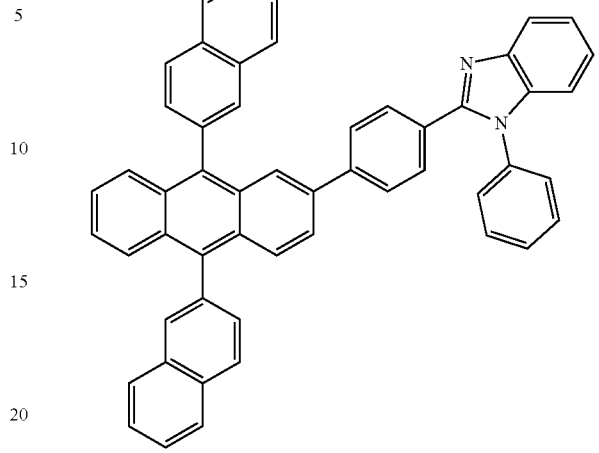

ET1

ET2

A thickness of the ETL may be in a range of about 100 Å to about 1,000 Å, for example, about 150 Å to about 500 Å. When the thickness of the ETL is within the range described above, the ETL may have satisfactory electron transportation characteristics without a substantial increase in driving voltage.

Also, the ETL may further include, in addition to the materials described above, a metal-containing material.

The metal-containing material may include a $L_1$ complex. The $L_1$ complex may include, for example, Compound ET-D1 (lithium quinolate, LiQ) or ET-D2.

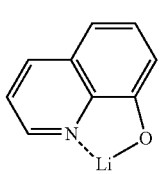

ET-D1

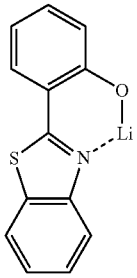
ET-D2

The electron transport region may include an EIL that allows electrons to be easily provided from the second electrode 19.

The EIL may include at least one compound selected from LiF, NaCl, CsF, $Li_2O$, and BaO.

A thickness of the EIL may be in a range of about 1 Å to about 100 Å, for example, about 3 Å to about 90 Å. When the thickness of the EIL is within the range described above, the EIL may have satisfactory electron transportation characteristics without a substantial increase in driving voltage.

The second electrode 19 is disposed on the organic layer 15 having the structure described above. The second electrode 19 may be a cathode that is an electron injection electrode, and in this regard, a material for forming the second electrode 19 may be a material having a low work function, and such a material may be a metal, an alloy, an electrically conductive compound, or a mixture thereof. Detailed examples of the material for forming second electrode 19 are lithium (Li), magnesium (Mg), aluminum (Al), aluminum-lithium (Al—Li), calcium (Ca), magnesium-indium (Mg—In), and magnesium-silver (Mg—Ag). Alternatively, ITO or IZO may be may be used to form a transmissive second electrode 19 to manufacture a top emission light-emitting device.

Hereinbefore, the organic light-emitting device has been described with reference to the FIGURE, but is not limited thereto.

A $C_1$-$C_{60}$ alkyl group used herein refers to a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene used herein refers to a divalent group having the same structure as the $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl group). Detailed examples thereof are a methoxy group, an ethoxy group, and an isopropyloxy group.

A $C_2$-$C_{60}$ alkenyl group used herein refers to a hydrocarbon group formed by substituting at least one carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group used herein refers to a divalent group having the same structure as the $C_2$-$C_{60}$ alkenyl group.

A $C_2$-$C_{60}$ alkynyl group used herein refers to a hydrocarbon group formed by substituting at least one carbon triple bond in the middle or at the terminal of the $C_2$-$C_{60}$ alkyl group. Detailed examples thereof are an ethynyl group and a propynyl group. A $C_2$-$C_{60}$ alkynylene group used herein refers to a divalent group having the same structure as the $C_2$-$C_{60}$ alkynyl group.

A $C_3$-$C_{10}$ cycloalkyl group used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_3$-$C_{10}$ heterocycloalkyl group used herein refers to a monovalent monocyclic group having at least one heteroatom selected from N, O, P, and S as a ring-forming atom and 3 to 10 carbon atoms. Detailed examples thereof are tetrahydrofuranyl and tetrahydrothiophenyl. A $C_3$-$C_{10}$ heterocycloalkylene group used herein refers to a divalent group having the same structure as the $C_3$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromaticity. Detailed examples thereof are a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_2$-$C_{10}$ heterocycloalkenyl group used herein refers to a monovalent monocyclic group that has at least one heteroatom selected from N, O, P, and S as a ring-forming atom, 2 to 10 carbon atoms, and at least one double bond in its ring. Detailed examples of the $C_2$-$C_{10}$ heterocycloalkenyl group are a 2,3-dihydrofuranyl group and a 2,3-dihydrothiophenyl group. A $C_2$-$C_{10}$ heterocycloalkenylene group used herein refers to a divalent group having the same structure as the $C_2$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_2$-$C_{60}$ heteroaryl group used herein refers to a monovalent group having a carbocyclic aromatic system that has at least one heteroatom selected from N, O, P, and S as a ring-forming atom, and 2 to 60 carbon atoms. A $C_2$-$C_{60}$ heteroarylene group used herein refers to a divalent group having a carbocyclic aromatic system that has at least one heteroatom selected from N, O, P, and S as a ring-forming atom, and 2 to 60 carbon atoms. Detailed examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other.

A $C_6$-$C_{60}$ aryloxy group used herein indicates —$OA_{102}$ (wherein $A_{102}$ is the $C_6$-$C_{60}$ aryl) and a $C_6$-$C_{60}$ arylthio group used herein indicates —$SA_{103}$ (wherein $A_{103}$ is the $C_6$-$C_{60}$ aryl group).

A monovalent non-aromatic condensed polycyclic group (for example, having 8 to 60 carbon atoms) used herein refers to a monovalent group that has two or more rings condensed to each other, only carbon atoms as ring-forming atoms, wherein the molecular structure as a whole is non-aromatic. A detailed example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group (for example, having 2 to 60 carbon atoms) used herein refers to a monovalent group that has two or more rings condensed to each other, has a heteroatom selected from N, O P, and S, other than carbon atoms, as a ring forming atom, wherein the molecular structure as a whole is non-aromatic. Detailed examples of the monovalent non-aromatic condensed heteropolycyclic group are a carbazolyl group. A divalent non-aromatic condensed heteropolycyclic group used herein refers to a divalent group having the same structure as the monovalent non-aromatic condensed heteropolycyclic group.

Hereinafter, an organic light-emitting device according to an embodiment will be described in detail with reference to Synthesis Examples and Examples. The wording "B was used instead of A" used in describing Synthesis Examples means that a molar equivalent of A was identical to a molar equivalent of B.

EXAMPLE

Synthesis Example 1: Synthesis of Compound 813

Synthesis of Intermediate B

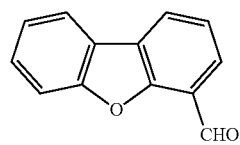

Molecular Weight: 196.20

Intermediate A

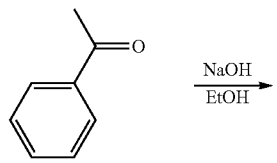

Molecular Weight: 120.15

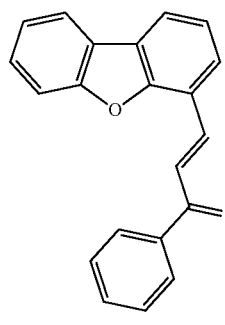

Molecular Weight: 296.33

Intermediate B 44.0 g (224.3 mmol) of Intermediate A, 126.9 g (224.3 mmol) of acetophenone, and 9.0 g (224.3 mmol) of sodium hydroxide were added in 670 mL of ethanol in a 1,000 mL round bottom flask and then stirred in nitrogen atmosphere for 2 hours at room temperature to prepare a mixture. Crystallized solids in the mixture were filtered to obtain Intermediate B (59.2. g and yield 88.0%). Element analysis results of Intermediate B are as follows.

calcd. $C_{21}H_{14}O_2$: C, 84.54; H, 4.73; 0, 10.73. found: C, 84.51; H, 4.75; O, 10.71.

Synthesis of Intermediate C

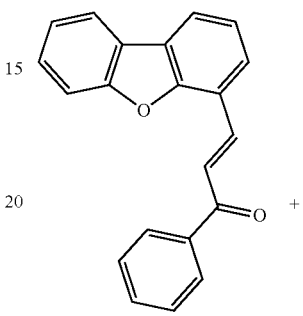

Molecular Weight: 296.33

Intermediate B

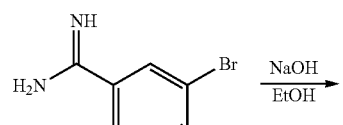

Molecular Weight: 235.51

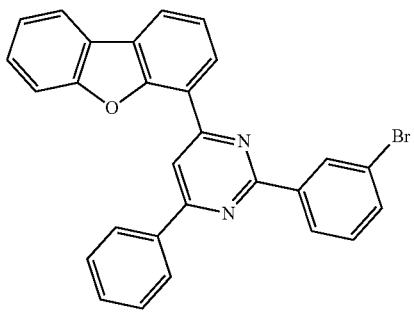

Molecular Weight: 477.35

Intermediate C 13.0 g (106.2 mmol) of Intermediate B, 30.0 g (127.4 mmol) of 3-bromobenzimidamide, and 8.5 g (212.3 mmol) of sodium hydroxide were added in 500 ml of ethanol in a 1,000 mL round bottom flask, heated in a nitrogen atmosphere for 15 hours to reflux the same to prepare a mixture. Crystallized solids in the mixture were stirred with water and then filtered. The crystallized solids were stirred again by using ethanol and then filtered to obtain Intermediate C (23.8 g, yield 47%). Element analysis results of the Intermediate C are as follows.

calcd. $C_{28}H_{17}BrN_2O$: C, 70.45; H, 3.59; Br, 16.74; N, 5.87; O, 3.35. found C, 70.43; H, 3.60; Br, 16.72; N, 5.85; O, 3.36.

Synthesis of Compound 813

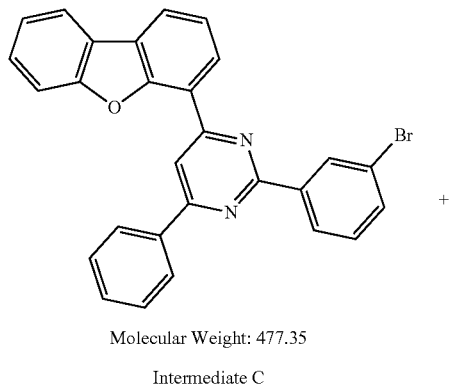

Molecular Weight: 477.35

Intermediate C

Molecular Weight: 167.21

Molecular Weight: 563.66

Compound 813

Synthesis Example 2: Synthesis of Compound 814

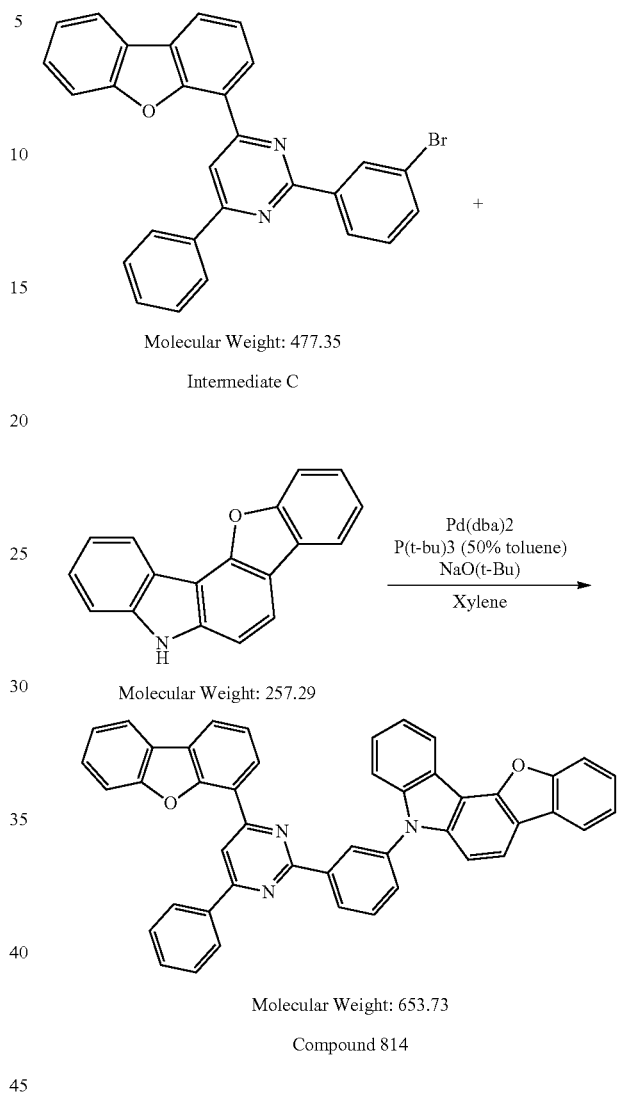

Molecular Weight: 477.35

Intermediate C

Molecular Weight: 257.29

Molecular Weight: 653.73

Compound 814

23.8 g (49.9 mmol) of Intermediate C, 7.0 g (41.6 mmol) of 9H-carbazole, 8.0 g (83.1 mmol) of sodium t-butoxide, 3.8 g (4.2 mmol) of Pd(dba)$_2$, and 4.2 mL (8.3 mmol) of tri-t-butyl phosphine (50% in toluene solution) were added to 166.2 mL of xylene in a 500 mL round bottom flask, and heated in a nitrogen atmosphere for 15 hours to reflux the same to prepare a mixture. The mixture was added to 1,000 mL of methanol to filter crystallized solids, dissolved in monochlorobenzene to filter the same by using a silica gel/celite, a suitable amount of organic solvent was removed therefrom, and then the same was recrystallized with methanol to obtain Compound 813 (11.7 g and yield 50%). Element analysis results and NMR analysis results of Compound 813 are as follows.

calcd. $C_{40}H_{25}N_3O$: C, 85.24; H, 4.47; N, 7.46; O, 2.84. found C, 85.22; H, 4.46; N, 7.47; O, 2.83.

300 MHz (CDCl$_3$, ppm): δ 8.960 (m, 1H), 8.865 (m, 2H), 8.657 (dd, 1H), 8.359 (dd, 2H), 8.196 (d, 2H), 8.081 (dd, 1H), 7.999 (d, 1H), 7.816 (t, 1H), 7.659-7.727 (m, 2H), 7.381-7.601 (m, 10H), 7.316 (t, 2H)

15.0 g (31.4 mmol) of Intermediate C, 9.7 g (37.7 mmol) of 5H-benzofuro[3,2-c]carbazole, 6.0 g (62.9 mmol) of sodium t-butoxide, 2.9 g (3.1 mmol) of Pd(dba)$_2$, and 3.1 mL (6.3 mmol) of tri-t-butyl phosphine (50% in toluene solution) were added to 125.7 mL of xylene in a 500 mL round bottom flask, and heated in a nitrogen atmosphere for 15 hours to reflux the same to prepare a mixture. The mixture was added to 1,000 mL of methanol to filter crystallized solids, dissolved in dichlorobenzene to filter the same by using a silica gel/celite, a suitable amount of organic solvent was removed therefrom, and then the same was recrystallized with methanol to obtain Compound 814 (11.8 g, yield 57%). Element analysis results and NMR analysis results of Compound 814 are as follows.

calcd. $C_{46}H_{27}N_3O_2$: C, 84.51; H, 4.16; N, 6.43; O, 4.89. found C, 84.49; H, 4.17; N, 6.44; O, 4.87.

300 MHz (CDCl$_3$, ppm): δ 9.023 (t, 1H), 8.905-8.959 (m, 2H), 8.797 (dd, 1H), 8.666 (dd, 1H), 8.392 (m, 2H), 8.110 (dd, 1H), 8.012 (m, 3H), 7.684-7.884 (t, 4H), 7.362-7.627 (m, 12H)

Synthesis Example 3: Synthesis of Compound 815

Synthesis of Intermediate D

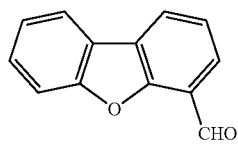

Molecular Weight: 196.20

Intermediate A

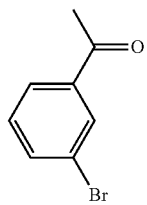

Molecular Weight: 199.04

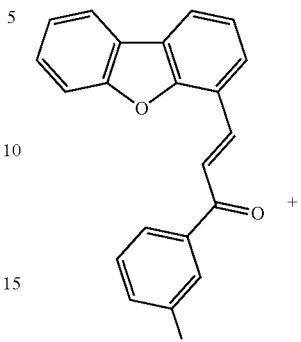

Molecular Weight: 377.23

Intermediate D 30.0 g (152.9 mmol) of Intermediate A, 30.4 g (152.9 mmol) of 1-(3-bromophenyl)ethanone, and 6.1 g (152.9 mmol) of sodium hydroxide were added to 458.7 mL of ethanol in a 1,000 mL round bottom flask and then stirred in a nitrogen current for 2 hours at room temperature to prepare a mixture. Crystallized solids in the mixture were filtered to obtain Intermediate D (46.2 g, yield 80.0%). Element analysis results of Intermediate D are as follows.

calcd. $C_{21}H_{13}BrO_2$: C, 66.86; H, 3.47; Br, 21.18; O, 8.48. found C, 66.83; H, 3.45; Br, 21.17; O, 8.49.

Synthesis of Intermediate E

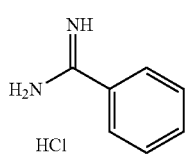

Molecular Weight: 156.61

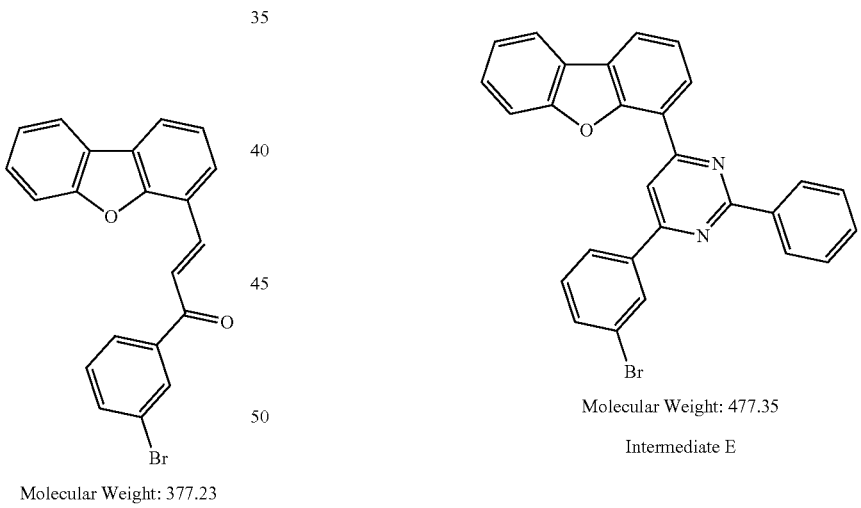

Molecular Weight: 477.35

Intermediate E 80.3 g (212.9 mmol) of Intermediate D, 40.0 g (255.4 mmol) of benzimidamide, and 17 g (425.7 mmol) of sodium hydroxide were added to 1,000 ml of ethanol in a 2,000 mL round bottom flask and then heated in a nitrogen atmosphere for 15 hours to reflux the same to prepare a mixture. Crystallized solids in the mixture were filtered and then stirred with water to filter the same. The crystallized solids were stirred again with ethanol and then filtered to obtain Intermediate E (45.8 g, yield 45%). Element analysis results of Intermediate E are as follows.

calcd. $C_{28}H_{17}BrN_2O$: C, 70.45; H, 3.59; Br, 16.74; N, 5.87; O, 3.35. found C, 70.44; H, 3.61; Br, 16.71; N, 5.84; O, 3.35.

Synthesis of Compound 815

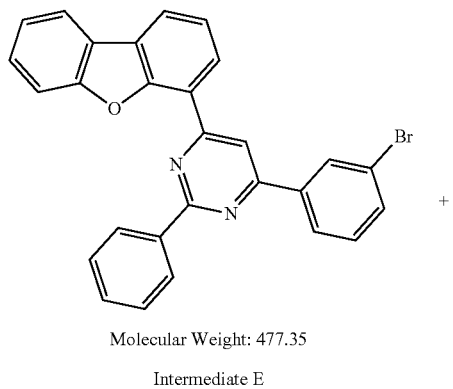

Molecular Weight: 477.35

Intermediate E

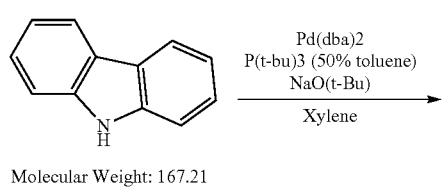

Molecular Weight: 167.21

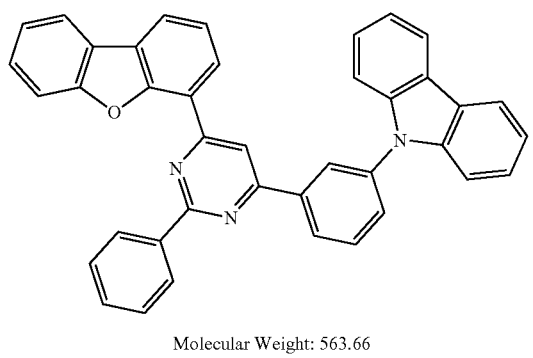

Molecular Weight: 563.66

Compound 815

34.3. g (71.8 mmol) of Intermediate E, 10.0 g (60.0 mmol) of 9H-carbazole, 11.5 g (119.6 mmol) of sodium t-butoxide, 5.5 g (6.0 mmol) of Pd(dba)$_2$, and 2.9 mL (12.0 mmol) of tri-t-butyl phosphine (50% in toluene solution) were added to 239.2 mL of xylene in a 500 mL round bottom flask and then heated in a nitrogen atmosphere for 15 hours to reflux the same to prepare a mixture. The mixture was added to 1,000 mL of methanol to filter crystallized solids, which were dissolved in monochlorobenzene to be filtered by using a silica gel/celite, a suitable amount of organic solvent was removed therefrom and then recrystallized with methanol to obtain Compound 815 (22.2 g, yield 66%). Element analysis results and NMR analysis results of Compound 815 are as follows.

calcd. $C_{40}H_{25}N_3O$: C, 85.24; H, 4.47; N, 7.46; O, 2.84. found C, 85.21; H, 4.47; N, 7.48; O, 2.86.

300 MHz (CDCl$_3$, ppm): δ 8.905 (s, 1H), 8.745 (m, 3H), 8.635 (t, 1H), 8.473 (tt, 1H), 8.208 (d, 2H), 8.120 (dd, 1H), 8.016 (d, 1H), 7.802-7.885 (m, 2H), 7.317-7.600 (m, 13H)

Synthesis Example 4: Synthesis of Compound 816

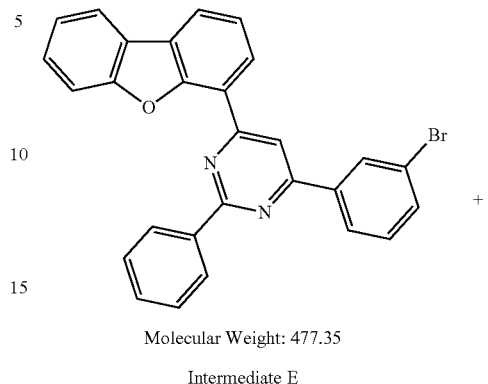

Molecular Weight: 477.35

Intermediate E

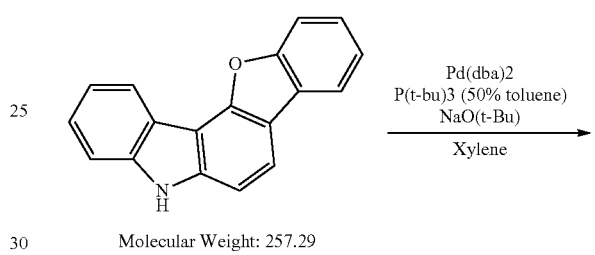

Molecular Weight: 257.29

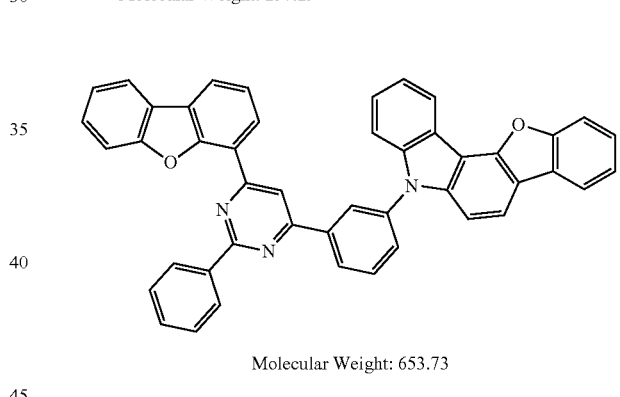

Molecular Weight: 653.73

Compound 816

19.0 g (56.0 mmol) of Intermediate E, 12.0 g (46.6 mmol) of 5H-benzofuro[3,2-c]carbazole, 6.7 g (70.0 mmol) of sodium t-butoxide, 1.3 g (1.4 mmol) of Pd(dba)$_2$, and 2.1 mL (4.2 mmol) tri t-butylphosphine (50% in toluene) were added to 182.9 mL of xylene in a 500 mL round bottom flask and then heated in a nitrogen atmosphere for 15 hours to reflux the same to prepare a mixture. The mixture was added to 1,000 mL of methanol to filter crystallized solids, dissolved in dichlorobenzene to filter the same by using a silica gel/celite, a suitable amount of organic solvent was removed therefrom, and then the same was recrystallized with methanol to obtain Compound 816 (14.7 g, yield 48%). Element analysis results and NMR analysis results of Compound 816 are as follows.

calcd. $C_{46}H_{27}N_3O_2$: C, 84.51; H, 4.16; N, 6.43; O, 4.89. found C, 84.53; H, 4.18; N, 6.42; O, 4.87.

300 MHz (CDCl$_3$, ppm): δ 8.903 (s, 1H), 8.739 (d, 3H), 8.641 (t, 2H), 8.506 (d, 1H), 8.096 (d, 1H), 7.976 (m, 3H), 7.868 (m, 2H), 7.763 (d, 1H), 7.347-7.634 (m, 13H)

Synthesis Example 5: Synthesis of Compound 506

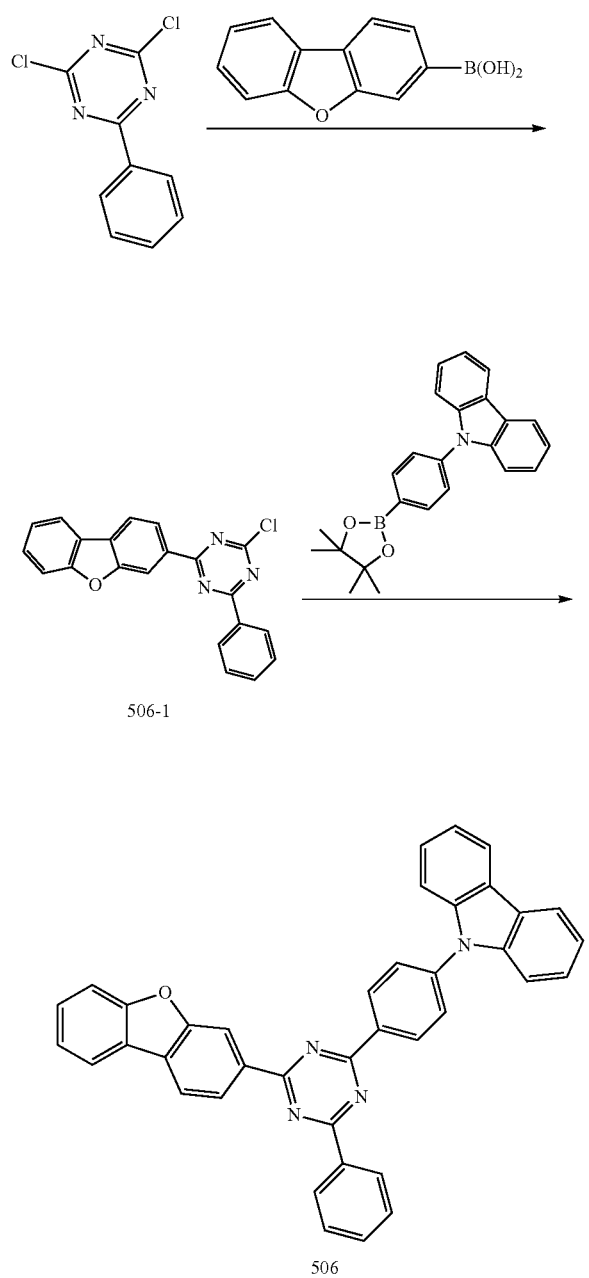

506-1

506 a) Synthesis of Intermediate 506-1

22.6 g (100 mmol) of 2,4-dichloro-6-phenyltriazine was added to 100 mL of tetrahydrofuran, 100 mL of toluene, and 100 mL of distilled water in a 500 mL round-bottom flask, and then, 0.9 equivalent weights of dibenzofuran-3-boronic acid, 0.03 equivalent weights of tetrakistriphenylphosphine palladium, and 2 equivalent weights of potassium carbonate were added thereto, followed by heating while refluxing in a nitrogen atmosphere. After 6 hours, the reaction solution was cooled, the water layer was removed, and the organic layer was dried under reduced pressure. The resulting solid was washed with water and hexane, and the solid was recrystallized by using 200 ml of toluene to complete the preparation of Intermediate 506-1 at a yield of 60%.

b) Synthesis of Compound 506

8.01 g (22.4 mmol) of Intermediate 506-1 synthesized above was added to 80 mL of tetrahydrofuran and 40 mL of distilled water in a 500 mL round-bottom flask, and 1.0 equivalent weight of 9-(4-(4,4,5,5-tetramethyl-1,3,2-dioxaborolan-2-yl)-phenyl)-carbazole (CAS: 785051-54-9), 0.03 equivalent weights of tetrakistriphenylphosphine palladium, and 2 equivalent weights of potassium carbonate were added thereto, followed by heating while refluxing in a nitrogen atmosphere. After 18 hours, the reaction solution was cooled and the precipitated solid was filtered and washed with 500 mL of water. The solid was recrystallized by using 500 mL of monochlorobenzene to complete the preparation of 10.12 g of Compound 506.

LC/MS calculated for: $C_{39}H_{24}N_4O$ Exact Mass: 564.1950 found for: 565.20.

Synthesis Example 6: Synthesis of Compound 825

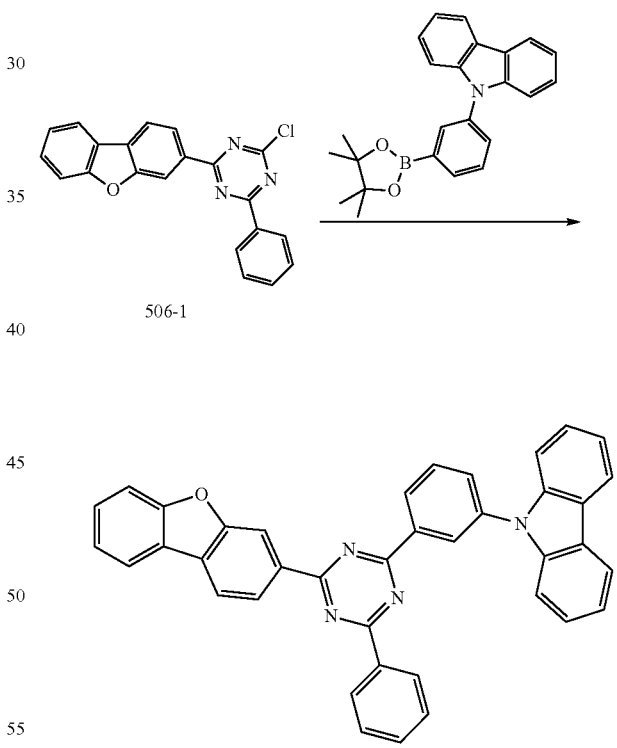

506-1

825

Compound 825 was synthesized in the same manner as in the same manner as in "b)" of Synthesis Example 5, except that 9-(3-(4,4,5,5-tetramethyl-1,3,2-dioxaborolan-2-yl)-phenyl)-carbazole (CAS: 870119-58-7) was used in an equivalent weight of 1.0 instead of 9-(4-(4,4,5,5-tetramethyl-1,3,2-dioxaborolan-2-yl)-phenyl)-carbazole.

LC/MS calculated for: $C_{39}H_{24}N_4O$ Exact Mass: 564.1950 found for: 565.20.

Comparative Synthesis Example 1: Synthesis of Comparative Compound R1
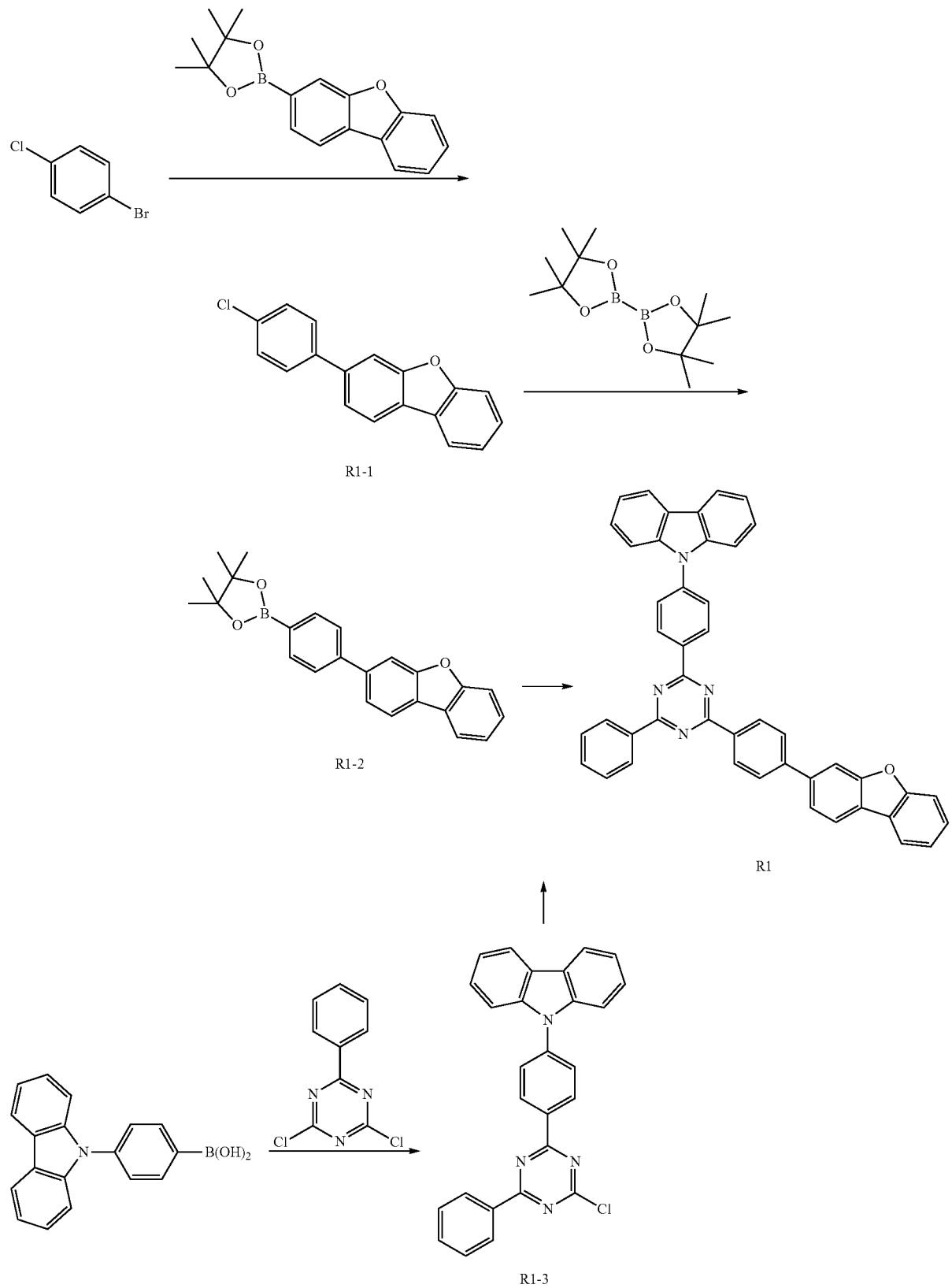

a) Synthesis of Intermediate R1-1

Intermediate R1-1 was synthesized in the same manner as in "b)" of Synthesis Example 5, except that each of 3-(4,4,5,5-tetramethyl-1,3,2-dioxaborolan-2-yl)-dibenzofuran and 1-bromo-4-chloro-benzene was used in an equivalent weight of 1 instead of Intermediate 506-1 and 9-(4-(4,4,5,5-tetramethyl-1,3,2-dioxaborolan-2-yl)-phenyl)-carbazole.

b) Synthesis of Intermediate R1-2

One equivalent weight of Intermediate R1-1 synthesized above was added to 150 mL of xylene in a 500 mL round-bottom flask, and 0.05 equivalent weights of dichlorodiphenylphosphinoferrocene palladium, 1.2 equivalent weights of bis(pinacolato)diboron, and 2 equivalent weights of potassium acetate were added thereto, followed by heating while refluxing for 18 hours in a nitrogen atmosphere. After cooling the reaction solution, the resultant solution was washed with water through extraction, the organic layer was treated with activated carbon and filtered through silica gel, and the filtrate was concentrated. The concentrated solid was stirred with a small amount of hexane, and then the solid was filtered therefrom to complete the preparation of Intermediate R1-2 at a yield of 75%.

c) Synthesis of Intermediate R1-3

Intermediate R1-3 was synthesized in the same manner as in "a)" of Synthesis Example 5, except that 0.9 equivalent weights of [4-(9H-carbazol-9-yl)phenyl]boronic acid was used instead of dibenzofuran-3-boronic acid.

d) Synthesis of Comparative Compound R1

Comparative Compound R1 was synthesized in the same manner as in "a)" of Synthesis Example 5, except that Intermediate R1-2 and Intermediate R1-3 was used in an equivalent weight of 1 instead of 2,4-dichloro-6-phenyltriazine and dibenzofuran-3-boronic acid.

LC/MS calculated for: $C_{45}H_{28}N_4O$ Exact Mass: 640.2263 found for: 641.23.

Comparative Synthesis Example 2: Synthesis of Comparative Compound R2

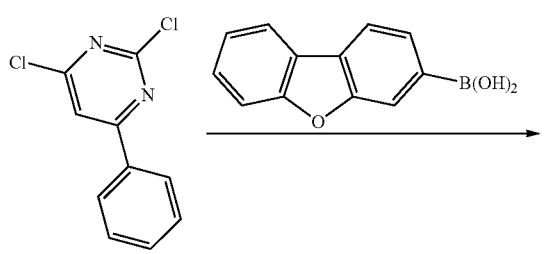

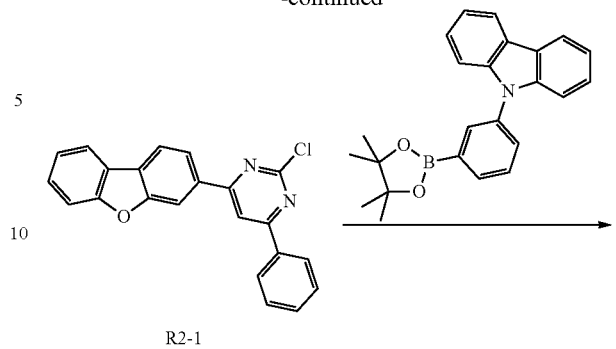

R2-1

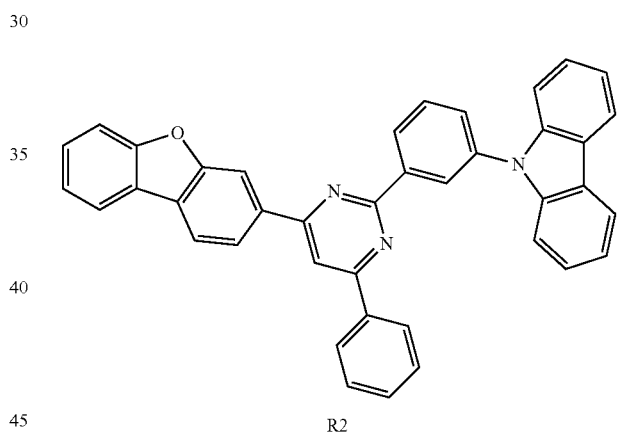

R2 a) Synthesis of Intermediate R2-1

Intermediate R2-1 was synthesized in the same manner as in "a)" of Synthesis Example 5, except that 2,4-dichloro-6-phenylpyrimidine was used in an equivalent weight of 1 instead of 2,4-dichloro-6-phenyltriazine.

b) Synthesis of Comparative Compound R2

Comparative Compound R2 was synthesized in the same manner as in "b)" of Synthesis Example 5, except that each of Intermediate R2-1 synthesized above was used in an equivalent weight of 1.0 instead of Intermediate 506-1.

LC/MS calculated for: $C_{40}H_{25}N_3O$ Exact Mass: 563.1998 found for: 564.23.

Comparative Synthesis Example 3: Synthesis of Comparative Compound R3

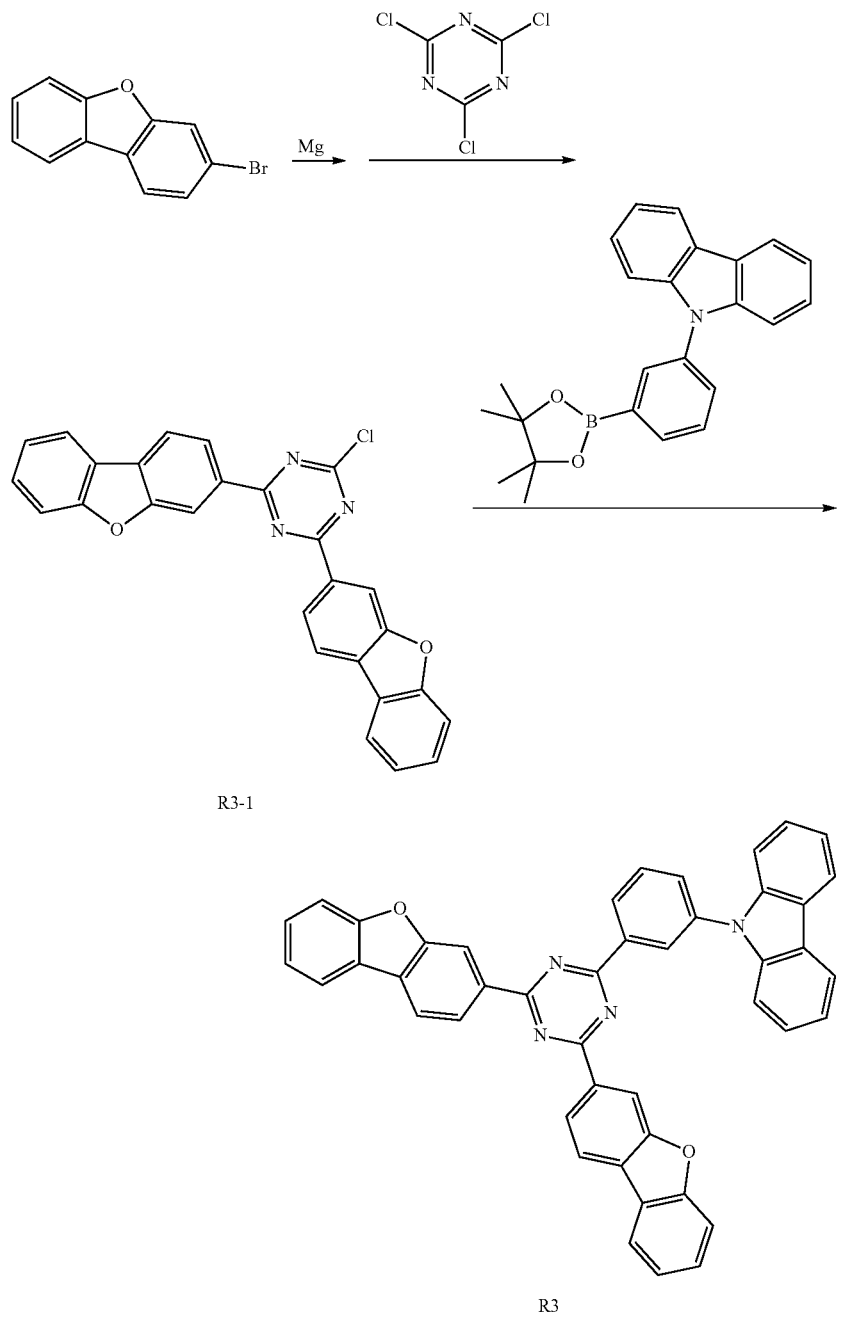

a) Synthesis of Intermediate R3-1

In a nitrogen atmosphere, 7.86 g (323 mmol) of magnesium and 1.64 g (6.46 mmol) of iodine were added to 0.1 L of tetrahydrofuran (THF) and stirred for 30 minutes, and then, 80 g (323 mmol) of 3-bromodibenzofuran dissolved in 0.3 L of THF was slowly added dropwise thereto at a temperature of 0° C. for 30 minutes. The resulting mixed solution was slowly added dropwise to 29.5 g (160 mmol) of cyanuric chloride dissolved in 0.5 L of THF at a temperature of 0° C. for 30 minutes. The reaction temperature was raised to room temperature, followed by 1 hour of stirring. Then, in the refluxing condition, the resultant solution was additionally stirred for 12 hours. After cooling the reaction mixture, water was added slowly to terminate the reaction, and the organic solvent was concentrated under reduced pressure to obtain a solid. This was stirred with 200 mL of acetone and then filtered to complete the preparation of Intermediate R3-1 at a yield of 40%.

b) Synthesis of Comparative Compound R3

Comparative Compound R3 was synthesized in the same manner as in "b)" of Synthesis Example 5, except that each of Intermediate R3-1 synthesized above was used in an equivalent weight of 1.0 instead of Intermediate 506-1.

LC/MS calculated for: $C_{45}H_{26}N_4O_2$ Exact Mass: 654.2056 found for: 655.2089.

Evaluation Example 1: Evaluation of HOMO, LUMO, and Triplet (T1) Energy Levels of Compounds HOMO, LUMO, and triplet (T1) energy levels of Compounds 813 to 824 were evaluated by using a DFT method of a Gaussian program (optimized at B3LYP and 6-31G(d,p) levels) and the results obtained therefrom are shown in Table 1 below.

TABLE 1

| Compound No. | HOMO (eV) | LUMO (eV) | $T_1$ energy level (eV) |
| --- | --- | --- | --- |
| 813 | −5.236 | −1.880 | 2.994 |
| 815 | −5.355 | −1.802 | 3.096 |
| 817 | −5.252 | −1.877 | 3.002 |
| 819 | −5.435 | −1.894 | 3.089 |
| 814 | −5.150 | −1.894 | 2.9 |
| 816 | −5.344 | −1.909 | 3.02 |
| 820 | −5.303 | −1.925 | 2.959 |
| 818 | −5.139 | −1.885 | 2.904 |
| 821 | −5.188 | −1.893 | 2.945 |
| 822 | −5.350 | −1.934 | 2.997 |
| 823 | −5.206 | −1.897 | 2.951 |
| 824 | −5.394 | −1.913 | 3.063 |

Thereafter, HOMO, LUMO, S1 energy level, and T1 energy level of Compounds 813 to 816 obtained according to the method in Table 2 and the results thereof are shown in Table 3.

TABLE 2

| | |
| --- | --- |
| An evaluation method of a HOMO energy level | Each compound was diluted in $CHCl_3$ at a concentration of $1 \times 10^{-5}$ M to measure UV absorption spectrum by using a Shimadzu UV-350 Spectrometer at room temperature and then a HOMO energy level was calculated by using an optical band gap (Eg) from an edge of the absorption spectrum. |
| An evaluation method of a LUMO energy level | Cyclic voltammetry (CV) (electrolyte: 0.1M $Bu_4NClO_4$/solvent: $CH_2Cl_2$/ electrode: a 3-electrode system (working electrode: GC, standard electrode: Ag/AgCl, and supply electrode: Pt)) was used to obtain a voltage (V)-current (A) graph for each compound and a LUMO energy level was calculated from a reduction onset of the graph. |
| An evaluation method of evT1 energy level | A mixture of toluene and each compound (1 mg of each compound was dissolved in 3 cc of toluene) was added to a quartz cell and liquid nitrogen (77 K) was added thereto, a photoluminescence measurement device was used to measure photoluminescence spectrum, which was compared to a conventional room temperature photoluminescence spectrum to only analyze the peak observed only at low temperature and calculate a T1 energy level. |

TABLE 3

| Compound No. | HOMO (eV) | LUMO (eV) | T1 energy level (eV) |
| --- | --- | --- | --- |
| 813 | −5.432 | −1.901 | 2.994 |
| 815 | −5.665 | −1.972 | 3.096 |
| 814 | −5.451 | −1.998 | 2.9 |
| 816 | −5.643 | −1.942 | 3.02 |

It may be concluded from Tables 1 and 3 that the condensed-cyclic compounds have suitable electrical properties to be used as a material for an organic light-emitting device.

Evaluation Example 2: Evaluation of Thermal Properties of Synthesized Compounds compounds 813 to 816 were subjected to thermal analyses by using Thermo Gravimetric Analysis (TGA) and Differential Scanning calorimetry (DSC) ($N_2$ atmosphere and temperature range for TGA: room temperature ~800° C. (10° C./min), for DSC: from room temperature to 400° C., Pan Type: for TGA: Pt Pan in a disposable Al Pan, for DSC: a disposable Al pan) and results obtained therefrom are shown in Table 4. From Table 4, it may be concluded that Compounds 813 to 816 have excellent thermal stabilities.

TABLE 4

| Compound No. | Tc (° C.) | Tm (° C.) | Tg (° C.) |
| --- | --- | --- | --- |
| 813 | — | — | 101.21 |
| 815 | 218.72 | 241.72 | 102.57 |
| 814 | — | 312.38 | — |
| 816 | — | — | 139.38 |

Example 1

An ITO glass substrate was cut to a size of 50 mm×50 mm×0.5 mm, and the ITO glass substrate was ultrasonically washed using isopropyl alcohol and pure water for 15 minutes each, followed by irradiation of UV and exposure to ozone for cleaning for about 30 minutes.

m-MTDATA was vacuum deposited on the ITO glass substrate to form an HIL having a thickness of 600 Å, and α-NPB was vacuum deposited at a rate of 1 Å/sec on the HIL to form an EML having a thickness of 300 Å. Thereafter, $Ir(ppy)_3$ (dopant) and Compound 813 (host) were co-deposited at a rate of 0.1 Å/sec and 1 Å/sec, respectively, on the HTL to form an EML having a thickness of 400 Å. BAlq was vacuum deposited on the EML at a rate of 1 Å/sec to form an HBL having a thickness of 50 Å and then $Alq_3$ was vacuum deposited on the HBL to form an ETL having a thickness of 300 Å. Then, LiF 10 Å (EIL) and Al 2000 Å (cathode) were sequentially vacuum deposited on the ETL to manufacture an organic light-emitting device.

Example 2

An organic light-emitting device was manufactured in the same manner as in Example 1, except that Compound 815 was used as a host instead of Compound 813 when forming an EML.

Example 3

An organic light-emitting device was manufactured in the same manner as in Example 1, except that Compound 814 was used as a host instead of Compound 813 when forming an EML.

Example 4

An organic light-emitting device was manufactured in the same manner as in Example 1, except that Compound 816 was used as a host instead of Compound 813 when forming an EML.

Comparative Example 1

An organic light-emitting device was manufactured in the same manner as in Example 1, except that Compound A was used as a host instead of Compound 813 when forming an EML.

Compound A

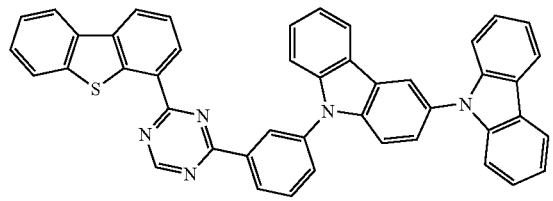

Comparative Example 2

An organic light-emitting device was manufactured in the same manner as in Example 1, except that Compound B was used as a host instead of Compound 813 when forming an EML.

Compound B

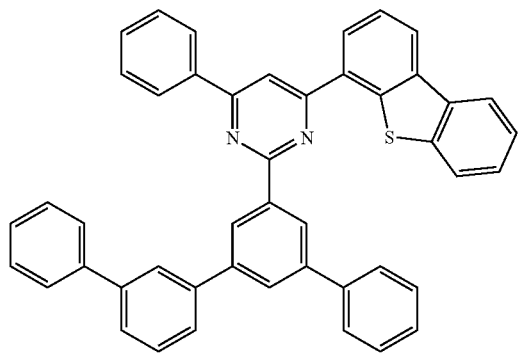

Comparative Example 3

An organic light-emitting device was manufactured in the same manner as in Example 1, except that Compound C was used as a host instead of Compound 813 when forming an EML.

Compound C

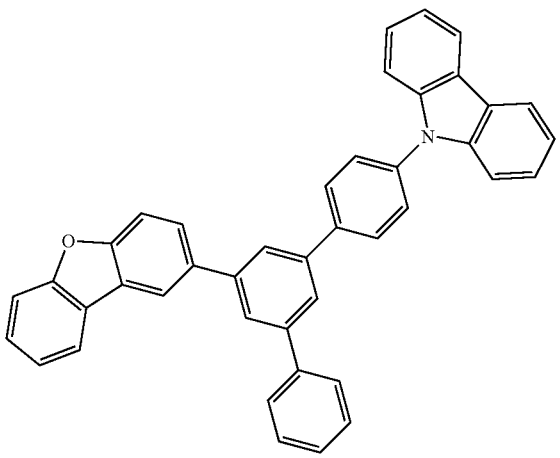

Evaluation Example 2: Evaluation of Characteristics of Organic Light-Emitting Device Changes in current density and brightness, and emission efficiency of each organic light-emitting device manufactured in Examples 1 to 4 and Comparative Examples 1 to 3 were measured. A detailed method of measurement is as described below and results obtained therefrom are shown in Table 5 below:

(1) Measurement of Changes in Current Density According to Changes in Voltage

For each organic light-emitting device, voltage was increased from 0 volts (V) to 10 V to measure current that flows through a unit cell therein by using a voltage-current meter (Keithley 2400) and the current was divided by surface area to obtain a current density.

(2) Measurement of Changes in Brightness According to Changes in Voltage

For each organic light-emitting device, brightness was measured while increasing voltage from 0 V to 10 V to by using Cs-1000A (a product of Minolta).

(3) Measurement of Emission Efficiency

Brightness, current density, and voltage measured from (1) and (2) were used to calculate current efficiency (candelas per ampere (cd/A)) at the same current density (10 milliamperes per square centimeter ($mA/cm^2$)).

TABLE 5

| | Host | Dopant | Driving voltage (V) | Current density (cd/A) | Brightness ($cd/m^2$) |
|---|---|---|---|---|---|
| Example 1 | Compound 813 | $Ir(ppy)_3$ | 3.7 | 40.3 | 3500 |
| Example 2 | Compound 815 | $Ir(ppy)_3$ | 3.4 | 46.2 | 3500 |
| Example 3 | Compound 814 | $Ir(ppy)_3$ | 4.1 | 36.1 | 3500 |
| Example 4 | Compound 816 | $Ir(ppy)_3$ | 3.8 | 33.8 | 3500 |
| Comparative Example 1 | Compound A | $Ir(ppy)_3$ | 4.4 | 32.6 | 3500 |
| Comparative Example 2 | Compound B | $Ir(ppy)_3$ | 4.3 | 31.5 | 3500 |
| Comparative Example 3 | Compound C | $Ir(ppy)_3$ | 4.2 | 32.9 | 3500 |

From Table 5, it may be concluded that the organic light-emitting devices of Examples 1 to 4 have lower driving voltage, high efficiency, and high brightness compared the organic light-emitting devices of Comparative Examples 1 to 3.

Examples 5 and 6

An organic light-emitting device was manufactured in the same manner as in Example 1, except that Compound 506 and 825, respectively, was used as a host instead of Compound 813 when forming an EML.

Comparative Examples R1 to R3

An organic light-emitting device was manufactured in the same manner as in Example 1, except that Compound R1 to R3, respectively, was used as a host instead of Compound 813 when forming an EML.

Evaluation Example 3

Driving voltage, luminous power efficiency and lifespan (T90@24K) of each organic light-emitting device manufactured in Example 5 and Comparative Example R1 were measured. A detailed method of measurement is as described below and results obtained therefrom are shown as a relative value (%) in Table 6 below. The relative value of the driving voltage, the luminous power efficiency and the lifespan of the organic light-emitting device of Comparative Example R1 were regarded as "100%."

(1) Measurement of Current Density Change Depending on Voltage Change

Current values flowing in the unit device of the manufactured organic light emitting diodes were measured for, while increasing the voltage from 0 V to 10 V using a current-voltage meter (Keithley 2400), and the measured current values were divided by an area to provide the results.

(2) Measurement of Luminance Change Depending on Voltage Change

Luminance of the manufactured organic light emitting diodes was measured for luminance, while increasing the voltage from 0 V to 10 V using a luminance meter (Minolta Cs-1000A).

(3) Measurement of Luminous Power Efficiency

Luminous Power efficiency (lm/W) at the same current density (10 mA/cm$^2$) was calculated by using the luminance, current density, and voltages (V) from the items (1) and (2).

(4) Measurement of Driving Voltage

Driving voltages (V) of each device were measured at 15 mA/cm$^2$ using a current-voltage meter (Keithley 2400).

(5) Measurement of Lifespan (T90@24K)

$T_{90}$ was measured an amount of time that lapsed when 100% of the initial luminance (2400 cd/m$^2$) was decreased to 90% at 24K using a Polanonix life-span measurement system.

TABLE 6

| Host | | Driving voltage (relative value) | Luminous Power Efficiency (relative value) | $T_{90}$@24K (relative value) |
|---|---|---|---|---|
| Example 5 | Compound 506 | 91% | 137% | 288% |
| Comparative Example R1 | Comparative Compound R1 | 100% | 100% | 100% |

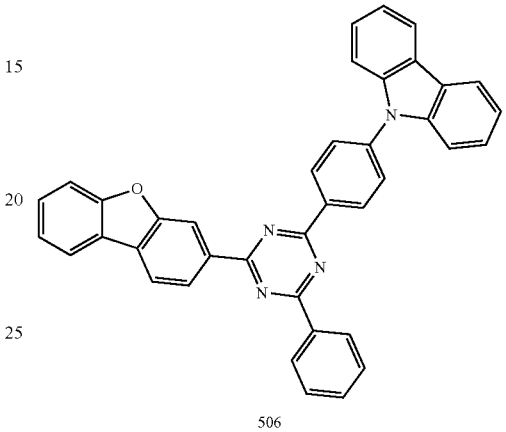

506

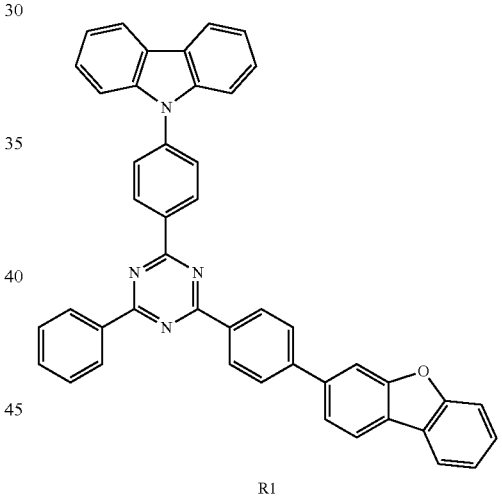

R1

From Table 6, it may be concluded that the organic light-emitting device of Example 5 has lower driving voltage, higher luminous power efficiency, and longer lifespan compared the organic light-emitting devices of Comparative Example R1.

Evaluation Example 4

Driving voltage and lifespan (T90@24K) of each organic light-emitting device manufactured in Example 6 and Comparative Example R2 were measured. A detailed method of measurement is as described in Evaluation Example 3 and results obtained therefrom are shown as a relative value (%) in Table 7 below. The relative value of the driving voltage and the lifespan of the organic light-emitting device of Comparative Example R2 were regarded as "100%."

TABLE 7

| | Host | Driving voltage (relative value) | T$_{90}$@24K (relative value) |
|---|---|---|---|
| Example 6 | Compound 825 | 96% | 162% |
| Comparative Example R2 | Comparative Compound R2 | 100% | 100% |

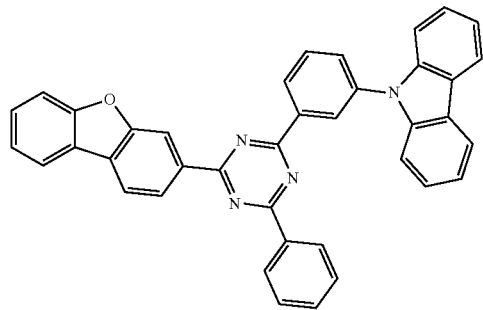

825

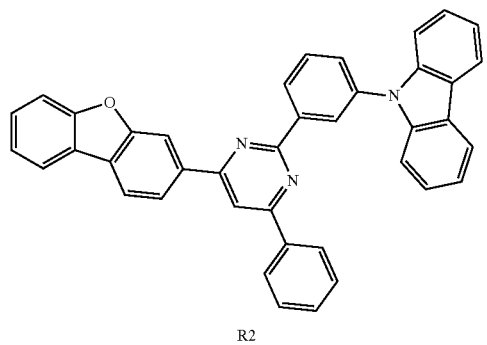

R2

From Table 7, it may be concluded that the organic light-emitting device of Example 6 has lower driving voltage, and longer lifespan compared the organic light-emitting devices of Comparative Example R2.

Evaluation Example 5

Driving voltage and lifespan (T90@24K) of each organic light-emitting device manufactured in Example 6 and Comparative Example R3 were measured. A detailed method of measurement is as described in Evaluation Example 3 and results obtained therefrom are shown as a relative value (%) in Table 8 below. The relative value of the driving voltage and the lifespan of the organic light-emitting device of Comparative Example R3 were regarded as "100%."

TABLE 8

| | Host | Driving voltage (relative value) | T$_{90}$@24K (relative value) |
|---|---|---|---|
| Example 6 | Compound 825 | 105% | 141% |
| Comparative Example R3 | Comparative Compound R3 | 100% | 100% |

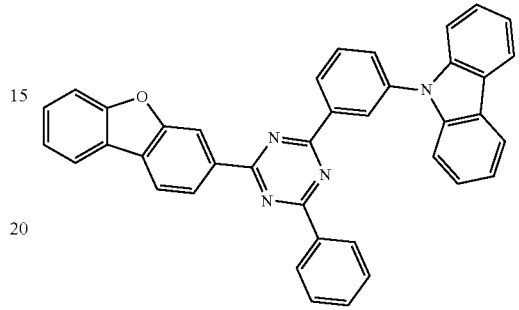

825

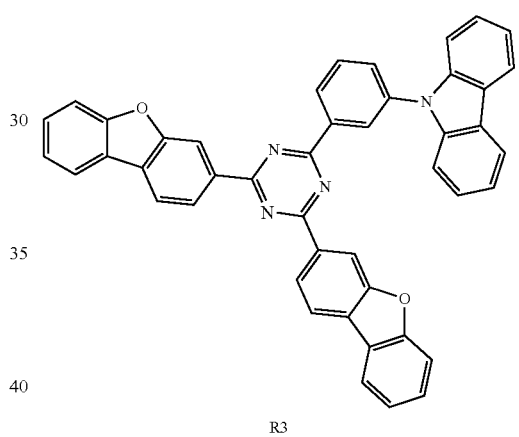

R3

From Table 8, it may be concluded that the organic light-emitting device of Example 6 has longer lifespan compared the organic light-emitting devices of Comparative Example R2.

As described above, according to the one or more of the above embodiments, the condensed-cyclic compound have excellent electrical properties and thermal stability and thus, an organic light-emitting device including the condensed-cyclic compound may have low driving voltage, high efficiency, high brightness, and a long lifespan.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope of the present disclosure as defined by the following claims.

What is claimed is:

1. A condensed-cyclic compound represented by Formula 1A:

Formula 1A

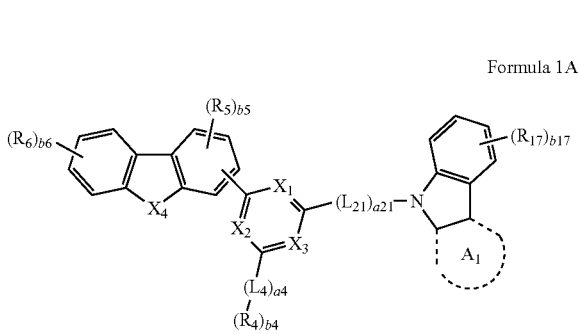

wherein in Formula 1A,
ring $A_1$ is represented by Formula 1D;

Formula 1D

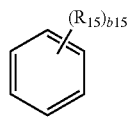

$X_1$ to $X_3$ is N;
$X_4$ is O or S;
$L_4$ and $L_{21}$ are each independently selected from groups represented by Formulae 2-1, 2-2 and 2-34;

Formula 2-1

Formula 2-2

Formula 2-34

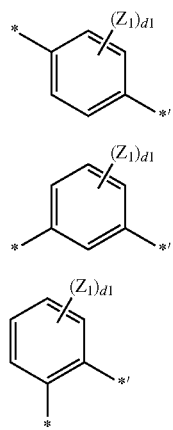

wherein in Formulae 2-1, 2-2 and 2-34, $Z_1$ is selected from a hydrogen and a deuterium, and d1 is selected from integers of 1 to 4;
a4 is selected from integers 0 to 3 and a21 is 0, 1, or 2;
$R_5$, $R_6$, $R_{15}$ and $R_{17}$ are each independently selected from a hydrogen and a deuterium;
$R_4$ is selected from:
a phenyl group; and
a phenyl group, substituted with at least one of a deuterium, and a phenyl group;
b4 to b6, b15 and b17 are each independently selected from integers of 1 to 3.

2. The condensed-cyclic compound of claim 1, wherein the condensed-cyclic compound is represented by one of Formulae 1A(1) to 1A(4):

Formula 1A(1)

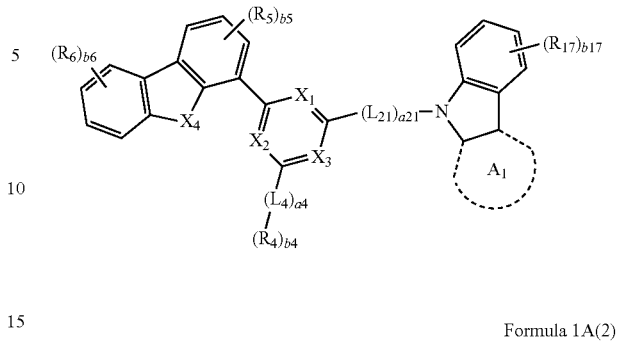

Formula 1A(2)

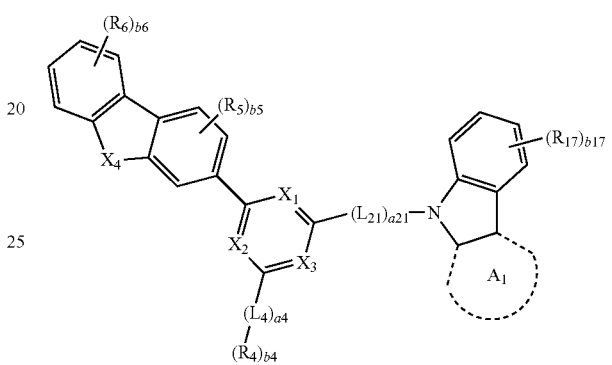

Formula 1A(3)

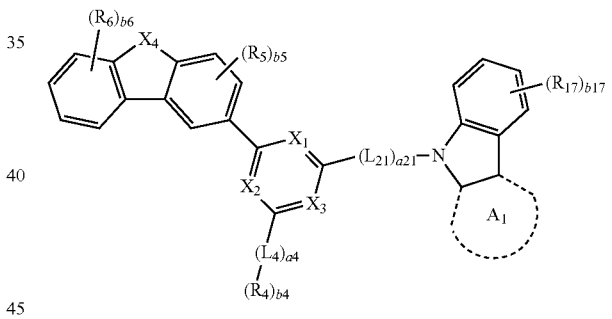

Formula 1A(4)

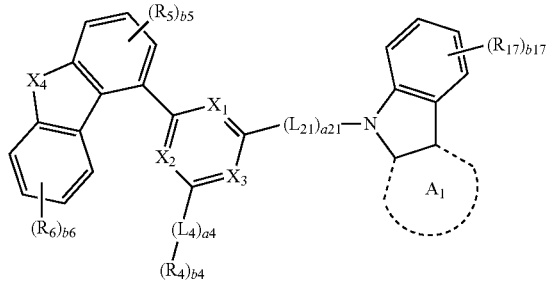

wherein in Formulae 1A(1) to 1A(4), descriptions of ring $A_1$, $X_1$ to $X_4$, $L_4$, $L_{21}$, a1, a21, $R_4$ to $R_6$, $R_{15}$, $R_{17}$, b4 to b6, b15 and b17 are the same as described in claim 1.

3. The condensed-cyclic compound of claim 1, wherein the condensed-cyclic compound is one of Compounds 1, 85, 169, 253, 337, 421, 505, 506, 575, 659, 660, 729 and 825:

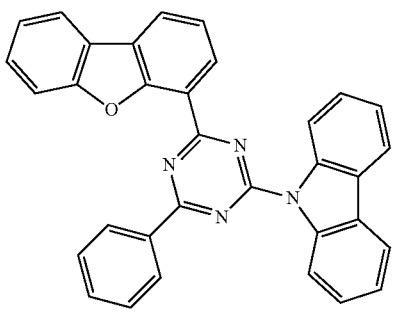
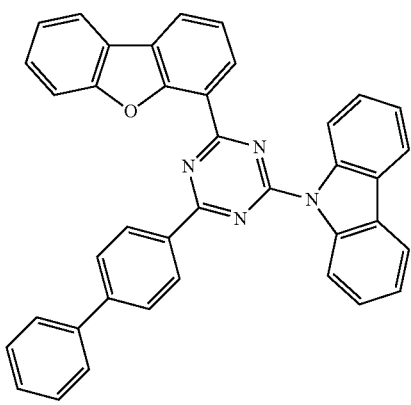
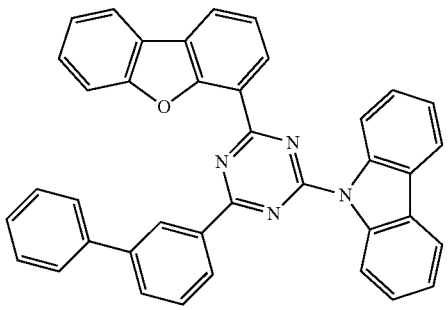
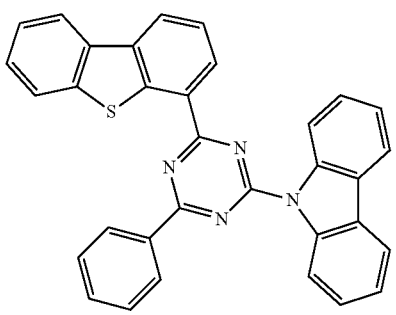
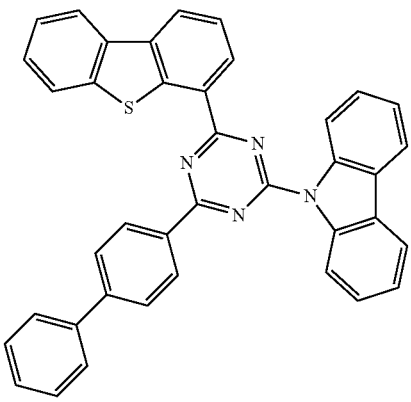
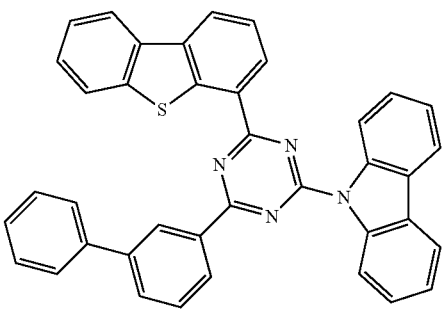
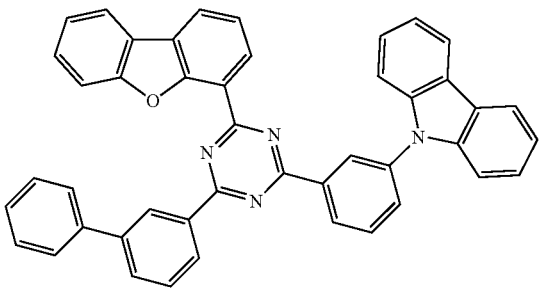
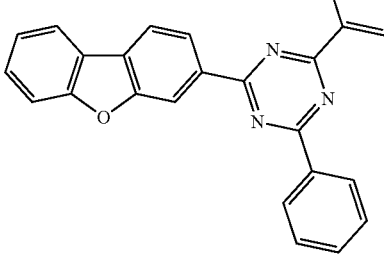

575 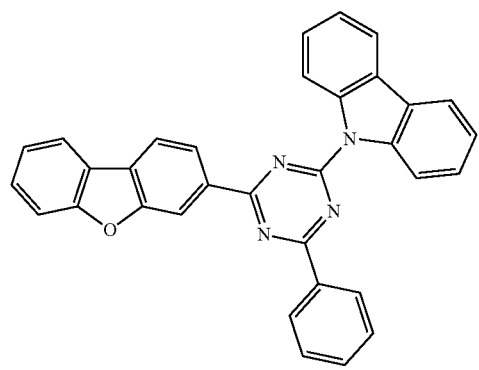

659 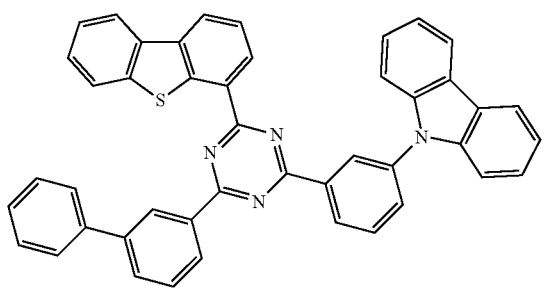

660 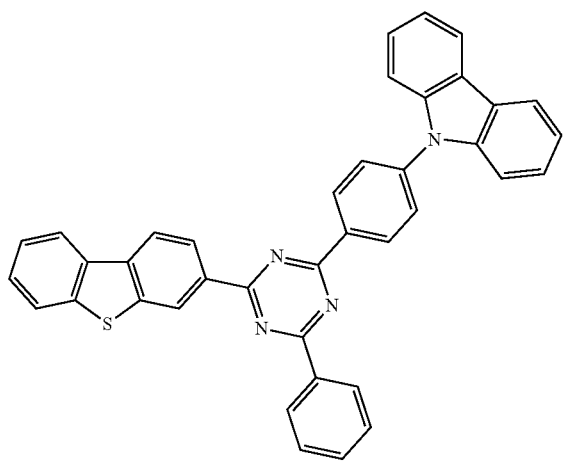

729 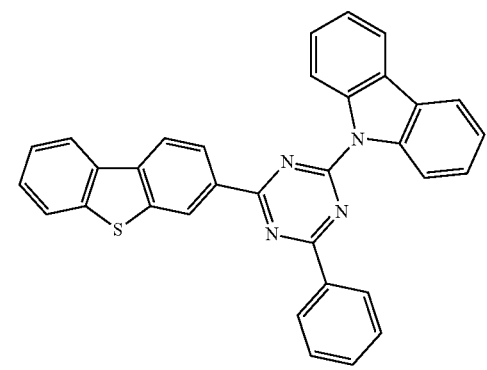

825 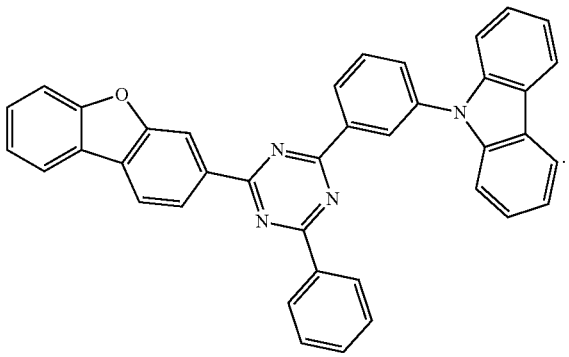

4. An organic light-emitting device comprising
a first electrode;
a second electrode; and
an organic layer disposed between the first electrode and the second electrode,
wherein the organic layer comprises an emission layer and the condensed-cyclic compound of claim 1.

5. The organic light-emitting device of claim 4, wherein
the first electrode is an anode and
the second electrode is a cathode,
wherein the organic layer comprises
i) a hole transport region disposed between the first electrode and the emission layer,
wherein the hole transport region comprises at least one of a hole-injection layer, a hole-transporting layer, and an electron-blocking layer; and
ii) an electron transport region disposed between the emission layer and the second electrode,
wherein the electron transport region comprises at least one layer selected from a hole-blocking layer, an electron-transporting layer, and an electron-injecting layer.

6. The organic light-emitting device of claim 4, wherein the emission layer comprises the condensed-cyclic compound.

7. The organic light-emitting device of claim 6, wherein the emission layer further comprises an organometallic compound represented by Formula 81:

Formula 81

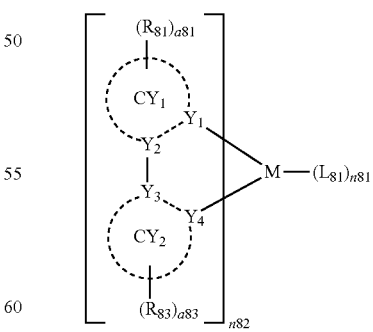

wherein in Formula 81,
M is selected from Ir, Pt, Os, Ti, Zr, Hf, Eu, Tb, and Tm;
$Y_1$ to $Y_4$ are each independently C or N;
$Y_1$ and $Y_2$ are connected by a single bond or a double bond and $Y_3$ and $Y_4$ are connected by a single bond or a double bond;

$CY_1$ and $CY_2$ are each independently selected from a benzene, a naphthalene, a fluorene, a spiro-fluorene, an indene, a pyrrole, a thiopene, a furan, an imidazole, a pyrazole, a thiazole, an isothiazole, an oxazole, an isooxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiopene, an isobenzothiopene, a benzooxazole, an isobenzooxazole, a triazole, a tetrazole, an oxadiazole, a triazine, a dibenzofuran, and a dibenzothiopene, wherein $CY_1$ and $CY_2$ are optionally bound to each other by a single bond or an organic linking group;

$R_{81}$ and $R_{82}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic hetero-condensed polycyclic group, —$N(Q_1)(Q_2)$, —$Si(Q_3)(Q_4)(Q_5)$, and —$B(Q_6)(Q_7)$;

a81 and a82 are each independently selected from integers of 1 to 5;

n81 is selected from integers of 0 to 4;

n82 is 1, 2, or 3; and $L_{81}$ is selected from a monovalent organic ligand, a divalent organic ligand, and a trivalent organic ligand, wherein $Q_1$ to $Q_7$ are each independently selected from a hydrogen, a $C_1$-$C_{60}$ alkyl group, a $C_2$-$C_{60}$ alkenyl group, a $C_2$-$C_{60}$ alkenyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, monovalent a non-aromatic condensed polycyclic group, and a monovalent non-aromatic hetero-condensed polycyclic group.

* * * * *